(12) United States Patent
Predki et al.

(10) Patent No.: US 10,640,822 B2
(45) Date of Patent: *May 5, 2020

(54) SYSTEMS AND METHODS FOR WRITING, READING, AND CONTROLLING DATA STORED IN A POLYMER

(71) Applicant: IRIDIA, INC., Carlsbad, CA (US)

(72) Inventors: Paul F. Predki, Carlsbad, CA (US); Maja Cassidy, Royal Exchange (AU)

(73) Assignee: IRIDIA, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/969,745

(22) Filed: May 2, 2018

(65) Prior Publication Data
US 2019/0136307 A1    May 9, 2019

Related U.S. Application Data

(63) Continuation-in-part of application No. PCT/US2017/059100, filed on Oct. 30, 2017, and a
(Continued)

(51) Int. Cl.
*C12Q 1/68* (2018.01)
*C12Q 1/6869* (2018.01)
(Continued)

(52) U.S. Cl.
CPC ............ *C12Q 1/6869* (2013.01); *C12P 19/34* (2013.01); *G01N 33/48721* (2013.01); *H01P 7/00* (2013.01); *H03H 7/06* (2013.01)

(58) Field of Classification Search
CPC ........ G11C 13/02; G16B 30/00; G06N 3/123; C12Q 1/6869; C12Q 1/68; B82Y 10/00
See application file for complete search history.

(56) References Cited

U.S. PATENT DOCUMENTS

| 5,605,662 A | 2/1997 | Heller et al. |
| 5,795,782 A | 8/1998 | Church et al. |

(Continued)

FOREIGN PATENT DOCUMENTS

| EP | 2843405 A2 | 3/2015 |
| WO | WO 2003/025123 A2 | 3/2003 |

(Continued)

OTHER PUBLICATIONS

Anderson, B.N., et al. "Probing Solid-State Nanopores with Light for the Detection of Unlabeled Analytes," ACS Nano (2014) 8(11):11836-11845.
(Continued)

*Primary Examiner* — Mohammed A Bashar
(74) *Attorney, Agent, or Firm* — Hoxie & Associates LLC

(57) ABSTRACT

The disclosure provides a novel system of storing information using a charged polymer, e.g., DNA, the monomers of which correspond to a machine-readable code, e.g., a binary code, and which can be synthesized and/or read using a novel nanochip device comprising nanopores; novel methods and devices for synthesizing oligonucleotides in a nanochip format; novel methods for synthesizing DNA in the 3' to 5' direction using topoisomerase; novel methods and devices for reading the sequence of a charged polymer, e.g., DNA, by measuring capacitive or impedance variance, e.g., via a change in a resonant frequency response, as the polymer passes through the nanopore; and further provides compounds, compositions, methods and devices useful therein.

27 Claims, 94 Drawing Sheets

Specification includes a Sequence Listing.

Related U.S. Application Data continuation-in-part of application No. 15/690,189, filed on Aug. 29, 2017, said application No. PCT/US2017/059100 is a continuation-in-part of application No. 15/690,189, which is a continuation-in-part of application No. PCT/US2017/020044, filed on Feb. 28, 2017.

(60) Provisional application No. 62/415,430, filed on Oct. 31, 2016, provisional application No. 62/301,538, filed on Feb. 29, 2016.

(51) Int. Cl.
| | |
|---|---|
| C12P 19/34 | (2006.01) |
| G01N 33/487 | (2006.01) |
| H01P 7/00 | (2006.01) |
| H03H 7/06 | (2006.01) |

(56) References Cited

U.S. PATENT DOCUMENTS

| | | |
|---|---|---|
| 6,312,911 B1 | 11/2001 | Bancroft et al. |
| 6,355,420 B1 | 3/2002 | Chan |
| 6,403,311 B1 | 6/2002 | Chan |
| 6,905,586 B2 | 6/2005 | Lee et al. |
| 7,217,562 B2 | 5/2007 | Cao et al. |
| 7,932,025 B2 | 4/2011 | Can et al. |
| 8,003,319 B2 | 8/2011 | Polonsky et al. |
| 8,137,569 B2 | 3/2012 | Harnack et al. |
| 8,262,998 B2 | 9/2012 | Vlahovic et al. |
| 8,273,532 B2 | 9/2012 | Gershow et al. |
| 8,324,914 B2 | 12/2012 | Chen et al. |
| 8,333,934 B2 | 12/2012 | Cao et al. |
| 8,461,854 B2 | 6/2013 | Chen et al. |
| 8,500,982 B2 | 8/2013 | Akeson et al. |
| 8,663,780 B2 | 3/2014 | Harnack et al. |
| 8,673,550 B2* | 3/2014 | Gundlach .............. C07K 14/35 435/4 |
| 8,702,929 B2 | 4/2014 | Leburton et al. |
| 8,828,208 B2 | 9/2014 | Canas et al. |
| 8,936,763 B2 | 1/2015 | Rothberg et al. |
| 8,961,763 B2 | 2/2015 | Dunbar et al. |
| 8,962,242 B2 | 2/2015 | Chen |
| 8,986,629 B2 | 3/2015 | Deierling et al. |
| 9,041,420 B2 | 5/2015 | Chen et al. |
| 9,127,313 B2 | 9/2015 | Brown et al. |
| 9,170,230 B2 | 10/2015 | Gundlach et al. |
| 9,222,082 B2 | 12/2015 | Jayasinghe et al. |
| 9,377,437 B2 | 6/2016 | Chen et al. |
| 9,384,320 B2 | 7/2016 | Church |
| 9,447,152 B2 | 9/2016 | Clarke et al. |
| 9,494,554 B2 | 11/2016 | Davis et al. |
| 9,551,023 B2 | 1/2017 | Turner et al. |
| 9,551,338 B2 | 1/2017 | Jones et al. |
| 9,551,697 B2 | 1/2017 | Chen |
| 9,557,294 B2 | 1/2017 | Chen et al. |
| 9,593,370 B2 | 3/2017 | Jones |
| 9,617,591 B2 | 4/2017 | Moysey et al. |
| 9,617,593 B2 | 4/2017 | Davis et al. |
| 9,651,519 B2 | 5/2017 | Brown et al. |
| 2001/0026918 A1 | 10/2001 | Collins et al. |
| 2004/0001371 A1 | 1/2004 | Mansuripur et al. |
| 2005/0053968 A1 | 3/2005 | Bharadwaj et al. |
| 2006/0073489 A1 | 4/2006 | Li et al. |
| 2007/0012783 A1 | 1/2007 | Mercolino |
| 2007/0190542 A1 | 8/2007 | Ling et al. |
| 2007/0194225 A1 | 8/2007 | Zorn |
| 2009/0098119 A1 | 4/2009 | Lu et al. |
| 2009/0203000 A1 | 8/2009 | Mutharasan et al. |
| 2009/0221443 A1 | 9/2009 | Heller et al. |
| 2011/0037486 A1 | 2/2011 | Zhang et al. |
| 2011/0120868 A1 | 5/2011 | Lindsay et al. |
| 2011/0287414 A1 | 11/2011 | Chen et al. |
| 2012/0058468 A1 | 3/2012 | McKeown |
| 2012/0322109 A1 | 12/2012 | Shuman et al. |
| 2012/0326732 A1 | 12/2012 | Cho et al. |
| 2013/0233709 A1 | 9/2013 | Dunbar et al. |
| 2013/0237460 A1 | 9/2013 | Deierling et al. |
| 2013/0264207 A1 | 10/2013 | Ju et al. |
| 2014/0099726 A1 | 4/2014 | Heller |
| 2014/0174927 A1 | 6/2014 | Bashir et al. |
| 2014/0266147 A1* | 9/2014 | Blick .............. G01N 33/48721 324/71.1 |
| 2014/0329225 A1 | 11/2014 | Morin |
| 2015/0001084 A1 | 1/2015 | Peter et al. |
| 2015/0107996 A1 | 4/2015 | Chen |
| 2015/0153303 A1 | 6/2015 | Chen |
| 2015/0269313 A1 | 9/2015 | Church |
| 2016/0025655 A1 | 1/2016 | Blick et al. |
| 2016/0169865 A1 | 6/2016 | Rosenstein et al. |
| 2016/0223538 A1 | 8/2016 | McAlpine et al. |
| 2016/0340719 A1 | 11/2016 | Chen et al. |
| 2016/0358055 A1 | 12/2016 | Church |
| 2017/0074855 A1 | 3/2017 | Morin et al. |
| 2017/0275678 A1 | 9/2017 | Sharaf et al. |
| 2018/0023115 A1 | 1/2018 | Morin et al. |
| 2018/0137418 A1 | 5/2018 | Roquet et al. |
| 2019/0033286 A1* | 1/2019 | Davidson .............. C12Q 1/6869 |

FOREIGN PATENT DOCUMENTS

| | | |
|---|---|---|
| WO | WO 2004/088585 A2 | 10/2004 |
| WO | WO 2006/028508 A2 | 3/2006 |
| WO | WO 2011/097028 A1 | 8/2011 |
| WO | WO 2012/042399 A1 | 4/2012 |
| WO | WO 2013/101672 A2 | 7/2013 |
| WO | WO 2013/178801 A2 | 12/2013 |
| WO | WO 2014/014991 A2 | 1/2014 |
| WO | WO 2015/090879 A1 | 6/2015 |

OTHER PUBLICATIONS

Ando, G., et al., "Directly Observing the Motion of DNA Molecules near Solid-State Nanopores," ACS Nano (2012) 6(11):10090-10097.

Arafat, A., "Covalent Biofunctionalization of Silicon Nitride Surfaces," Langmuir (2007) 23(11):6233-6244 (Abstract Only) 1 page.

Bancroft et al., "Long-Term Storage of Information in DNA", Science (2001) 293(5536):1763-1765, 12 pages.

Bell, N.A., et al., "DNA origami nanopores," Nano Lett. (2012) 12(1):512-517 (Abstract Only) 1 page.

Bell, N., et al., "Digitally encoded DNA nanostructures for multiplexed, single-molecule protein sensing with nanopores," Nat Nanotechnol. (2016) 11(7):645-51.

Benner S., et al., "Sequence-specific detection of indvidual DNA polymerase complexes in real time using a nanopore," Nature Nanotechnology (2007) 2(11):718-724.

Bornholt, J., et al., "A DNA-Based Archival Storage System," ASPLOS 2016 (2016) 637-649.

Briggs, K., et al., "Automated fabrication of 2-nm solid-state nanopores for nucleic acid analysis," Small (2014) 10(10):2077-86 (Abstract Only) 1 page.

Cao, H., et al., "Fabrication of Gradient Fluidic Structures Interfacing Microfluids and Nanofluids," Applied Physics Letters (2002) 81:3058.

Carlsen, A.T., et al., "Selective Detection and Quantification of Modified DNA with Solid-State Nanopores," Nano Letters (2014) 14(10):A-E, 6 pages.

Carminati, M., et al., "ZeptoFarad resolution CMOS read-out circuit for nanosensors," Procedia Engineering (2010) 5:1123-1126.

Cassidy, M.C., et al., "Demonstration of an ac Josephson junction laser," Science (2017) 355:939-942, 5 pages.

Chen, Z., "DNA translocation through an array of kinked nanopores," Nat Mater. (2010) 9(8):667-75 (Abstract Only) 1 page.

Cherf et al., "Automated forward and reverse ratcheting of DNA in a nanopore at 5-Å precision," Nature Biotechnology (2012) 30(4):344-348.

(56) References Cited

OTHER PUBLICATIONS

Church, G.M., et al., "Next-Generation Digital Information Storage in DNA," Science, 2012, 337:1628.
Clarke, J., et al., "Continuous base identification for single-molecule nanopore DNA sequencing," Nature Nanotechnology (2009) 4:265-270.
Cox et al., "Long-term data storage in DNA," Trends in Biotechnology (2001) 19(7):247-250 (Abstract Only) 1 page.
Dalmay, C., et al., "Ultra Sensitive Biosensor Based on Impedance Spectroscopy at Microwave Frequencies for Cell Scale Analysis," Procedia Chemistry (2009) 1:742-745.
Denef, N., et al., "RF detection of DNA based on CMOS inductive and capacitive sensors," 34$^{th}$ European Mircrowave Conference—Amsterdam, (2004) 669-672.
DeRouin et al., "A Wireless Inductive-Capacitive Resonant Circuit Sensor Array for Force Monitoring," Journal of Sensor Technology (2013) 3:63-69.
Derrington, I.M., et al., "Nanopore DNA sequencing with MspA," PNAS (2010) 107(37): 16060-16065, Supporting Information located on pp. 1-8.
Ervin, E.N., "Creating a Single Sensing Zone within an Alpha-Hemolysin Pore Via Site Directed Mutagenesis," Bionanoscience (2014) 4(1):78-84.
Esfandiari, L., "Sequence-specific Nucleic Acid Detection from Binary Pore Conductance Measurement," J. Am. Chem. Soc. (2012) 134:15880-15886.
Extance, A., "Could the Molecule Known for Storing Genetic Information Also Store the World's Data?" Nature (2016) 537:22-24.
Feng, et al., "Identification of single nucleotides in MoS2 nanopores," Nat Nanotechnol. (2015) 10(12):1070-1076.
Fyta, M., et al., "Threading DNA through nanopores for biosensing application," J. Phys. Condens. Matter (2015) 27(273101):1-18.
Garaj, S., et al., "Graphene as a subnanometre trans-electrode membrane," Nature (2010) 467 (7312):190-193.
Garaj, S., et al., "Molecule-hugging graphene nanopores," PNAS (2013) 110(30):12192-12196.
Gershow et al., "Recapturing and Trapping Single Molecules with a Solid State Nanopore," Nat Nanotechnol. (2007) 2(12):775-779 (Abstract Only) 1 page.
Gilbert, et al., "Fabrication of Atomically Precise Nanopores in Hexagonal Boron Nitride," eprint arXiv:1702.01220 (2017).
Goldman, N., et al., "Toward practical high-capacity low-maintenance storage of digital information in synthesised DNA," Nature (2013) 494(7435):77-80, 9 pages.
Goldstein, B., et al., "CMOS Low Current Measurement System for Nanopore Sensing Applications," 4 pages.
Goyal et al., "Structural and mechanistic insights into the bacterial amyloid secretion channel CsgG," Nature (2014) S16:250-253, 18 pages.
Gracheva, M.E., et al., "Electrical signatures of single-stranded DNA with single base mutations in a nanopore capacitor," Nanotechnology (2006) 17:3160-3165.
Gracheva, M.E., et al., "Simulation of the electric response of DNA translocation through a semiconductor nanopore-capacitor," Nanotechnology (2006) 17(3): 622-633.
Hall, A.R. et al., "Hybrid pore formation by directed insertion of a-haemolysin into solid-state nanopores," Nature Nanotechnology (2010) 5:874-877.
Heerema, S.J., et al, "Graphene nanodevices for DNA sequencing," Nature Nanotechnology (2016) 11:127-136.
Heng et al., "Beyond the gene chip," Bell System Technical Journal (2005) 10(3):5-22.
Heng, J.B., et al., "Sizing DNA Using a Nanometer-Diameter Pore," Biophys. J (2004) 87(4):2905-11.
Henley, et al. "Electrophoretic Deformation of Individual Transfer RNA Molecules Reveals Their Identity," Nano Lett. (2016) 16:138-144.
Heron, A.J., et al., "Simultaneous Measurement of Ionic Current and Fluorescence from Single Protein Pores," J. Am. Chem. Soc. (2009) 131:1652-1653.
Holmes, I., et al., "Modular non-repeating codes for DNA storage," posted online: Jun. 7, 2016, doi: http://dx.doi.org/10.1101/057448, 39 pages.
Hossein Tabatabaei Yazdi, S.M., et al., "A Rewritable, Random-Access DNA-Based Storage System," Scientific Reports (2015) 5:14138:1-10.
Huang, S., et al., "High-throughput optical sensing of nucleic acids in a nanopore array," Nature Nanotechnology (2015) 10:986-992.
International Preliminary Report on Patentability and Written Opinion of the International Searching Authority, International Application No. PCT/US2013/050815, prepared by the International Searching Authority, dated Jan. 20, 2015, 7 pages.
International Search Report of International Application No. PCT/US2017/059100, prepared by the International Searching Authority, dated Jan. 18, 2018, 3 pages.
International Search Report of International Application No. PCT/US2017/020044, prepared by the International Searching Authority, dated Aug. 16, 2017, 4 pages.
Ivankin, A., et al., "Label-Free Optical Detection of Biomolecular Translocation through Nanopore Arrays," ACS Nano (2014) 8(10:10774-10781.
Johnson, R.P., et al., "Base Flipping within the α-Hemolysin Latch Allows Single-Molecule Identification of Mismatches in DNA," JACS (2015) 138:594-603.
Ju, J., "Four-color DNA sequencing by synthesis using cleavable fluorescent nucleotide reversible terminators," Proc Natl Acad Sci U S A. (2006) 103(52):19635-40.
Kalff, F.E., et al., "A kilobyte rewritable atomic memory," Nature Nanotechnology (2016) 11:926-929, 5 pages.
Kasianowicz, J.J., et al., "Characterization of individual polynucleotide molecules using a membrane channel," Proc. Natl. Acad. Sci. (1996) 93:13770-13773.
Kennedy, E., "Reading the primary structure of a protein with 0.07 nm3 resolution using a subnanometre-diameter pore," Nature Nanotechnology (2016) 11(11):968-976, 11 pages.
Kim, Y. et al., "Development of LC resonator for label-free biomolecule detection," Sensors and Actuators A 143 (2008) 279-285.
Kolb, et al., "Click Chemistry: Diverse Chemical Function from a Fe Good Reactions," Angew. Chem. Int. Ed. (2001) 40:2004-2021.
Kulkarni, G., et al., "Detection beyond the Debye Screening Length in a High-Frequency Nanoelectronic Biosensor," Nano Letters (2012) 12:719-723.
Kwok, et al., "Nanopore Fabrication by Controlled Dielectric Breakdown," PLOS ONE (2014) 9(3):e92880, 6 pages.
Laborde, C., et al., "Real-Time imaging of microparticles and living cells with CMOS nanocapacitor arrays," Nat Nano. (2015) 10(9):791-5.
Lemay, S., et al., "High-Frequency Nanocapacitor Arrays: Concept, Recent Developments, and Outlook," Acc. Chem. Res. (2016) 49:2355-2362.
Li, J. et al, "Solid-state nanopore for detecting individual biopolymers," Methods Mol Biol. (2009) 544:81-93.
Liu, X. et al., "High-throughput impedance spectroscopy biosensor array chip," Philosophical Transactions of The Royal Society A (2013) 372:1-14.
Liu, Z., et al., "Solid-State Nanopore-Based DNA Sequencing Technology," Journal of Nanomaterials (2016) Articled ID 5284786, 13 pages.
Lu, J., et al., "Nucleotide Capacitance Calculation for DNA Sequencing," Biophysical Journal: Biophysical Letters (2008) doi: 10.1529/biophysj.108.140749, L60-L62.
Malyshev, D., et al., "A semi-synthetic organism with an expanded genetic alphabet", Nature (2014) 509:385-388.
Manrao, E., et al., "Reading DNA at single-nucleotide resolution with a mutant MspA nanopore and phi29 DNA polymerase," Nature Biotechnology (2012) 30(4):349-354.
McNally et al., "Optical recognition of converted DNA nucleotides for single molecule DNA sequencing using nanopore arrays," Nano Lett. (2010) 10(6): 2237-2244.

(56) References Cited

OTHER PUBLICATIONS

Mikheyev, A.S., et al., "A first look at the Oxford Nanopore MinION sequencer," Mol. Ecol. Resour. (2014) 14:1097-1102 (Abstract Only) 1 page.
Minkah, N., et al., "Variola Virus Topoisomerase: DNA Cleavage Specificity and Distribution of Sites in Poxvirus Genomes," Virology (2007) 365(1):60-69.
Nam, et al., "Graphene Nanopore with a Self-Integrated Optical Antenna," Nano Lett. (2014) 14:5584-5589 (Abstract Only) 1 page.
Nishigaki, K., Type II restriction endonucleases cleave single-stranded DNAs in general, Nucleic Acids Res. (1985) 13(16):5747-5760.
Palaniyar, N., et al., "SFV topoisomerase: sequence specificity in a genetically mapped interval," Virology (1996) 221(2):351-4.
Patel, P., "Tech Turns to Biology as Data Storage Needs Explode: Interest by Microsoft and others in DNA-based storage could deliver post-silicon electronic memory within a decade," Scientific American (May 31, 2016) 7 pages.
Paunescu, D., et al., "Reversible DNA encapsulation in silica to produce ROS-resistant and heat-resistant synthetic DNA 'fossils'," Nature Protocols (2013) 8:2440-2448 (Abstract Only) 4 pages.
Pevarnik, M., et al., "Polystyrene Particles Reveal Pore Substructure As They Translocate," ACS Nano (2012) 6(8):7295-7302.
Plesa, C., et al., "Direct observation of DNA knots using a solid-state nanopore," Nature Nanotechnology, 2016, 11(12):1093-1097, 6 pages.
Plesa, C., "Solid-state nanopores for probing DNA and protein," Casimir PhD Series 2014-36, Delft-Leiden, pp. 1-203, 216 pages.
Rodriguez-Manzo et al., "DNA Translocation in Nanometer Thick Silicon Nanopores," ACS Nano (2015) 9(6):6555-6564.
Rothberg et al., "An integrated semiconductor device enabling non-optical genome sequencing," Nature (2011) 475:348-352.
Schneider et al., "DNA sequencing with nanopores," Nature Biotechnology (2012) 30(4):326-328.
Schneider et al., "Tailoring the hydrophobicity of graphene for its use as nanopores for DNA translocation," Nature Communications (2013) 4:2619, 7 pages.
Shankaraiah, G., et al., "Rapid and selective deallylation of allyl ethers and esters using iodine in polyethylene glycol-400," Green Chem. (2011)13: 2354-2358 (Abstract Only) 1 page.
Shuman, S., "Novel Approach to Molecular Cloning and Polynucleotide Synthesis Using Vaccinia DNA Topoisomerase*," J Biol Chem. (1994) 269(51):32678-84.
Sigalov et al., "Detection of DNA sequences using an alternating electric field in a nanopore capacitor," Nano Letters (2008) 8(1):56-63.
Smeets, R.M., et al., "Noise in solid-state nanopores," PNAS (2008) 105(2):417-21.
Smolyanitsky, A., et al., "A MoS2-based capacitive displacement sensor for DNA sequencing," (2016) ACS Nano 10(9) pp. 1-21, Supplementary Information provided on pp. S1-S7.
Stahl, P.L., et al., "Visualization and analysis of gene expression in tissue section by spatial transcriptomics," Science (2016) 353(6294):78-82, 6 pages.
Stivers, J.T., et al., "Vaccinia DNA Topoisomerase I: Single-Turnover and Steady-State Kinetic Analysis of the DNA Strand Cleavage and Ligation Reactions," Biochemistry (1994) 33(1):327-339.
Stoddart, D., "Single-nucleotide discrimination in immobilized DNA oligonucleotides with a biological nanopore," PNAS (2009) 106(19):7702-7707.
Storm, A.J., et al., "Fabrication of solid-state nanopores with single-nanometre precision," Nature Materials (2003) 2:537-540 (Abstract Only) 1 page.
Storm, A.J. et al., "Translocation of double-stranded DNA through a silicon oxide nanopore," Phys. Rev. E (2005) 71:051903.
Tan, S., et al., "DNA-functionalized silicon nitride nanopores for sequence-specific recognition of DNA biosensor," Nanoscale Research Letters (2015) 10(205):1-10.

Thompson, D., et al., "Amplification free detection of Herpes Simplex Virus DNA," Analyst (2011) 136(8):1599-1607.
Toumazou et al., "Simultaneous DNA amplification and detection using a pH-sensing semiconductor system," Nature Methods (2013) 10:641-646.
Traversi et al., "Detecting the translocation of DNA through a nanopore using graphene nanoribbons," Nature Nanotechnology (2013) 8:939-945.
Tsutsui, M., et al., "Identifying single nucleotides by tunnelling current," Nature Nanotechnology (2010) 5:286-290.
Ud-Dean, "A theoretical model for template-free synthesis of long DNA sequence," Syst Synth Biol (2008) 2:67-73.
Uddin, et al., "Integration of solidstate nanopores in a 0.5 µm CMOS foundry process," Nanotechnology (2013) 24(15):155501, 22 pages.
Venkatesan, B.M., "Nanopore sensors for nucleic acid analysis," Nature Nanotechnology (2011) 6:615-624.
Venta, K., et al., "Differentiation of Short, Single-Stranded DNA Homopolymers in Solid-State Nanopores," ACS Nano. (2013) 7(5):4629-36.
Vitarelli, M. J., et al., "Determining Nanocapillary Geometry from Electrochemical Impedance Spectroscopy Using a Variable Topology Network Circuit Model," Anal. Chem., (2011) 83:533-541.
Vitarelli, M.J., et al., "Theoretical models for electrochemical impedance spectroscopy and local-potential of unfolded proteins in nanopores," The Journal of Chemical Physics (2013) 139(105101):1-8.
Wang et al., "Multi-Channel Capacitive Sensor Arrays," Sensors (2016) 16:150.
Wang, Y., et al., "Nanopore-based detection of circulating microRNAs in lung cancer patients," Nature Nanotechnology (2011) 6:668-674.
Wanunu, M., "Electrostatic Focusing of Unlabelled DNA into Nanoscale Pores using a Salt Gradient," Nat Nanotechnol. (2010) 5(2):160-5.
Widdershoven, "CMOS Pixelated Capacitive Sensor platform for biosensing and many other applications," Smart sensors NEREID workshop, Presentation (Oct. 21, 2016) 35 pages.
Yang, C., et al., "Compact Low-Power Impedance-to-Digital Converter for Sensor Array Microsystems," IEEE Journal of Solid-State Circuits, vol. 44, No. 10, (2009) 2844-2855.
Zahid, O.K., "Sequence-Specific Recognition of MicroRNAs and Other Short Nucleic Acids with Solid-State Nanopores," Nano Letters (2016) 16:2033-2039.
Bagiante, S., et al., "Giant Electric Field Enhancement in Split Ring Resonators Featuring Nanometer-Sized Gaps," Scientific Reports (2015) vol. 5, No. 8051, pp. 1-5; DOI: 10.1038/srep08051.
Bhat, A., et al., "Radio Frequency Tank Circuit for Probing Planar Lipid Bilayers," Soft Nanoscience Letters (2013) vol. 3, 6 pages; http://dx.doi.org/10.4236/snl.2013.34016.
Kim, H "Radio-Frequency Response of Single Pores and Artificial Ion , Channels," New Journal of Physics (2011) vol. 13, 17 pages; DOI: 10.1088/1367-2630/13/9/093033.
Meller, A.,"Towards Optical Dna Sequencing Using Nanopore Arrays," J Biomol Tech. (2011) 22(Suppl): S8-S9.
Anonymous, "Orthogonal Frequency-Division Multiplexing," Wikipedia (2018), 11 pages.
Reddy, N., et al., "Split Ring Resonator and its Evolved Structures over the Past Decade," National Institute of Technology, Department of Electronics and Communication, Trichy India, (2014) 6 pages.
Stava, E., et al., "Mechanical Actuation of Ion Channels using a Piezoelectric Planar Patch Clamp System," Lab Chip (2013), vol. 12, pp. 80-87; DOI: 10.1039/C1LC20636B.
Stava, E., et al., "Rapid Fabrication and Piezoelectric Tuning of Micro- and Nanopores in Single Crystal Quartz," Lab Chip (2013), vol. 13, pp. 156-160; DOI: 10.1039/C2LC40925A.
Wanunu, M., "Nanopores: A Journey Towards Dna Sequencing," Phys Life Rev. (2012) vol. 9, No. 2, pp. 125-158; DOI: 10.1016/J.PLREV.2012.05.010.

* cited by examiner

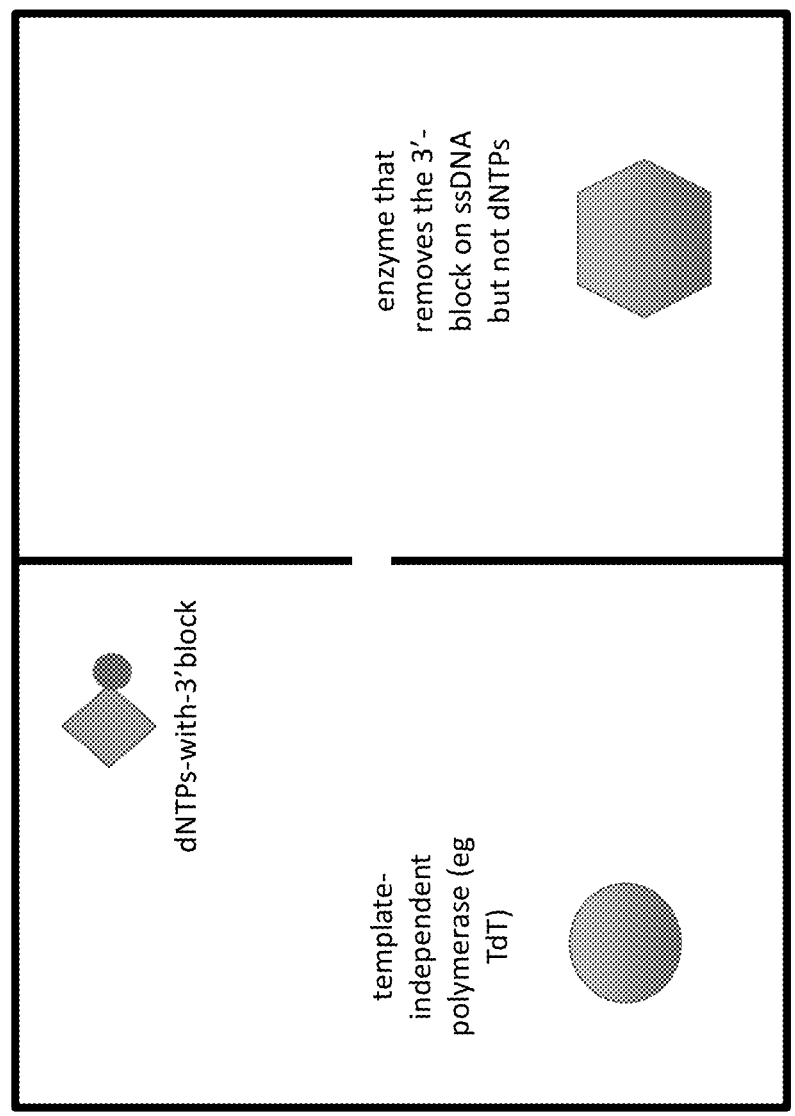
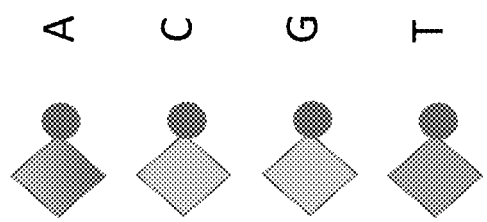
FIG. 6

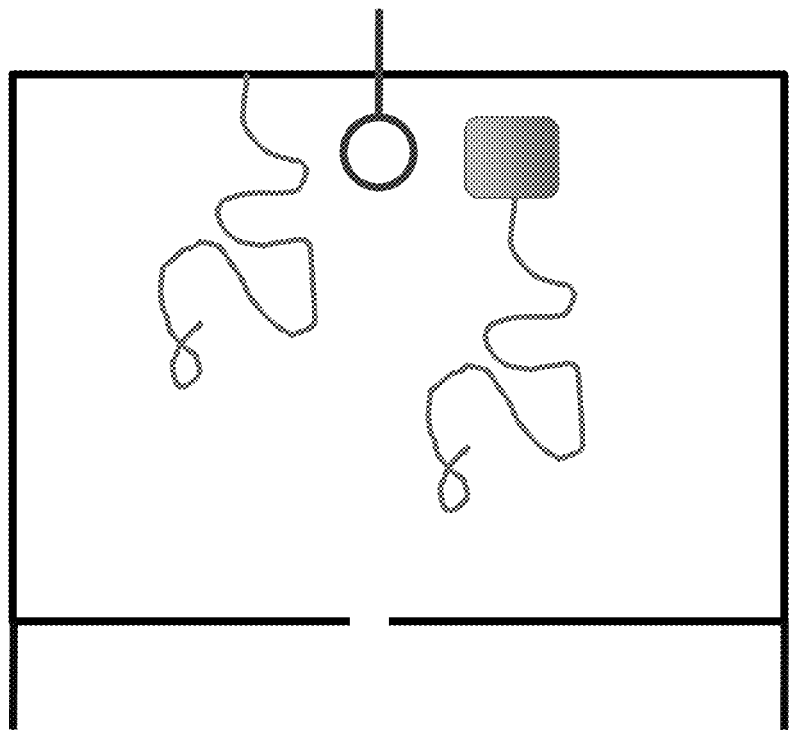
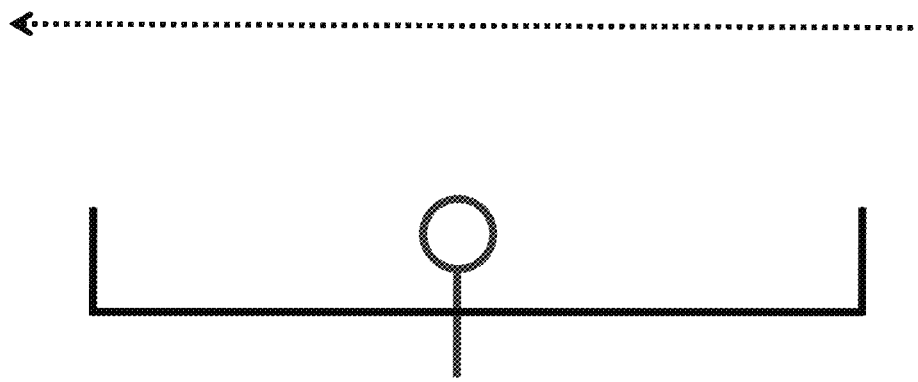
FIG. 11

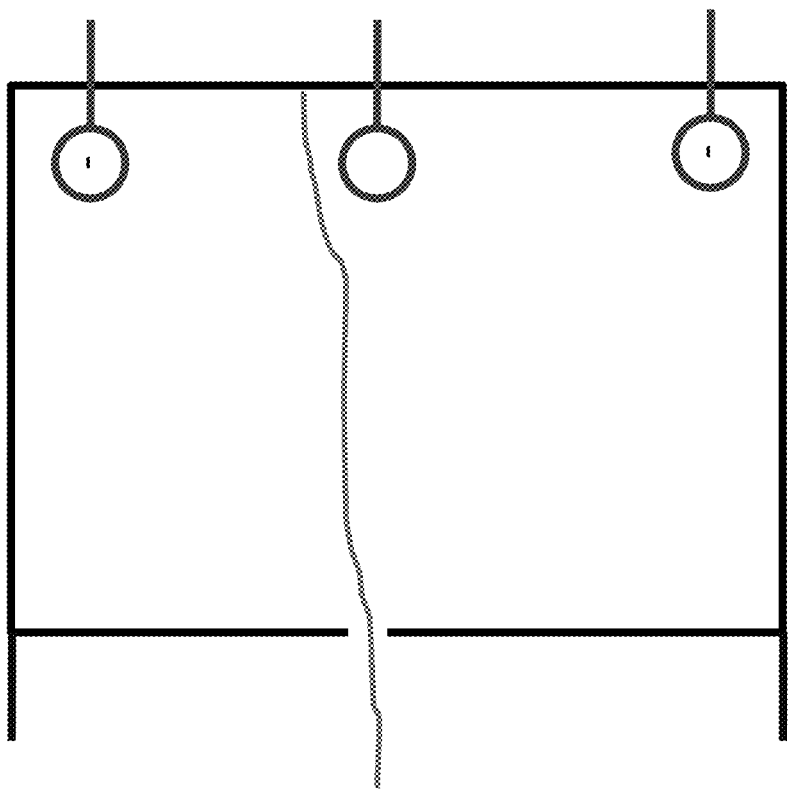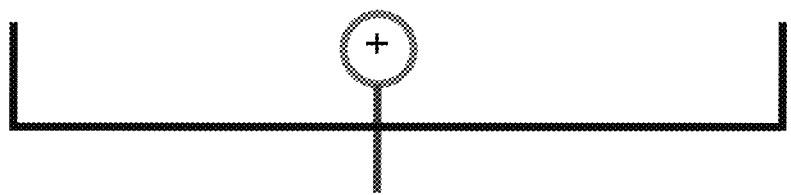
FIG. 12

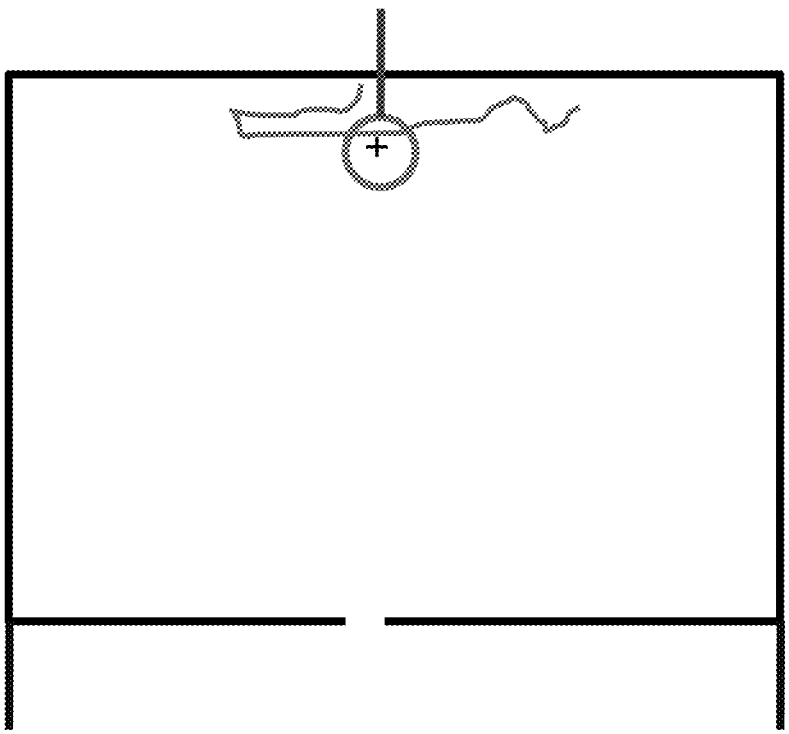
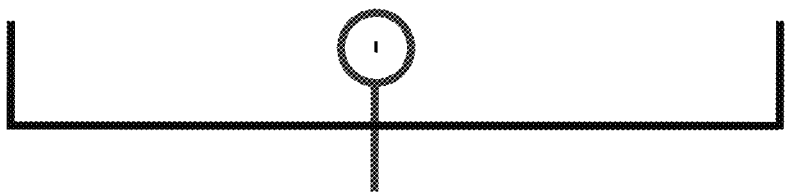
FIG. 13

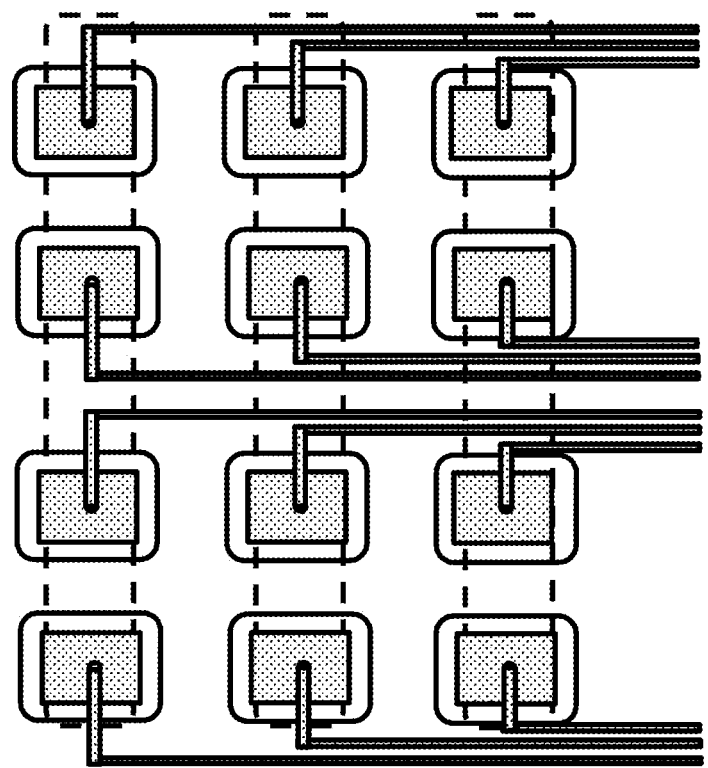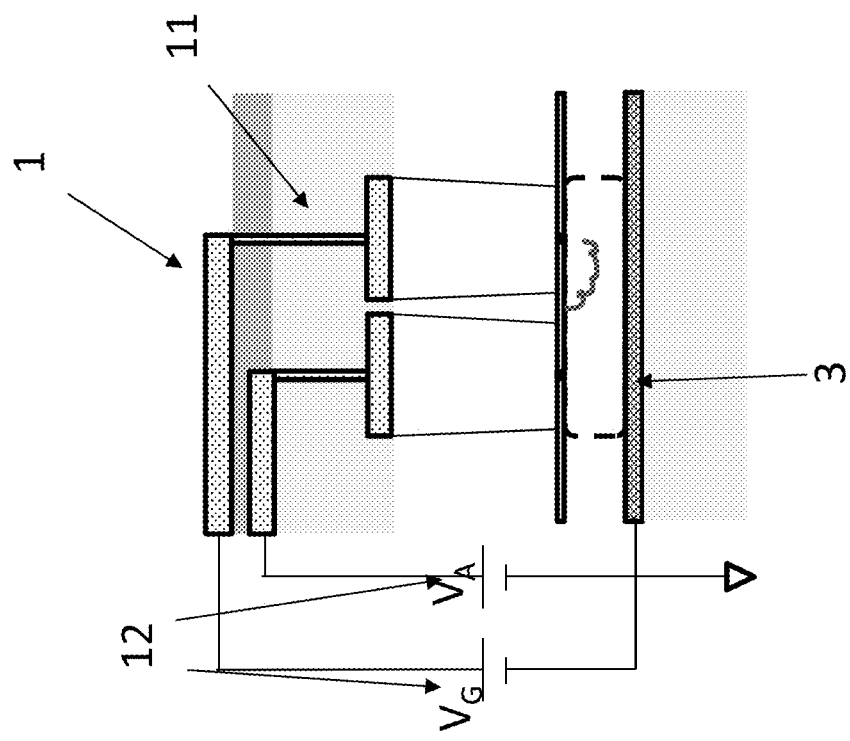
Fig. 28

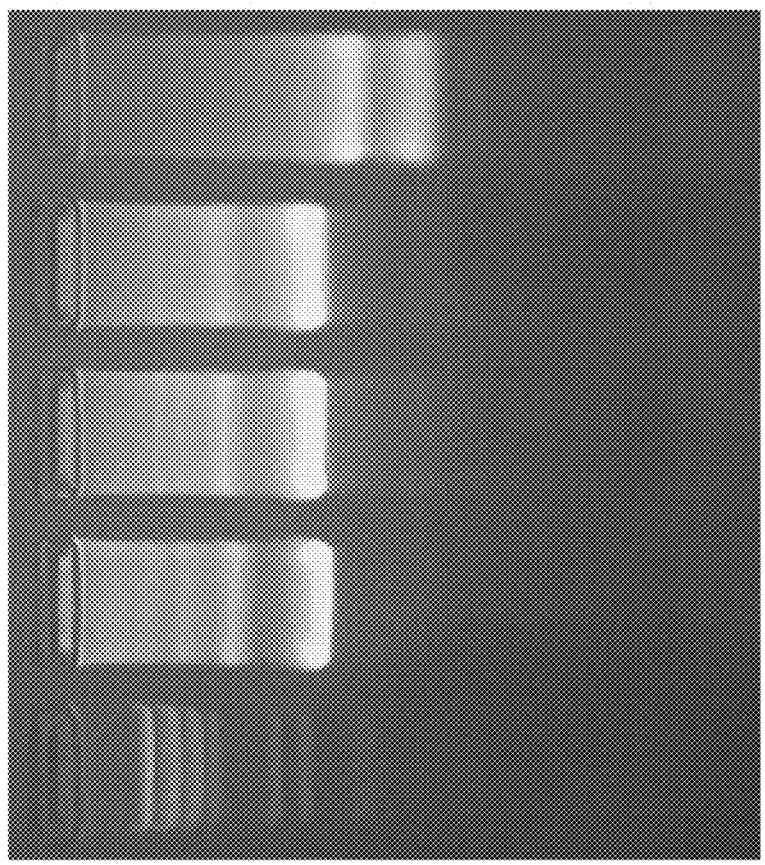
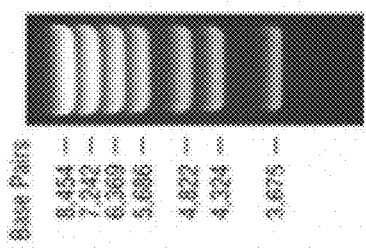
Fig. 37

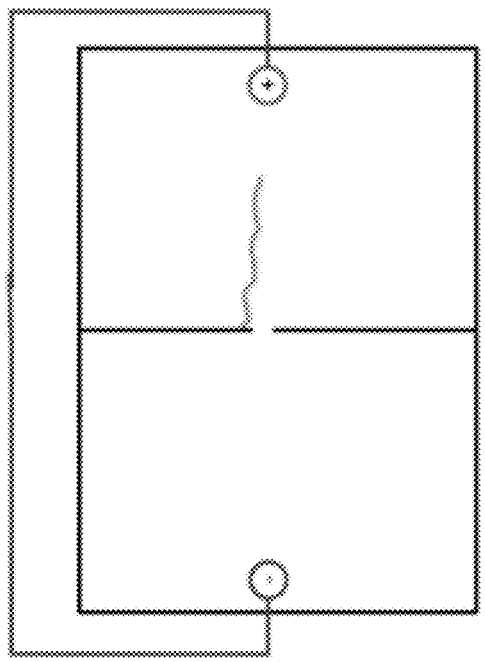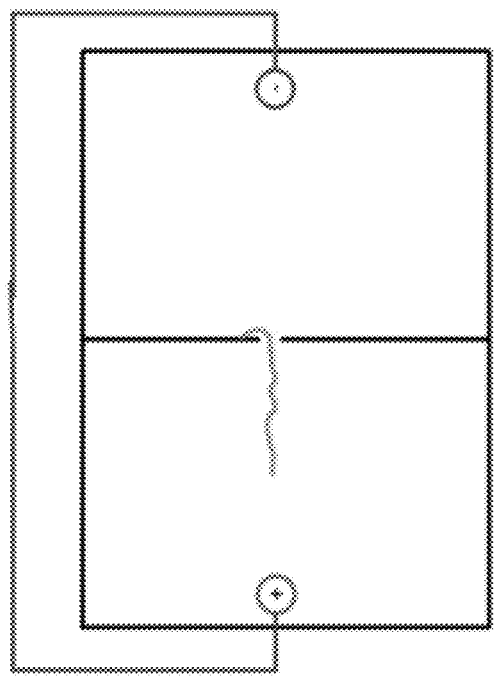
Fig. 45

| Step | Controller Action | Result |
|---|---|---|
| Writing/Adding a "1" bit to DNA string (Assume string starts in a common "deblock" chamber) & Optional DNA Reading | | |
| 1 | Apply positive voltage to RIGHT "addition" chamber ("1" bit or Add "1") electrode and 0 volts to the LEFT "addition" chamber (or Add "0" electrode). | The unattached (loose) end of the DNA is pulled via electric field through nanopore from the common "deblock" chamber to the RIGHT "addition" chamber, and a "1" bit is added to the loose end of the DNA string. Also, the base sequence of the DNA string may be read (or sequenced) while the DNA is being pulled through the nanopore. |
| 2 | Wait X milliseconds (or seconds) | Allow for DNA transport and the "addition" chemical reaction to complete. |
| 3 | Apply negative voltage to RIGHT "addition" chamber (or Add "1") electrode AND and 0 volts to the LEFT "addition" chamber (or Add "0" electrode). | The unattached (loose) end of the DNA is pulled via electric field back through nanopore from the RIGHT "addition" chamber to the common "deblock" chamber. Also, the base sequence of the DNA string may be read (or sequenced) while the DNA is being pulled back through the nanopore. |
| 4 | Wait X milliseconds (or seconds) | Allow for DNA transport and the "deblock" chemical reaction to complete. |
| Writing/Adding a "0" bit to DNA string (Assume string starts in "reserve/deblock" chamber) & Optional DNA Reading | | |
| 1 | Apply positive voltage to LEFT "addition" chamber ("0" bit or Add "0") electrode and 0 volts to the RIGHT "addition" chamber (or Add "1" electrode). | The unattached (loose) end of the DNA is pulled via electric field through nanopore from the common "deblock" chamber to the LEFT "addition" chamber, and a "0" bit is added to the loose end of the DNA string. Also, the base sequence of the DNA string may be read (or sequenced) while the DNA is being pulled through the nanopore. |
| 2 | Wait X milliseconds (or seconds) | Allow for DNA transport and the "addition" chemical reaction to complete. |
| 3 | Apply negative voltage to LEFT "addition" chamber ("0" bit or Add "0") electrode and 0 volts to the RIGHT "addition" chamber (or Add "1" electrode). | The unattached (loose) end of the DNA is pulled via electric field back through nanopore from the LEFT "addition" chamber to the common "deblock" chamber. Also, the base sequence of the DNA string may be read (or sequenced) while the DNA is being pulled back through the nanopore. |
| 4 | Wait X milliseconds (or seconds) | Allow for DNA transport and the "deblock" chemical reaction to complete. |

Note: This process is for a three-chamber cell structure (such as shown in Figs. 24, 25 or 28 or Fig. 66) having a common electrode on the bottom of the common "deblock" chamber connected to ground (0 volts), and two upper addition chambers (left and right) each with a individually controllable top electrode (Add "0" and Add "1" electrodes).

*FIG. 70B*

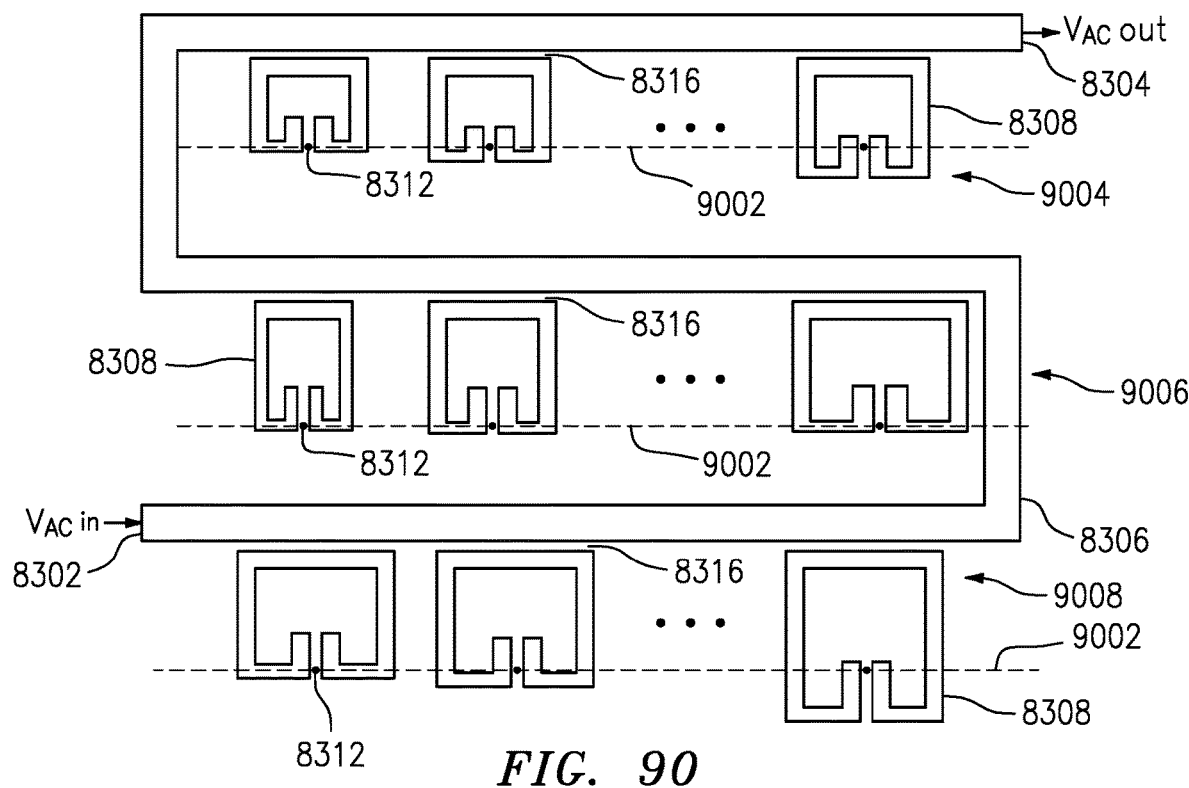
FIG. 90
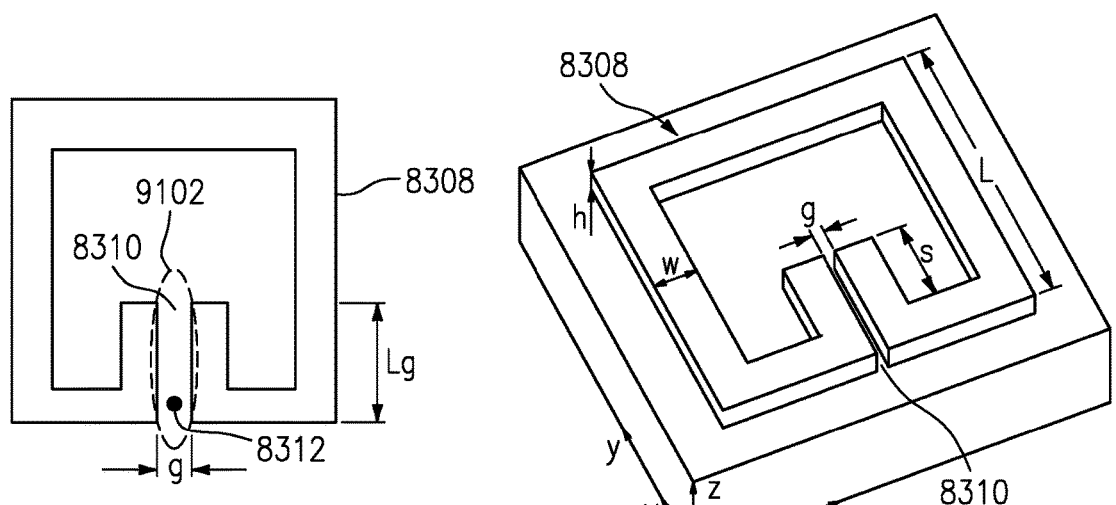
FIG. 91
FIG. 91A

SEQUENCE LISTING

<160> NUMBER OF SEQ ID NOS: 35

<210> SEQ ID NO 1
<211> LENGTH: 30
<212> TYPE: DNA
<213> ORGANISM: Artificial Sequence
<220> FEATURE:
<223> OTHER INFORMATION: Donor Oligonucleotide
<220> FEATURE:
<221> NAME/KEY: misc_feature
<222> LOCATION: (1)..(30)
<223> OTHER INFORMATION: n is a, c, g, t, or absent
<220> FEATURE:
<221> NAME/KEY: misc_feature
<222> LOCATION: (8)..(19)
<223> OTHER INFORMATION: n (located from base position 8 to 19) refers
      to Informational Sequence A or B, which can be from 3 to 12
      nucleotides

<400> SEQUENCE: 1
cgaagggnnn nnnnnnnnng tcgacnnnnn                                    30

<210> SEQ ID NO 2
<211> LENGTH: 25
<212> TYPE: DNA
<213> ORGANISM: Artificial Sequence
<220> FEATURE:
<223> OTHER INFORMATION: Topoisomerase Ligation Site
<220> FEATURE:
<221> NAME/KEY: misc_feature
<222> LOCATION: (1)..(25)
<223> OTHER INFORMATION: n is a, c, g, t, or absent
<220> FEATURE:
<221> NAME/KEY: misc_feature
<222> LOCATION: (8)..(19)
<223> OTHER INFORMATION: n (located from base position 8 to 19) refers
      to Informational Sequence A or B, which can be from 3 to 12
      nucleotides

<400> SEQUENCE: 2
cgaagggnnn nnnnnnnnng tcgac                                         25

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(21)
<223> OTHER INFORMATION: n is a, c, g, t, or absent
<220> FEATURE:
<221> NAME/KEY: misc_feature
<222> LOCATION: (8)..(19)
<223> OTHER INFORMATION: n (located from base position 8 to 19) refers
      to Informational Sequence A or B, which can be from 3 to 12
      nucleotides

<400> SEQUENCE: 3
cgaagggnnn nnnnnnnnng t                                             21

<210> SEQ ID NO 4
<211> LENGTH: 81
<212> TYPE: DNA
<213> ORGANISM: Artificial Sequence
<220> FEATURE:
<223> OTHER INFORMATION: BAB (synthesized sequence)

<400> SEQUENCE: 4
cgatagtcta ggcactgttt gctgcgccct tgtccgtgtc gcccttatct acttaagaga   60
tcatacagca ttgcgagtac g                                              81

<210> SEQ ID NO 5
<211> LENGTH: 35
<212> TYPE: DNA
<213> ORGANISM: Artificial Sequence
<220> FEATURE:
<223> OTHER INFORMATION: B2 (synthesized sequence)

<400> SEQUENCE: 5
atctacttaa gagatcatac agcattgcga gtacg                               35

<210> SEQ ID NO 6
<211> LENGTH: 30
<212> TYPE: DNA
<213> ORGANISM: Artificial Sequence
<220> FEATURE:
<223> OTHER INFORMATION: TA2 (synthesized sequence)

<400> SEQUENCE: 6
agggcgacac ggacagtttg aatcataccg                                     30

<210> SEQ ID NO 7
<211> LENGTH: 71
<212> TYPE: DNA
<213> ORGANISM: Artificial Sequence
<220> FEATURE:
<223> OTHER INFORMATION: TA3b (synthesized sequence)

<400> SEQUENCE: 7
aacttagtat gacggtatga ttcaaactgt ccgtgtcgcc cttattccga tagtgactac    60
agcggcatga g                                                         71

<210> SEQ ID NO 8
<211> LENGTH: 30
<212> TYPE: DNA
<213> ORGANISM: Artificial Sequence
<220> FEATURE:
<223> OTHER INFORMATION: TB2 (synthesized sequence)

<400> SEQUENCE: 8
agggcgcagc aaacagtgcc tagactatcg                                     30

<210> SEQ ID NO 9
<211> LENGTH: 71
<212> TYPE: DNA
<213> ORGANISM: Artificial Sequence
<220> FEATURE:
<223> OTHER INFORMATION: TB3b (synthesized sequence)

<400> SEQUENCE: 9
aacttagtat gacgatagtc taggcactgt ttgctgcgcc cttattccga tagtgactac    60
agcggcatga g                                                         71

<210> SEQ ID NO 10
<211> LENGTH: 17
<212> TYPE: DNA
<213> ORGANISM: Artificial Sequence
<220> FEATURE:
<223> OTHER INFORMATION: FP1 (synthesized sequence)

<400> SEQUENCE: 10
cacgtactcg caatgct                                                   17

```
<210> SEQ ID NO 11
<211> LENGTH: 21
<212> TYPE: DNA
<213> ORGANISM: Artificial Sequence
<220> FEATURE:
<223> OTHER INFORMATION: FP2 (synthesized sequence)

<400> SEQUENCE: 11
cggtatgatt caaactgtcc g                                              21

<210> SEQ ID NO 12
<211> LENGTH: 15
<212> TYPE: DNA
<213> ORGANISM: Artificial Sequence
<220> FEATURE:
<223> OTHER INFORMATION: FP3 (synthesized sequence)

<400> SEQUENCE: 12
gcccttgtcc gtgtc                                                     15

<210> SEQ ID NO 13
<211> LENGTH: 50
<212> TYPE: DNA
<213> ORGANISM: Artificial Sequence
<220> FEATURE:
<223> OTHER INFORMATION: NAT1 (synthesized sequence)

<400> SEQUENCE: 13
cacgtcaggc gtatccatcc cttcacgtac tcgcaatgct gtatggcgat               50

<210> SEQ ID NO 14
<211> LENGTH: 21
<212> TYPE: DNA
<213> ORGANISM: Artificial Sequence
<220> FEATURE:
<223> OTHER INFORMATION: NAT9x (synthesized sequence)

<400> SEQUENCE: 14
atcgccatac agcattgcga g                                              21

<210> SEQ ID NO 15
<211> LENGTH: 28
<212> TYPE: DNA
<213> ORGANISM: Artificial Sequence
<220> FEATURE:
<223> OTHER INFORMATION: NAT9 (synthesized sequence)

<400> SEQUENCE: 15
acgtgaaggg atggatacgc ctgacgtg                                       28

<210> SEQ ID NO 16
<211> LENGTH: 31
<212> TYPE: DNA
<213> ORGANISM: Artificial Sequence
<220> FEATURE:
<223> OTHER INFORMATION: Nat9Acc (synthesized sequence)

<400> SEQUENCE: 16
cacgtagcag caaacagtgc ctagactatc g                                   31

<210> SEQ ID NO 17
<211> LENGTH: 20
<212> TYPE: DNA
<213> ORGANISM: Artificial Sequence
<220> FEATURE:
<223> OTHER INFORMATION: Nat1P (synthesized sequence)
```

```
<400> SEQUENCE: 17
cacgtcaggc gtatccatcc                                               20

<210> SEQ ID NO 18
<211> LENGTH: 21
<212> TYPE: DNA
<213> ORGANISM: Artificial Sequence
<220> FEATURE:
<223> OTHER INFORMATION: FP4 (synthesized sequence)

<400> SEQUENCE: 18
cgatagtcta ggcactgttt g                                             21

<210> SEQ ID NO 19
<211> LENGTH: 28
<212> TYPE: DNA
<213> ORGANISM: Artificial Sequence
<220> FEATURE:
<223> OTHER INFORMATION: NAT9c (synthesized sequence)

<400> SEQUENCE: 19
gtgcagtccg cataggtagg gaagtgca                                      28

<210> SEQ ID NO 20
<211> LENGTH: 47
<212> TYPE: DNA
<213> ORGANISM: Artificial Sequence
<220> FEATURE:
<223> OTHER INFORMATION: o1 (synthesized sequence)

<400> SEQUENCE: 20
ctggaacggt aaattcagag actgcgcttt ccattctggc tttaatg                 47

<210> SEQ ID NO 21
<211> LENGTH: 24
<212> TYPE: DNA
<213> ORGANISM: Artificial Sequence
<220> FEATURE:
<223> OTHER INFORMATION: o3 (synthesized sequence)

<400> SEQUENCE: 21
ggaaagcgca gtctctgaat ttac                                          24

<210> SEQ ID NO 22
<211> LENGTH: 37
<212> TYPE: DNA
<213> ORGANISM: Artificial Sequence
<220> FEATURE:
<223> OTHER INFORMATION: N1 (synthesized sequence)

<400> SEQUENCE: 22
cttactggaa cggctatcga tatcgcagca ggacaga                            37

<210> SEQ ID NO 23
<211> LENGTH: 34
<212> TYPE: DNA
<213> ORGANISM: Artificial Sequence
<220> FEATURE:
<223> OTHER INFORMATION: N2 (synthesized sequence)

<400> SEQUENCE: 23
gtcctgctgc gatatcgata gccgttccag taag                               34

<210> SEQ ID NO 24
```

-continued

```
<211> LENGTH: 47
<212> TYPE: DNA
<213> ORGANISM: Artificial Sequence
<220> FEATURE:
<223> OTHER INFORMATION: Oligonucleotide

<400> SEQUENCE: 24
ctggaacggt aaattcagag actgcgcttt ccattctggc tttaatg          47

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide

<400> SEQUENCE: 25
catttaagtc tctgacgcga aagg                                   24

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide

<400> SEQUENCE: 26
gcgcacggtc tcccggcgta tccatccctt                             30

<210> SEQ ID NO 27
<211> LENGTH: 84
<212> TYPE: DNA
<213> ORGANISM: Artificial Sequence
<220> FEATURE:
<223> OTHER INFORMATION: Oligonucleotide

<400> SEQUENCE: 27
cggcctcgca atgctgtatg gcgatggaat tccacagtca gcaggagcgt tacgacatac    60
cgctacctta aggtgtcagt cgtc                                          84

<210> SEQ ID NO 28
<211> LENGTH: 74
<212> TYPE: DNA
<213> ORGANISM: Artificial Sequence
<220> FEATURE:
<223> OTHER INFORMATION: Oligonucleotide

<400> SEQUENCE: 28
gcgcacggtc tcccggcgta tccatccctt cggcctcgca atgctgtatg gcgatggaat    60
tccacagtca gcag                                                     74

<210> SEQ ID NO 29
<211> LENGTH: 61
<212> TYPE: DNA
<213> ORGANISM: Artificial Sequence
<220> FEATURE:
<223> OTHER INFORMATION: Oligonucleotide

<400> SEQUENCE: 29
cggcgtatcc atcccttcgg cctcgcaatg ctgtatggcg atggaattcc acagtcagca    60
g                                                                   61

<210> SEQ ID NO 30
<211> LENGTH: 91
```

```
<212> TYPE: DNA
<213> ORGANISM: Artificial Sequence
<220> FEATURE:
<223> OTHER INFORMATION: Oligonucleotide

<400> SEQUENCE: 30
gcgcacggtc tcccggcgta tccatccctt cggcgtatcc atcccttcgg cctcgcaatg    60
ctgtatggcg atggaattcc acagtcagca g                                    91

<210> SEQ ID NO 31
<211> LENGTH: 16
<212> TYPE: DNA
<213> ORGANISM: Artificial Sequence
<220> FEATURE:
<223> OTHER INFORMATION: 7F-T

<400> SEQUENCE: 31
cggcagatct accctt                                                     16

<210> SEQ ID NO 32
<211> LENGTH: 16
<212> TYPE: DNA
<213> ORGANISM: Artificial Sequence
<220> FEATURE:
<223> OTHER INFORMATION: Topo

<400> SEQUENCE: 32
cggcagatct accctt                                                     16

<210> SEQ ID NO 33
<211> LENGTH: 16
<212> TYPE: DNA
<213> ORGANISM: Artificial Sequence
<220> FEATURE:
<223> OTHER INFORMATION: 7F-B1

<400> SEQUENCE: 33
gccgaagggt agatct                                                     16

<210> SEQ ID NO 34
<211> LENGTH: 11
<212> TYPE: DNA
<213> ORGANISM: Artificial Sequence
<220> FEATURE:
<223> OTHER INFORMATION: 7F-B2

<400> SEQUENCE: 34
caagtacgtg a                                                          11

<210> SEQ ID NO 35
<211> LENGTH: 23
<212> TYPE: DNA
<213> ORGANISM: Artificial Sequence
<220> FEATURE:
<223> OTHER INFORMATION: NAT9cI
<220> FEATURE:
<221> NAME/KEY: modified_base
<222> LOCATION: (1)..(1)
<223> OTHER INFORMATION: I (located before base position 1) refers to
      inosine, which consists of 5 inosine bases, which pair with base
      position 1

<400> SEQUENCE: 35
aagggatgga tacgcctgac gtg                                             23
```

SYSTEMS AND METHODS FOR WRITING, READING, AND CONTROLLING DATA STORED IN A POLYMER

CROSS-REFERENCE TO RELATED APPLICATIONS

This application (i) is a Continuation-in-Part of U.S. patent application Ser. No. 15/690,189, filed Aug. 29, 2017, which is a Continuation-in-Part of International Application No. PCT/US2017/020044, filed Feb. 28, 2017, which claims the benefit of U.S. Provisional Patent Application No. 62/301,538, filed Feb. 29, 2016, and also claims the benefit of U.S. Provisional Patent Application No. 62/415,430, filed Oct. 31, 2016, and (ii) is a Continuation-in-Part of International Application PCT/US2017/059100, filed Oct. 30, 2017, which application claims priority to U.S. application Ser. No. 15/690,189, filed Aug. 29, 2017, International Application No. PCT/US2017/020044, filed Feb. 28, 2017, and U.S. Provisional Patent Application No. 62/415,430, filed Oct. 31, 2016. The entire contents of each of these related applications are incorporated herein by reference, to the fullest extent permitted by law.

FIELD

The invention relates to novel methods, compositions and devices useful for information storage and retrieval, using nanopore devices to synthesize and sequence polymers, e.g., nucleic acids.

BACKGROUND

There is a continuing demand to store ever more data on or in physical media, with storage devices getting ever smaller as their capacity gets bigger. The amount of data stored is reportedly doubling in size every two years, and according to one study, by 2020 the amount of data we create and copy annually will reach 44 zetabytes, or 44 trillion gigabytes. Moreover, existing data storage media such as hard drives, optical media, and magnetic tapes, are relatively unstable and become corrupted after prolonged storage.

There is an urgent need for alternative approaches to storing large volumes of data for extended periods, e.g. decades or centuries.

Some have proposed using DNA to store data. DNA is extremely stable and could in theory encode vast amounts of data and store the data for very long periods. See, for example, Bancroft, C., et al., *Long-Term Storage of Information in DNA*, Science (2001) 293: 1763-1765. Additionally, DNA as a storage medium is not susceptible to the security risks of traditional digital storage media. But there has been no practical approach to implementing this idea.

WO 2014/014991, for example, describes a method of storing data on DNA oligonucleotides, wherein information is encoded in binary format, one bit per nucleotide, with a 96 bit (96 nucleotide) data block, a 19 nucleotide address sequence, and flanking sequences for amplification and sequencing. The code is then read by amplifying the sequences using PCR and sequencing using a high speed sequencer like the Illumina HiSeq machine. The data block sequences are then arranged in the correct order using the address tags, the address and flanking sequences are filtered out, and the sequence data is translated into binary code. Such an approach has significant limitations. For example, the 96 bit data block could encode only 12 letters (using the conventional one byte or 8 bits per letter or space). The ratio of useful information stored relative to "housekeeping" information is low—approximately 40% of the sequence information is taken up with the address and the flanking DNA. The specification describes encoding a book using 54,898 oligonucleotides. The ink-jet printed, high-fidelity DNA microchips used to synthesize the oligonucleotides limited the size of the oligos (159-mers described were at the upper limit). Furthermore, reading the oligonucleotides requires amplification and isolation, which introduces additional potential for error. See also, WO 2004/088585A2; WO 03/025123 A2; C. BANCROFT: "Long-Term Storage of Information in DNA", Science (2001) 293 (5536): 1763c-1765; COX J P L: "Long-term data storage in DNA", Trends in Biotechnology (2001)19(7): 247-250.

DNA sequencing devices include nanopore-based devices from Oxford Nanopore, Genia and others. In many of those devices, typically a nanopore is used in a fluid-filled cell to read the DNA data by measuring a change in current as the DNA passes through the nanopore, which are typically in the range of nano-amps. Measurements based on changes in capacitance have been proposed but are not commercial; the changes are in the range of pico/fempto/atto-farads. Accordingly, it is very difficult to reliably and repeatably detect such small changes, as they are difficult to distinguish over typical background noise. The difficulties are further enhanced in that DNA can move through a nanopore at the rate of approximately one million bases per second, which is too fast to read accurately using existing means, requiring the use of protein nanopores which slow the passage of DNA through the nanopore, and which are impractical for reading large amounts of data.

Existing nano-pore based DNA data readers do not overcome these problems and thus do not provide highly precise, repeatable, reliable, automated, and robust DNA data reading results. Thus, it would be desirable to have a device that provides high quality, reliable DNA data reading results and also provides a scalable approach to reliably read data stored on multiple DNA molecules simultaneously.

While the potential information density and stability of DNA make it an attractive vehicle for data storage, as has been recognized for over twenty-five years, there is still no practical approach to writing and reading large amounts of data in this form.

BRIEF SUMMARY

We have developed a new approach to nucleic acid storage, using nanofluidic systems to synthesize the nucleic acid sequences and nanopore readers to read the sequences. Our approach allows for the synthesis, storage and reading of DNA strands which are hundreds, thousands or even millions of bases long. Because the sequences are long, only a relatively small proportion of the sequence is taken up with identifying information, so that the information density is much higher than in the approach described above. Moreover, in some embodiments, the nucleic acid as synthesized will have a specific location on a nanochip, so the sequence can be identified even without identifying information. The sequencing carried out in nanochambers is very rapid, and reading the sequence through a nanopore can be extremely rapid, on the order of up to one million bases per second. Since only two base types are required, the sequencing can be faster and more accurate than sequencing procedures that must distinguish among four nucleotide base types (adenine, thymine, cytosine, guanine). In particular embodiments, the two bases will not pair with one another and form secondary structures and will also be of different sizes. For example, adenine and cytosine would be better for this purpose than adenine and thymine, which tend to hybridize, or adenine and guanine, which are of similar size.

In some embodiments, this system can be used to synthesize long polymers encoding data, which can be amplified and/or released, and then sequenced on a different sequencer. In other embodiments, the system can be used to provide custom DNA sequences. In still other embodiments, the system can be used to read DNA sequences.

The nanochips used in one embodiment contain at least two separate reaction compartments connected by at least one nanopore, which prevents at least some of the components from mixing, but allows as few as a single molecule of DNA, or other charged polymers, e.g., RNA or peptide nucleic acid (PNA), to cross from one reaction compartment into another in a controllable manner. The transfer of the polymer (or at least the end of the polymer to which monomers are added) from one compartment to another permits sequential manipulations/reactions to the polymer, such as addition of bases, using enzymes which are prevented from crossing through the nanopore, for example because they are too large or because they are tethered to a substrate or bulky portion. Nanopore sensors report back on the movement or location of the polymer and its state, for example its sequence and whether the attempted reaction was successful. This allows data to be written, stored, and read, for example wherein the base sequence corresponds to a machine readable code, for example a binary code, with each base or group of bases corresponding to a 1 or 0.

Accordingly, the invention includes, inter alia, the following embodiments,

A nanochip for synthesis of an electrically charged polymer, e.g., DNA, comprising at least two distinct monomers, the nanochip comprising two or more reaction chambers separated by one or more nanopores, wherein each reaction chamber comprises an electrolytic fluid, one or more electrodes to draw the electrically charged polymer into the chamber and one or more reagents to facilitate addition of monomers or oligomers to the polymer. The nanochip may optionally be configured with functional elements to guide, channel and/or control the DNA, it may optionally be coated or made with materials selected to allow smooth flow of DNA or to attach the DNA, and it may comprise nanocircuit elements to provide and control electrodes proximate to the nanopores. For example, the one or more nanopores may optionally each be associated with electrodes which can control the movement of the polymer though the nanopore and/or detect changes in electric potential, current, resistance or capacitance at the interface of the nanopore and the polymer, thereby detecting the sequence of the polymer as it passes through the one or more nanopores. In particular embodiments, the oligomers are synthesized using polymerases or site specific recombinases. In some embodiments, the polymer is sequenced during the course of synthesis, to allow for the detection and optionally correction of mistakes. In some embodiments, the polymer thus obtained is stored on the nanochip and can be sequenced when it is desired to access the information encoded in the polymer sequence.

Methods and devices for determining the sequence of a polymer, e.g., DNA, in a nanopore chip by measuring the capacitive variance in a resonant RF circuit as the DNA is drawn through the nanopore by a DC bias.

A method of synthesizing a polymer, e.g., DNA, using a nanochip as described.

A single stranded DNA molecule wherein the sequence consists essentially of only nonhybridizing nucleotides, for example adenine and cytosine nucleotides (As and Cs), which are arranged in sequence to correspond to a binary code, e.g., for use in a method of data storage.

A double stranded DNA comprising a series of nucleotide sequences corresponding to a binary code, wherein the double stranded DNA further comprises A method of reading binary code encoded in DNA, comprising using a nanopore sequencer.

A method of data storage and devices therefor, using the above nanochip to make an electrically charged polymer, e.g., DNA, comprising at least two distinct monomers, wherein the monomers are arranged in sequence to correspond to a binary code.

Methods and systems for storing and reading data on a memory string (such as DNA or a polymer) in situ in a nanopore-based chip, includes providing a cell having at least three chambers, having an Add "1" chamber arranged to add a "1" bit to the polymer and an Add "0" chamber arranged to add a "0" bit to the polymer, and a "deblock" chamber arranged to enable the polymer to receive the "1" bit and "0" bit when the polymer enters the Add "1" or Add "0" chambers, respectively, successively steering the polymer from the "deblock" chamber through the nanopore to the Add "1" chamber or to the Add "0" chamber based on a predetermined digital data pattern to create the digital data pattern on the polymer, and reading the digital data stored on the polymer as it passes through the nanopore using a resonance frequency response of a nanopore-polymer resonator (NPR) on the chip.

Methods and systems for reading data stored in a polymer include providing a resonator having an inductor and a cell, the cell having a nano-pore and a polymer that can traverse through the nanopore, the resonator having an AC output voltage frequency response at a probe frequency in response to an AC input voltage at the probe frequency, providing the AC input voltage having at least the probe frequency, and monitoring the AC output voltage at least at the probe frequency, the AC output voltage at the probe frequency being indicative of the data stored in the polymer at the time of monitoring, wherein the polymer includes at least two monomers having different properties causing different resonant frequency responses.

Further aspects and areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6 shows a two chamber nanochip design for DNA synthesis, in which a polymerase enzyme is located in one chamber, a de-blocking enzyme is in the other chamber, and neither can pass through the nanopore.

FIG. 11 shows an approach to keeping the DNA associated with its chamber, by attaching to the chamber (upper DNA fragment in figure) or by coupling to a bulky group that cannot get through the nanopore (lower DNA fragment in figure). In this system, the end of the DNA can still move into the flow chamber and receive additional nucleotides, but the other end remains in the retaining chamber.

FIG. 12 shows a configuration where the DNA is attached to the wall of the chamber and controlled by multiple electrodes.

FIG. 13 shows how the DNA can be retained in the chamber when desired, simply by controlling the polarity of the electrodes.

FIG. 28 depicts further details of the wiring for the dual addition chamber layouts. The electrical control layer (1) includes wiring made from metal or polysilicon. The wiring density is increased by 3D stacking, with electrical isolation provided by dielectric deposition (e.g., via PECVD, sputtering, ALD etc). The contact (11) to the top electrode by in the addition chamber in in one embodiment is made using Through Silicon Via (TSV) by Deep Reactive Ion Etch (DRIE) (cryo or BOSCH process). Individual voltage control (12) allows for each addition chamber to be addressed individually, allowing fine control of the sequence of multiple polymers in parallel. The right side of the figure depicts a top view illustrating wiring to multiple addition cells. The electrical ground layer (3) may be common (as shown) or split to reduce cross coupling between the cells.

(Note, in this case the TS buffer is used: 50 mM Tris, pH 8, 1M NaCl). Lambda DNA is used for this DNA translocation experiment.

Figure 35:
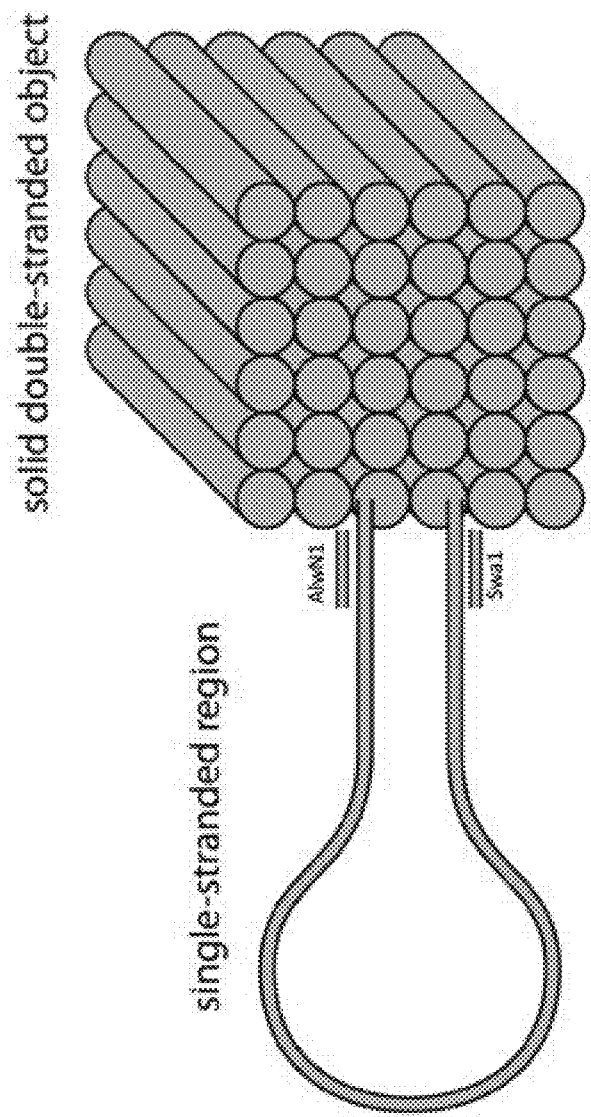

FIG. 35 depicts a simplified picture illustrating the main features of the DNA origami structure: a large single stranded region, the cubic origami structure, and the presence of 2 restriction sites (SwaI and AlwN1) near the origami structure.

Figure 36:
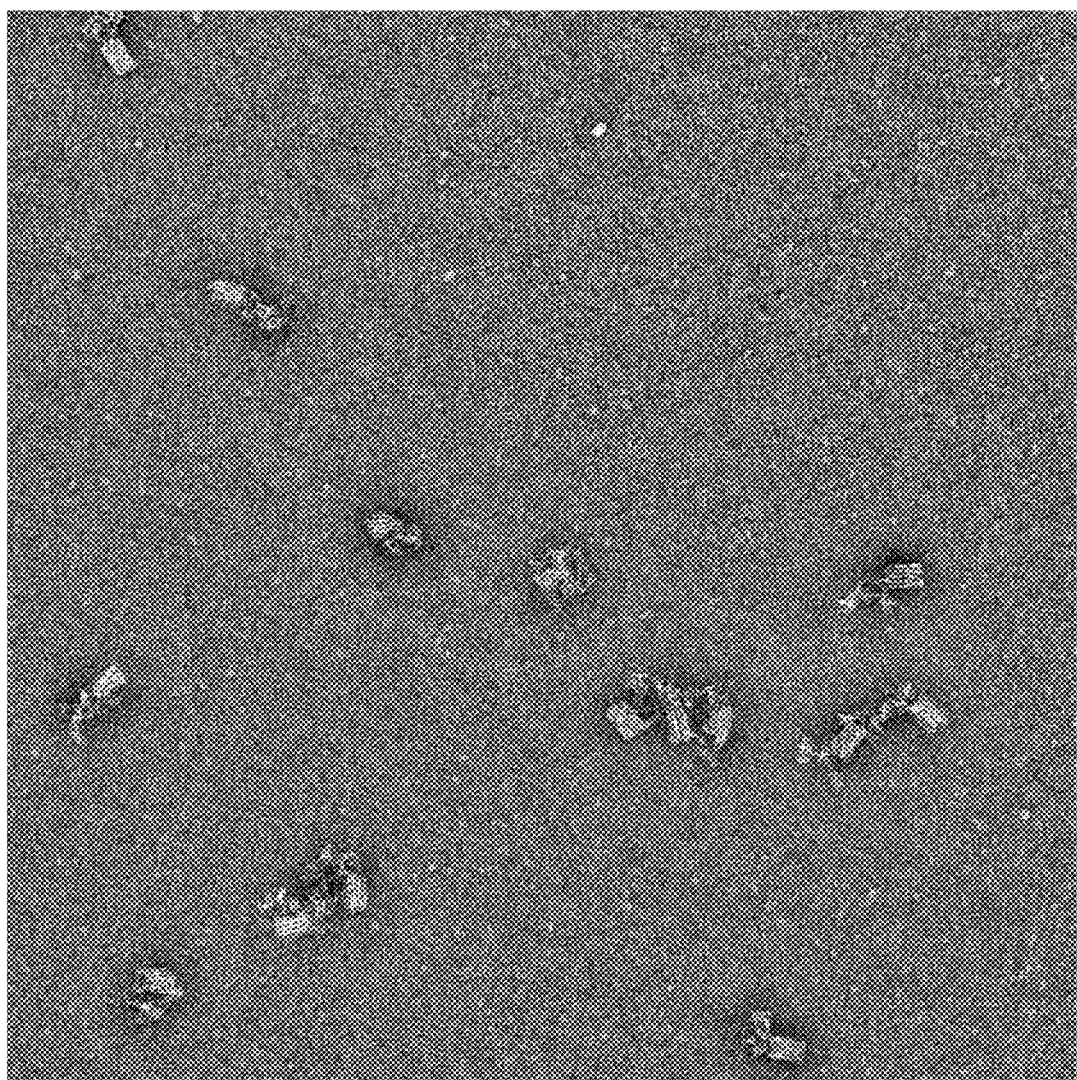

FIG. 36 depicts an electron microscope image of the manufactured DNA origami structure, and demonstrates the expected topology. Origami is made in 5 mM Tris base, 1 mM EDTA, 5 mM NaCl, 5 mM MgCl2. In order to maintain the origami structure, it is preferable to have $Mg^+$ concentrations of ~5 mM or $Na^+/K^+$ concentrations around 1M. The origami structure is stored at 4° C. at 500 nM.

FIG. 37 depicts a restriction digestion of the DNA origami to confirm correct assembly and function. The lane on the far left provides MW standards. The restriction sites are tested by digesting the origami with AlwN1 and Swa1. The four test lanes contain reagents as follows (units are microliters):

|  | 1 | 2 | 3 | 4 |
|---|---|---|---|---|
| origami | 10 | 10 | 10 | 10 |
| SwaI | — | 1 | — | 1 |
| AlwNI | — | — | 1 | 1 |
| NEB 3.1 10x | 2 | 2 | 2 | 2 |
| water | 8 | 7 | 7 | 6 |

Test lane (1) is a negative control; (2) is digestion with Swa1; (3) is digestion with AlwN1; (4) is double digestion with Swa1/AlwN1. Digestion is performed at room temperature for 60 minutes, followed by 37° C. for 90 minutes. Agarose gel ½×TBE-Mg (½×TBE with 5 mM MgCl2), visualized with ethidium bromide staining. Individual digestion with either enzyme shows no mobility effect in a gel, but digestion with both enzymes together (lane 4) results in two fragments of different lengths, as expected.

Figure 38:
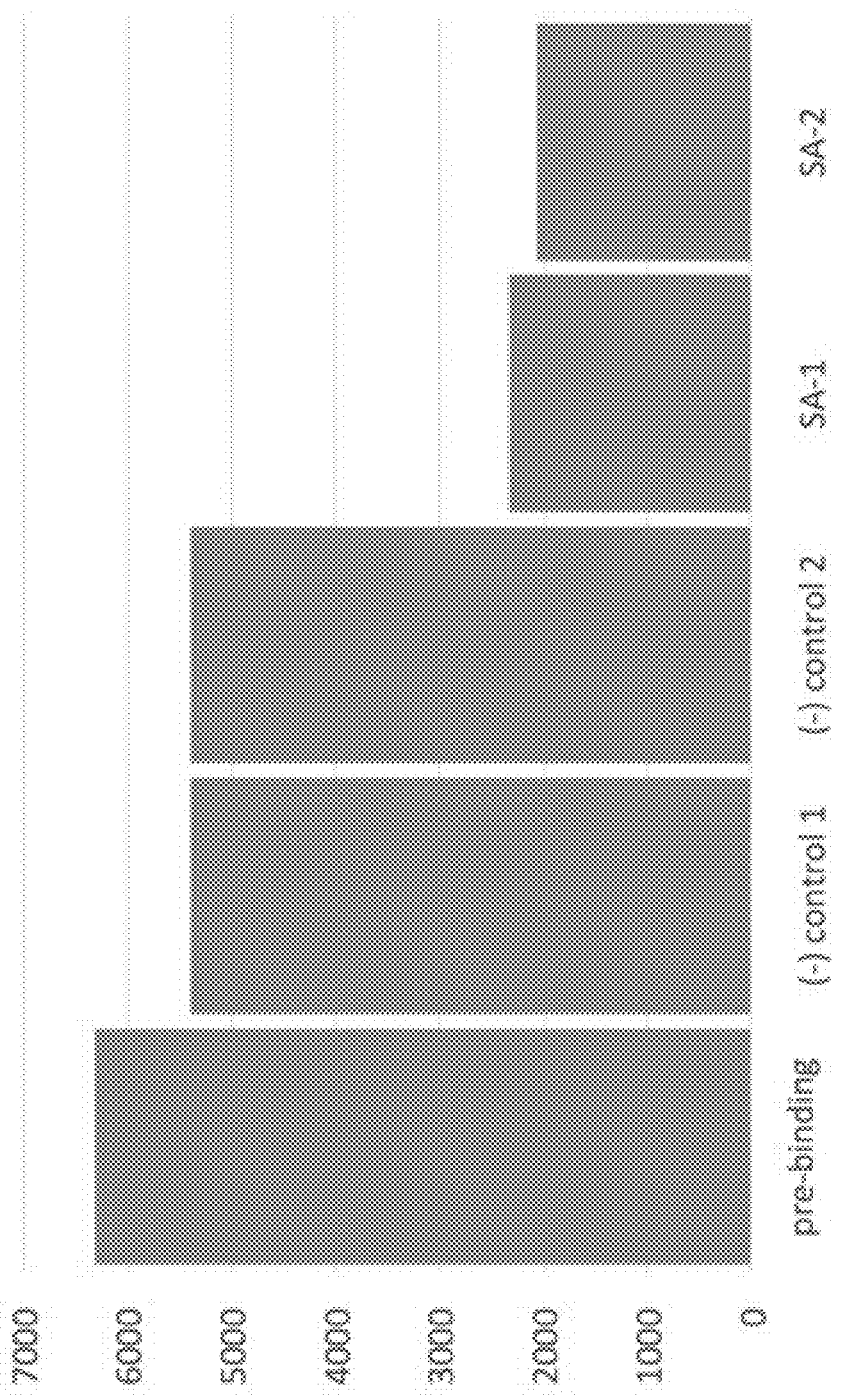

FIG. 38 depicts binding of biotin-labeled oligonucleotides to streptavadin-coated beads vs. binding to control BSA coated beads. The y-axis is fluorescence units, 'pre-binding' is oligo fluorescence from test solution prior to binding beads, (-) controls are fluorescence seen after binding to two different batches of BSA-conjugated beads, SA-1 and SA-2 are fluorescence seen after binding to 2 different batches of streptavidin-conjugated beads. A small apparent amount of binding is observed with BSA-conjugated beads, but much larger binding is seen with the streptavidin-conjugated beads.

Figure 39:
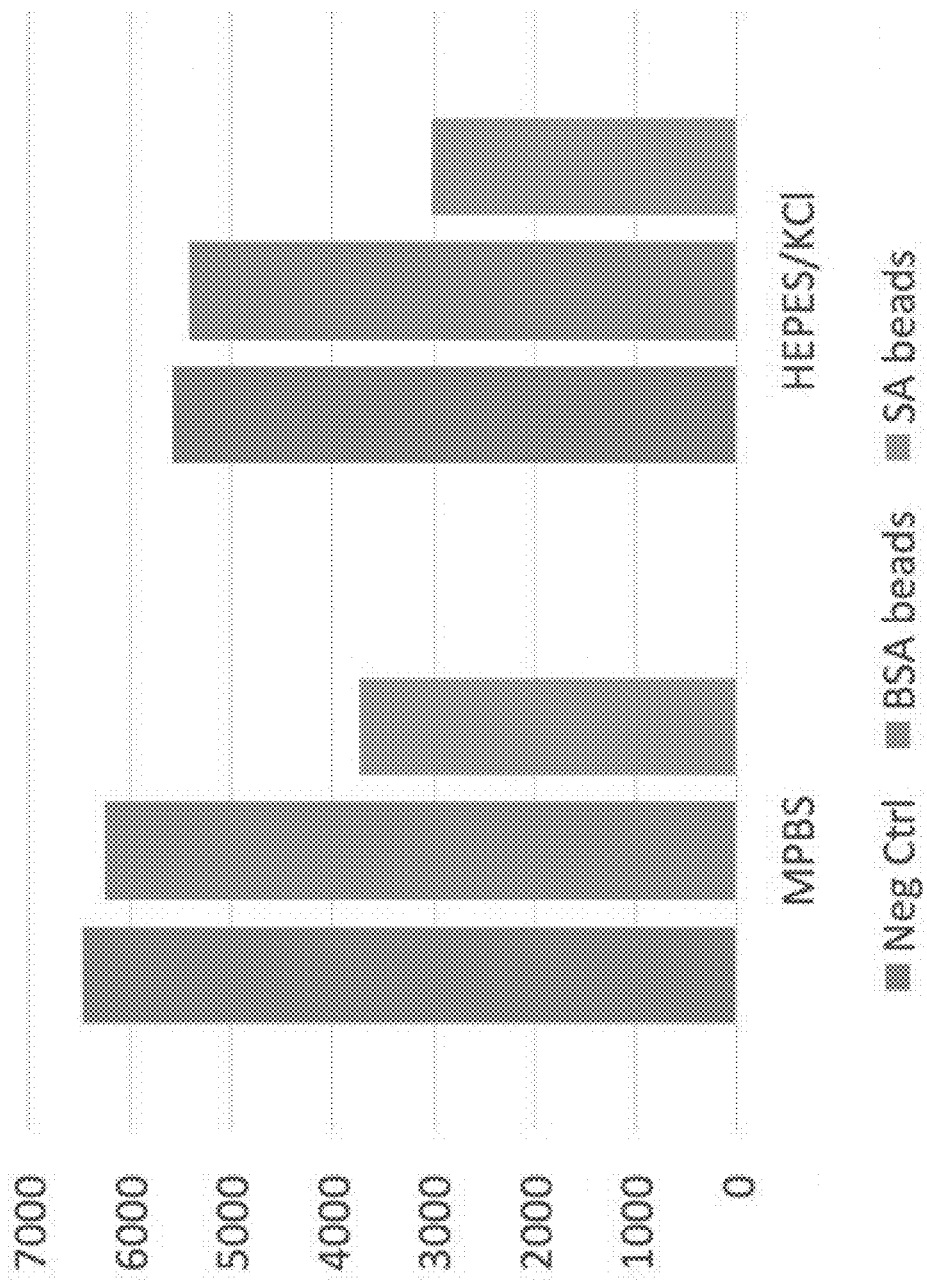

FIG. 39 depicts binding of biotin-labeled oligonucleotides to streptavadin-coated beads vs. binding to control BSA coated beads in different buffer systems, MPBS and HK buffer. The left bar 'Neg Ctrl' is the oligo fluorescence from test solution prior to binding the beads. Middle column shows fluorescence of 'BSA beads' and right column of 'SA beads' after binding to BSA or streptavidin beads respectively. In both buffer systems, the fluorescence is reduced by the streptavidin beads relative to controls, indicating that the biotin-labeled oligonucleotides are binding well to streptavadin-coated beads in different buffer systems.

Figure 40:
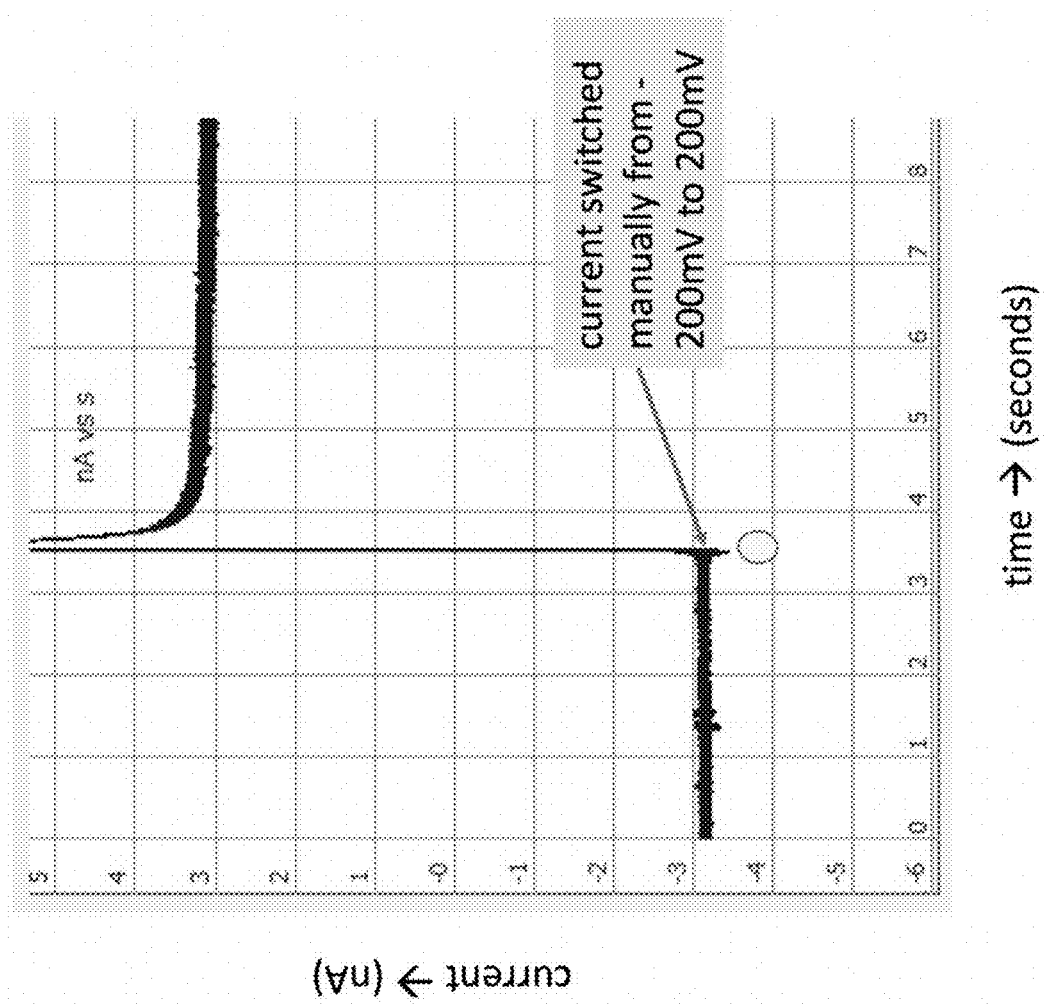

FIG. 40 depicts a functioning conjugated $SiO_2$ nanopore, wherein the surface is strepavidin coated on one side and BSA coated on the other. The x-axis is time and the y-axis is current. The dot shows the point where the current is reversed. There is a brief overshoot when the current is reversed, then the current settles to approximately the same absolute value. The nanopore shows a current of ~+3 nA at 200 mV and ~−3 nA at −200 mV.

Figure 41:
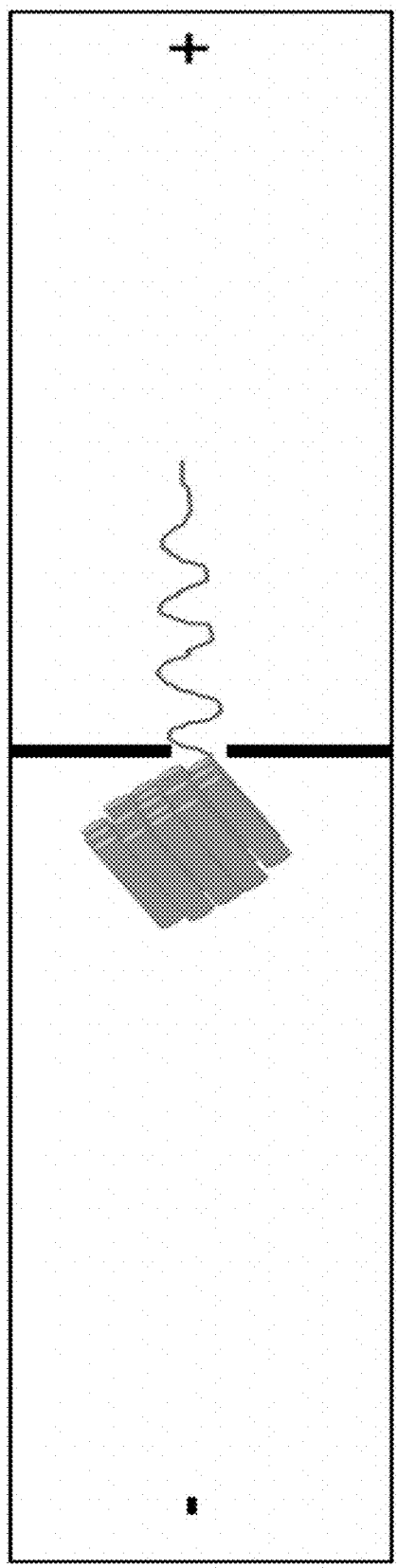

FIG. 41 shows a representation of an origami DNA structure inserted into a nanopore.

Figure 42:
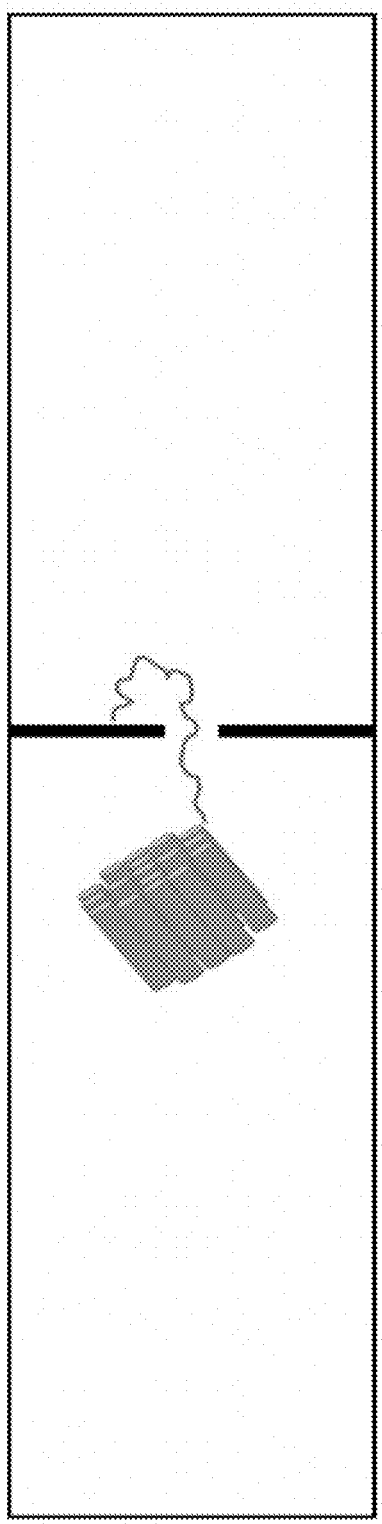

FIG. 42 shows a representation of attachment of the single stranded DNA to the streptavidin-coated surface adjacent to the nanopore.

Figure 43:
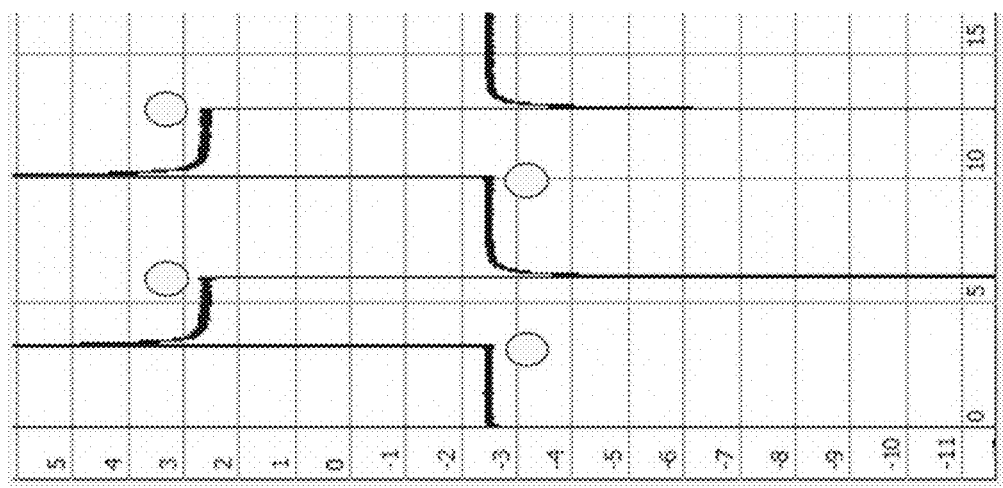

FIG. 43 shows experimental results of an origami DNA attached to the surface near a nanopore. Current is + or −~2.5 nA in both directions, which is less than the original current of +/−~3 nA, reflecting partial obstruction by the origami structure. The x-axis is time (s), y-axis is current (nA), circles represent voltage switch points.

Figure 44:
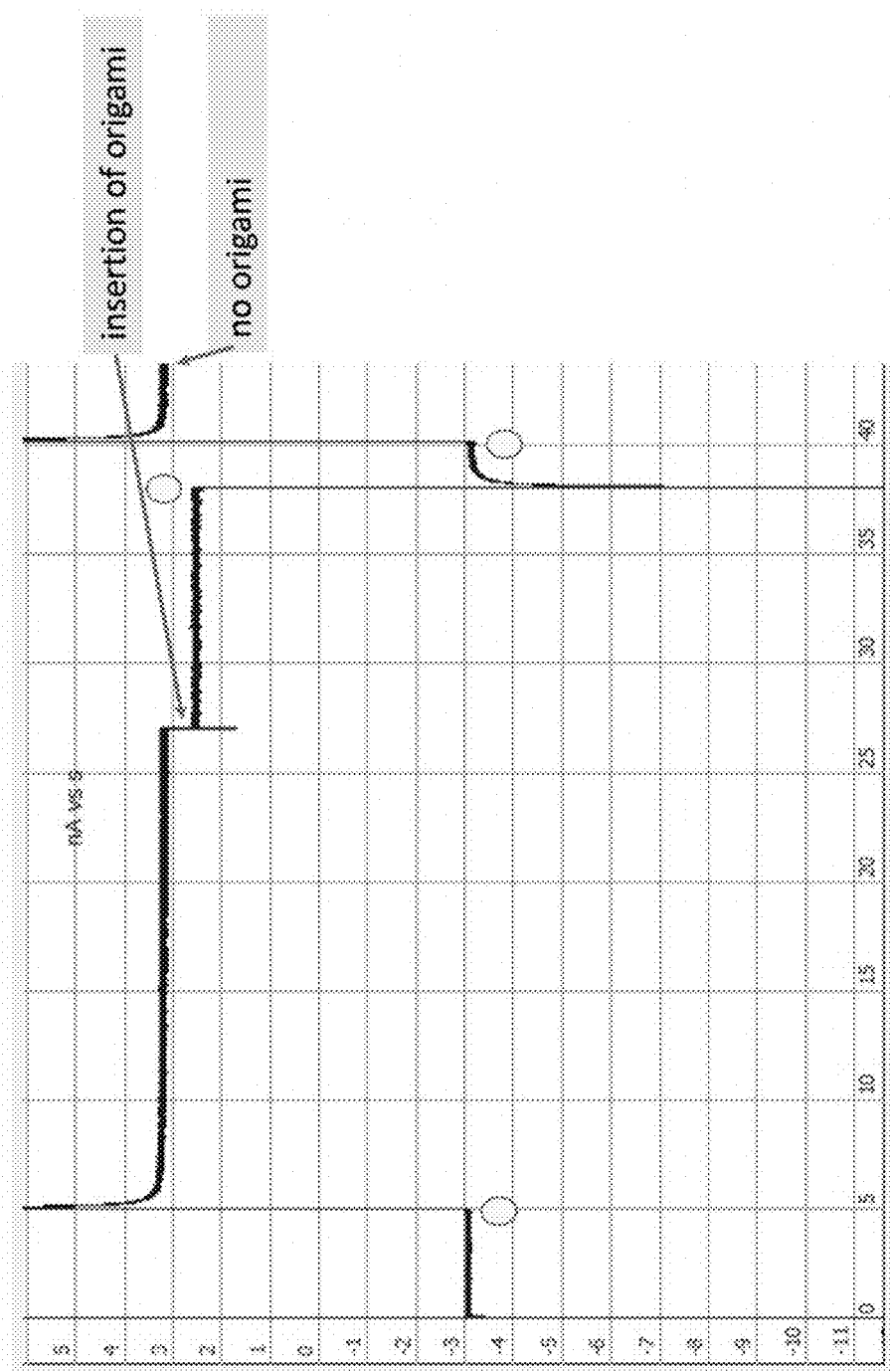

FIG. 44 shows the insertion of origami DNA, resulting in a slight drop in current. The origami immediately exits the nanopore when the current is released. The x-axis is time (s), y-axis is current (nA), circles represent voltage switch points.

FIG. 45 shows a representation of controlled movement of a DNA strand back and forth through a nanopore by application of current. On the left side the DNA is in the pore, so the observed current will be lower than if there was no DNA in the pore. When the current is reversed (right side) the is no DNA in the pore so the current will be unchanged.

Figure 46:
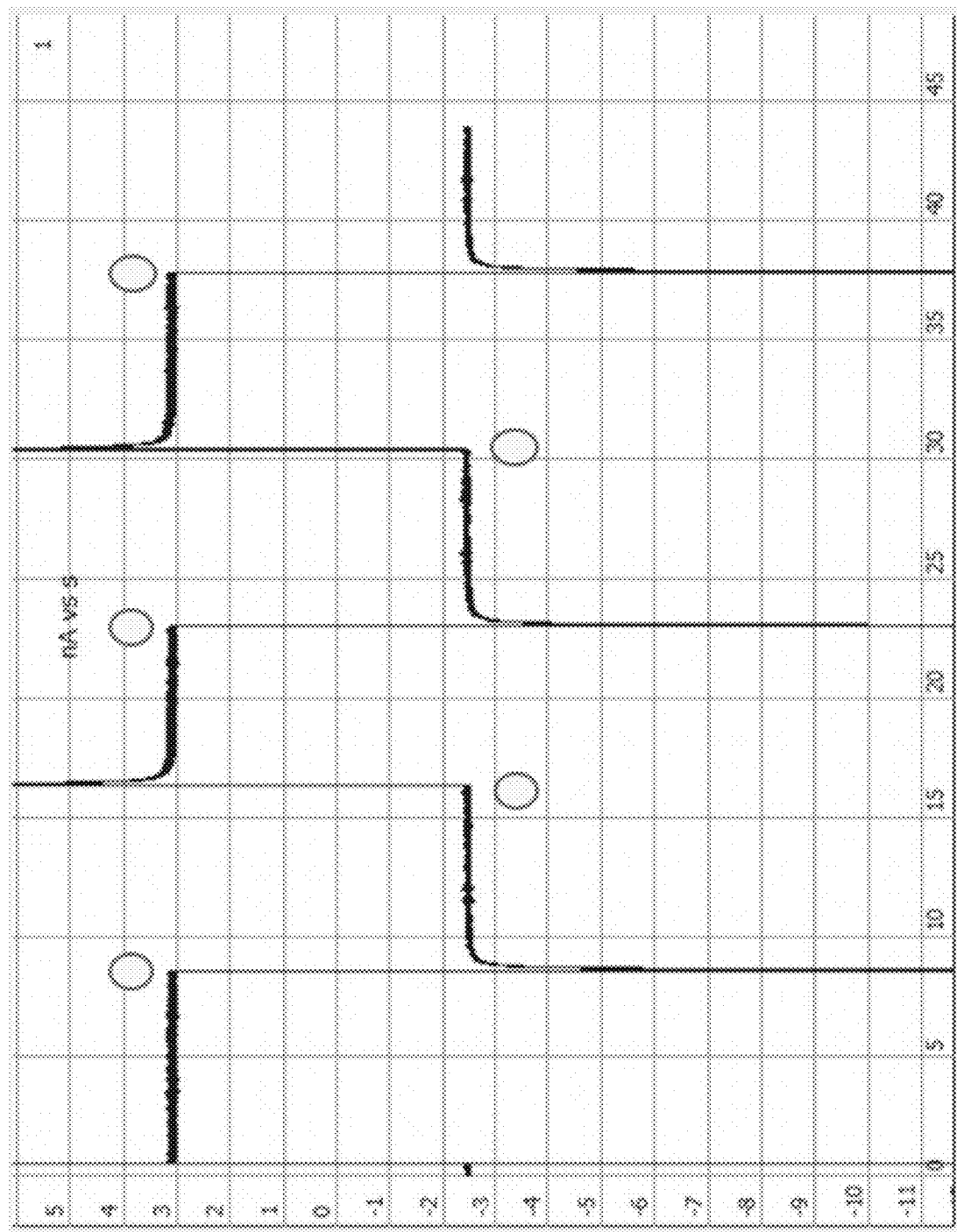

FIG. 46 shows experimental results confirming this representation. When a positive voltage is applied the current is ~3 nA, comparable to the current typically observed when the pore is open. When the voltage is reversed the current is ~−2.5 nA. This is lower than the current typically seen when the pore is open, and corresponds to the current typically observed when the pore is blocked by a strand of DNA. Several sequential voltage switches show consistent results, suggesting that the DNA is alternating in configuration as depicted in FIG. 45.

Figure 47:
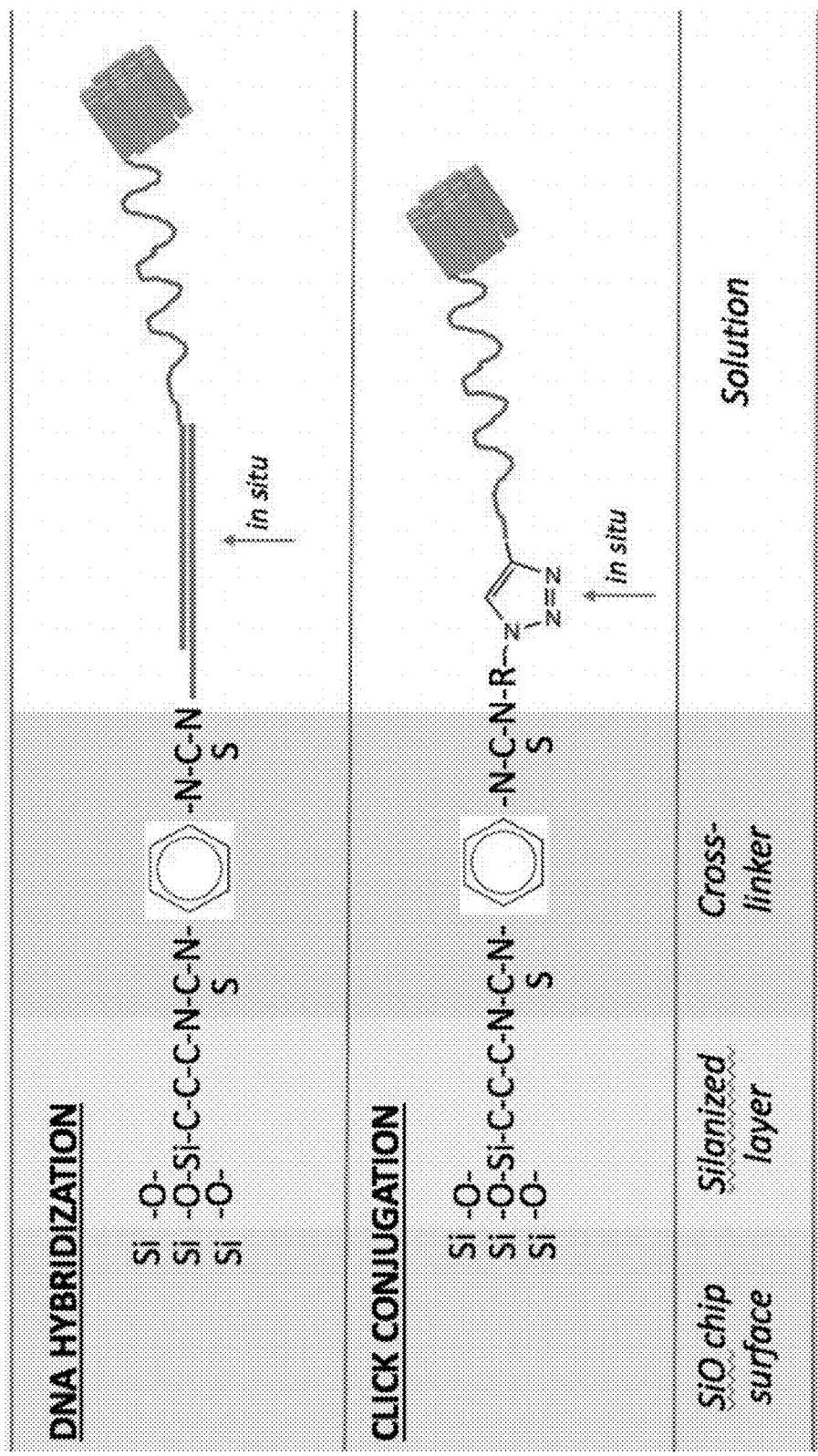

FIG. 47 shows different conjugation chemistries to link the DNA to the surface adjacent to the nanopore.

Figures 48A, 48B, 48C:
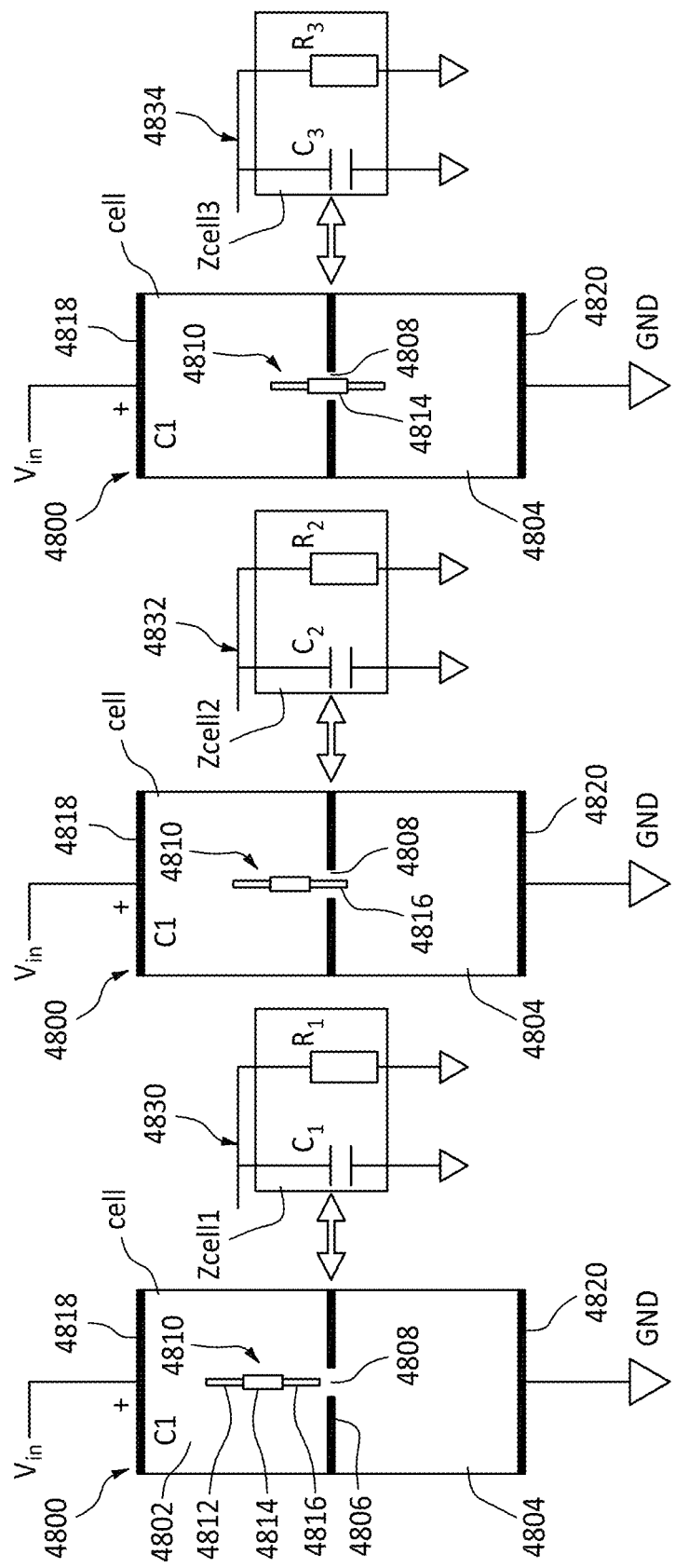

FIGS. 48A, 48B, and 48C are three views of a polymer and a nanopore and the equivalent circuit, in accordance with embodiments of the present invention.

Figure 49B:
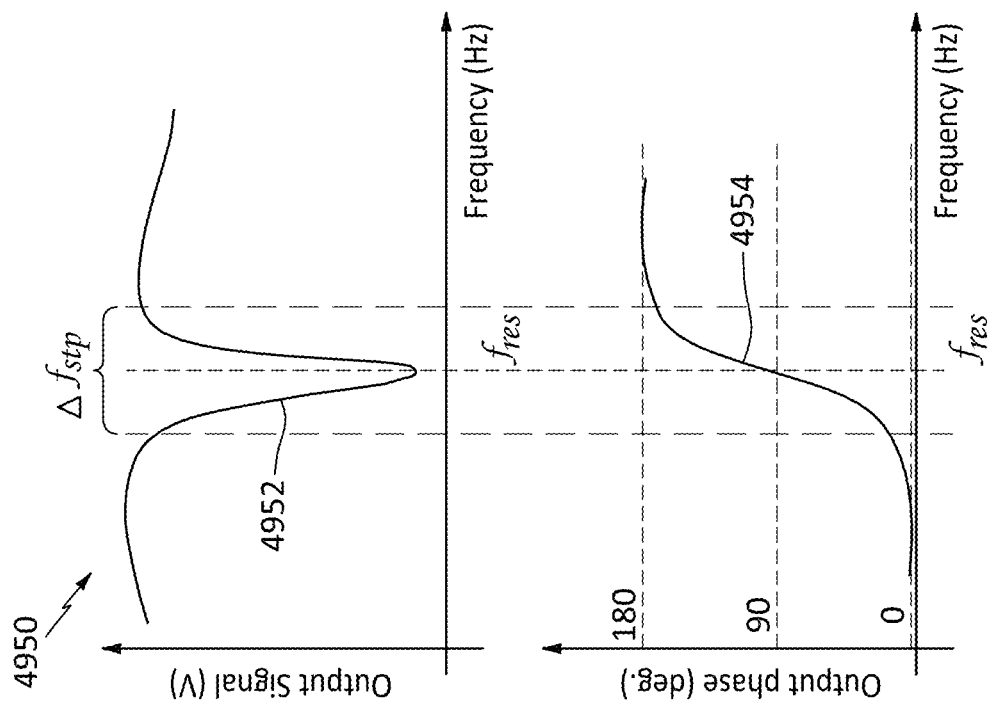
Figure 49A:
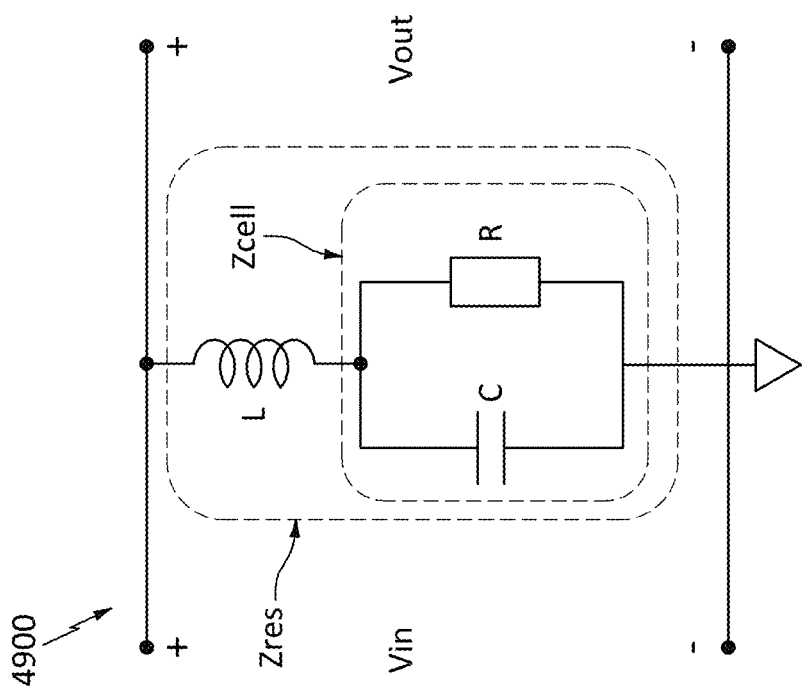

FIG. 49A is an equivalent circuit for a resonator made with a nanopore cell, in accordance with embodiments of the present invention.

FIG. 49B is a graph of magnitude and phase of the output response of the resonator of FIG. 49A, in accordance with embodiments of the present invention.

Figure 50:
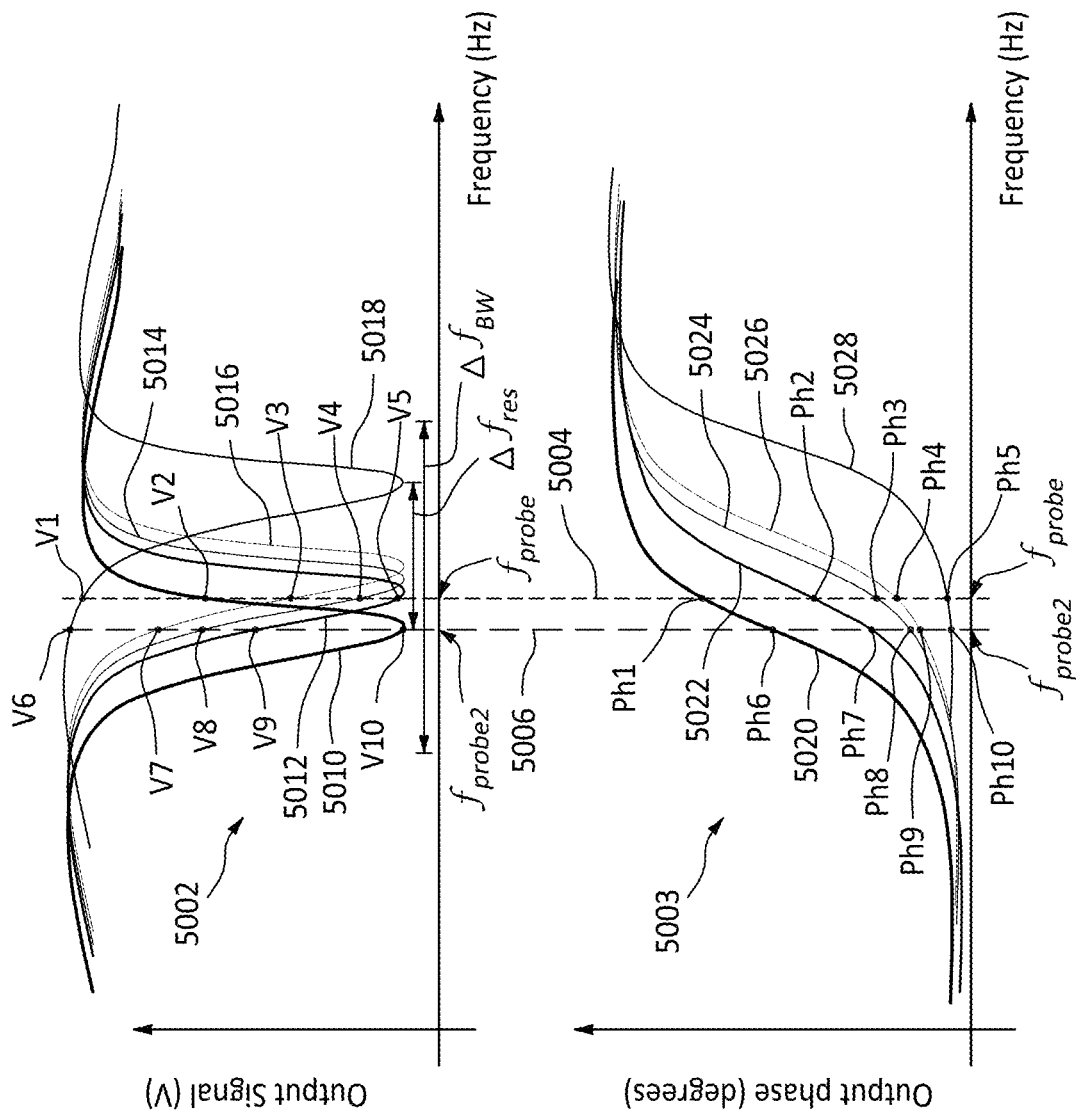

FIG. 50 is a family of curves showing a range of magnitude and phase of the output responses of the resonator of FIG. 49A, in accordance with embodiments of the present invention.

Figure 51:
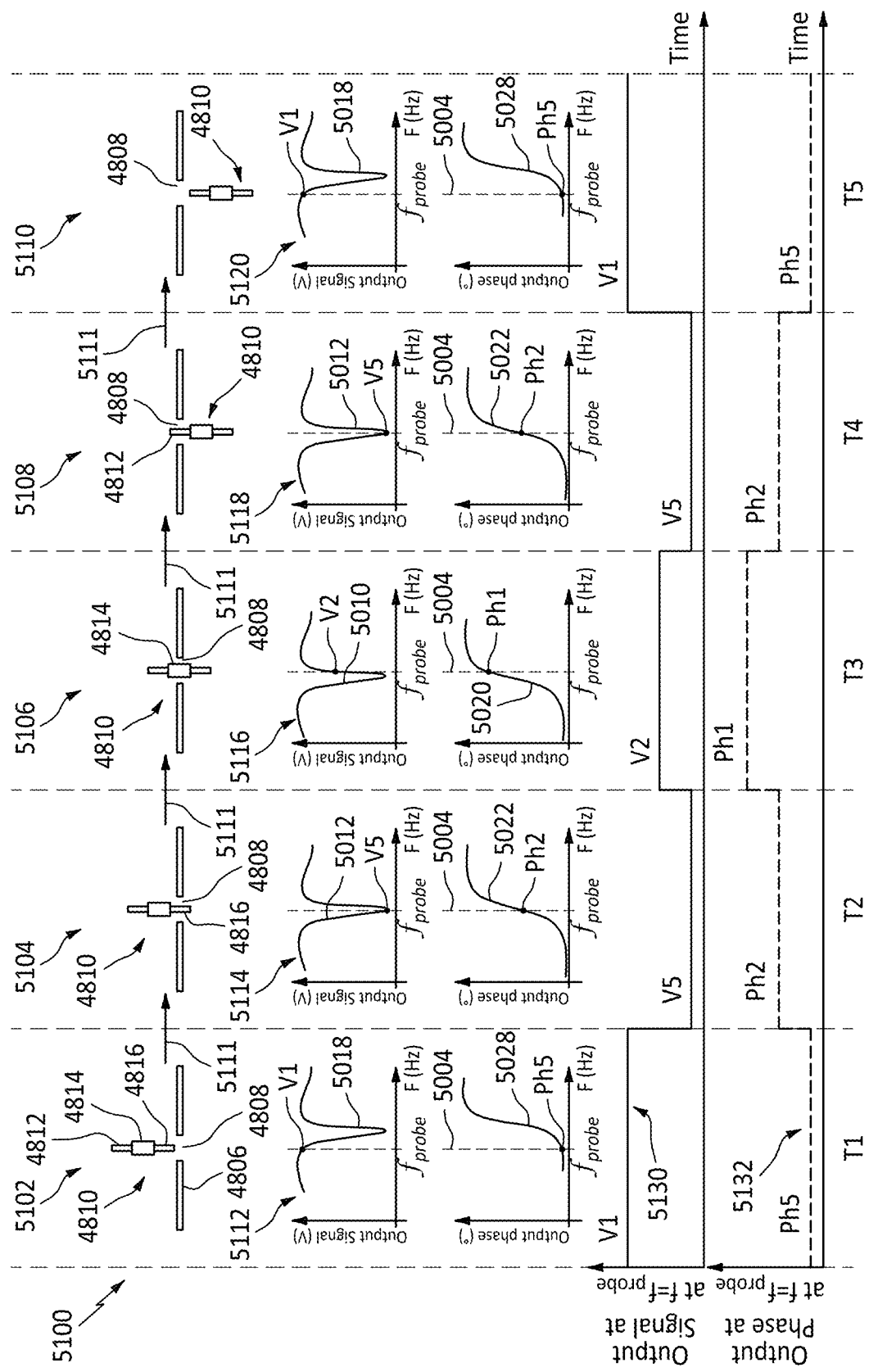

FIG. 51 is a time series showing a polymer passing through a nanopore and the resulting resonator magnitude and phase of the output responses at a probe frequency, in accordance with embodiments of the present invention.

Figure 52:
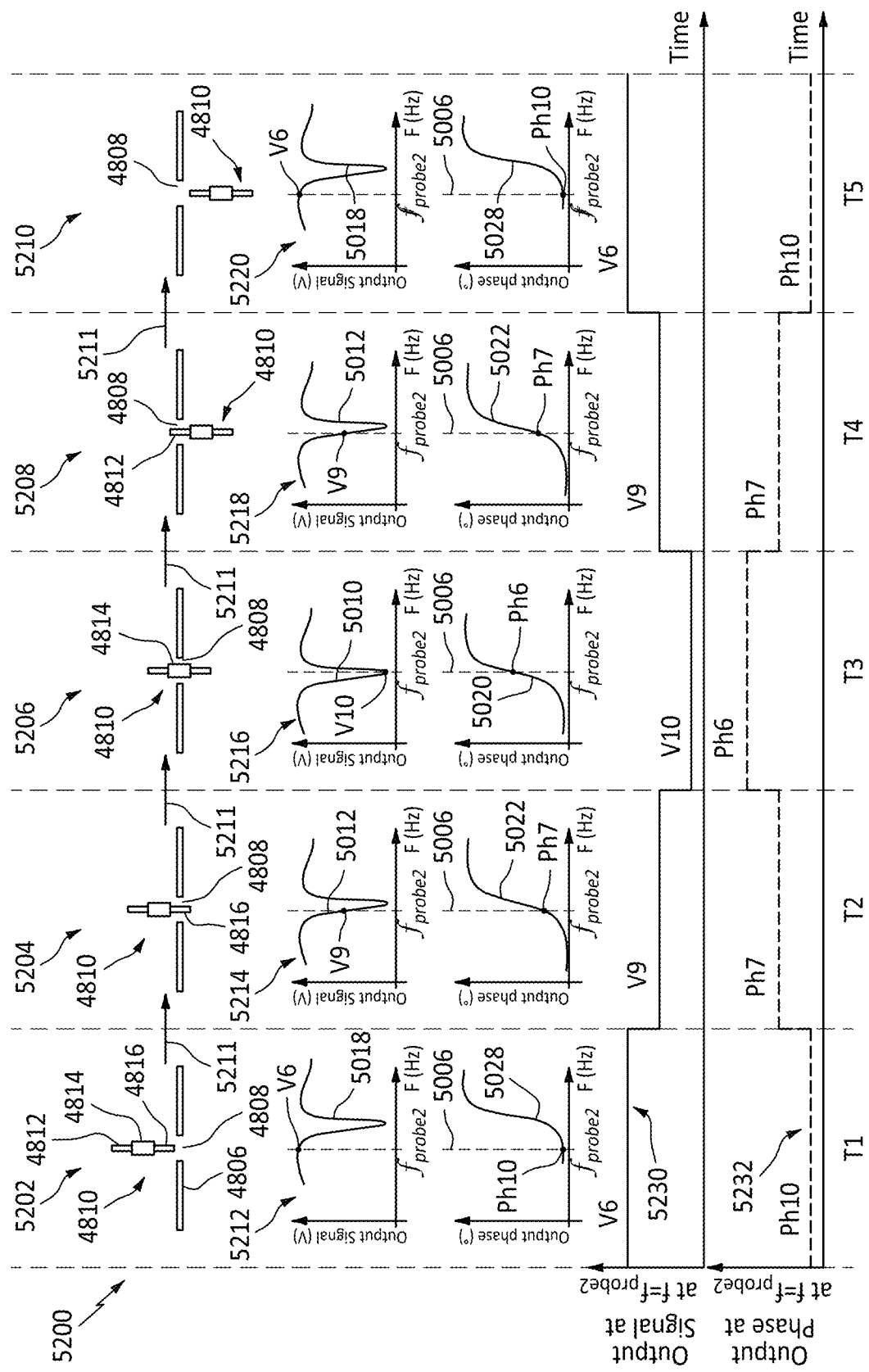

FIG. 52 is a time series showing a polymer passing through a nanopore and the resulting resonator magnitude and phase of the output responses at a second probe frequency, in accordance with embodiments of the present invention.

Figure 53:
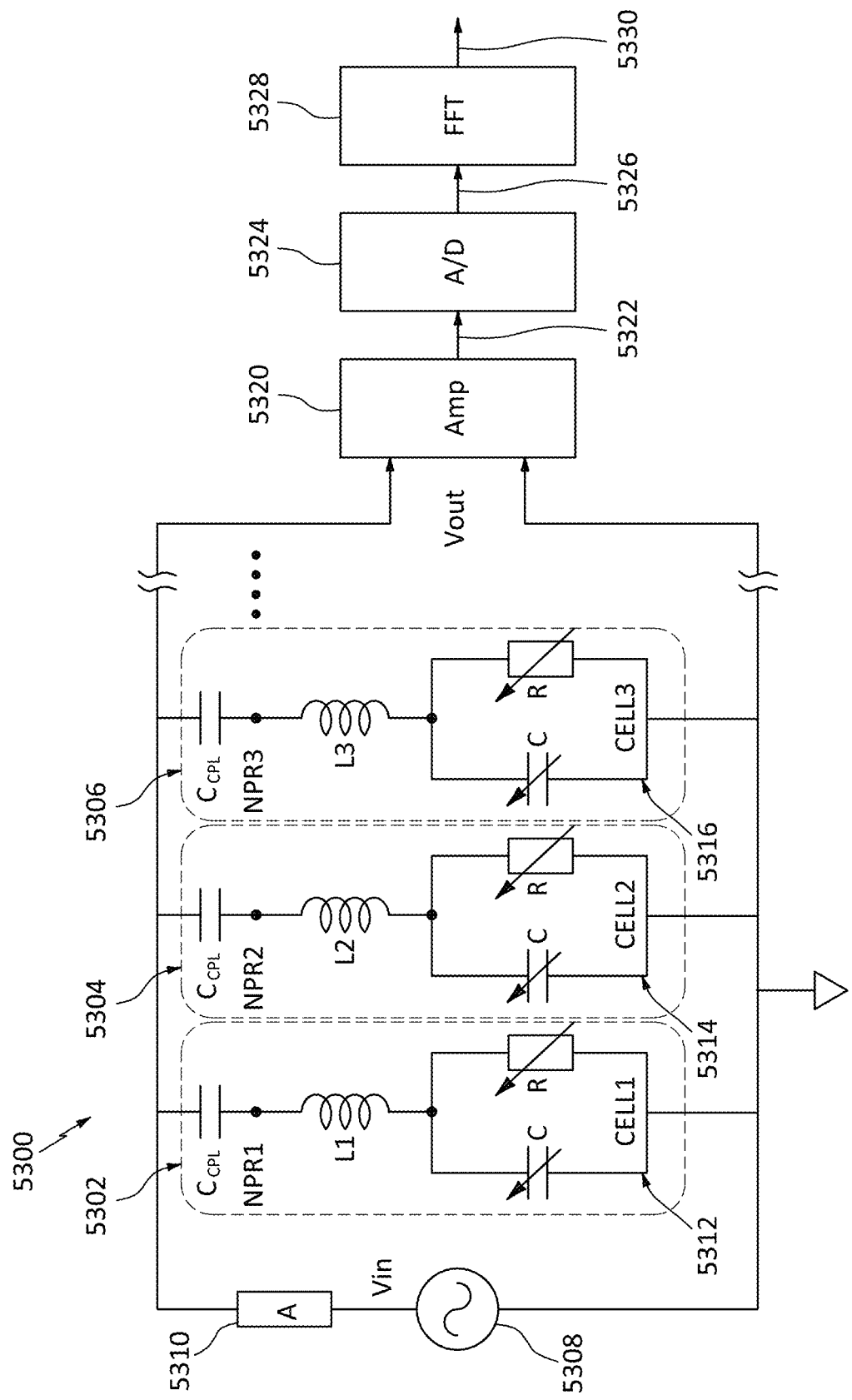

FIG. 53 is an equivalent circuit of a plurality of parallel nanopore-polymer resonators and signal processing, in accordance with embodiments of the present invention.

Figure 54:
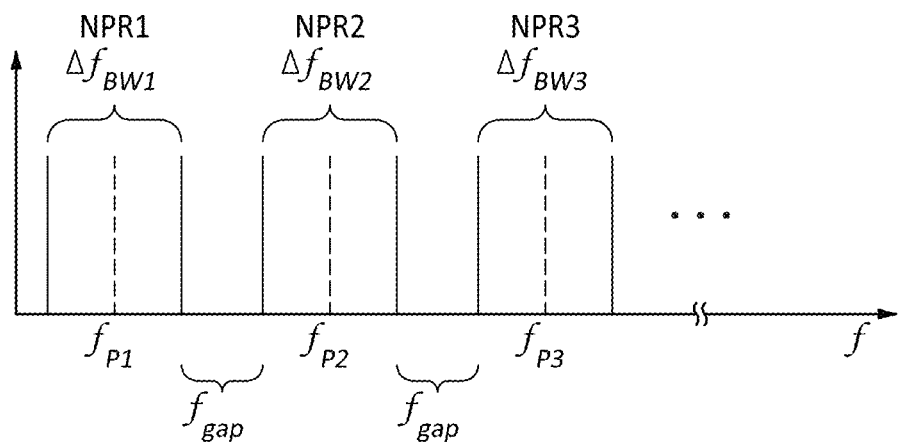

FIG. 54 is a frequency plot for several resonant frequency bandwidths, in accordance with embodiments of the present invention.

Figure 55A:
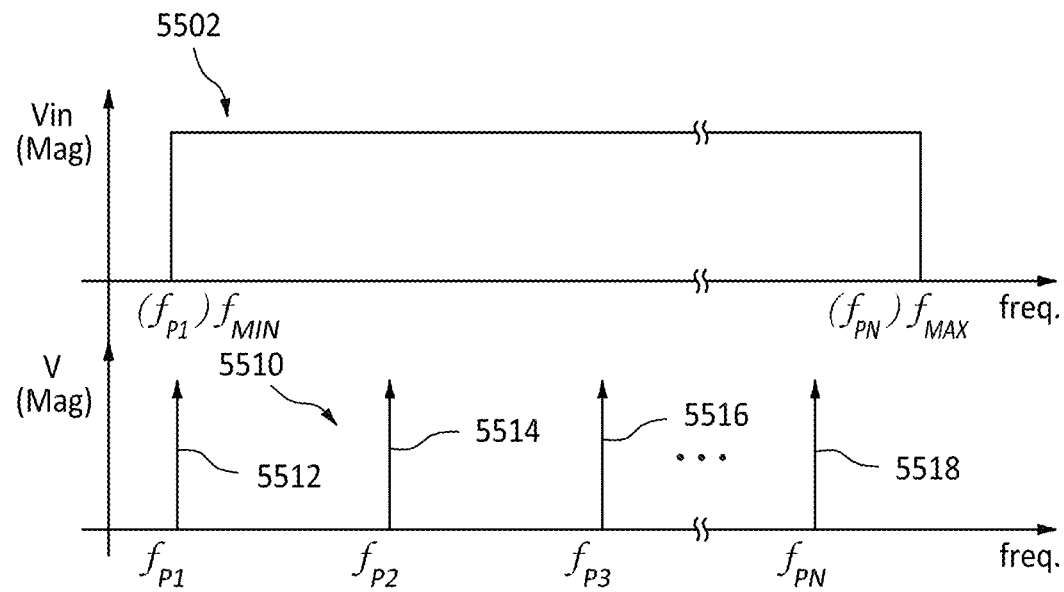

FIG. 55A are frequency plots for AC input voltages Vin, in accordance with embodiments of the present invention.

Figure 55B:
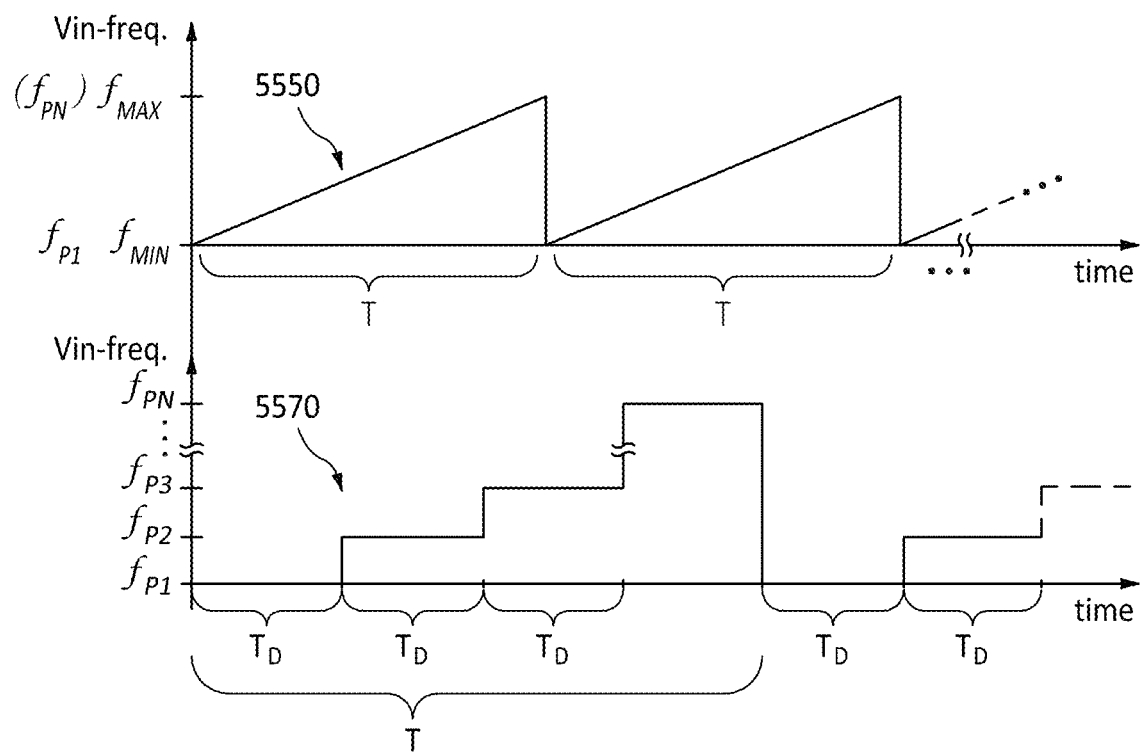

FIG. 55B are time & frequency plots for alternative AC input voltages Vin, in accordance with embodiments of the present invention.

Figure 56:
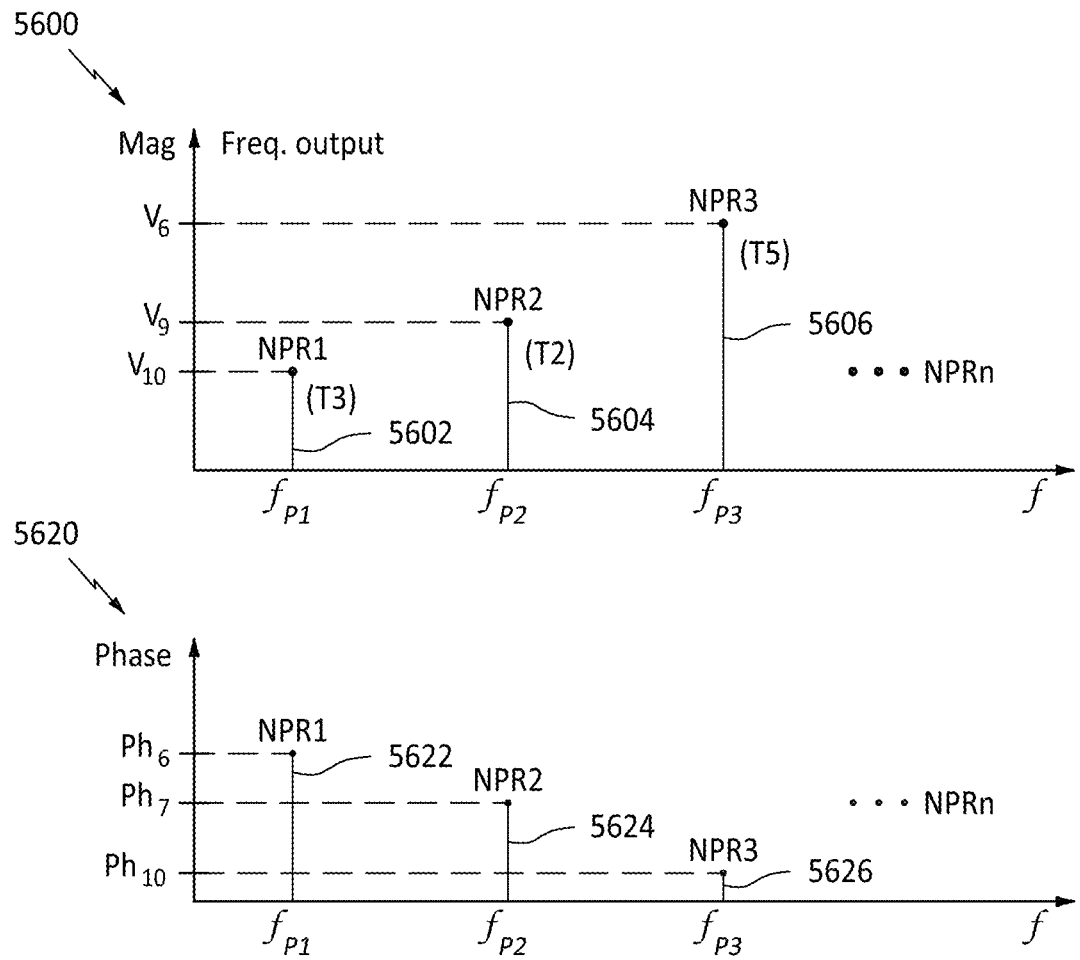

FIG. 56 are magnitude and phase frequency plots at three probe frequencies, in accordance with embodiments of the present invention.

Figure 57:
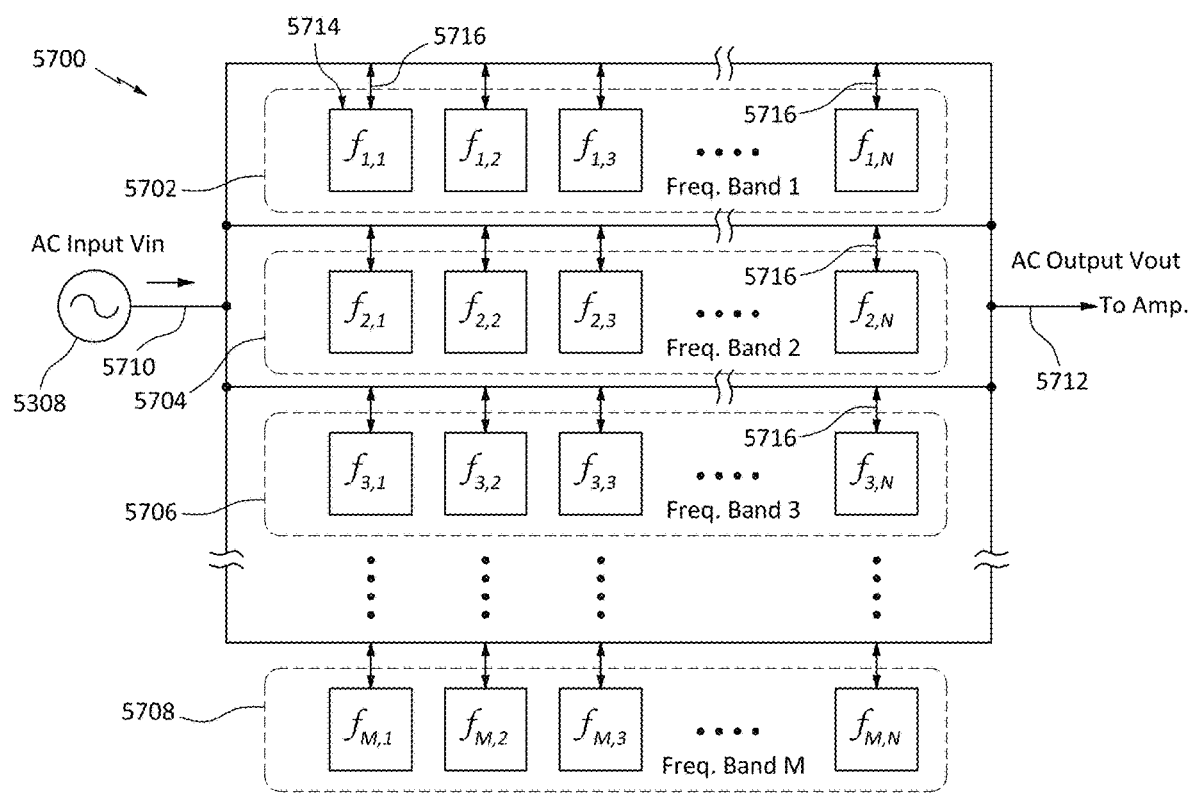

FIG. 57 is a block diagram of a 2D array of nanopore-polymer resonators, in accordance with embodiments of the present invention.

Figures 58, 59:
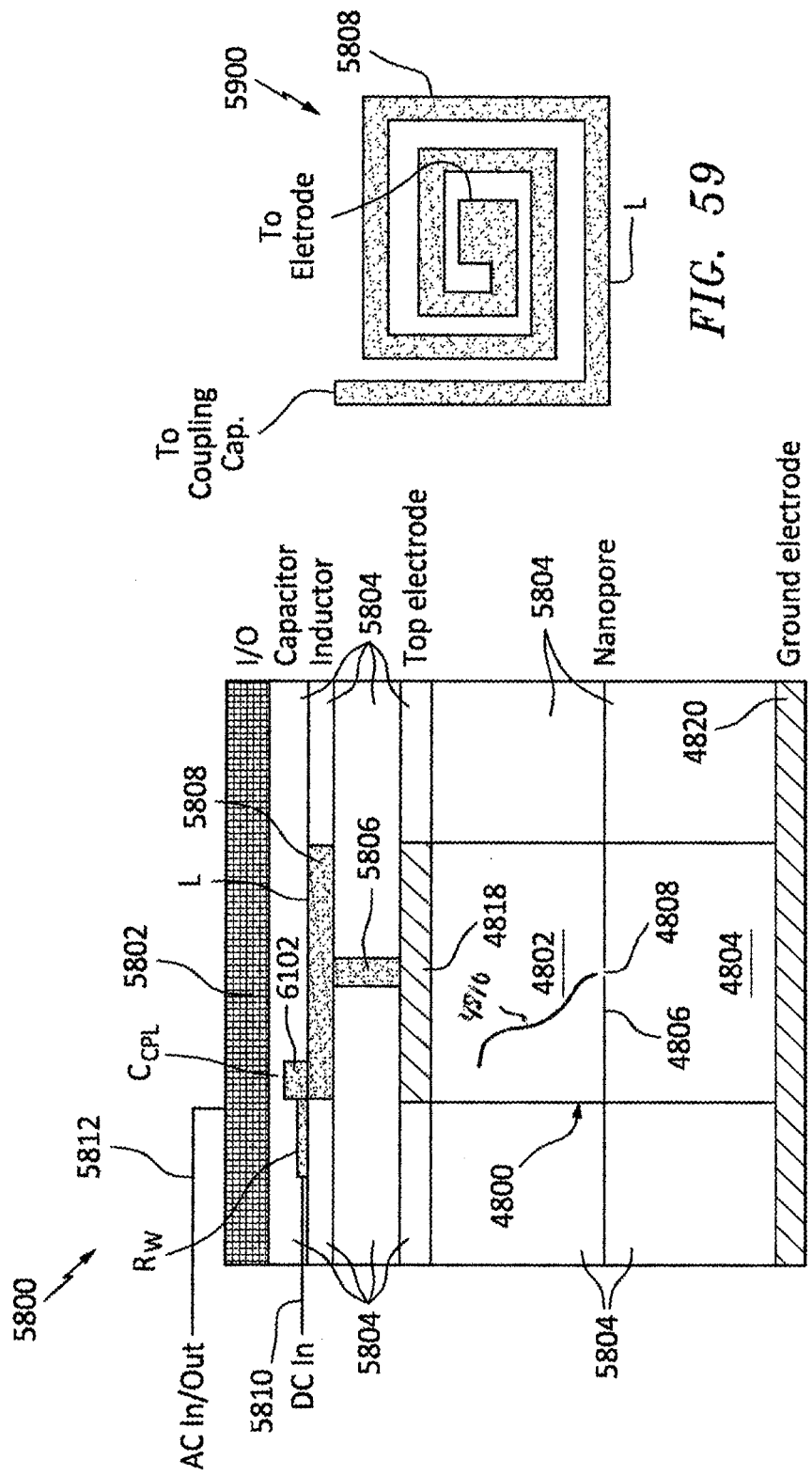

FIG. 58 is a side cross-sectional view of a nanopore memory chip, in accordance with embodiments of the present invention.

FIG. 59 is a top view of an inductor used in the chip of FIG. 58, in accordance with embodiments of the present invention.

Figure 60:
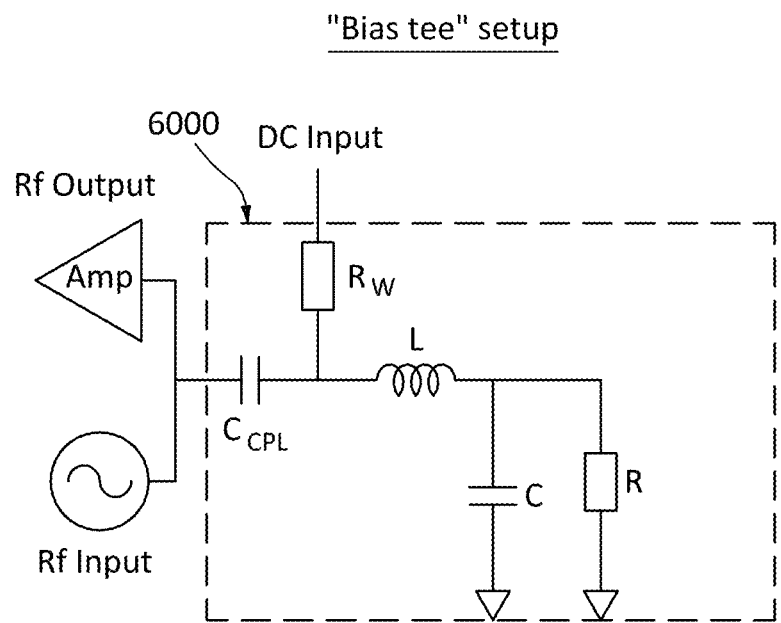

FIG. 60 is an equivalent circuit diagram of a "bias-tee" configuration to connect both AC and DC signals, in accordance with embodiments of the present invention.

Figure 61:
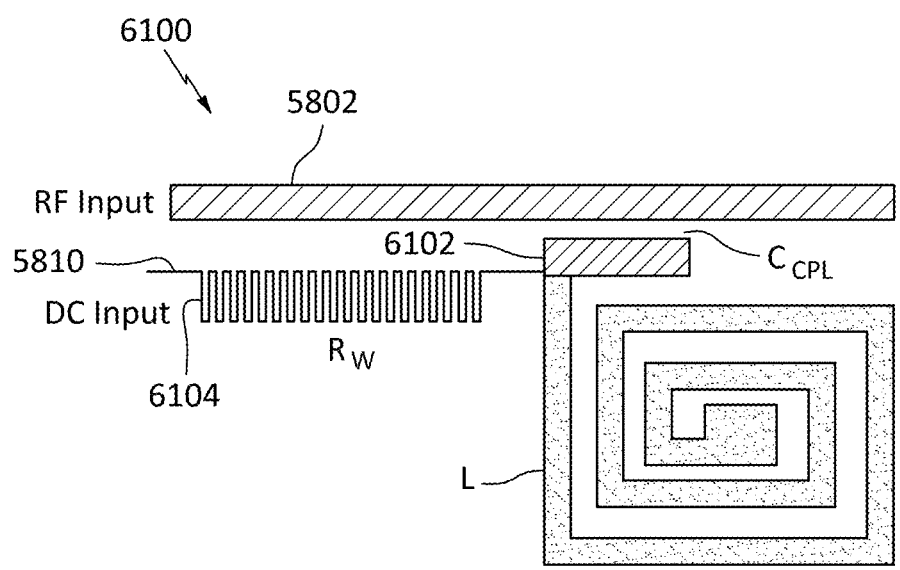

FIG. 61 is a diagram of a portion of the "bias-tee" configuration of FIG. 60, in accordance with embodiments of the present invention.

Figure 62:
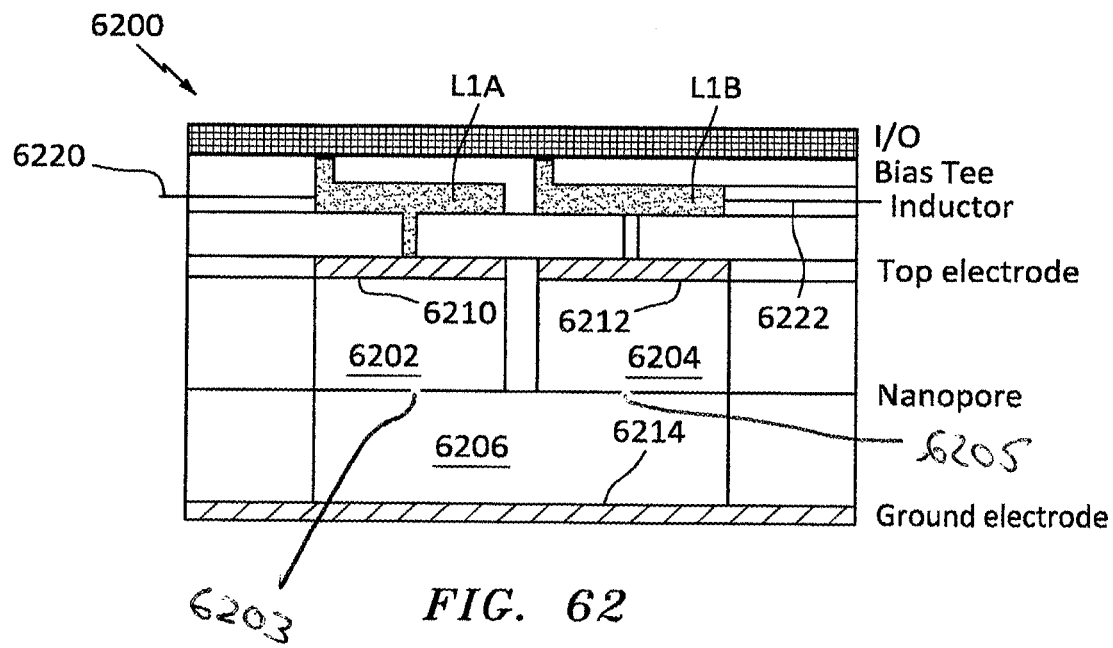

FIG. 62 is a side cross sectional view of another embodiment of nanopore memory chip having two inductors, one on each of the top Add chambers, in accordance with embodiments of the present invention.

Figure 63:
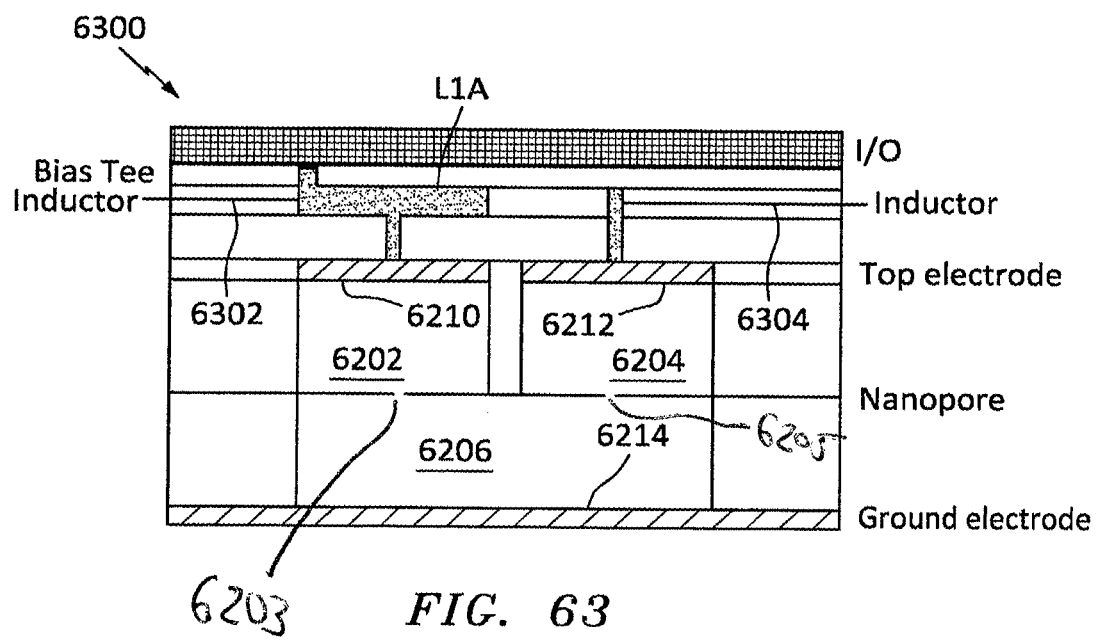

FIG. 63 is a side cross sectional view of another embodiment of nanopore memory chip having one inductor one of the top Add chambers, in accordance with embodiments of the present invention.

Figure 63A:
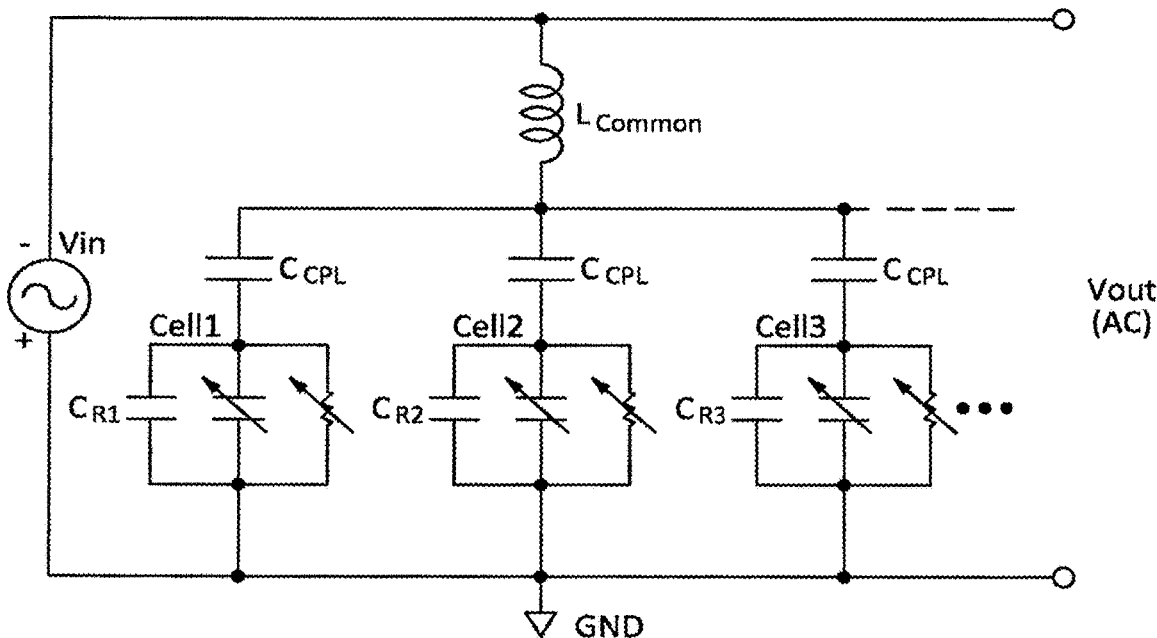

FIG. 63A is an equivalent circuit of a plurality of parallel nanopore-polymer resonators and signal processing having a single common inductor connected to the top electrodes of the resonator and fixed capacitance in each resonator cell, in accordance with embodiments of the present invention.

Figure 63B:
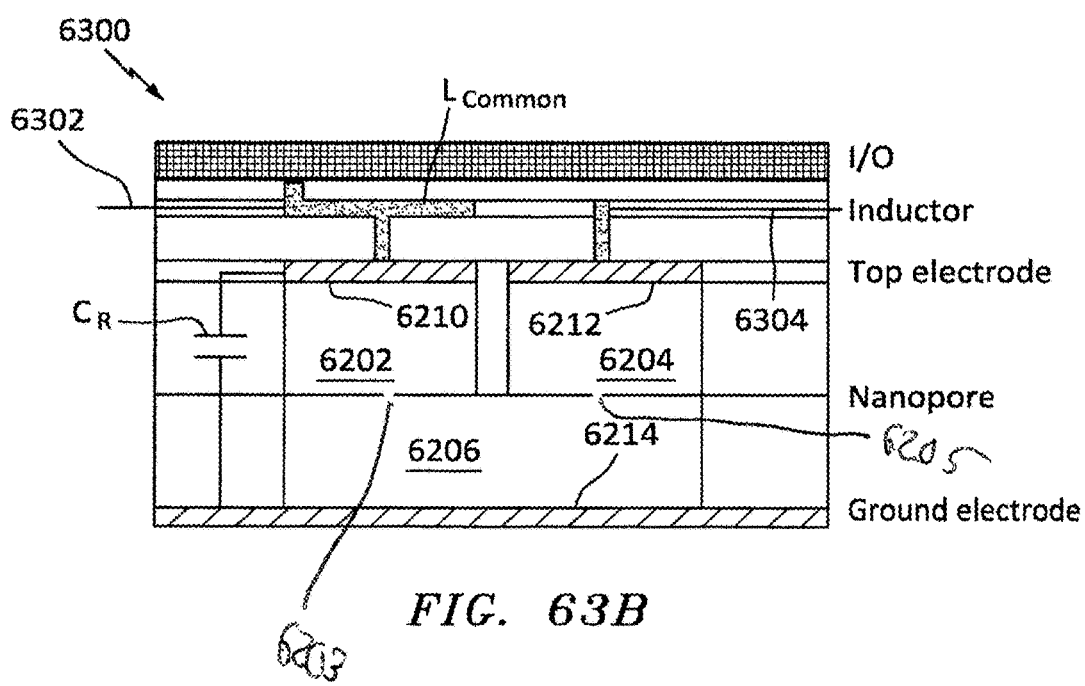

FIG. 63B is a side cross sectional view of another embodiment of nanopore memory chip having the configuration of FIG. 63A, in accordance with embodiments of the present invention.

Figure 64:
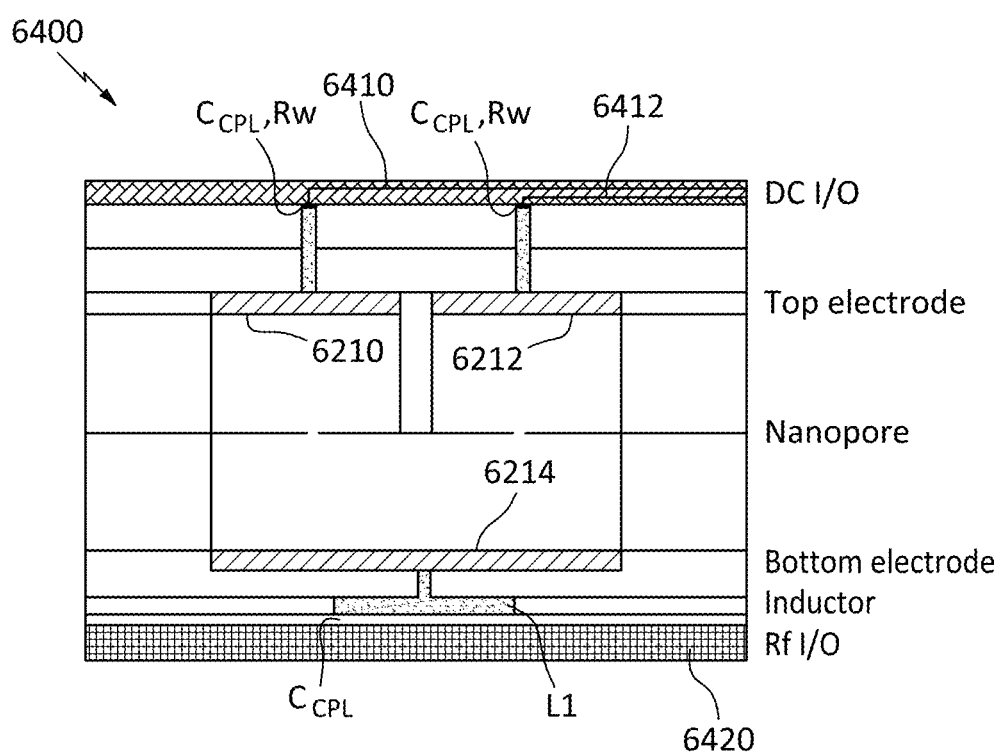

FIG. 64 is a side cross sectional view of another embodiment of nanopore memory chip having an inductor on the bottom of the deblock chamber, in accordance with embodiments of the present invention.

Figure 64A:
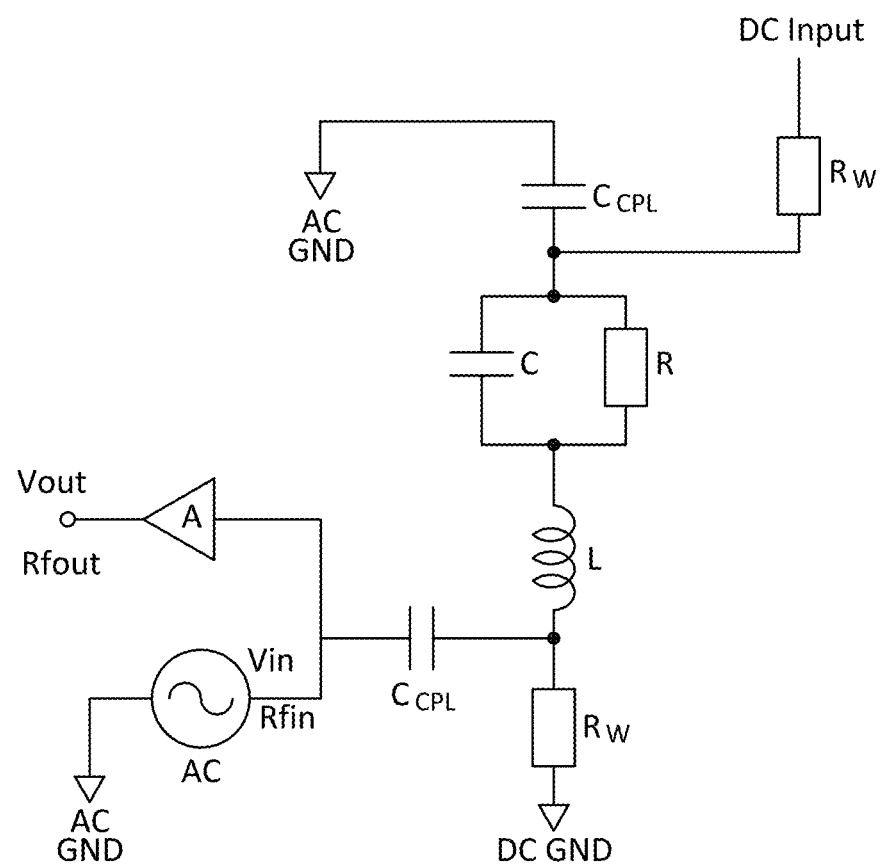

FIG. 64A is an equivalent circuit diagram of a "bias-tee" configuration to connect both AC and DC signals for the configuration of FIG. 64, in accordance with embodiments of the present invention.

Figure 64B:
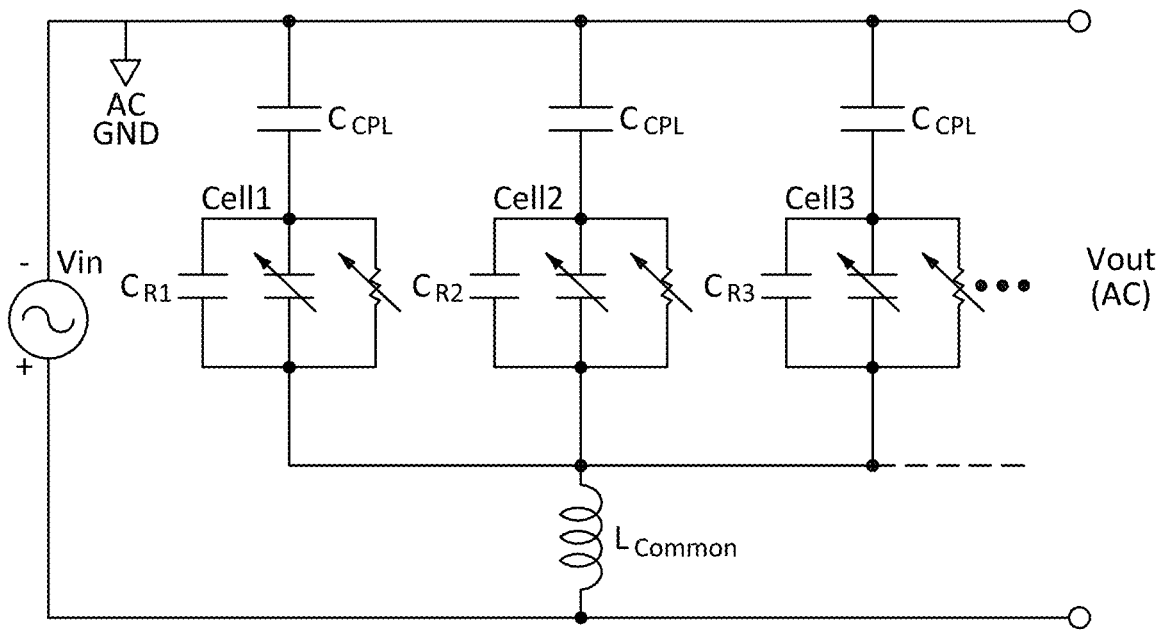

FIG. 64B is an equivalent circuit of a plurality of parallel nanopore-polymer resonators and signal processing having a single common inductor and fixed capacitance in each resonator cell, in accordance with embodiments of the present invention.

Figure 64C:
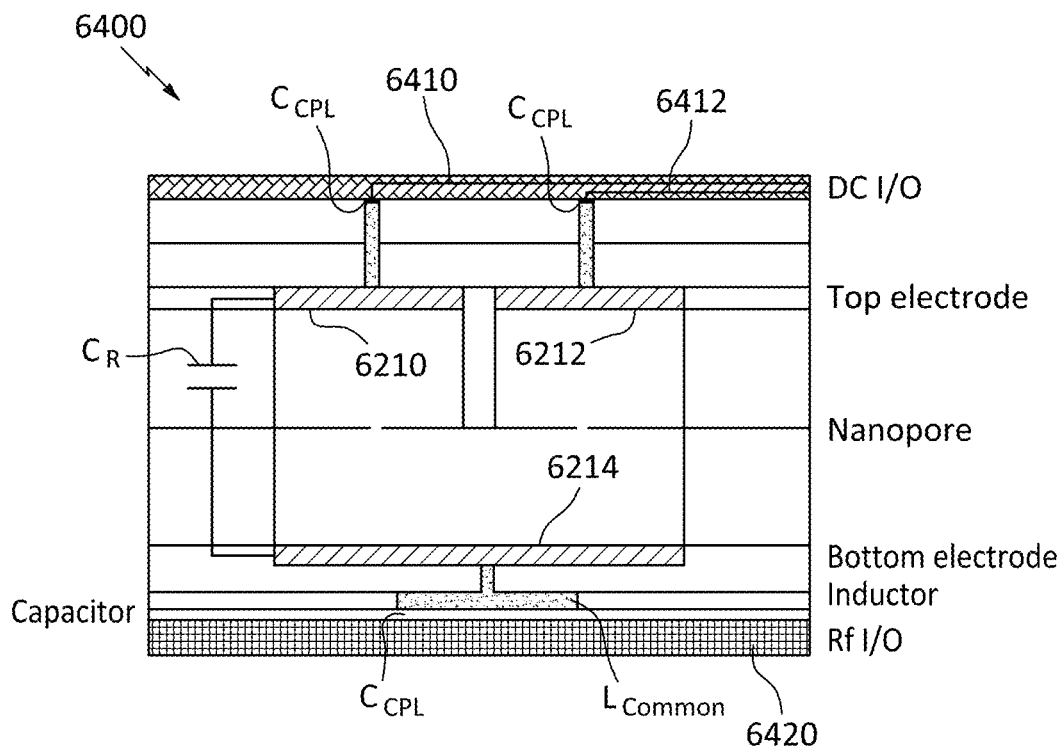

FIG. 64C is a side cross sectional view of another embodiment of nanopore memory chip having the configuration of FIG. 64B, in accordance with embodiments of the present invention.

Figure 65:
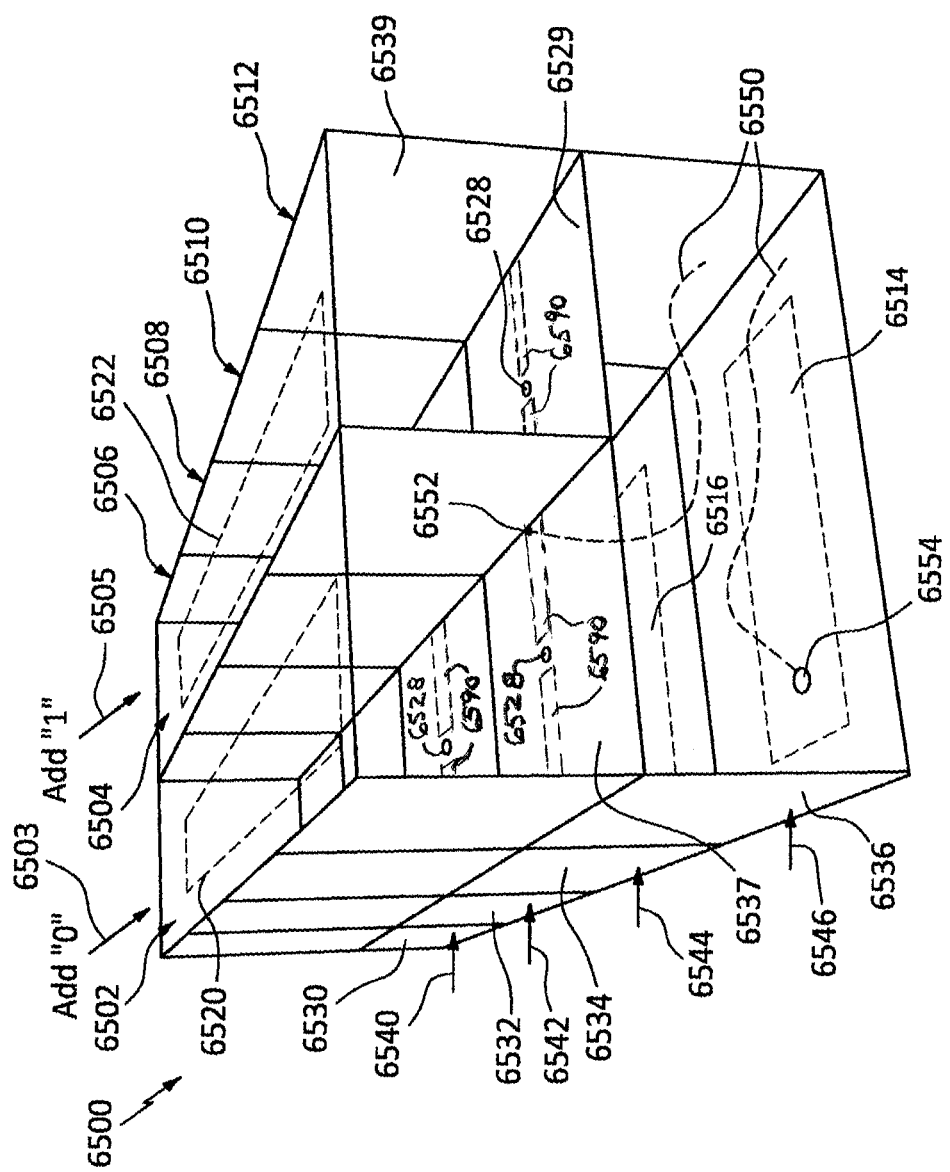

FIG. 65 is a partial perspective view of a group of connected 3-chamber cell nanopore devices having a transparent top and electrodes, in accordance with embodiments of the present invention.

Figure 66:
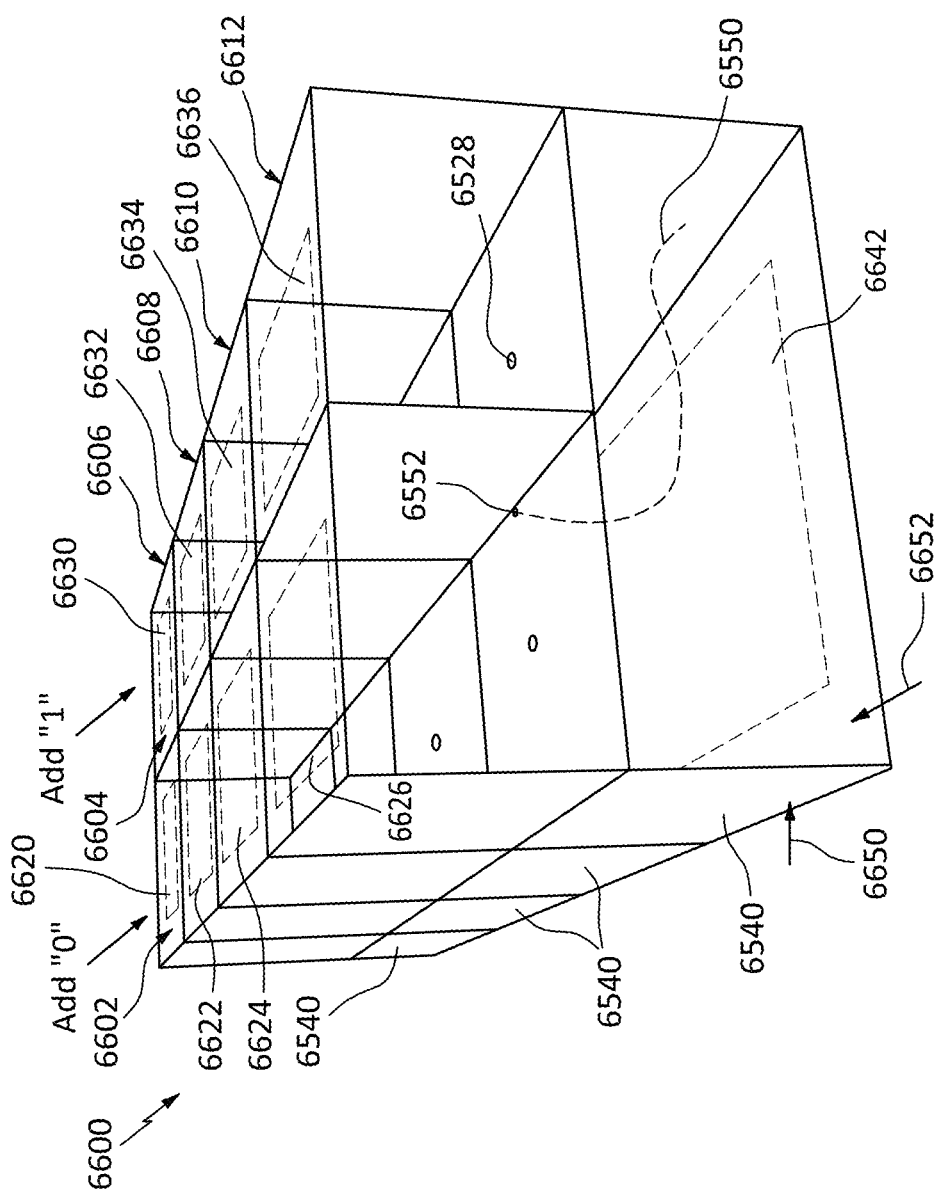

FIG. 66 is a partial perspective view of an alternative embodiment of a group of connected 3-chamber cell nanopore devices having a transparent top and electrodes, in accordance with embodiments of the present invention.

Figure 67:
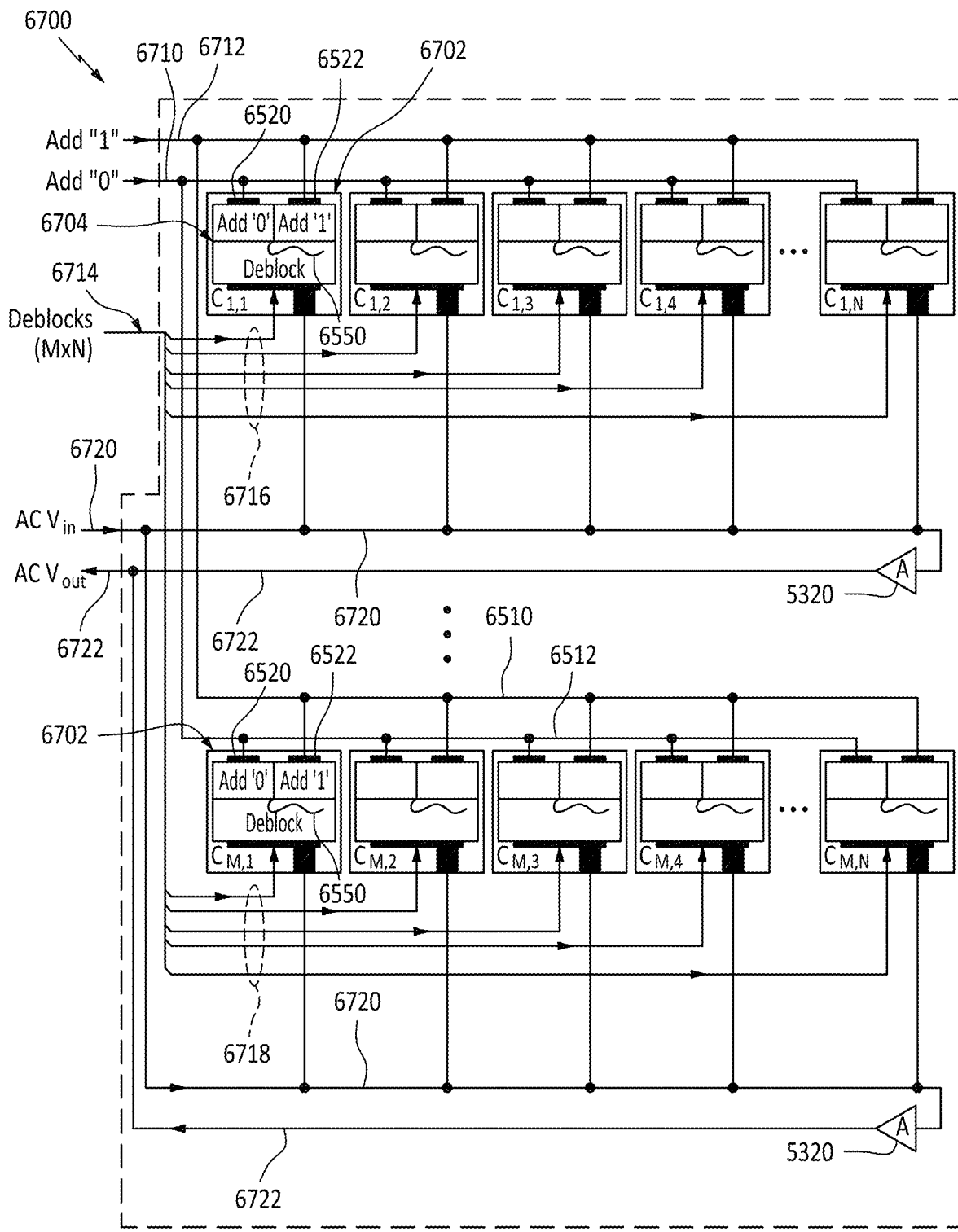

FIG. 67 is a circuit block diagram of an array of nanopore cells connected as per FIG. 65, in accordance with embodiments of the present invention.

Figure 68:
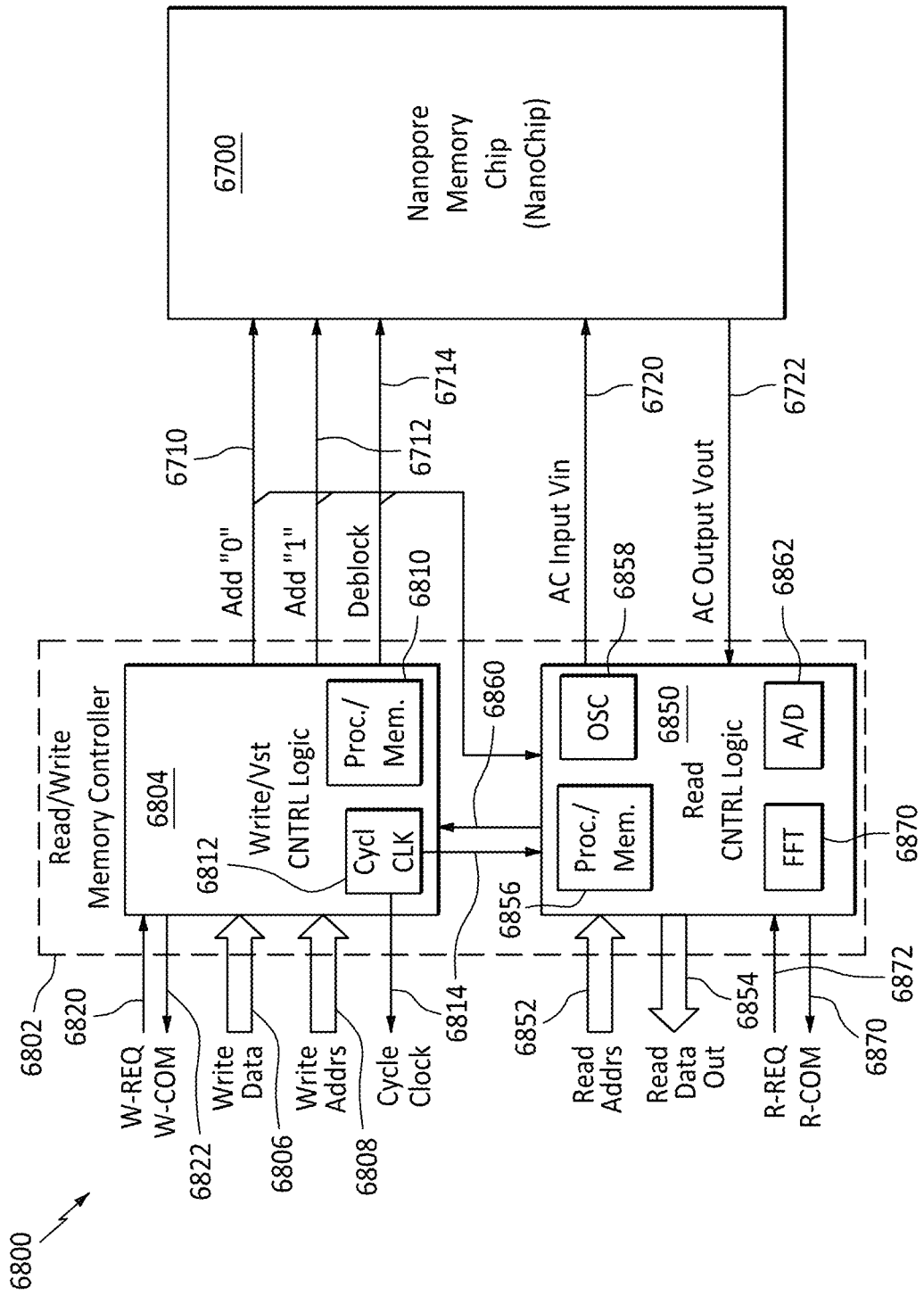

FIG. 68 is a block diagram of a read/write memory controller and a nanopore memory chip, in accordance with embodiments of the present invention.

Figure 68A:
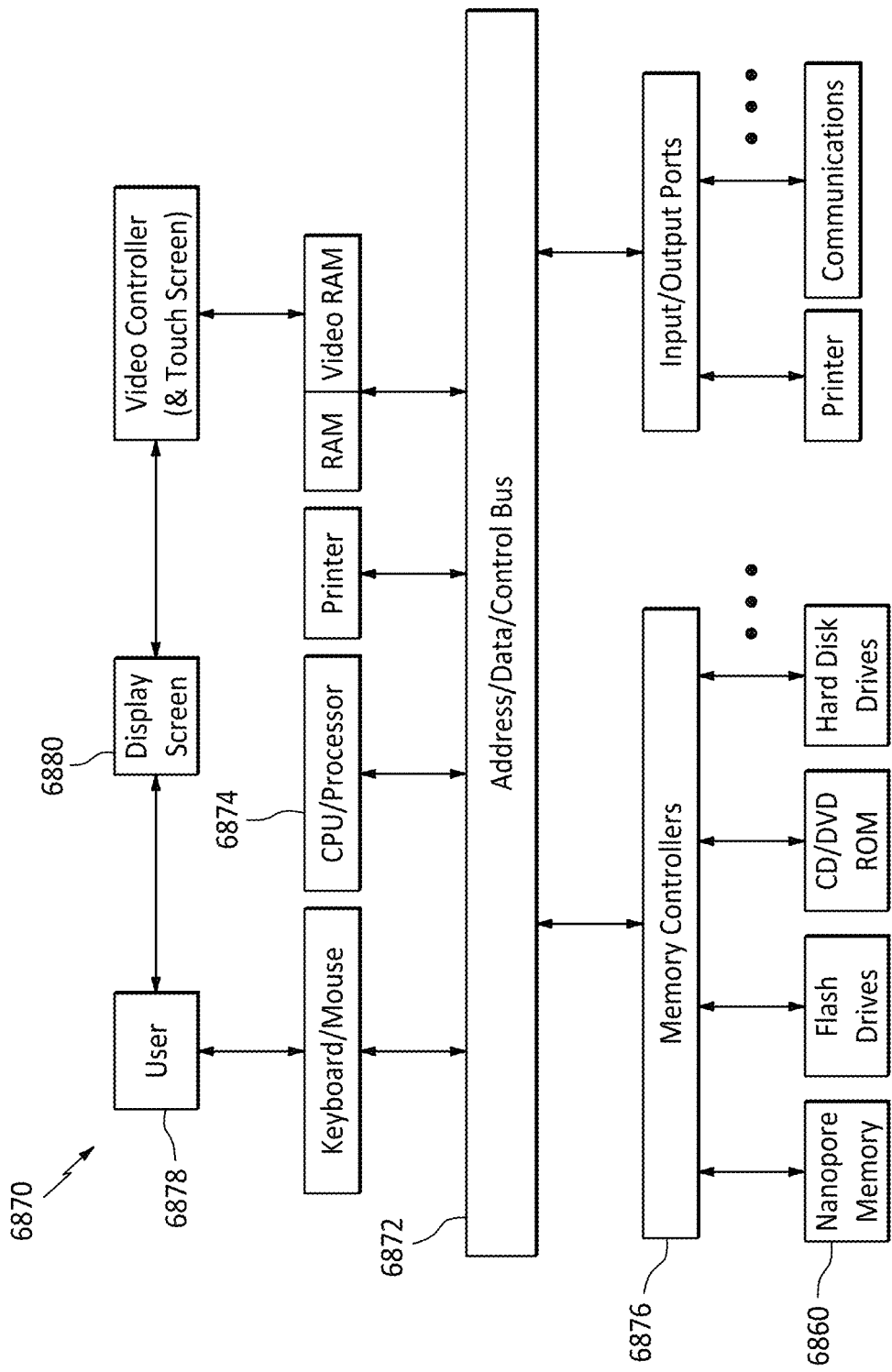

FIG. 68A is a block diagram of a computer system, in accordance with embodiments of the present invention.

Figure 69:
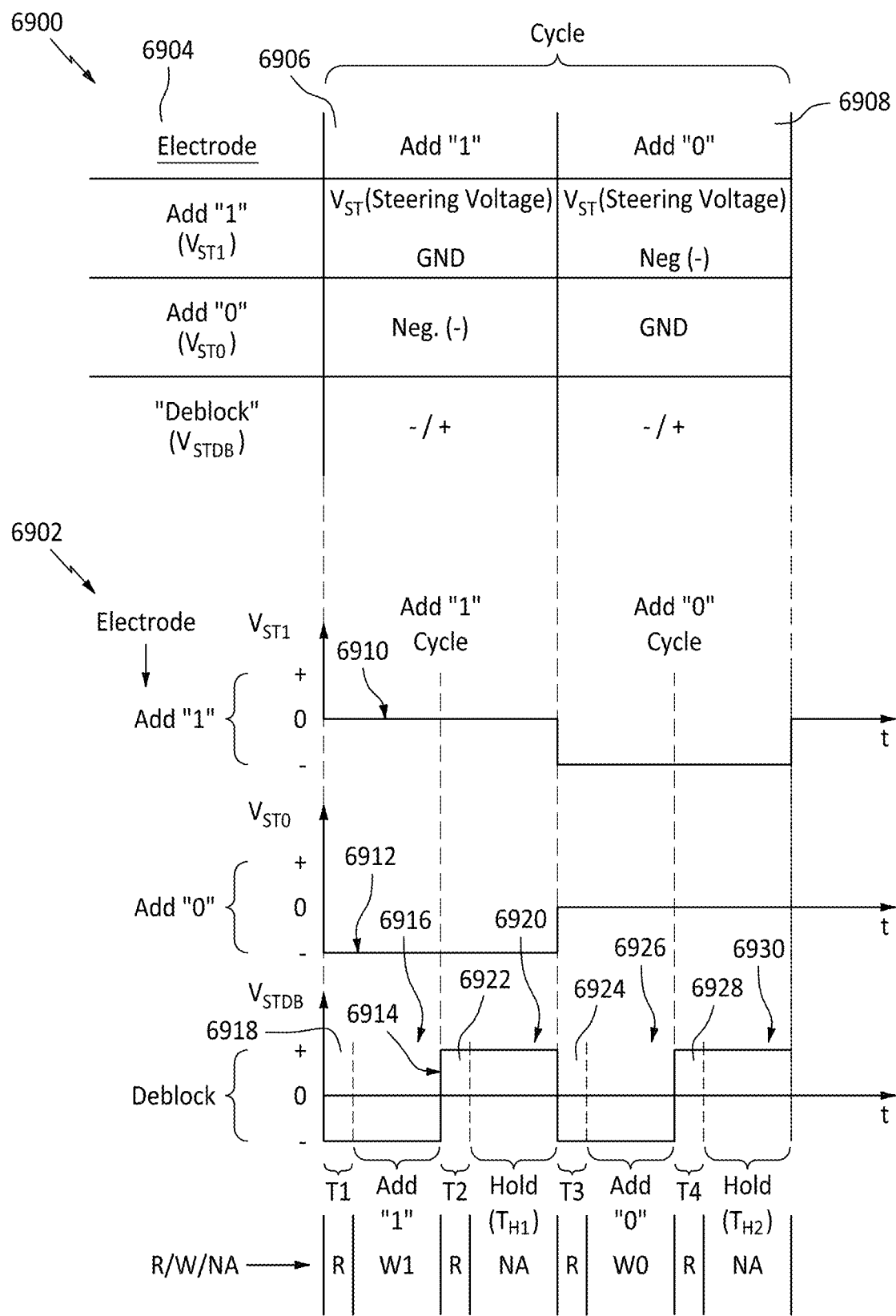

FIG. 69 is a table and graphs of memory add cycles and steering voltages needed to perform the cycles, in accordance with embodiments of the present invention.

Figure 70:
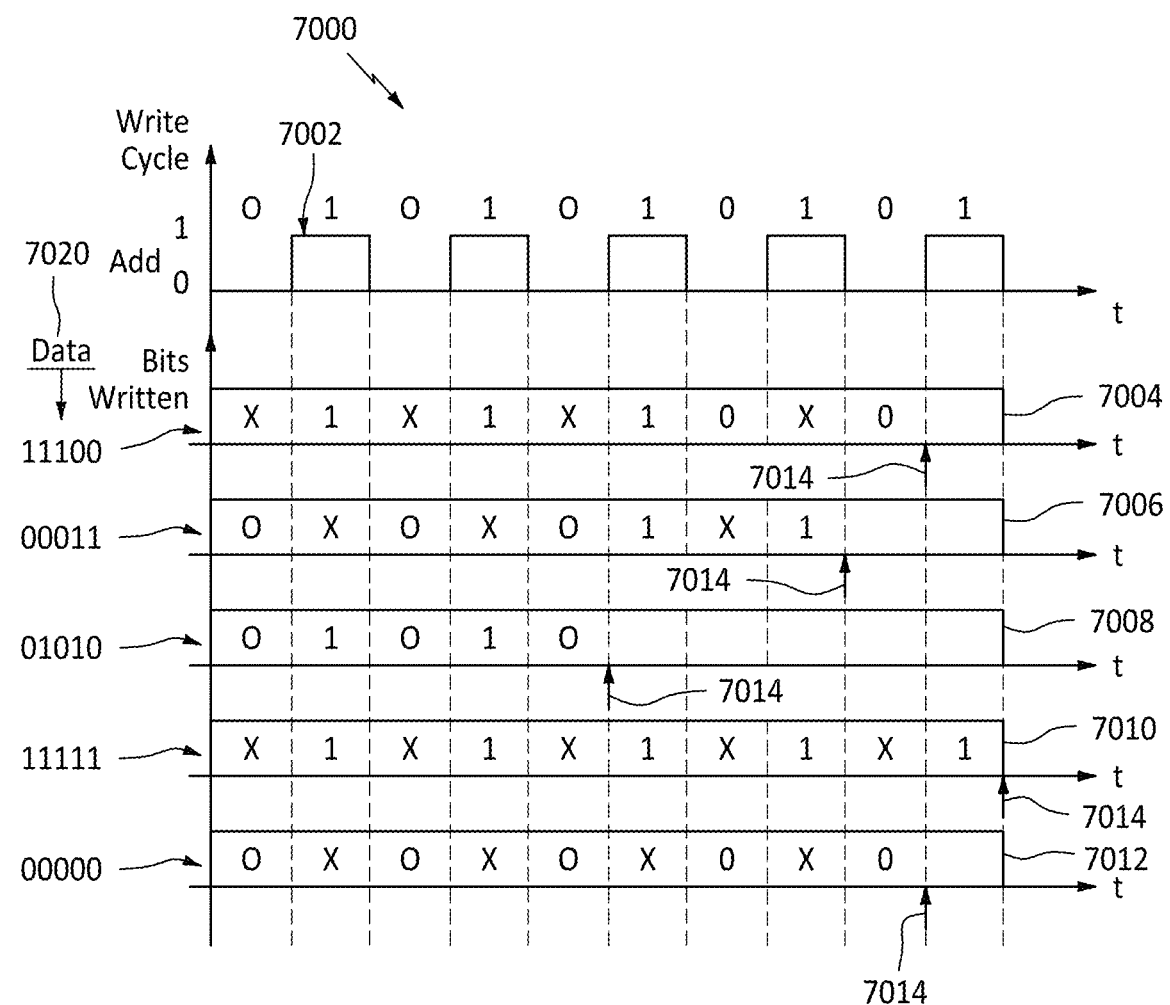

FIG. 70 is a graph and data map showing how memory is populated for various data inputs using alternating write cycles, in accordance with embodiments of the present invention.

Figure 70A:
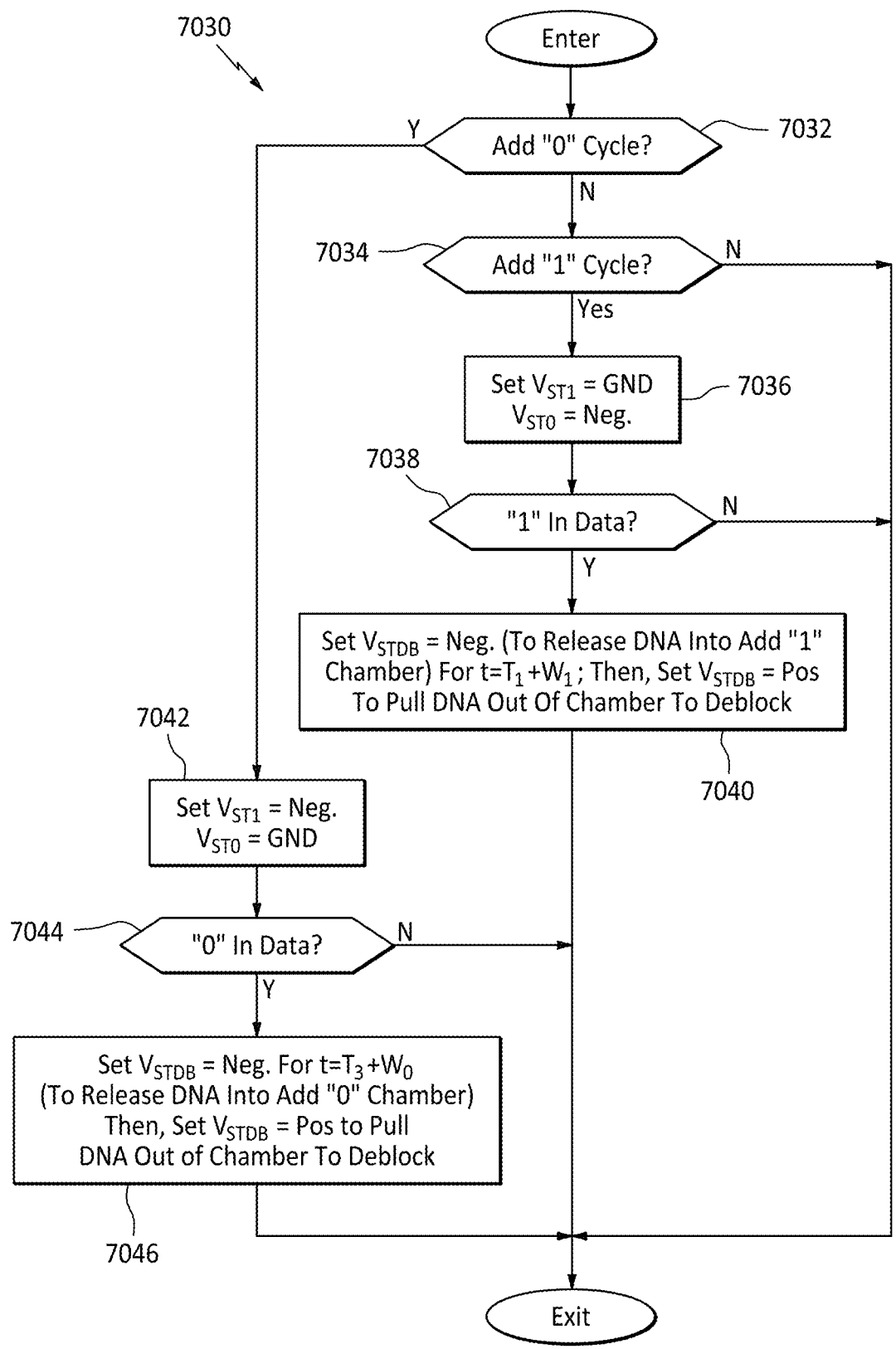

FIG. 70A is a flowchart of controller logic for performing the write cycles shown in FIG. 70, in accordance with embodiments of the present invention.

FIG. 70B is a table showing steps for writing "1" and "0" with the nanopore chip configured as shown in FIG. 66, in accordance with embodiments of the present invention.

Figure 71:
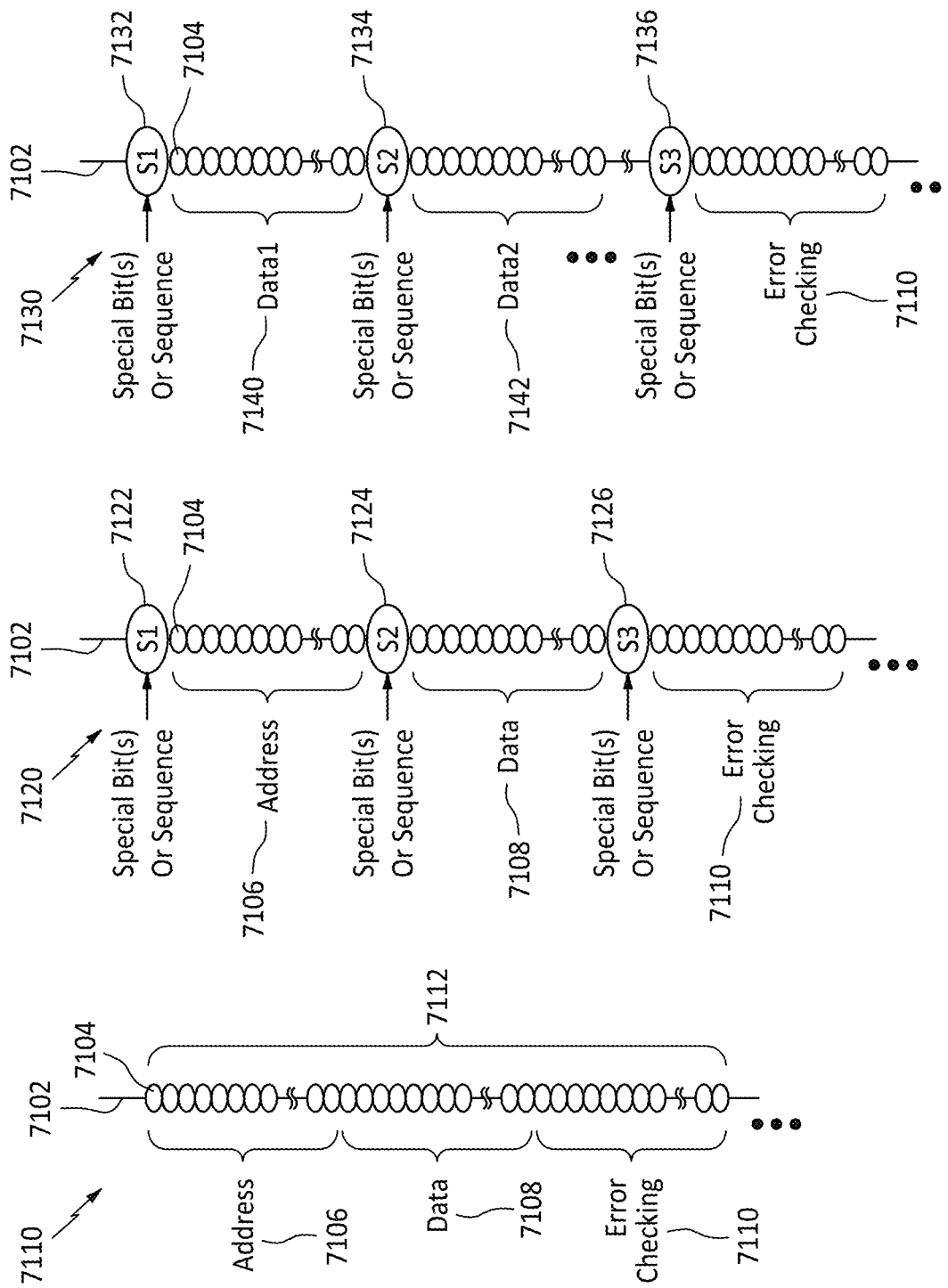

FIG. 71 shows three different data format listings of the bits on a memory string, in accordance with embodiments of the present invention.

Figure 72:
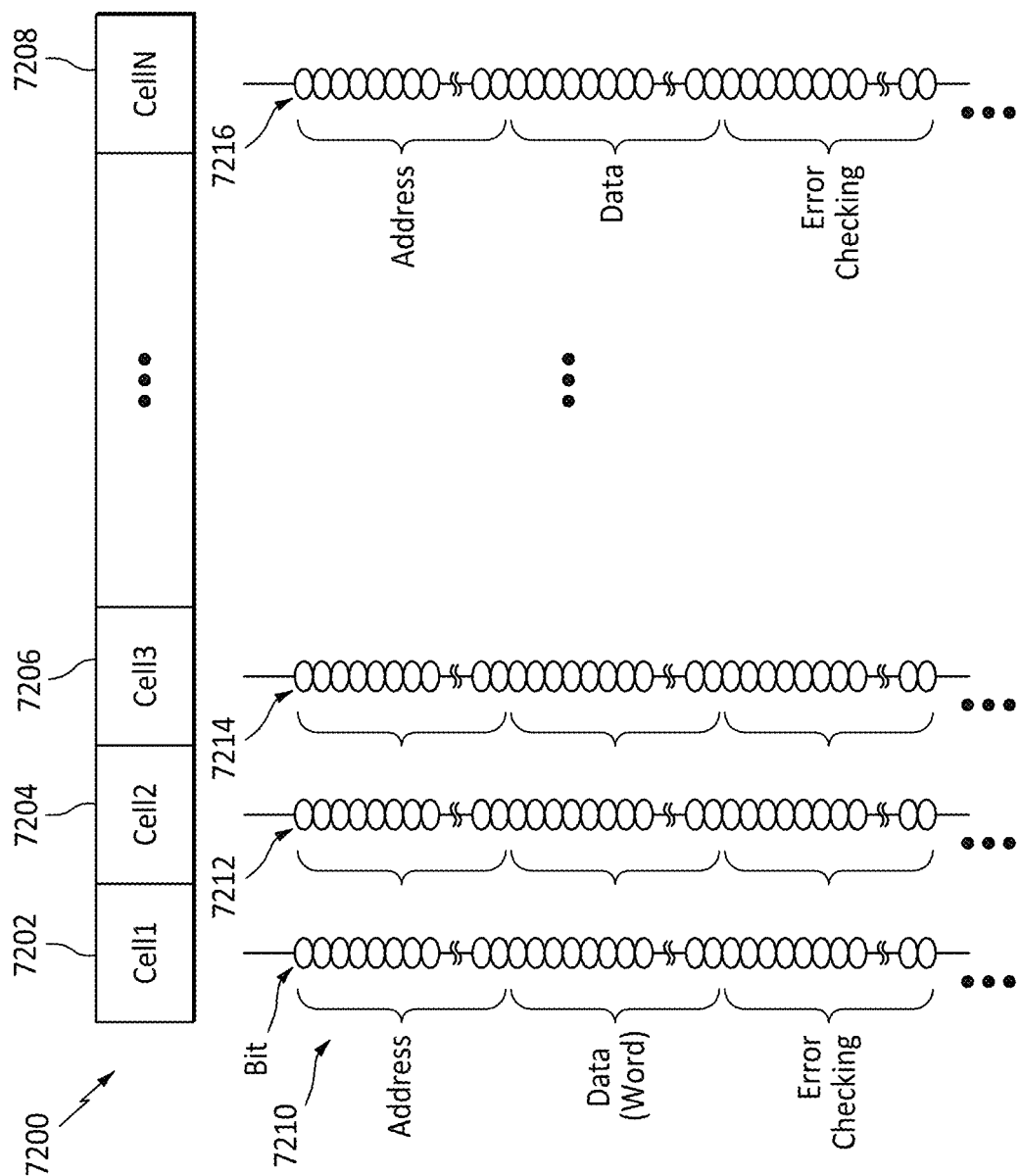

FIG. 72 shows a data format listing of the bits on a memory string for each cell in a row, in accordance with embodiments of the present invention.

Figure 73:
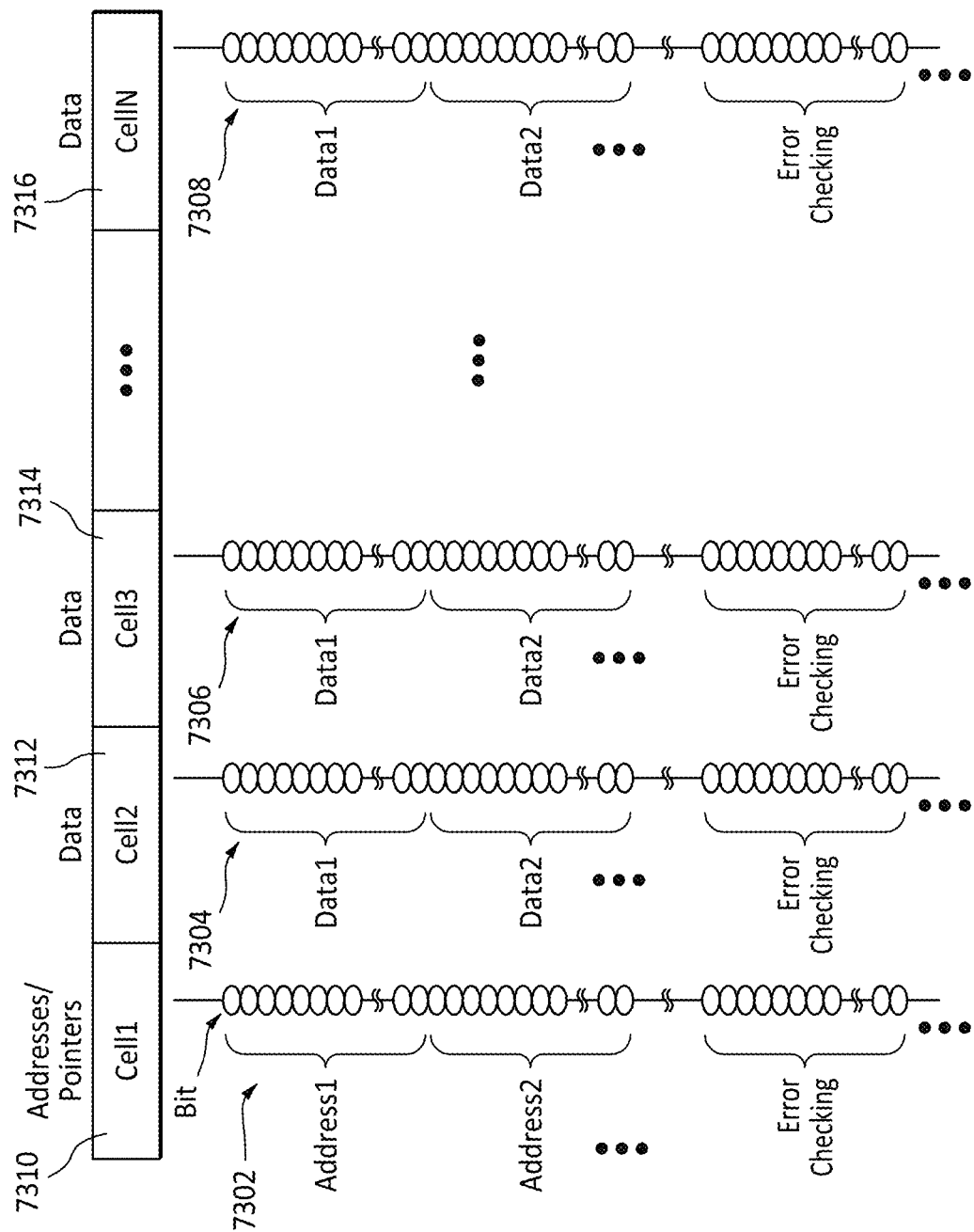

FIG. 73 shows an alternative data format listing of the bits on a memory string for each cell in a row, in accordance with embodiments of the present invention.

Figure 74:
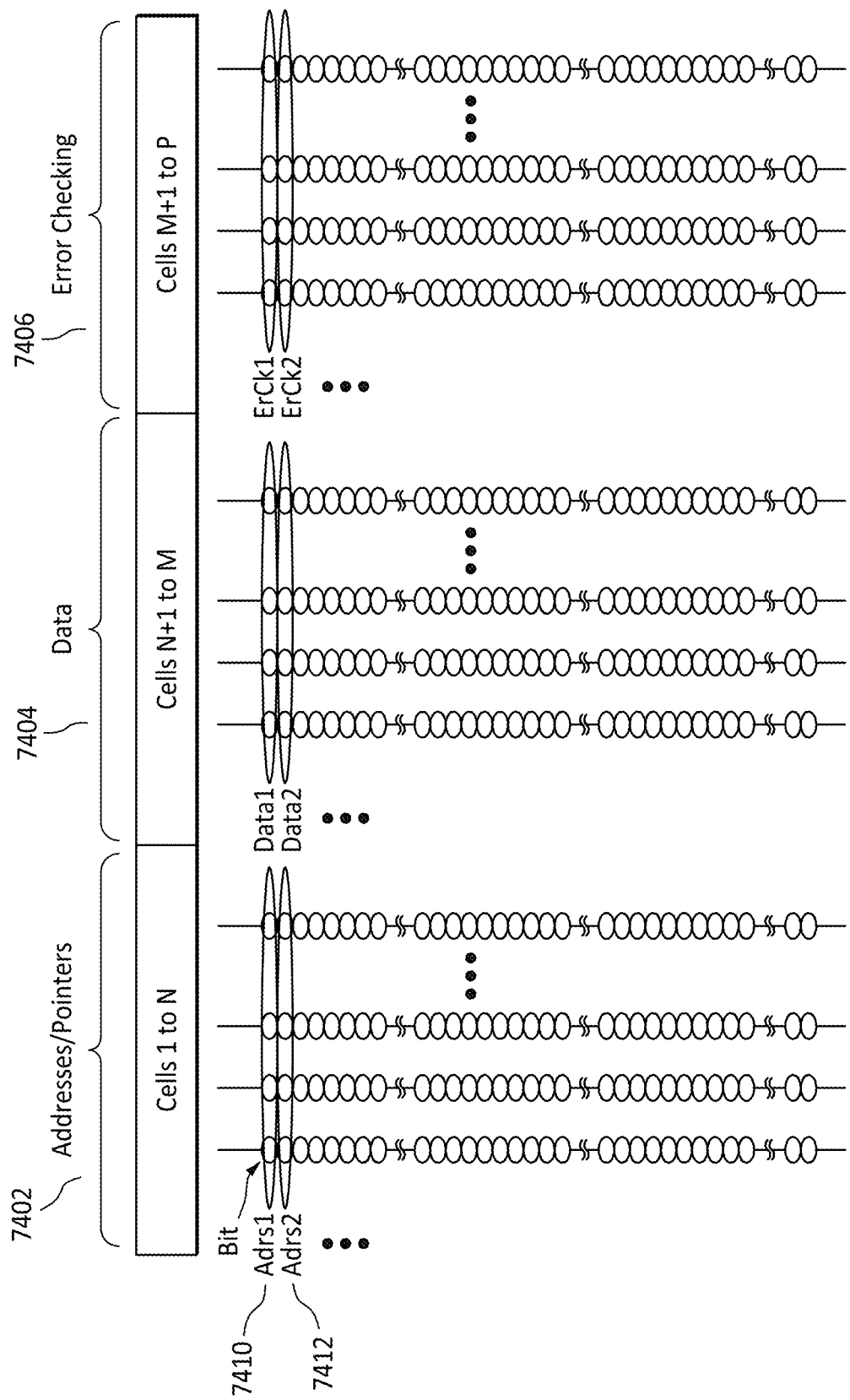

FIG. 74 shows an alternative parallel data storage format listing of the bits on a memory string for cells in a row, in accordance with embodiments of the present invention.

Figure 75:
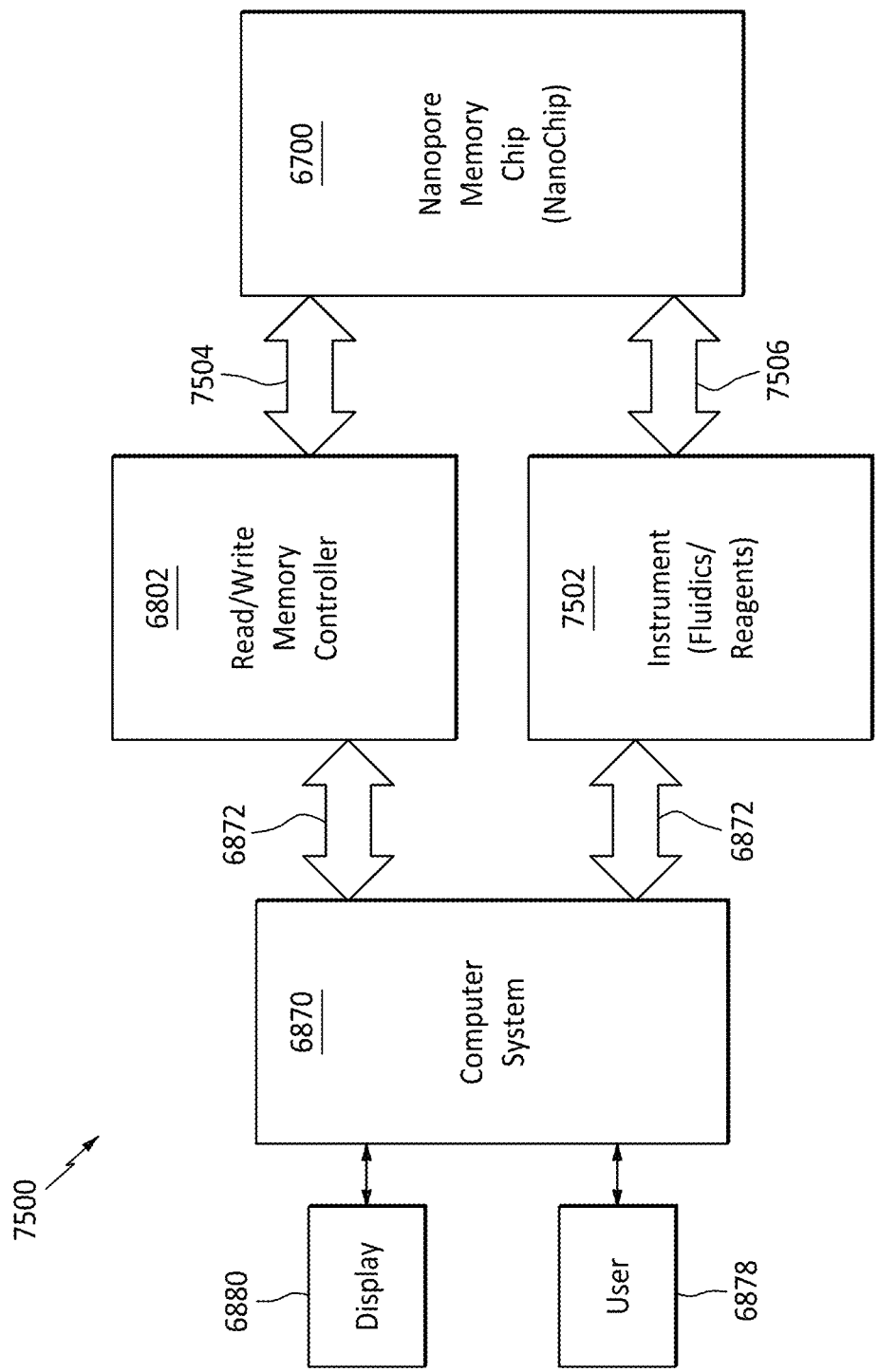

FIG. 75 is a block diagram showing a nanopore memory system showing a read/write memory controller and an instrument for fluidics/reagents, in accordance with embodiments of the present invention.

Figure 76:
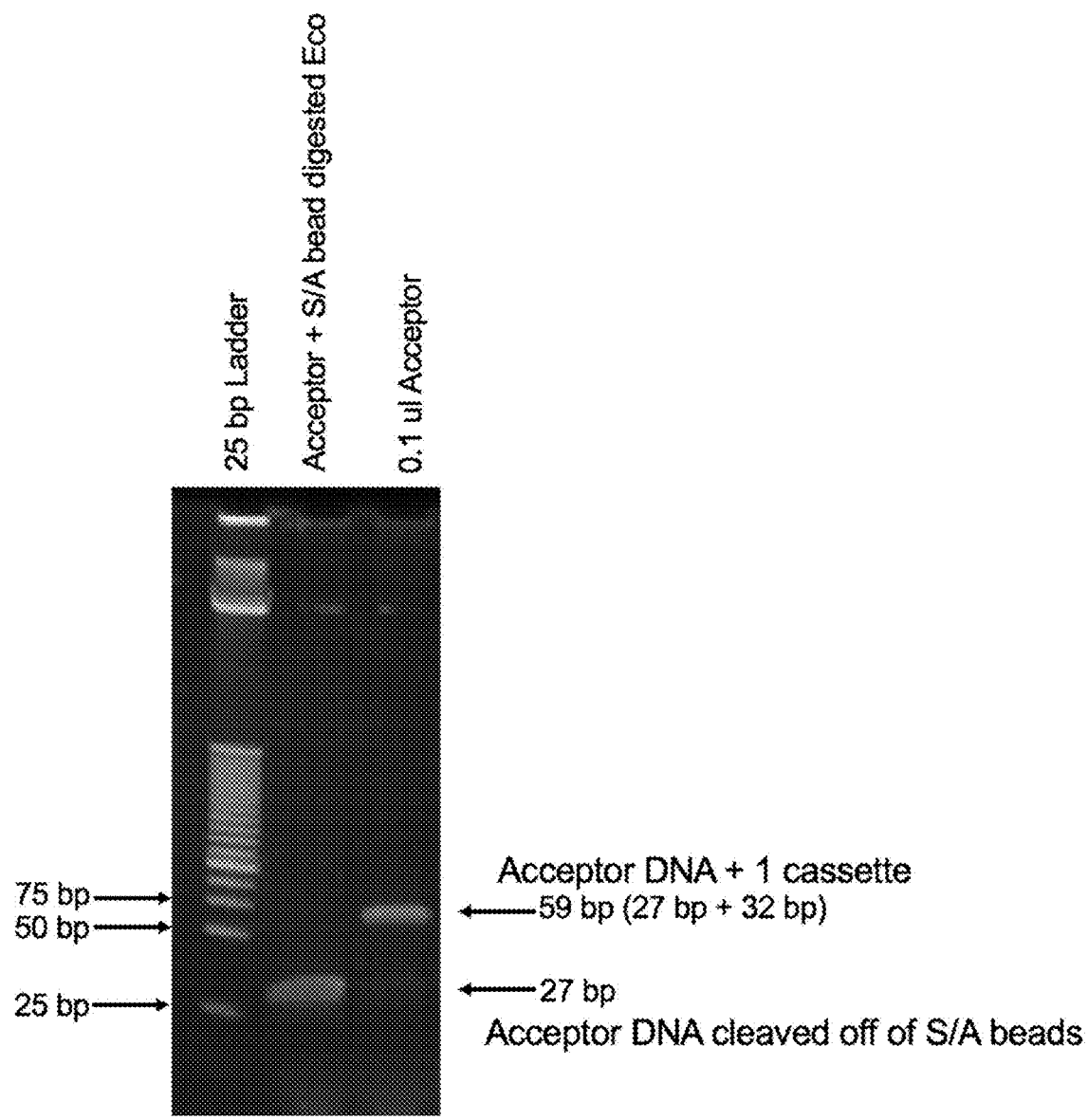

FIG. 76 is an gel electrophoresis preparation, showing topoisomerase-mediated addition of oligonucleotide cassettes ("bits") to a DNA molecule.

Figure 77:
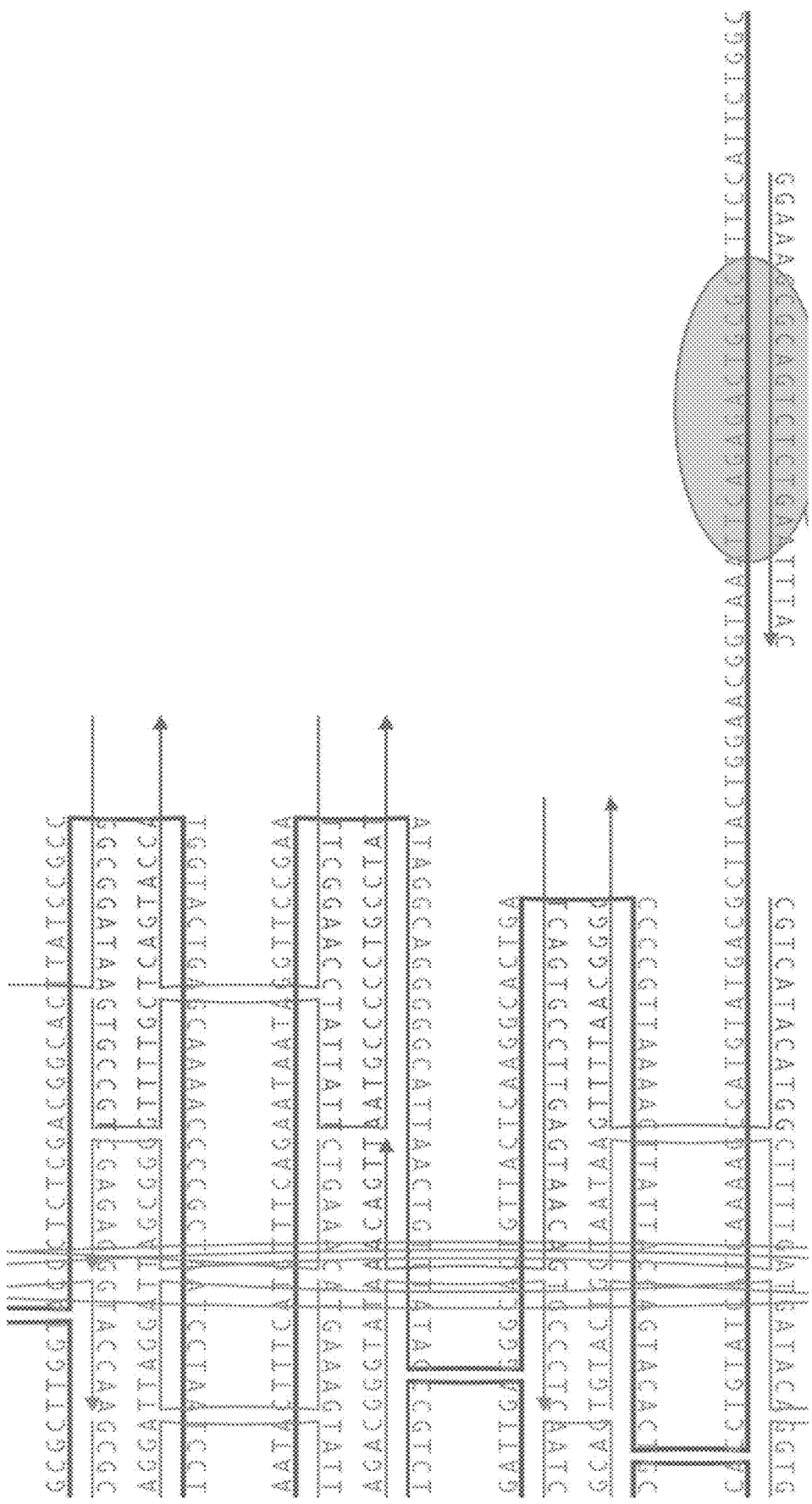

FIG. 77 depicts the DNA origami molecule of Example 7.

Figure 77A:
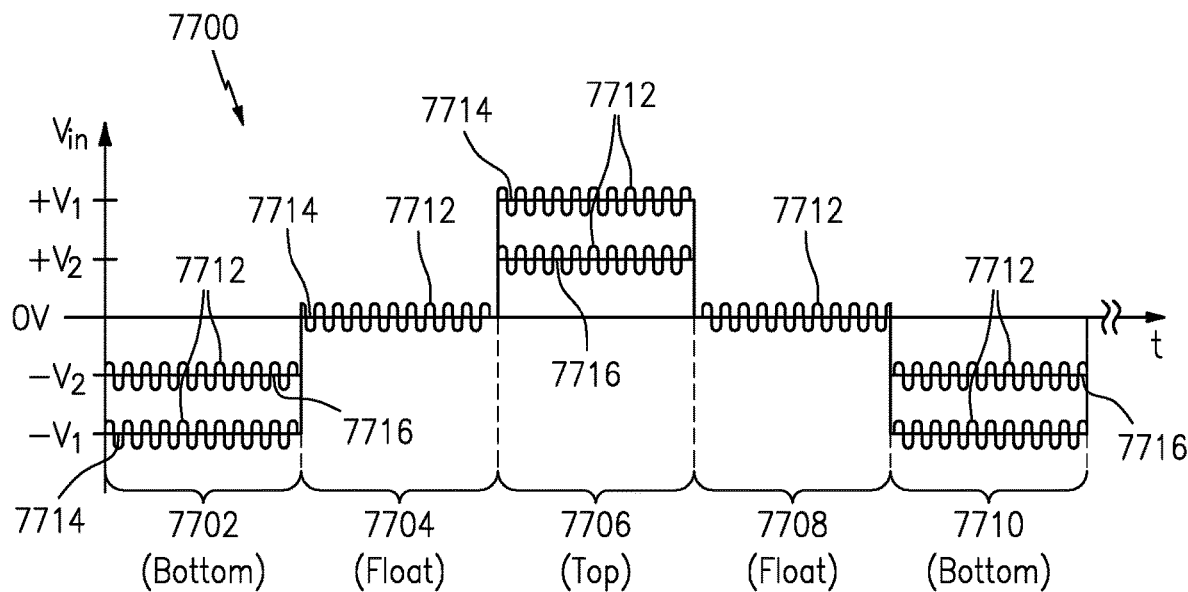

FIG. 77A is a graph of input voltage showing DC and AC voltage over time with different DC voltage levels, in accordance with embodiments of the present invention.

Figure 78A:
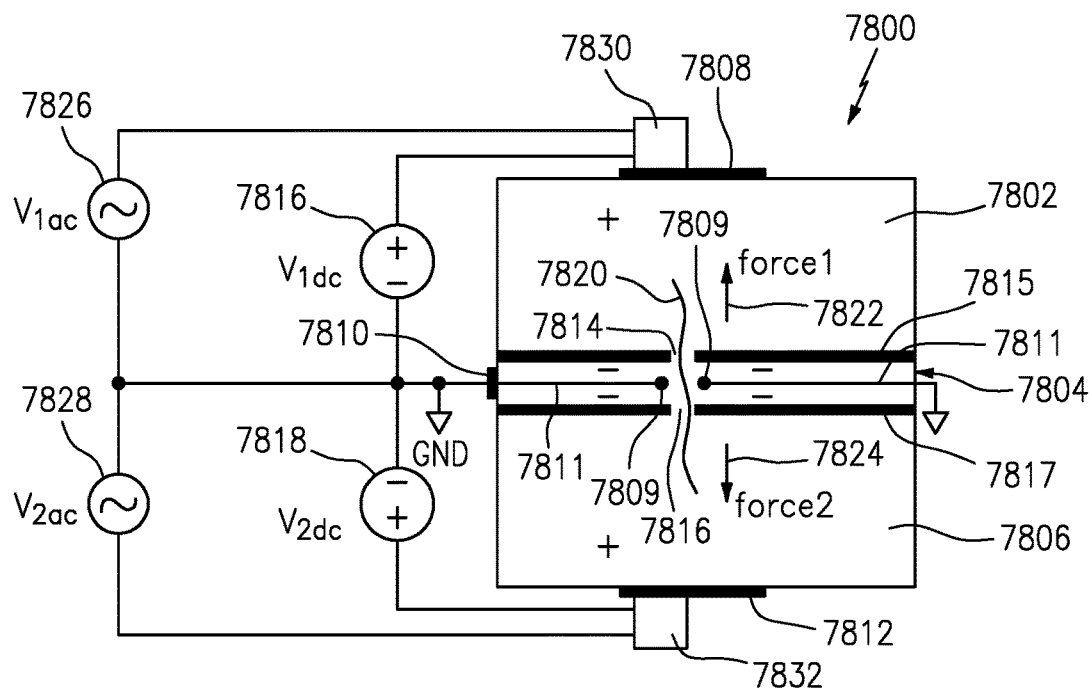

FIG. 78A is a side view of a dual-nanopore device having two longitudinal nanopore resonators, in accordance with embodiments of the present invention.

Figure 78B:
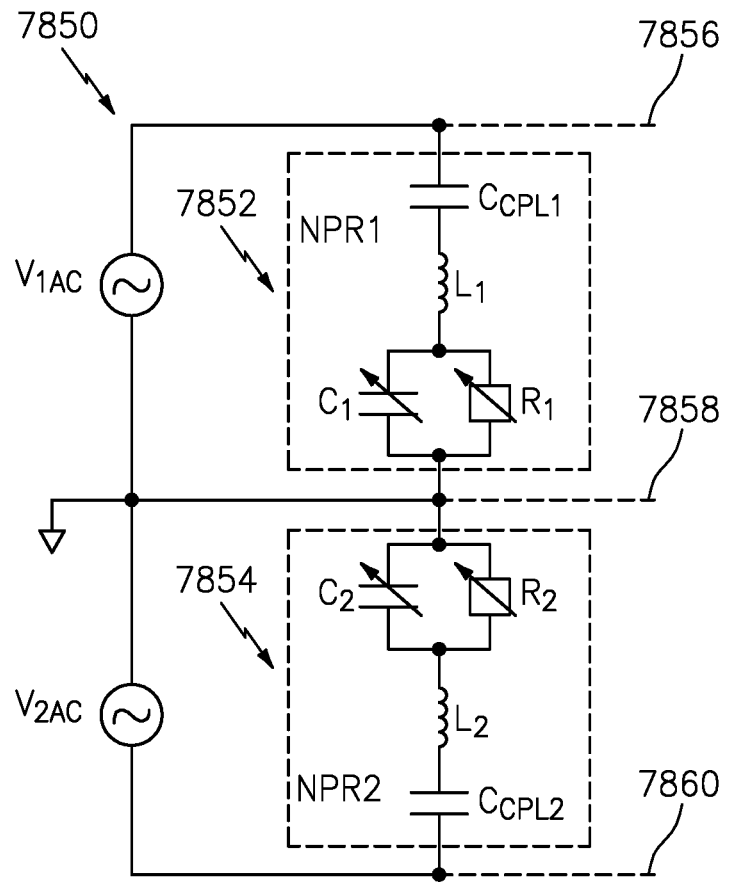

FIG. 78B is an equivalent circuit of the dual-nanopore device of FIG. 78A, in accordance with embodiments of the present invention.

Figure 79A:
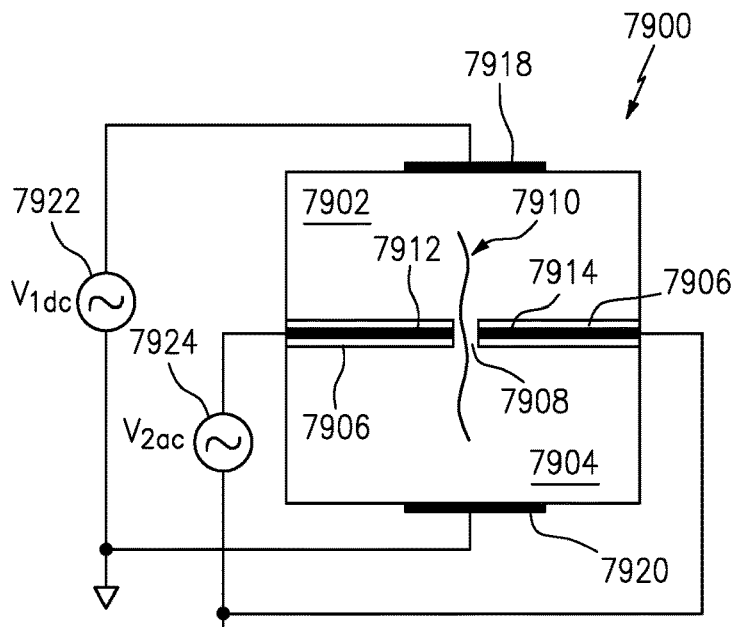

FIG. 79A is a side view of a dual chamber nanopore device having a transverse resonator, in accordance with embodiments of the present invention.

Figure 79B:
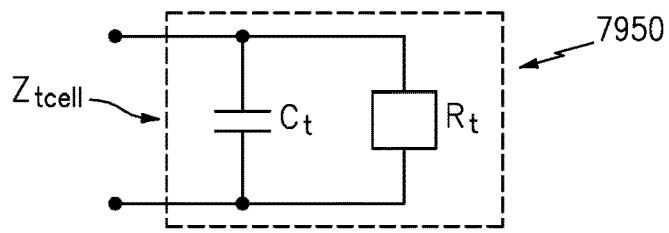

FIG. 79B is an equivalent circuit of a portion of the dual chamber device of FIG. 79A, in accordance with embodiments of the present invention.

Figure 79C:
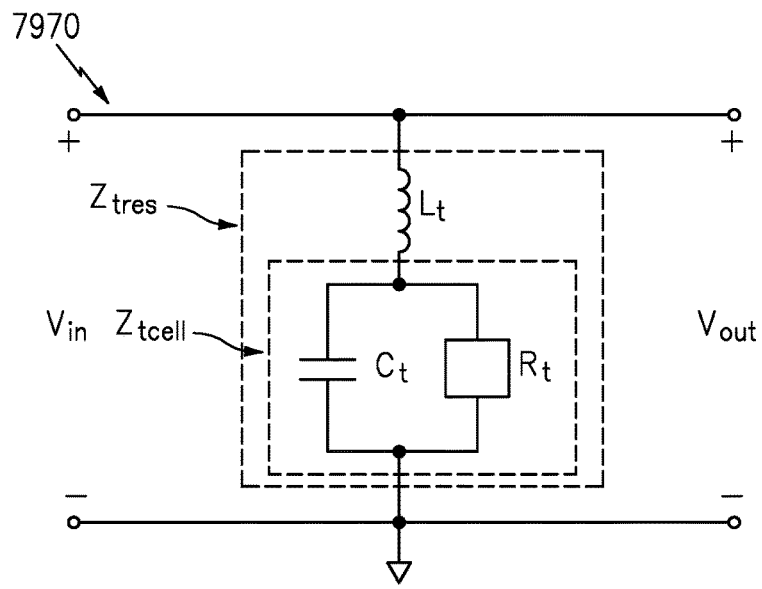

FIG. 79C is an equivalent circuit of the transverse resonator of FIG. 79A, in accordance with embodiments of the present invention.

Figure 80A:
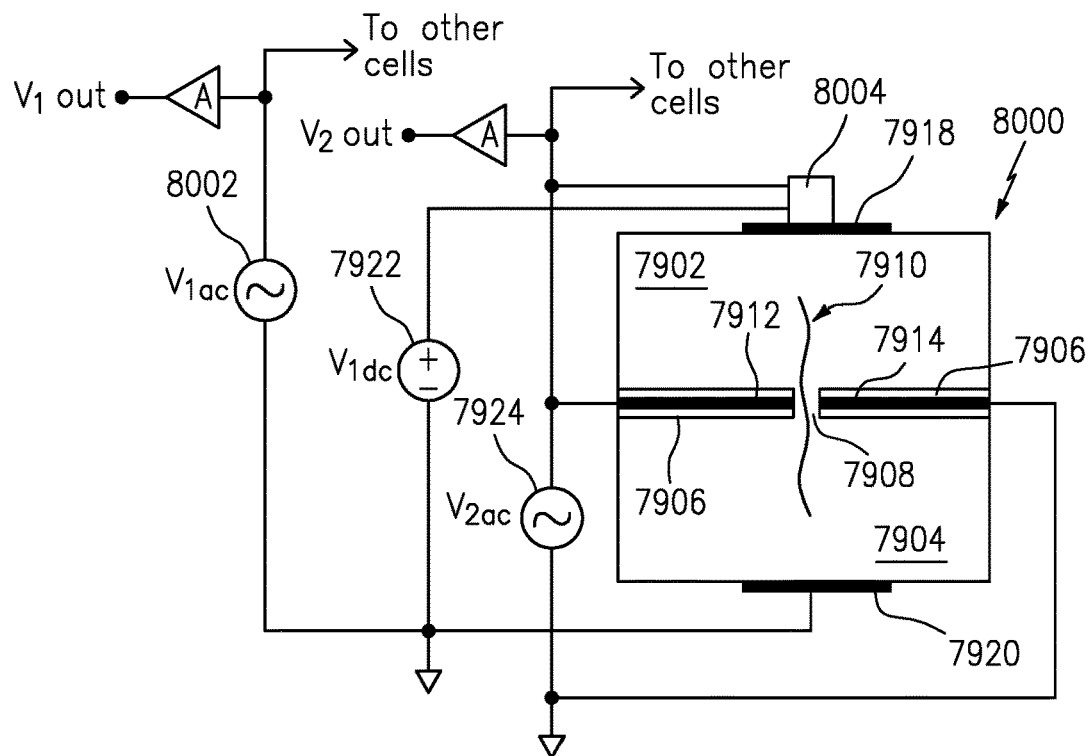

FIG. 80A is a side view of a dual chamber nanopore device having a transverse resonator and a longitudinal resonator using different AC sources, in accordance with embodiments of the present invention.

Figure 80B:
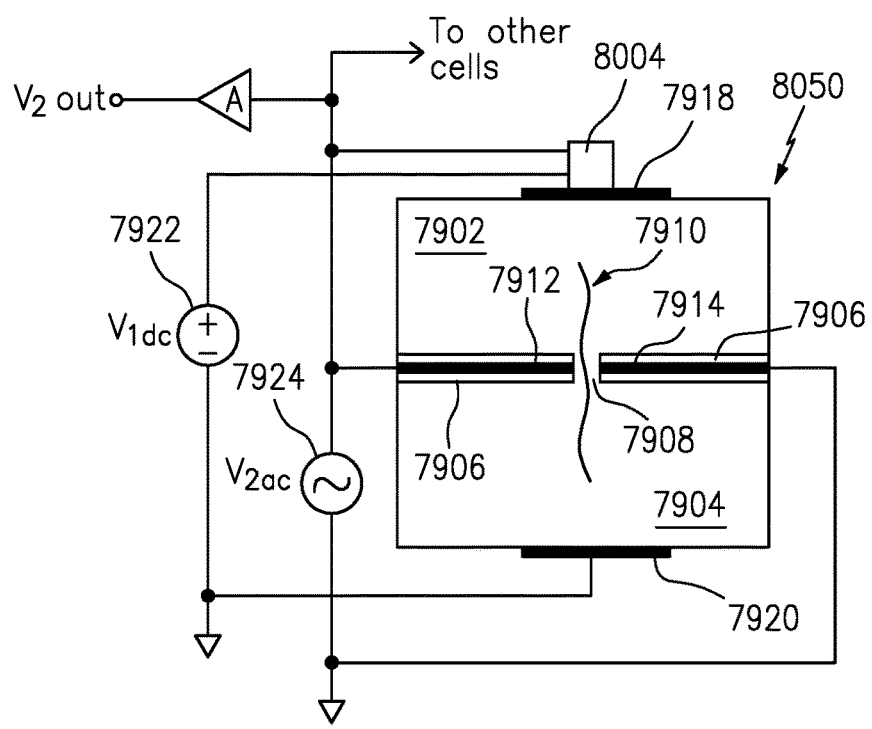

FIG. 80B is a side view of a dual chamber nanopore device of FIG. 80A having a transverse resonator and a longitudinal resonator using the same AC sources, in accordance with embodiments of the present invention.

Figure 81A:
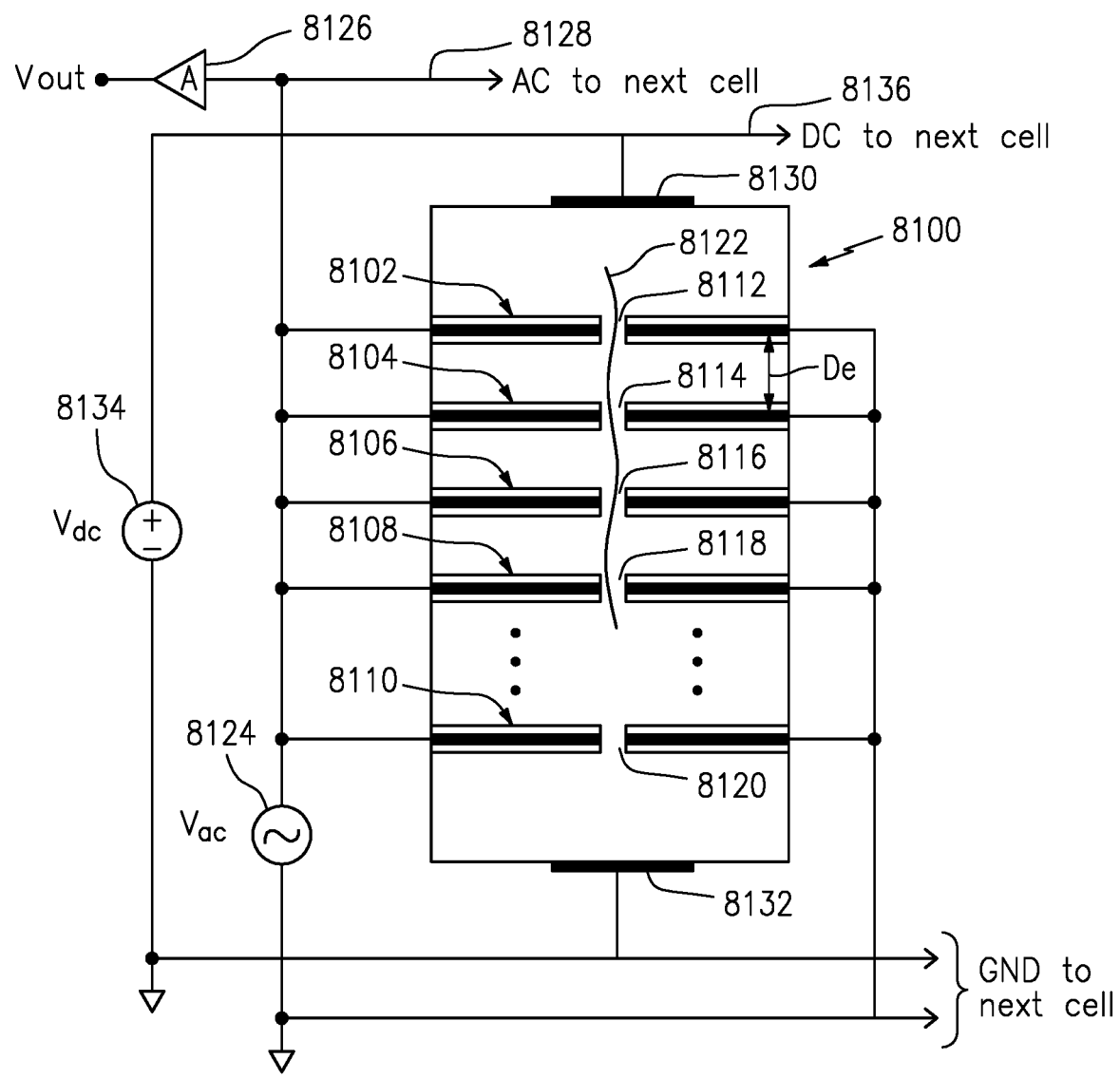

FIG. 81A is a side view of a nanopore device having a plurality of transverse resonators using the same AC source, in accordance with embodiments of the present invention.

Figure 81B:
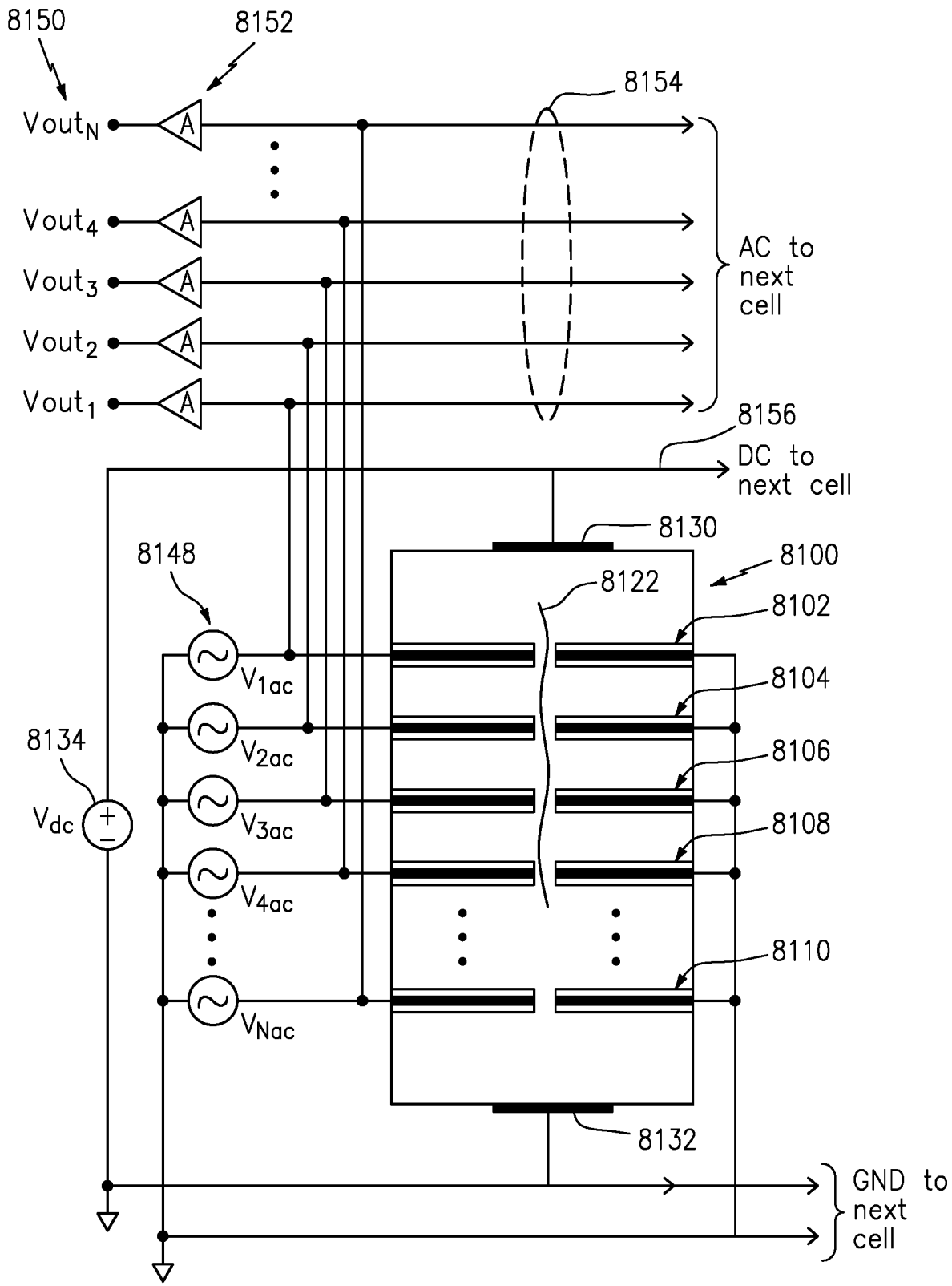

FIG. 81B is a side view of the nanopore device of FIG. 81A, having a plurality of transverse resonators using different AC sources for each transverse resonator, in accordance with embodiments of the present invention.

Figure 82A:
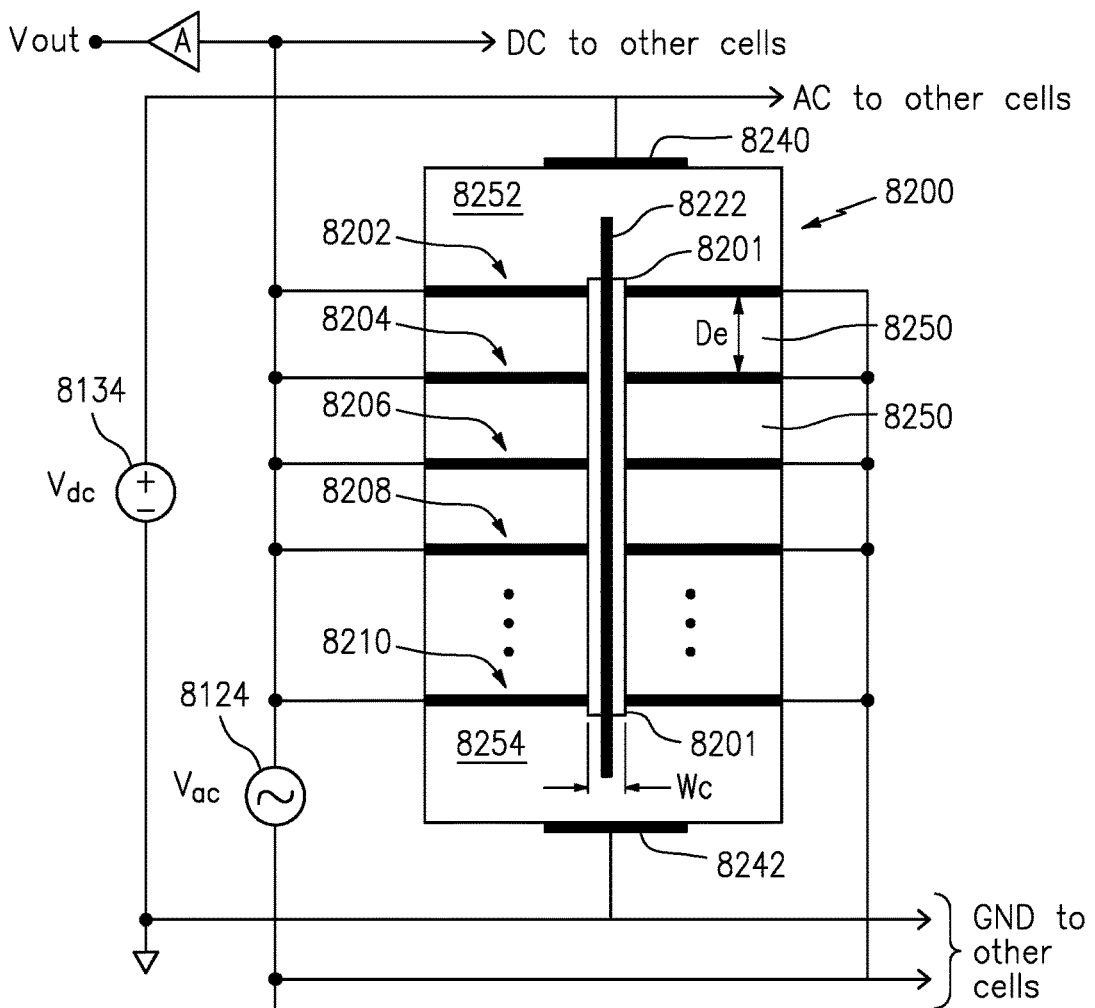

FIG. 82A is a side view of a device with a plurality of transverse resonators having a nano-channel and using the same AC source, in accordance with embodiments of the present invention.

Figure 82B:
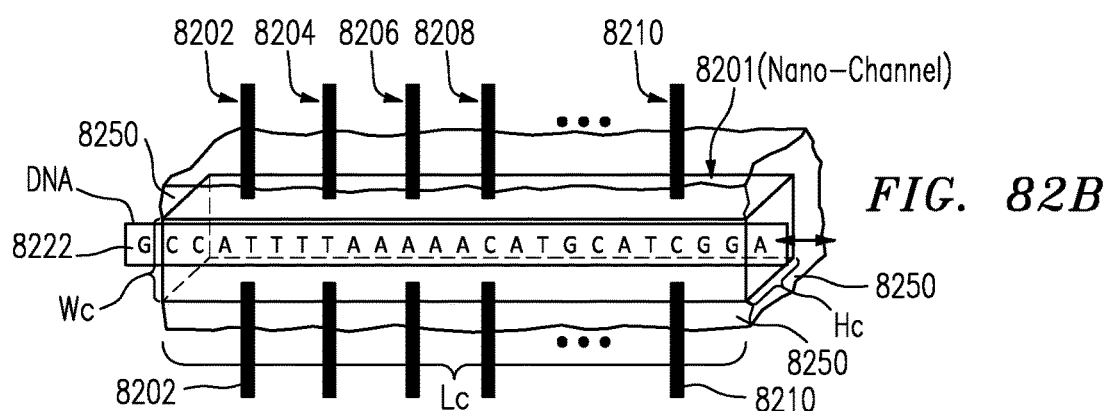

FIG. 82B is a side view of the nano-channel and electrodes of FIG. 82A, in accordance with embodiments of the present invention.

Figure 82C:
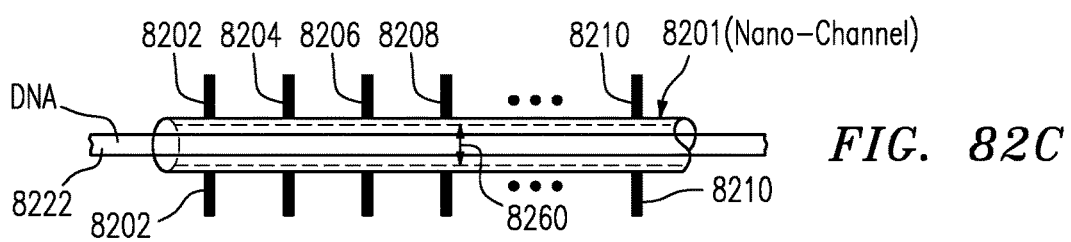

FIG. 82C is a side view of another embodiment of the nano-channel and electrodes of FIG. 82A, in accordance with embodiments of the present invention.

Figure 83:
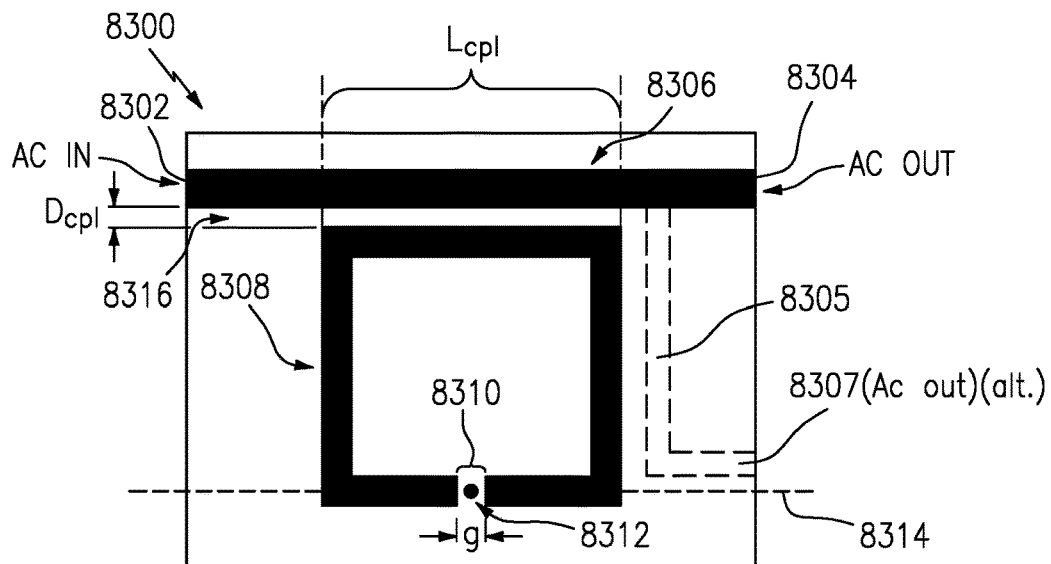

FIG. 83 is a top view of a split-ring resonator having a square split-ring, in accordance with embodiments of the present invention.

Figure 84:
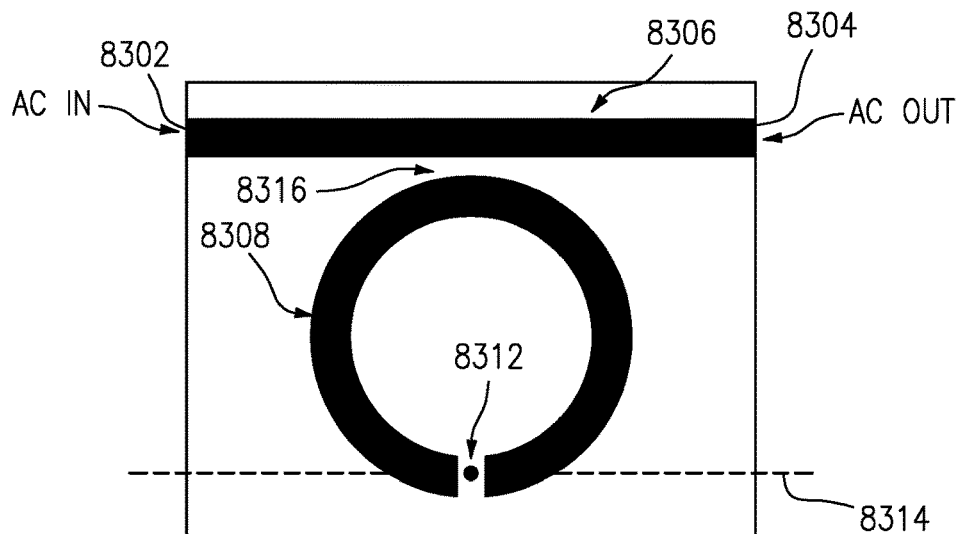

FIG. 84 is a top view of a split-ring resonator having a circular split-ring, in accordance with embodiments of the present invention.

Figure 85:
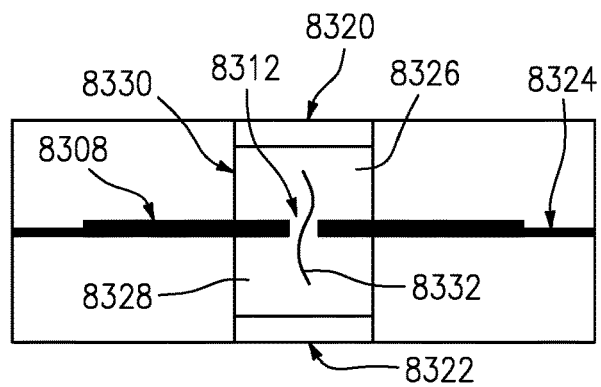

FIG. 85 is a side view of the split ring resonators of FIGS. 83 and 84 along a line 8314, in accordance with embodiments of the present invention.

Figure 86:
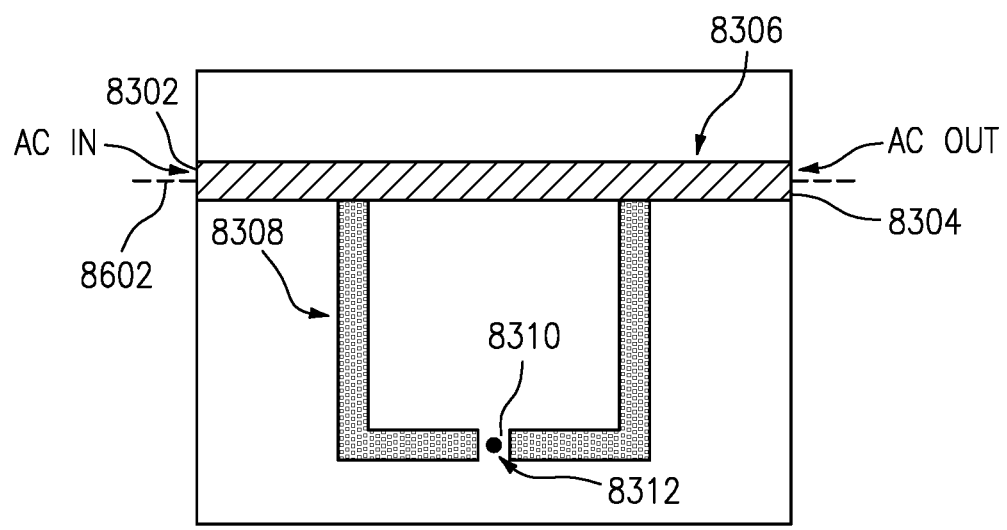

FIG. 86 is a top view of a split-ring resonator having a square split-ring and a feedline that is offset vertically, in accordance with embodiments of the present invention.

Figure 87:
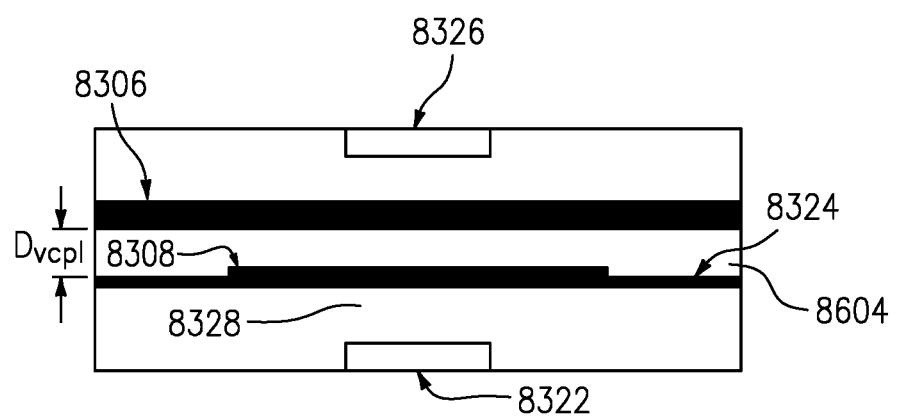

FIG. 87 is a side view of the split-ring resonator of FIG. 86 along a line 8304, in accordance with embodiments of the present invention.

Figure 88:
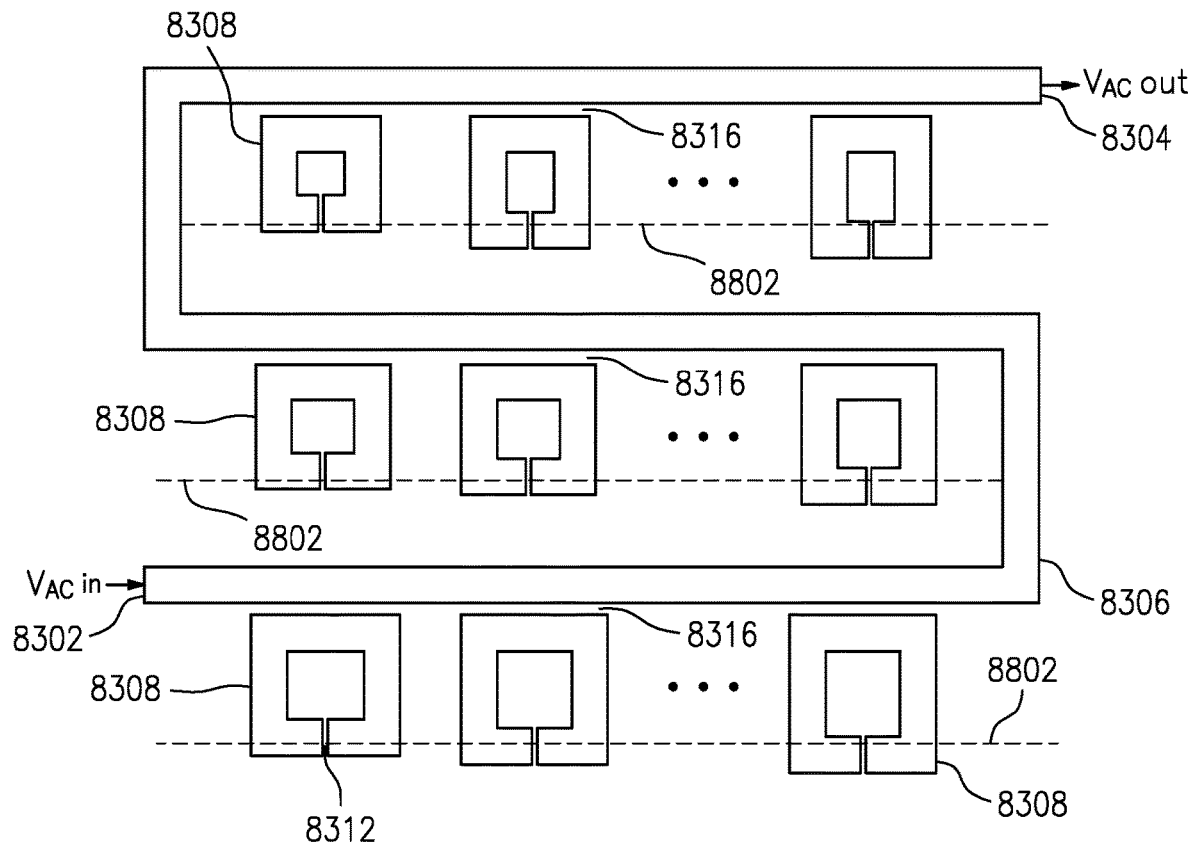

FIG. 88 is a top view of a plurality of split-ring resonators driven by a common feedline, in accordance with embodiments of the present invention.

Figure 89:
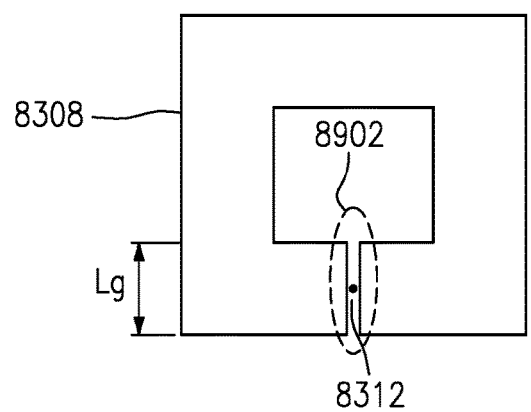

FIG. 89 is an expanded view of one of the resonators of FIG. 88, in accordance with embodiments of the present invention.

FIG. 90 is a top view of a plurality of alternative geometry split-ring resonators driven by a common feedline, in accordance with embodiments of the present invention.

FIG. 91 is an expanded view of one of the resonators of FIG. 90, in accordance with embodiments of the present invention.

FIG. 91A is perspective view of one of the resonators of FIG. 90, in accordance with embodiments of the present invention.

FIGS. 92A, 92B, 92C, 92D, 92E, 92F are top views of various geometries of the end of the transverse electrodes for the transverse resonators, in accordance with embodiments of the present invention.

Figure 92A:
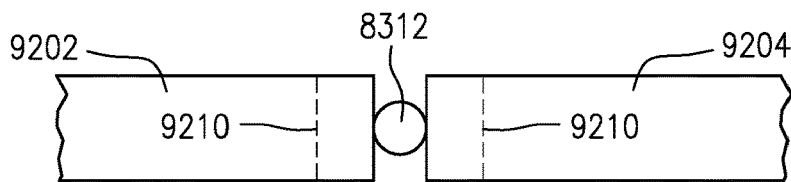
Figure 92B:
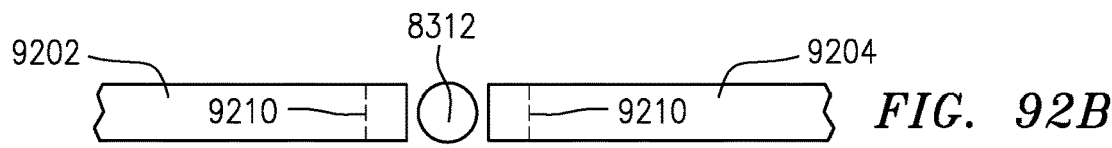
Figure 92C:
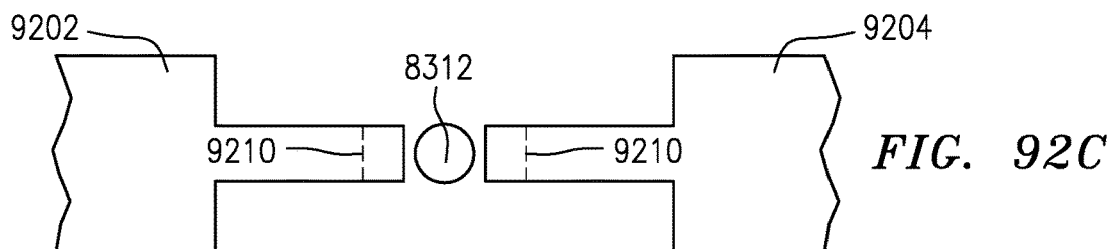
Figure 92D:
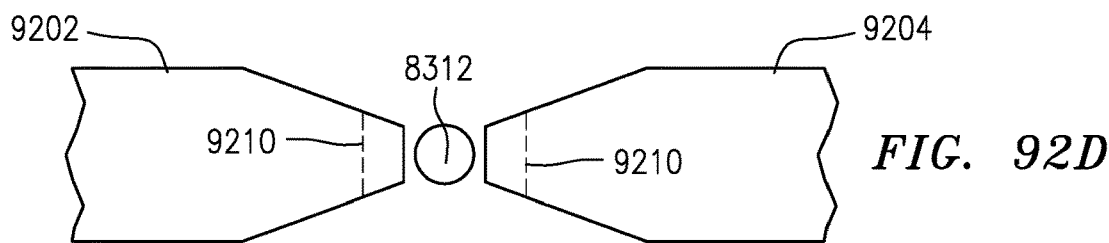
Figure 92E:
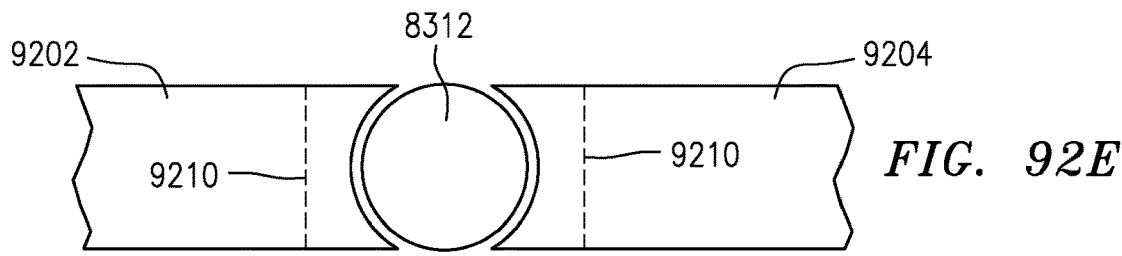
Figure 92F:
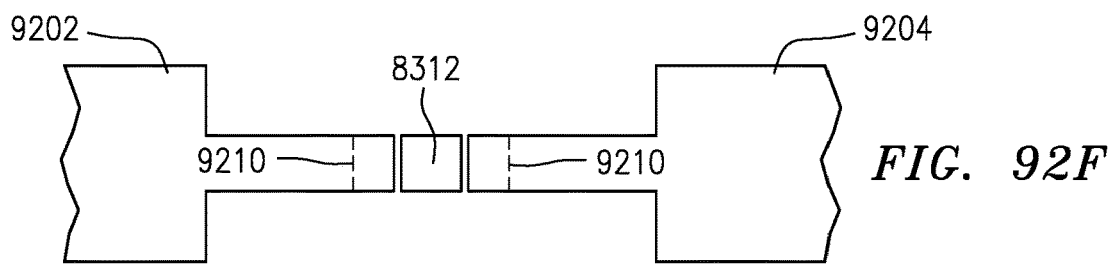
Figure 92G:
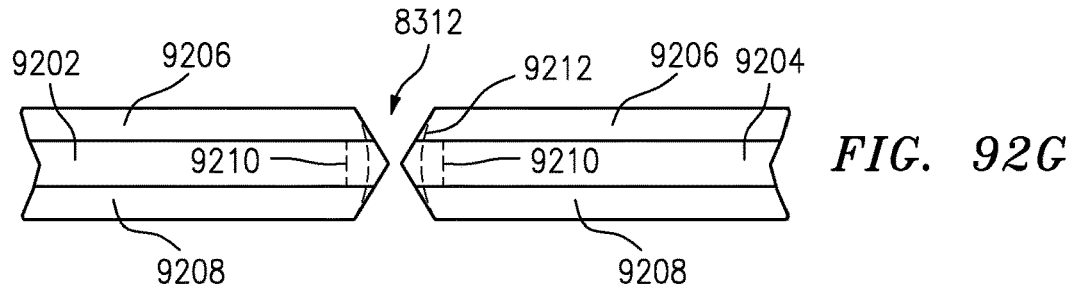

FIG. 92G is a side view of transverse electrodes for the transverse resonators, in accordance with embodiments of the present invention.

Figure 93:
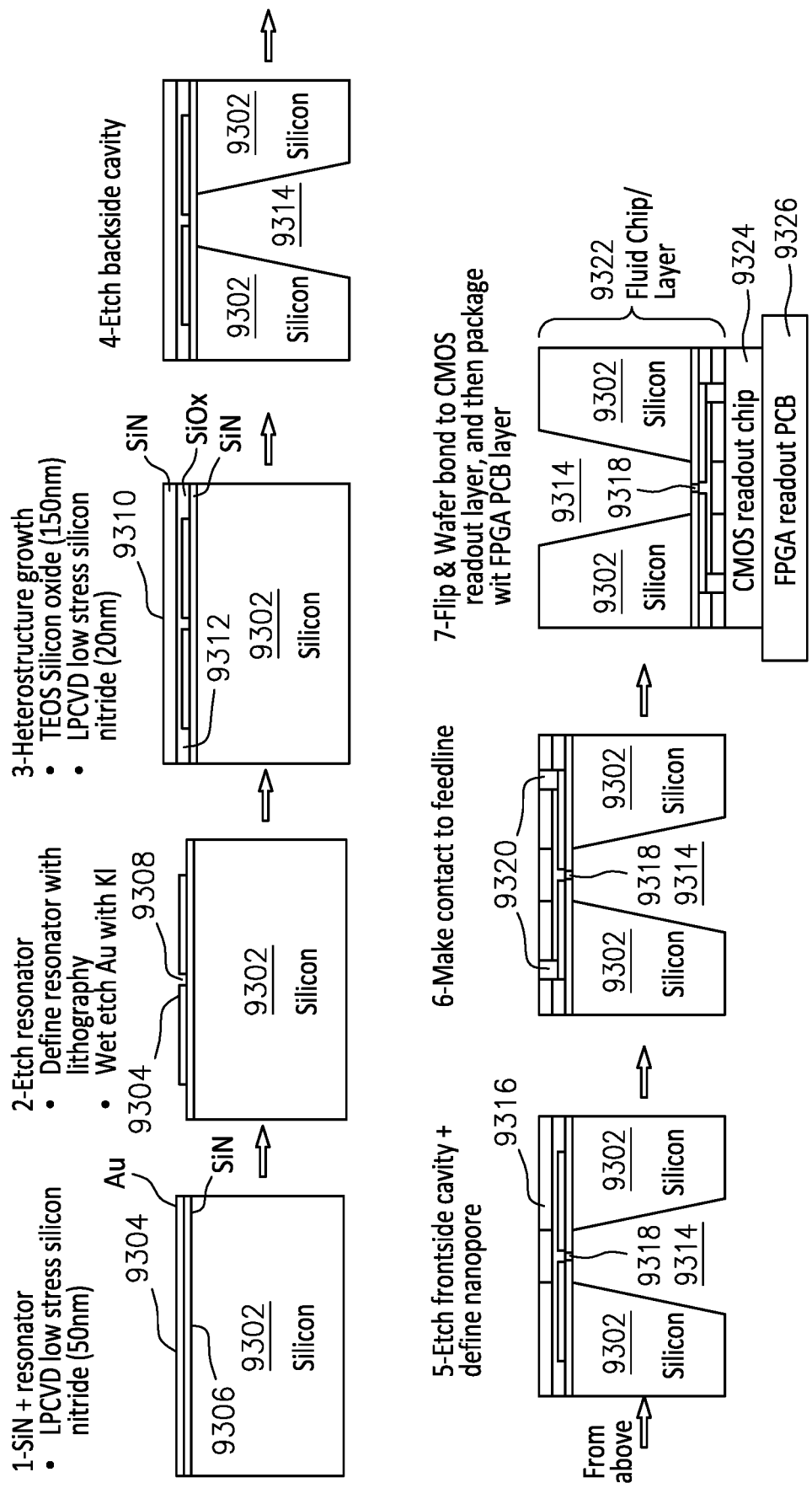

FIG. 93 is a fabrication process for a two-chamber cell using a split-ring resonator, in accordance with embodiments of the present invention.

Figure 94:
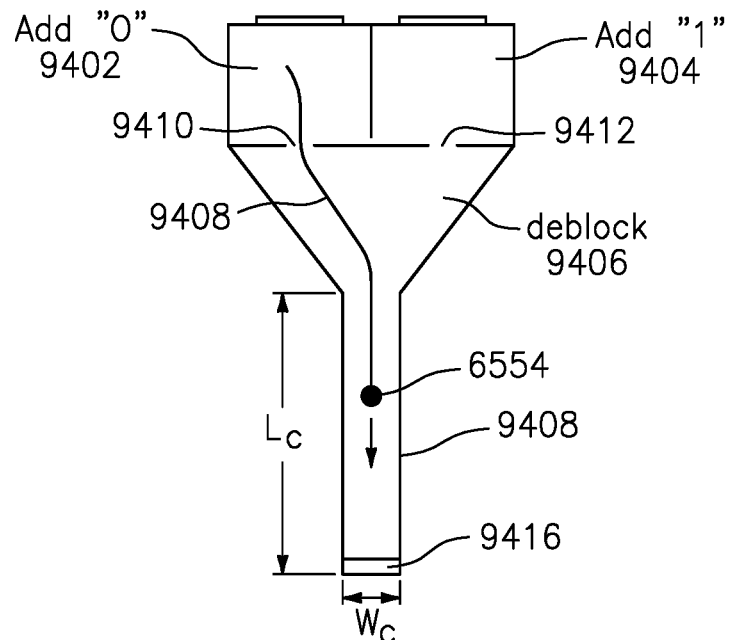

FIG. 94 is a side view of a three-chamber nanopore device having a nano-channel in the lower common channel, in accordance with embodiments of the present invention.

Figure 95:
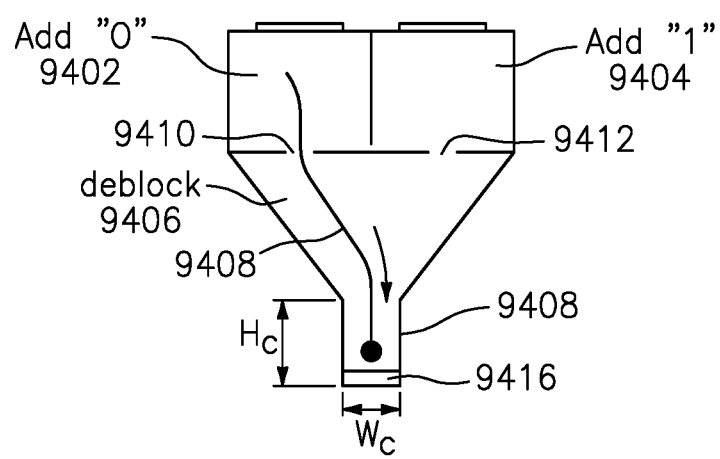

FIG. 95 is a side view of a three-chamber nanopore device having an alternative nano-channel configuration in the lower common channel, in accordance with embodiments of the present invention.

Figure 96:
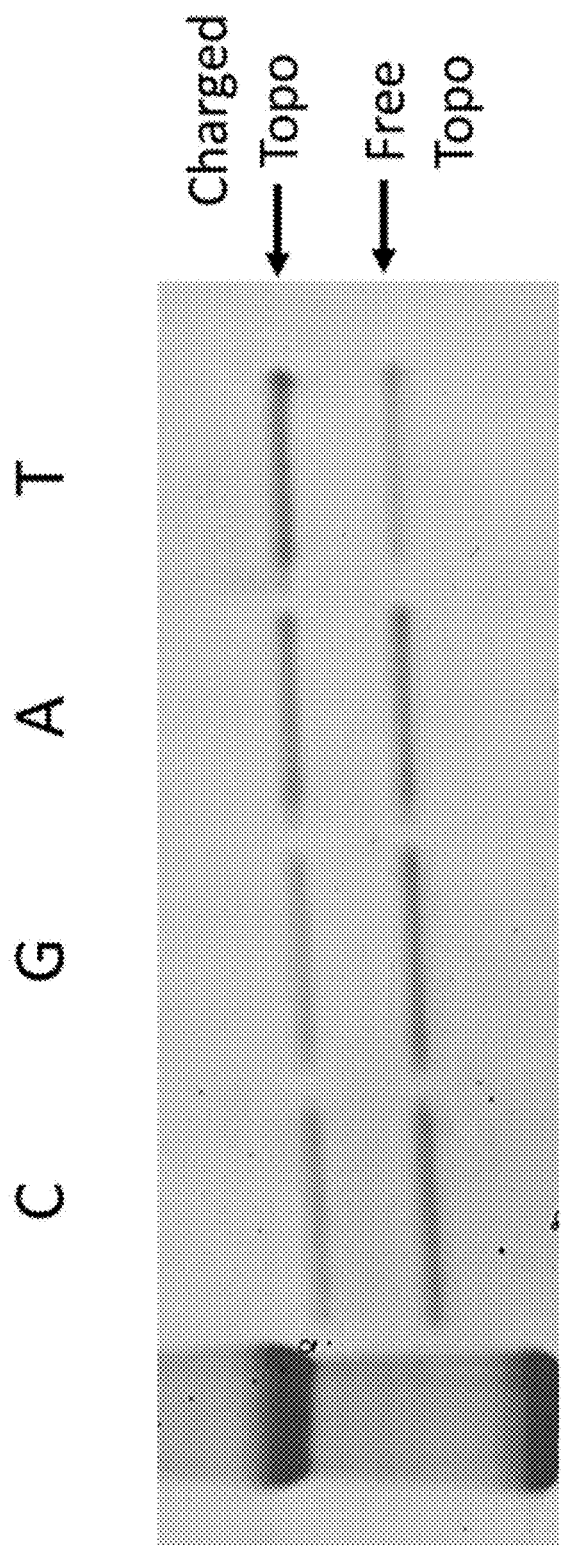

FIG. 96 depicts a SDS-PAGE of charged topoisomerase.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

"Nanochip" as used herein refers to a nanofluidic device, comprising multiple chambers containing fluid and optionally channels allowing for fluid flow, wherein the critical dimensions of the features of the nanochip, for example the width of the elements dividing the chambers from one another, are from one atom to 10 microns in thickness, e.g., smaller than one micron, e.g. 0.01-1 micron. The flow of materials in the nanochip may be regulated by electrodes. For example, as DNA and RNA are negatively charged, they will be drawn to a positively charged electrode. See, e.g., Gershow, M, et al., *Recapturing and Trapping Single Molecules with a Solid State Nanopore*, Nat Nanotechnol. (2007) 2(12): 775-779, incorporated herein by reference. The flow of fluids may in some cases also be regulated by gate elements, and by flushing, injecting, and/or suctioning fluids into or out of the nanochip. The system is capable of precise multiplexed analysis of nucleic acids (DNA/RNA). In certain embodiments, the nanochip can be made of a silicon material, for example silicon dioxide or silicon nitride. Silicon nitride (e.g., $Si_3N_4$) is especially desirable for this purpose because it is chemically relatively inert and provides an effective barrier against diffusion of water and ions even when only a few nm thick. Silicon dioxide (as used in the examples herein) is also useful, because it is a good surface to chemically modify. Alternatively, in certain embodiments, the nanochip, may be made in whole or in part out of materials which can form sheets as thin as a single molecule (sometimes referred to as single layered materials), for example graphene, e.g., as described in Heerema, S J, et al, *Graphene nanodevices for DNA sequencing*, Nature Nanotechnology (2016) 11: 127-136; Garaj S et al., *Graphene as a subnanometre trans-electrode membrane*, Nature (2010) 467 (7312), 190-193, the contents of each of which are incorporated herein by reference, or a transition metal dichalcogenide, e.g., molybendum disulfide ($MoS_2$) as described in Feng, et al., *Identification of single nucleotides in $MoS_2$ nanopores*, Nat Nanotechnol. (2015) 10(12):1070-1076, the contents of which are incorporated herein by reference, or boron nitride, as described in Gilbert, et al. Fabrication of Atomically Precise Nanopores in Hexagonal Boron Nitride, eprint arXiv:1702.01220 (2017).

In some embodiments, the nanochip comprises such a single layered material which is relatively stiff and inert, e.g., at least as inert and stiff as graphene, such as $MoS_2$. Single layered materials may, for example be used as all or part of the membrane comprising the nanopore. The nanochip may be lined in parts with metal, for example the walls may be layered (e.g. metal-silicon nitride-metal), and the metal can then be configured to provide a controllable pair of electrodes near the nanopore, so that the nucleic acid can be moved back and forth through the nanopore by electromotive force, and also can be sequenced by measuring the change in electric potential as the nucleic acid passes through the nanopore.

Nanochip nanofluidic devices for sequencing DNA are generally known, for example as described in Li, J., et al, *Solid-state nanopore for detecting individual biopolymers*, Methods Mol Biol. (2009)544:81-93; Smeets R M, et al. *Noise in solid-state nanopores*, PNAS (2008)105(2):417-21; Venta K, et al., *Differentiation of short, single-stranded DNA homopolymers in solid-state nanopores*, ACS Nano. (2013) 7(5):4629-36; Briggs K, et al. *Automated fabrication of 2-nm solid-state nanopores for nucleic acid analysis*, Small (2014)10(10):2077-86; and Chen Z, *DNA translocation through an array of kinked nanopores*, Nat Mater. (2010)9 (8):667-75; the entire contents of each of which are incorporated herein by reference, e.g. for their teachings on the design and manufacture of nanochips comprising nanopores.

"Nanopore" as used herein is pore having a diameter of less than 1 micron, e.g., 2-20 nm diameter, for example on the order of 2-5 nm. Single stranded DNA can pass through a 2 nm nanopore; single or double stranded DNA can pass through a 4 nm nanopore. Having a very small nanopore, e.g., 2-5 nm, allows the DNA to pass through, but not the larger protein enzymes, thereby allowing for controlled synthesis of the DNA (or other charged polymer). Where larger nanopores (or smaller protein enzymes) are used, the protein enzyme may be conjugated to a substrate that will prevent it from passing though the nanopore, e.g. to a larger molecule, such as a larger protein, to a bead, or to a surface in the chamber. Different types of nanopores are known. For example, biological nanopores are formed by assembly of a pore-forming protein in a membrane such as a lipid bilayer. For example, α-hemolysin and similar protein pores are found naturally in cell membranes, where they act as channels for ions or molecules to be transported in and out of cells, and such proteins can be repurposed as nanochannels. Solid-state nanopores are formed in synthetic materials such as silicon nitride or graphene e.g., by configuring holes in the synthetic membrane, e.g. using feedback controlled low energy ion beam sculpting (IBS) or high energy electron beam illumination. Hybrid nanopores can be made by embedding a pore-forming protein in synthetic material. Where there is a metal surface or electrode at either end or either side of the nanopore, a current flow across the nanopore may be established through the nanopore via an electrolyte media. Electrodes may be made of any conductive material, for example silver, gold, platinum, copper, titanium dioxide, for example silver coated with silver chloride.

Methods for configuring a nanopore in a solid state, e.g., silicon nitride, membrane, are known. In one approach, a silicon substrate is coated with the membrane material, e.g., silicon nitride, and the overall configuration of the membrane is created using photolithography and wet chemical etching, to provide silicon nitride membranes of the desired size for incorporation into a nanochip, e.g., about 25×25 microns. Initial 0.1 micron diameter holes or cavities are punched in the silicon nitride membrane using a focused ion beam (FIB). Ion beam sculpting can configure the nanopore either by shrinking a larger pore, e.g., by ion beam induced lateral mass transport on the membrane surface, or by removing membrane material by ion beam sputtering layer by layer from the flat side of the membrane containing a cavity from opposing sides, so that when the cavity is ultimately reached, there is a sharp-edged nanopore. The ion beam exposure is extinguished then the ion current transmitted through the pore is appropriate for the desired pore size. See, e.g. Li, J., et al., *Solid-state nanopore for detecting individual biopolymers*, Methods Mol Biol. (2009)544:81-93. Alternatively, the nanopores can be configured using high energy (200-300 keV) electron beam illumination in a TEM. Using semiconductor processing techniques, e-beam lithography, reactive-ion etching of SiO2 mask layers, and anisotropic KOH etching of Si, pyramidal 20×20 nm and larger pores are made in a 40 nm thick membrane. The electron beam in a TEM is used to shrink the larger 20 nm pores to smaller ones. The TEM allows the shrinking process to be observed in real-time. Using a thinner membrane (e.g., <10 nm thick) nanopores can be drilled with a high energy focused electron beam in a TEM. See, generally, Storm A J, et al. *Fabrication of solid-state nanopores with single-nanometre precision.* Nature Materials (2003) 2:537-540; Storm A J, et al. *Translocation of double-stranded DNA through a silicon oxide nanopore.* Phys. Rev. E (2005)71: 051903; Heng J B, et al. *Sizing DNA Using a Nanometer-Diameter Pore.* Biophys. J (2004) 87(4):2905-11; the contents of each of which are incorporated herein by reference.

In other embodiments, the nanopores are made using dielectric breakdown, using a relatively high voltage potential across the membrane, wherein the voltage is raised until current is detected, e.g., as described in Kwok, et al., "Nanopore Fabrication by Controlled Dielectric Breakdown," PLOS ONE (2014) 9(3): e92880, the contents of which are incorporated herein by reference.

Using these techniques, and depending of course on the exact technique used and the thickness and exact composition of the membrane, the overall shape of the nanopore in a solid material such a silicon nitride may roughly resemble two funnels with their apexes coming together at the narrowest point, i.e., the actual nanopore. Such a double cone shape is conducive to steering the polymer through the nanopore and back. Imaging techniques, for example atomic force microscopy (AFM) or transmission electron microscopy (TEM), particularly TEM, can be used to verify and measure the size, location and configuration of the nanomembranes, the FIB holes or cavities, and the final nanopores.

In some embodiments, one end of the polymer, e.g., DNA, is tethered near the nanopore or on the inner wall of the funnel leading to the nanopore. Since the polymer approaches the nanopore initially by diffusion, then is driven by the electrical gradient, the gradient-driven motion is maximized and the diffusive motion minimized, and speed and efficiency thereby enhanced, if one end of the polymer is tethered close to the nanopore. See, e.g. Wanunu M, *Electrostatic focusing of unlabelled DNA into nanoscale pores using a salt gradient,* Nat Nanotechnol. (2010) 5(2): 160-5; Gershow M., *Recapturing and trapping single molecules with a solid-state nanopore.* Nat Nanotechnol. (2007) 2(12):775-9; Gershow, M., *Recapturing and Trapping Single Molecules with a Solid State Nanopore.* Nat Nanotechnol. (2007) 2(12): 775-779.

In one embodiment, one end of the polymer, e.g., DNA, is attached to a bead and the polymer is driven through the pore. Attachment to the bead will stop the polymer from moving all the way through the nanopore on the opposite side of the dividing membrane in an adjacent chamber. The current is then turned off, and the polymer, e.g., DNA, attaches to the surface adjacent to the nanopore in a chamber on the other side of the dividing membrane. For example, in one embodiment, one end of ssDNA is covalently attached to a 50 nm bead, and the other end is biotinylated. Streptavidin is bound to the area at the desired point of attachment in the chamber on the other side of the dividing membrane. The DNA is pulled through the nanopore by an electrical potential, and the biotin attaches to the streptavidin. The attachments to the bead and/or the surface adjacent to the nanopore can be either covalent bonds or strong noncovalent bonds (like the biotin-streptavidin bond). The bead is then cut off with an enzyme and flushed away. In some embodiments, the single stranded DNA is cleaved with a restriction enzyme which cleaves single stranded DNA, e.g., as described in K. Nishigaki, *Type II restriction endonucleases cleave single-stranded DNAs in general.* Nucleic Acids Res. (1985) 13(16): 5747-5760, incorporated herein by reference. In other embodiments, a complementary oligonucleotide is provided to make a double-stranded restriction site, which can then be cleaved with the corresponding restriction enzyme.

As the polymer passes through the nanopore, the change in electric potential, capacitance or current across the nanopore caused by the partial blockage of the nanopore as the polymer passes through can be detected and used to identify the sequence of monomers in the polymer, as the different monomers can be distinguished by their different sizes and electrostatic potentials.

The use of nanochips comprising nanopores in a method of DNA fabrication, as described herein, is not disclosed in the art, but such chips are well known and commercially available for rapid sequencing of DNA. For example, the MinION (Oxford Nanopore Technologies, Oxford, UK) is small and can be attached to a laptop computer. As a single strand of DNA passes through a protein nanopore at 30 bases per second, the MinION measures the electrical current. The DNA strands in the pore disrupts the ionic flow, resulting in changes in current corresponding to the nucleotides in the sequence. Mikheyev, A S, et al. *A first look at the Oxford Nanopore MinION sequencer,* Mol. Ecol. Resour. (2014)14, 1097-1102. While the accuracy of the MinION is poor, requiring repeated resequencing, the speed and accuracy of the sequencing using the nanochips of the present invention can be greatly improved if the DNA being read contains only two easily distinguishable bases, e.g. A and C.

The membrane comprising the nanopores may, in some embodiments, have a trilayer configuration, with a metal surface on either side of an insulating core material, e.g. a silicon nitride membrane. In this embodiment, the metal surfaces are configured, e.g., by lithographic means, to provide a microcircuit with paired electrodes, one at each end of each nanopore, e.g., such that a current flows across the nanopore may be established between the electrodes and through the nanopore via an electrolyte media, which current can draw the polymer through the nanopore and by reversing the polarity, can draw it back. As the polymer passes through the nanopore, the electrodes can measure the change in electric potential across the nanopore so as to identify the sequence of monomers in the polymer.

In some embodiments, the sequence of the polymer is designed to store data. In some embodiments, the data is stored in a binary code (1's and 0's). In some embodiments each base corresponded to a 1 or 0. In other embodiments, an easily recognized sequence of two or more bases corresponds to a 1 and another easily recognized sequence of two or more bases corresponds to a 0. In other embodiments, the data is can be stored in a ternary, quaternary or other code. In a particular embodiment, the polymer is DNA, for example single stranded DNA, wherein the DNA contains only two base types and does not contain any bases capable of self-hybridizing, e.g., wherein the DNA comprises adenines and guanines, adenines and cytosines, thymidines and guanines, or thymidines and cytosines. In some embodiments, the two bases may be interspersed with one or more additional bases, for example A and C may contain a T to "punctuate" the sequence, e.g., by indicating a break in a coding sequence, at a frequency that does not result in significant self-hybridization. In other embodiments, e.g., where the nucleic acid is double stranded, some or all available bases may be employed.

The nucleotide bases may be natural or may in some embodiments consist of or include nonnatural bases, e.g. as described in Malyshev, D. et al. "A semi-synthetic organism with an expanded genetic alphabet", *Nature* (2014) 509: 385-388, incorporated herein by reference.

In one embodiment, the data is stored by addition of single monomers, e.g., single nucleotides in the case of DNA, to the polymer. In one embodiment, the polymer is DNA and the monomers are adenine (A) and cytosine (C) residues. A and C residues have an advantage because (i) A and C have a large size difference, so differentiation through the nanopore should be facilitated, (ii) A and C do not pair with one another so do not form significant secondary structure which could complicate interpretation of the nanopore signal, and (iii) for the same reason, G's are less preferred as they are know to form guanine tetrads. Nucleotides are added by terminal transferase (or polynucleotide phosphorylase), but the nucleotides are 3'-blocked so that only a single nucleotide is added at a time. The block is removed prior to addition of the next nucleotide.

In some embodiments, the DNA is left in the nanochip. In other embodiments, it is removed, and optionally converted to double stranded DNA and/or optionally converted to crystalline form, e.g. to enhance long term stability. In still other embodiments, DNA can be amplified and the amplified DNA removed for long term storage, while the original template DNA, for example DNA bound to the wall of a chamber in the nanochip, can be left in the nanochip, where it can be read and/or used as a template to make additional DNA.

Figure 1:
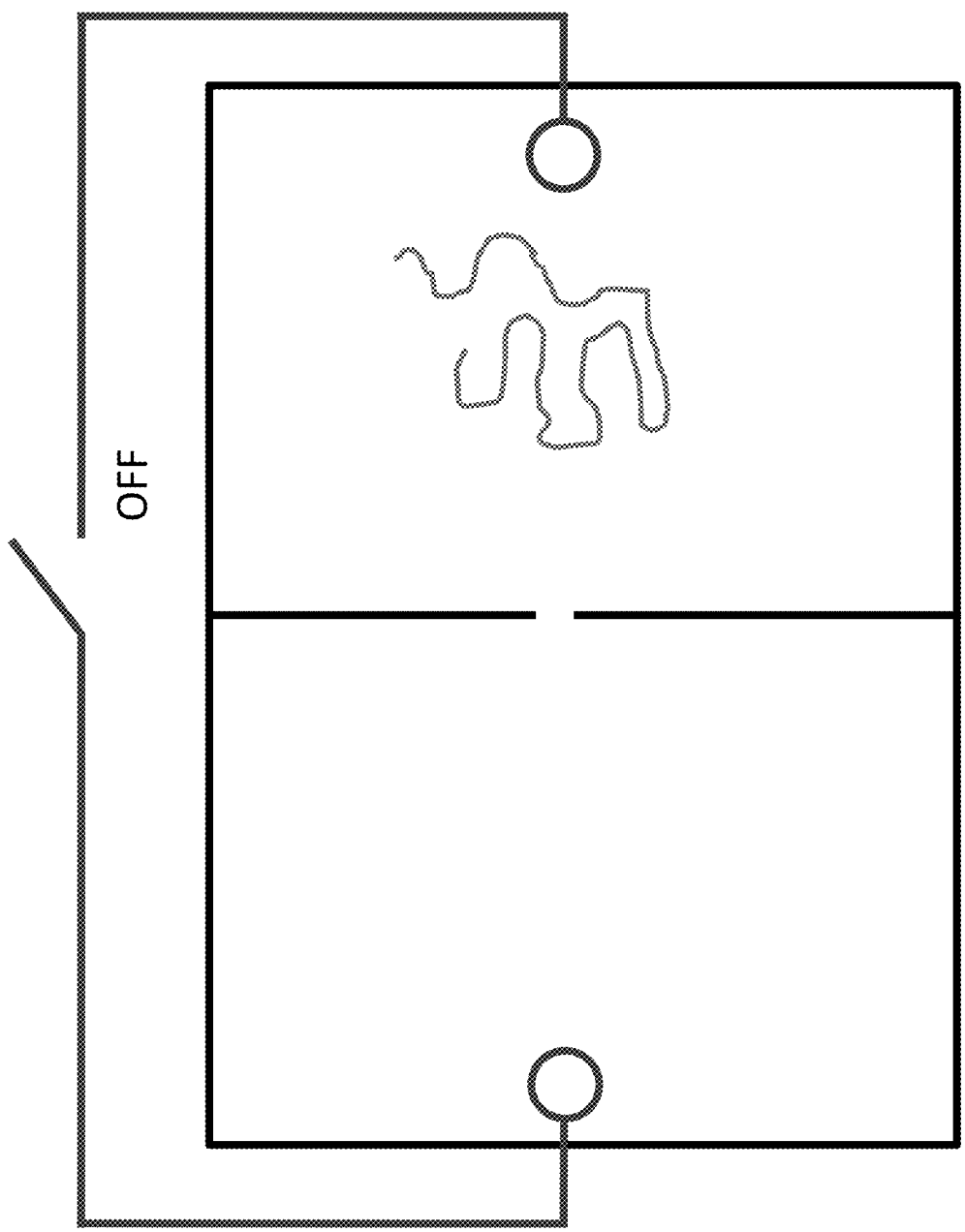
FIG. 1 shows a diagram of a simple two-chamber nanochip design, with a dividing membrane perforated by a nanopore, and electrodes on either side of the membrane.
Figure 2:
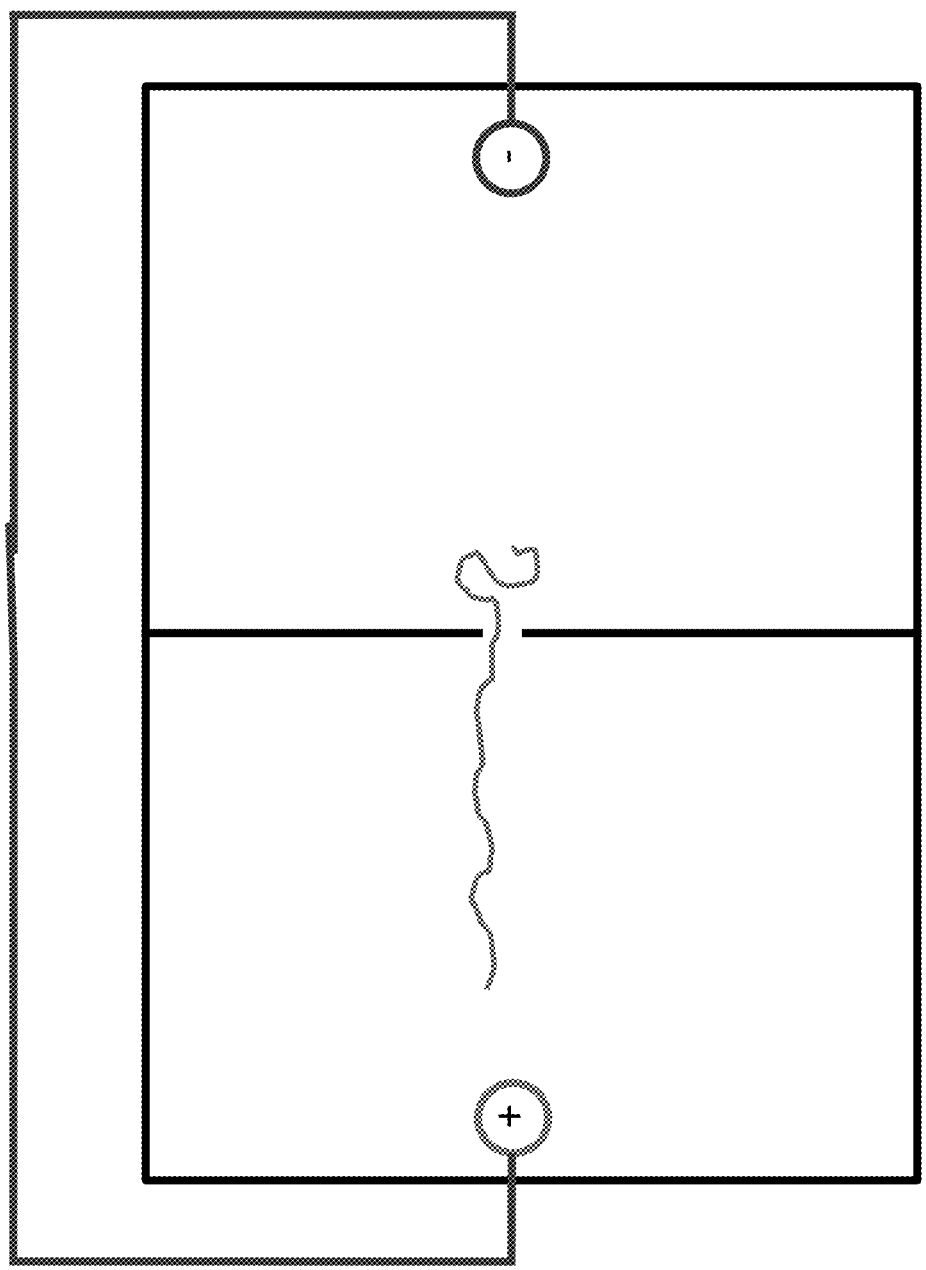
FIGS. 2 and 3 show how the charged polymer, e.g. DNA, is drawn towards the anode.
Figure 3:
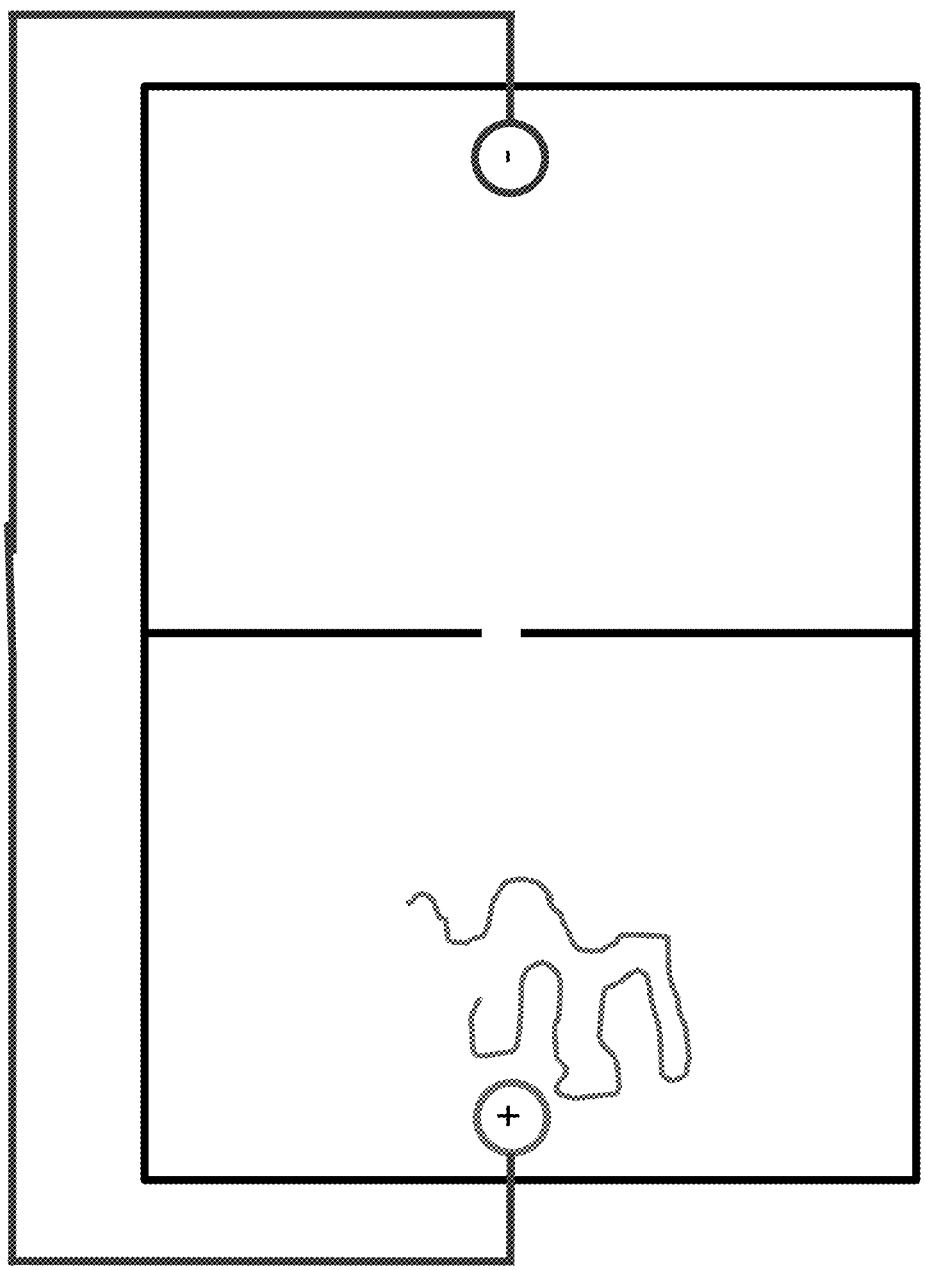
Figure 4:
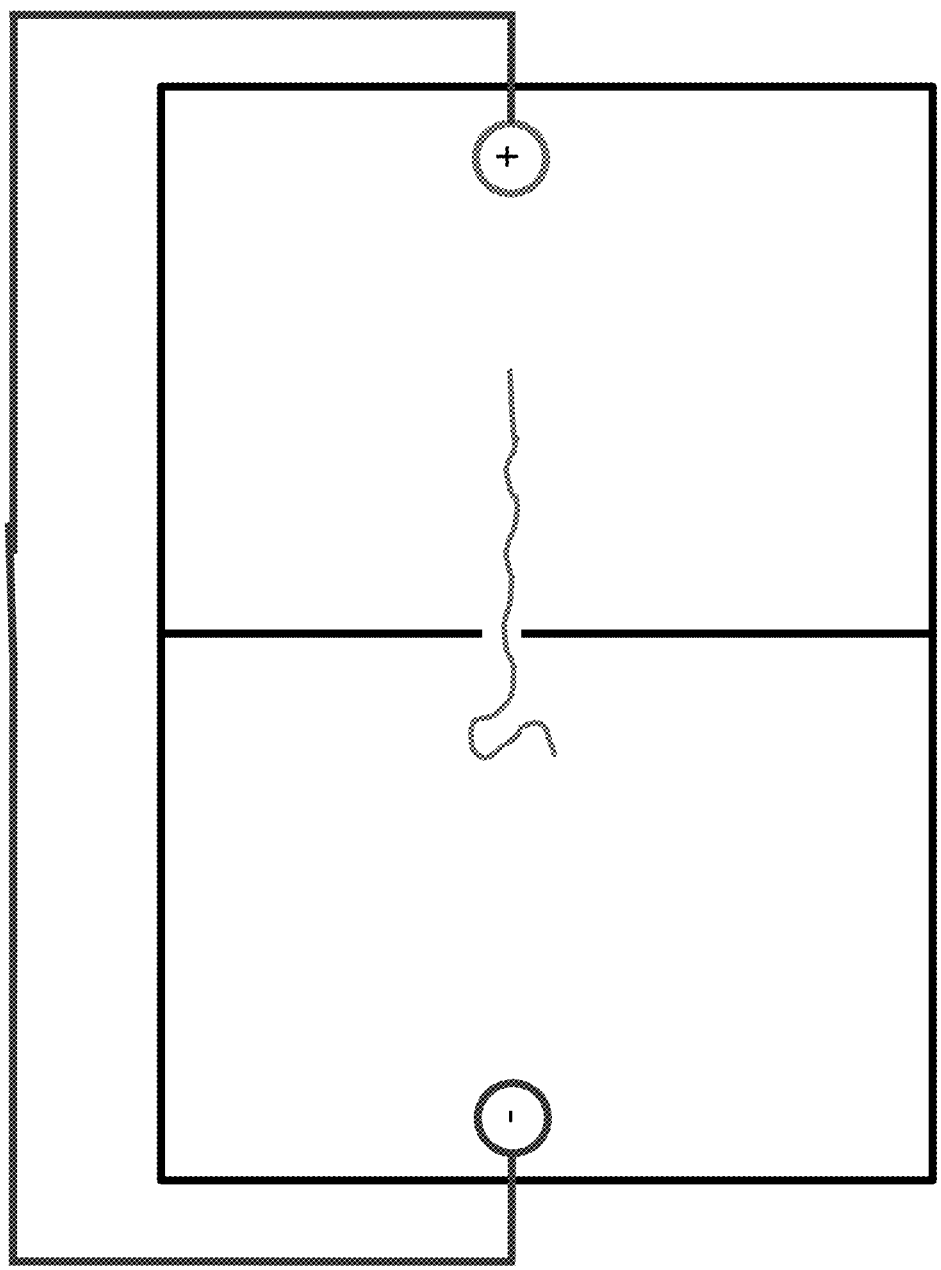
FIGS. 4 and 5 show that the polymer can be moved back by reversing the polarity of the electrodes.
Figure 5:
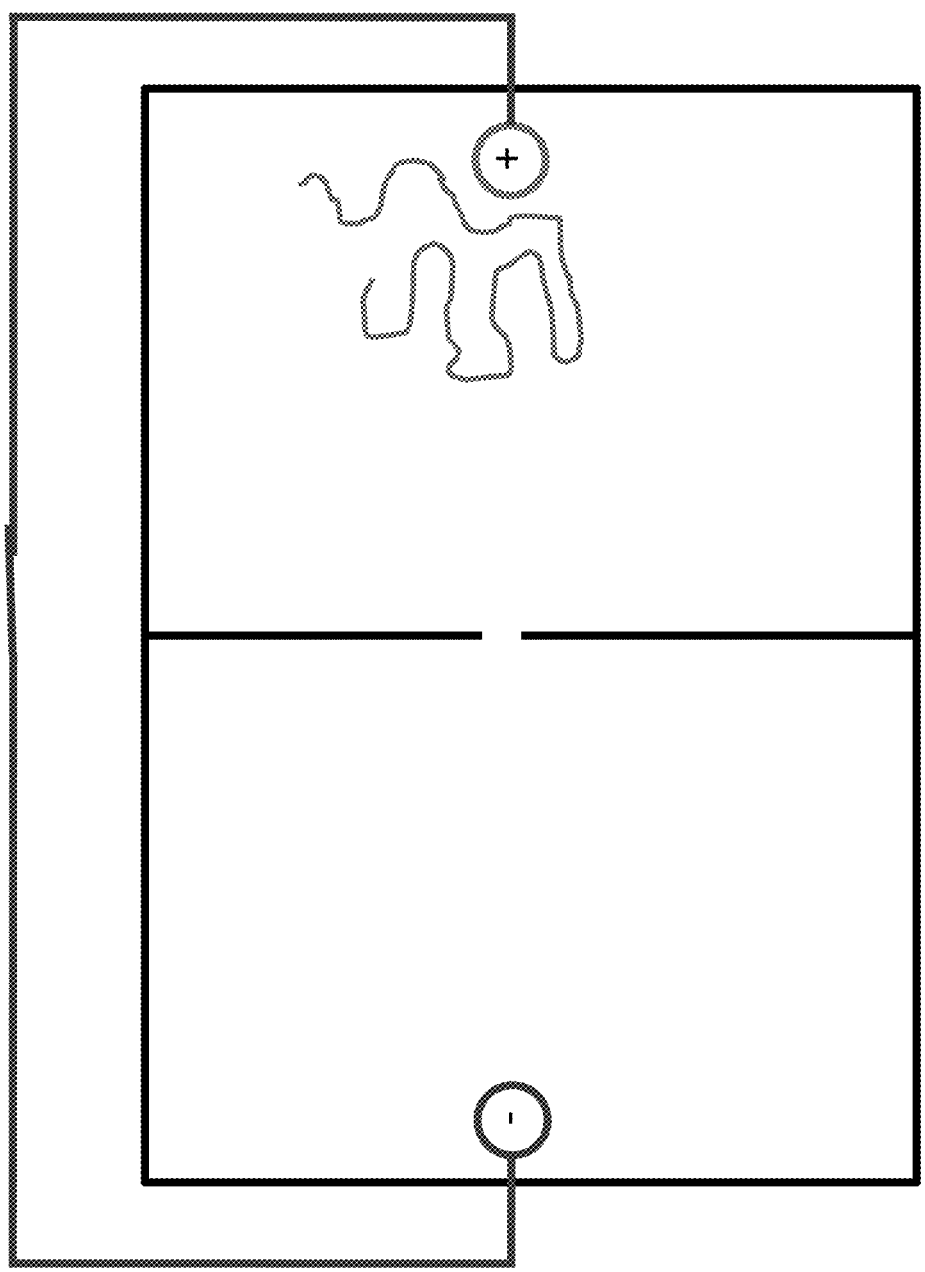
Figure 7:
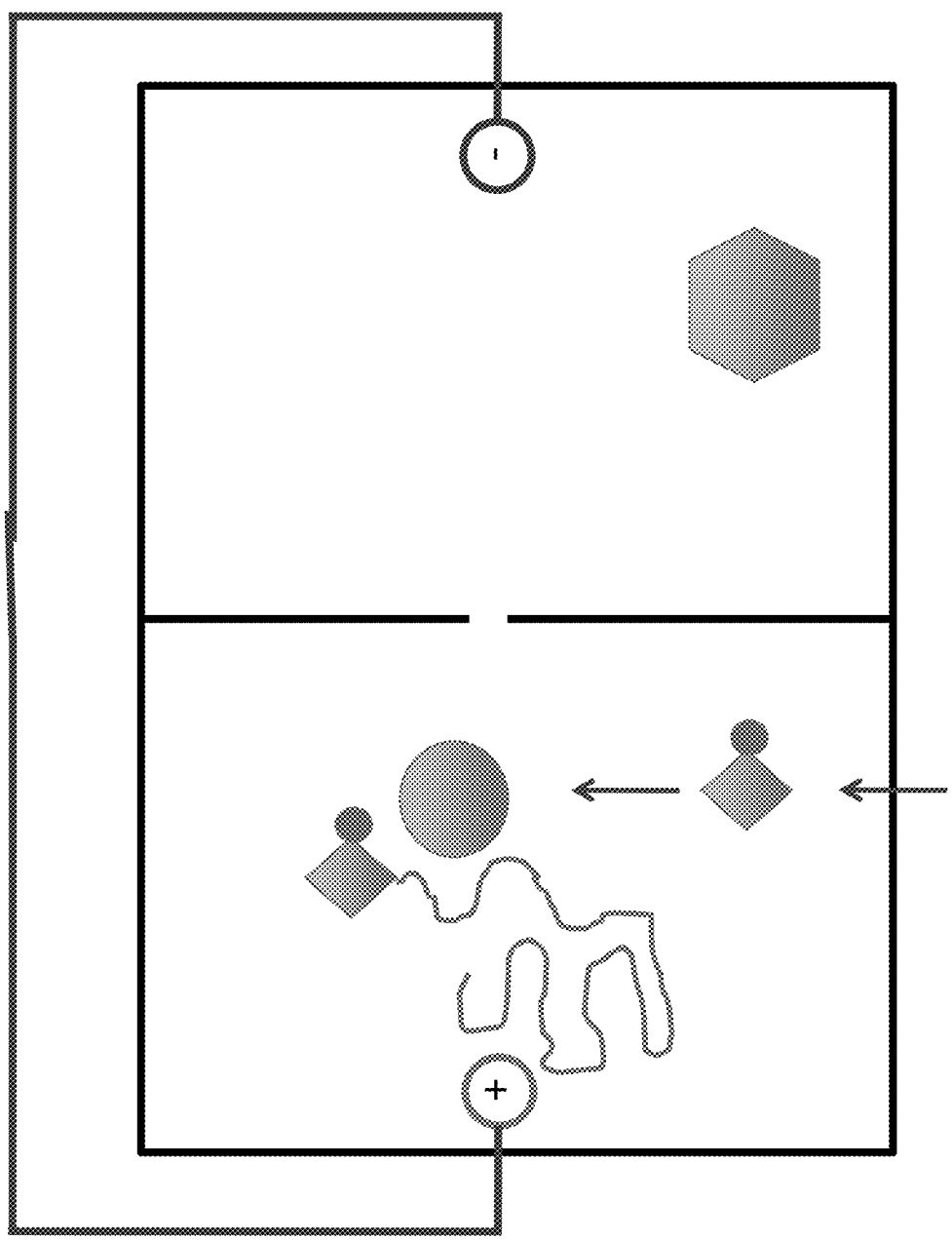
FIG. 7 shows addition of an adenine nucleotide when a 3'-blocked dATP (A) flows through left chamber, and the current is set 'forward' to bring the DNA into the chamber.
Figure 8:
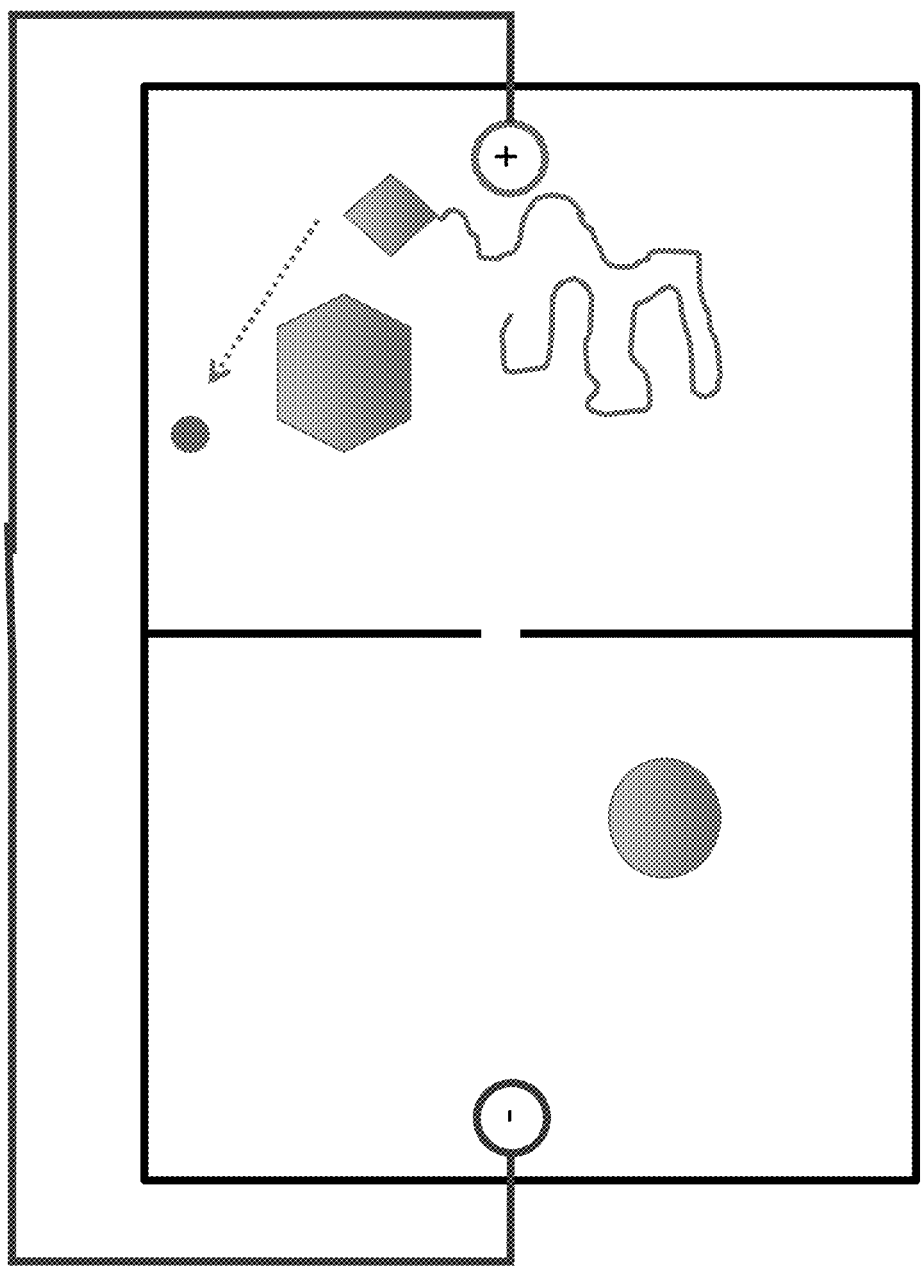
FIG. 8 shows deprotection of the oligonucleotide so an additional nucleotide can be added. For example, deprotection occurs after moving the DNA into the chamber by setting the current to 'reverse'.
Figure 9:
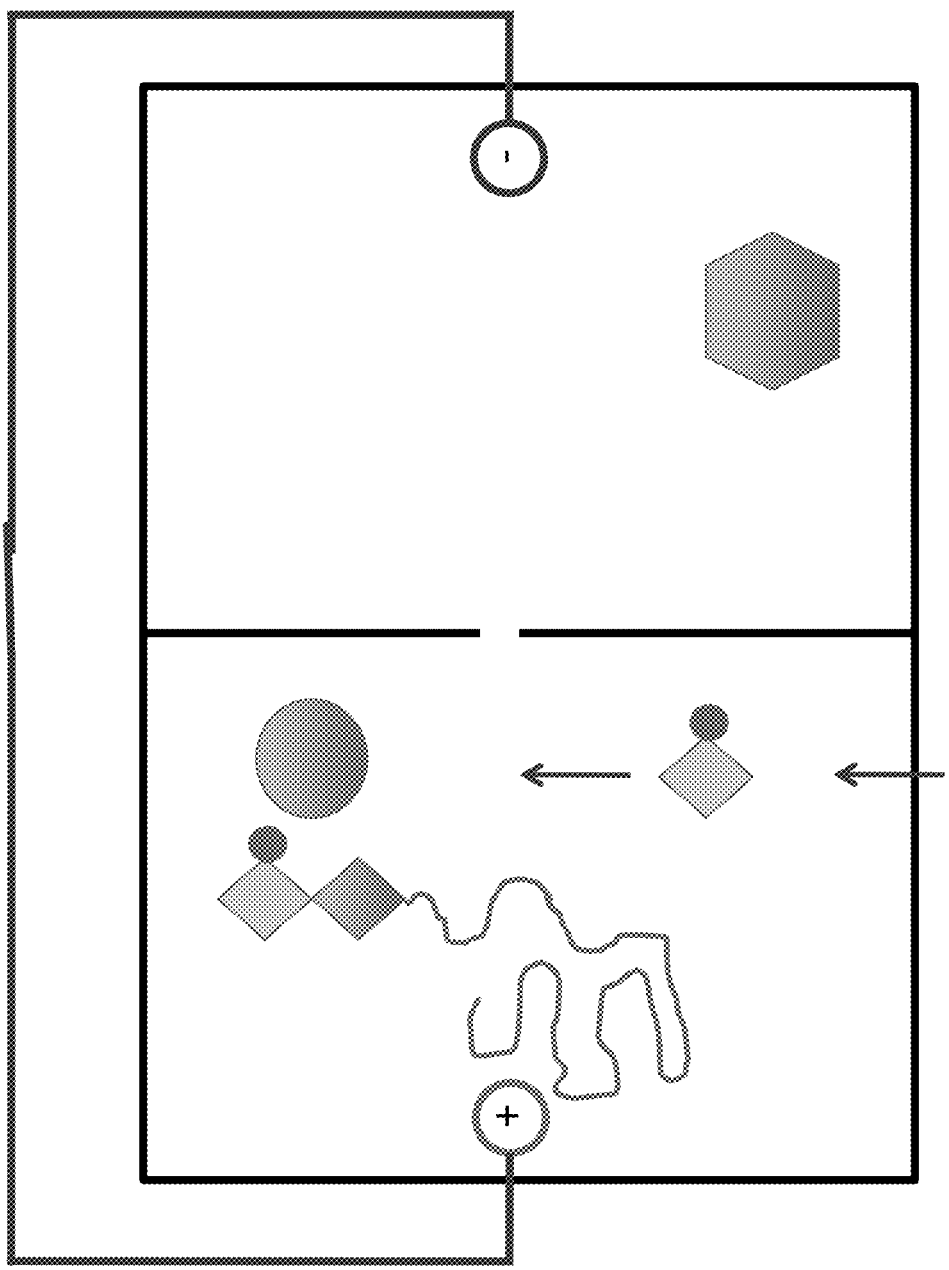
FIG. 9 shows addition of a 3'-blocked dCTP (C). In certain embodiments, fluid flow is used to exchange the contents of this chamber, e.g., as depicted, previously there was 'A' in this chamber.
Figure 10:
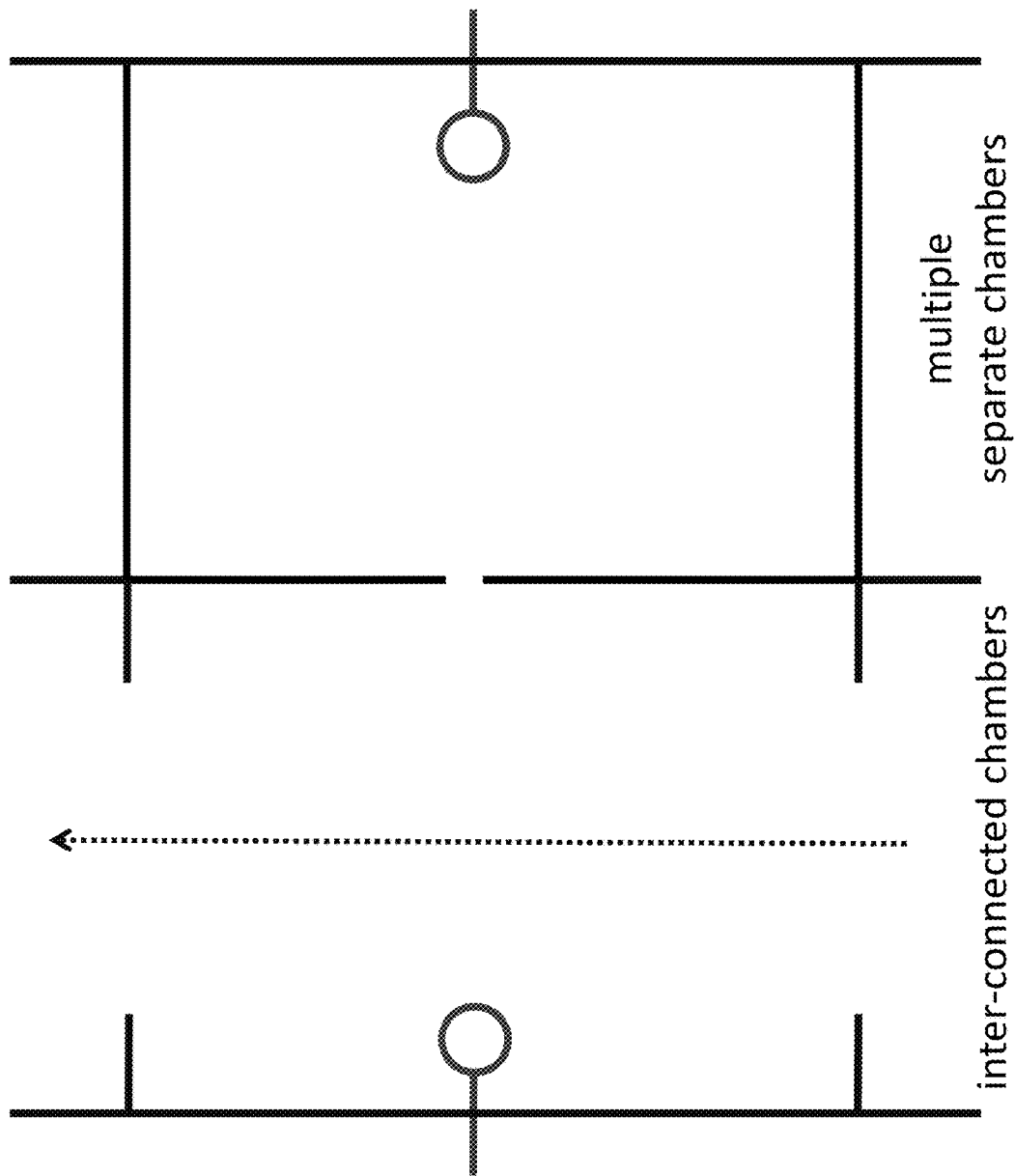
FIG. 10 shows how multiple separate retaining chambers can be provided while the flow chamber becomes a single lane to provide reagents.
Figure 14:
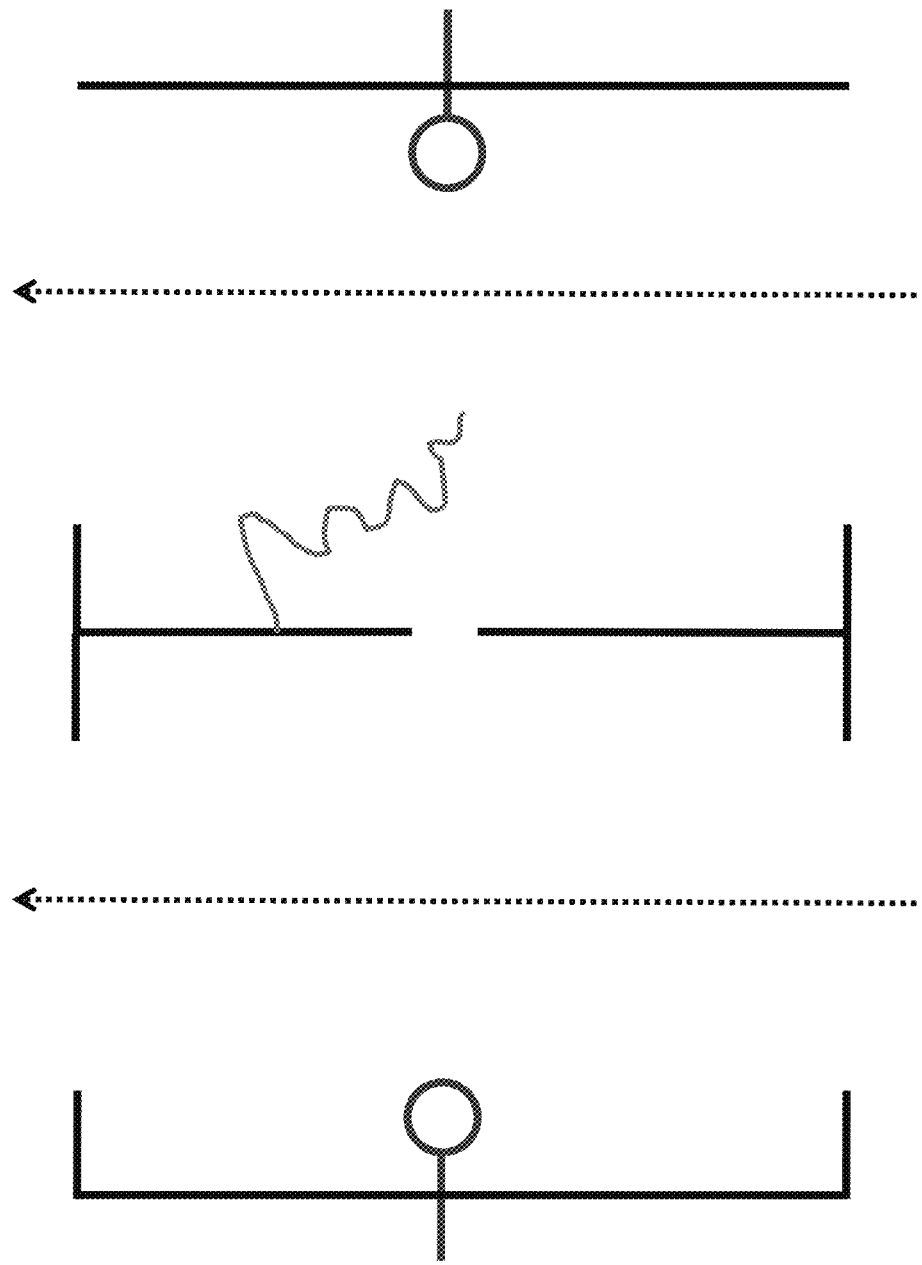
FIG. 14 shows an array with free-flowing reagents through both sides, with the DNA bound to the surface of a chamber.
Figure 15:
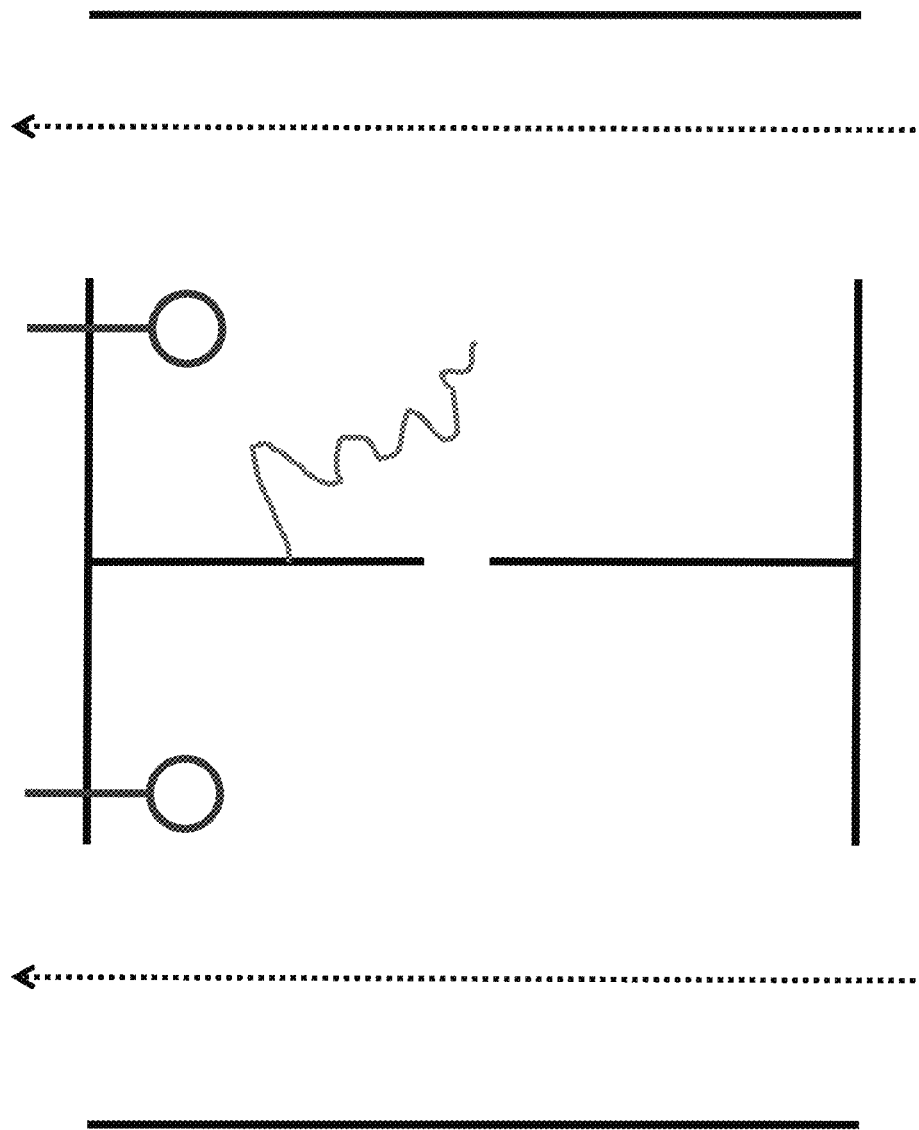
FIG. 15 shows an alternate design with the electrodes on the sides adjacent to the dividing membrane, which allows for less expensive manufacture.
Figure 16:
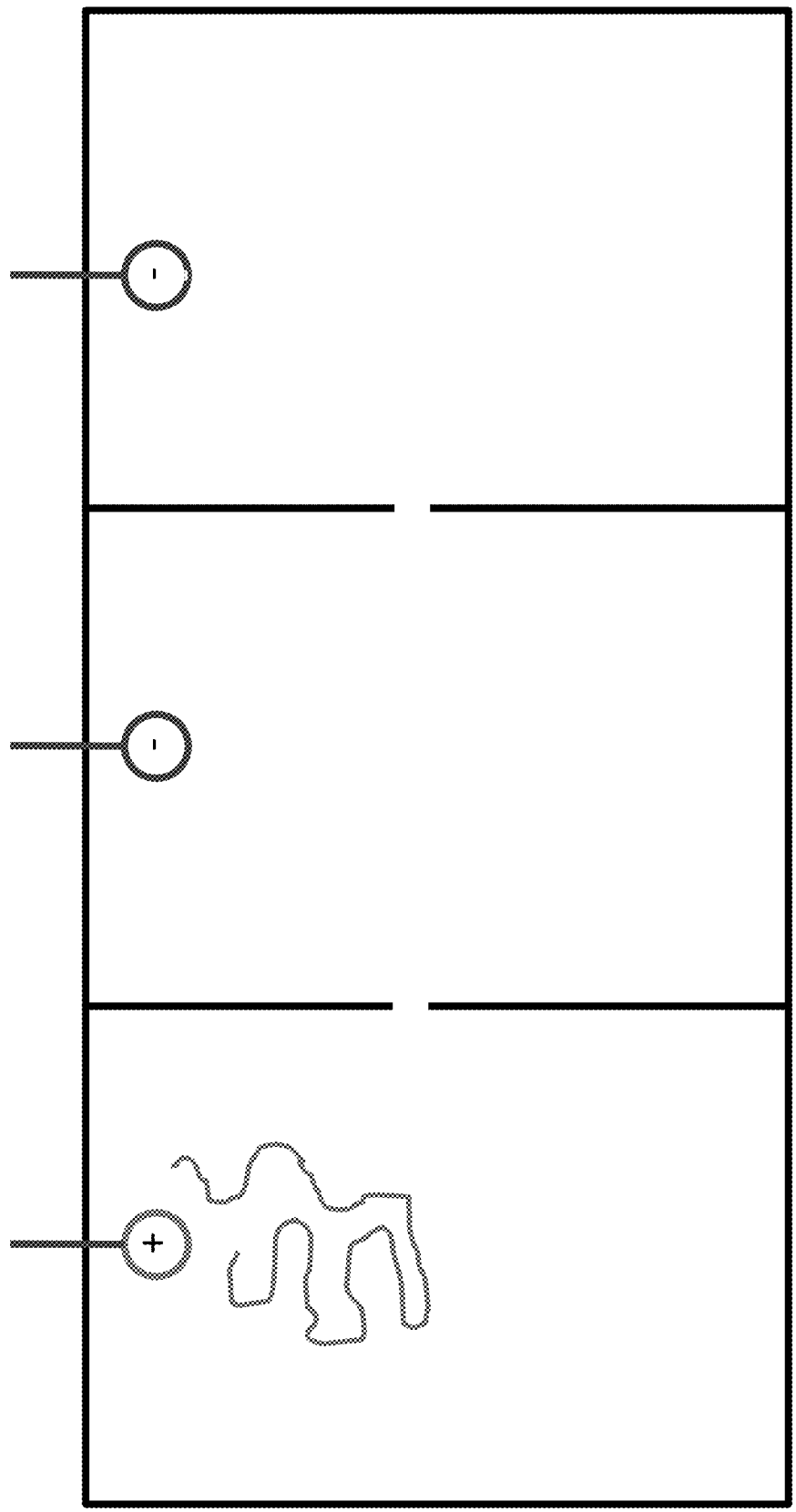
FIG. 16 shows a three-compartment arrangement, where the DNA can be moved from compartment to compartment by the electrodes. This system does not require significant flow of reagents during synthesis.
Figure 17:
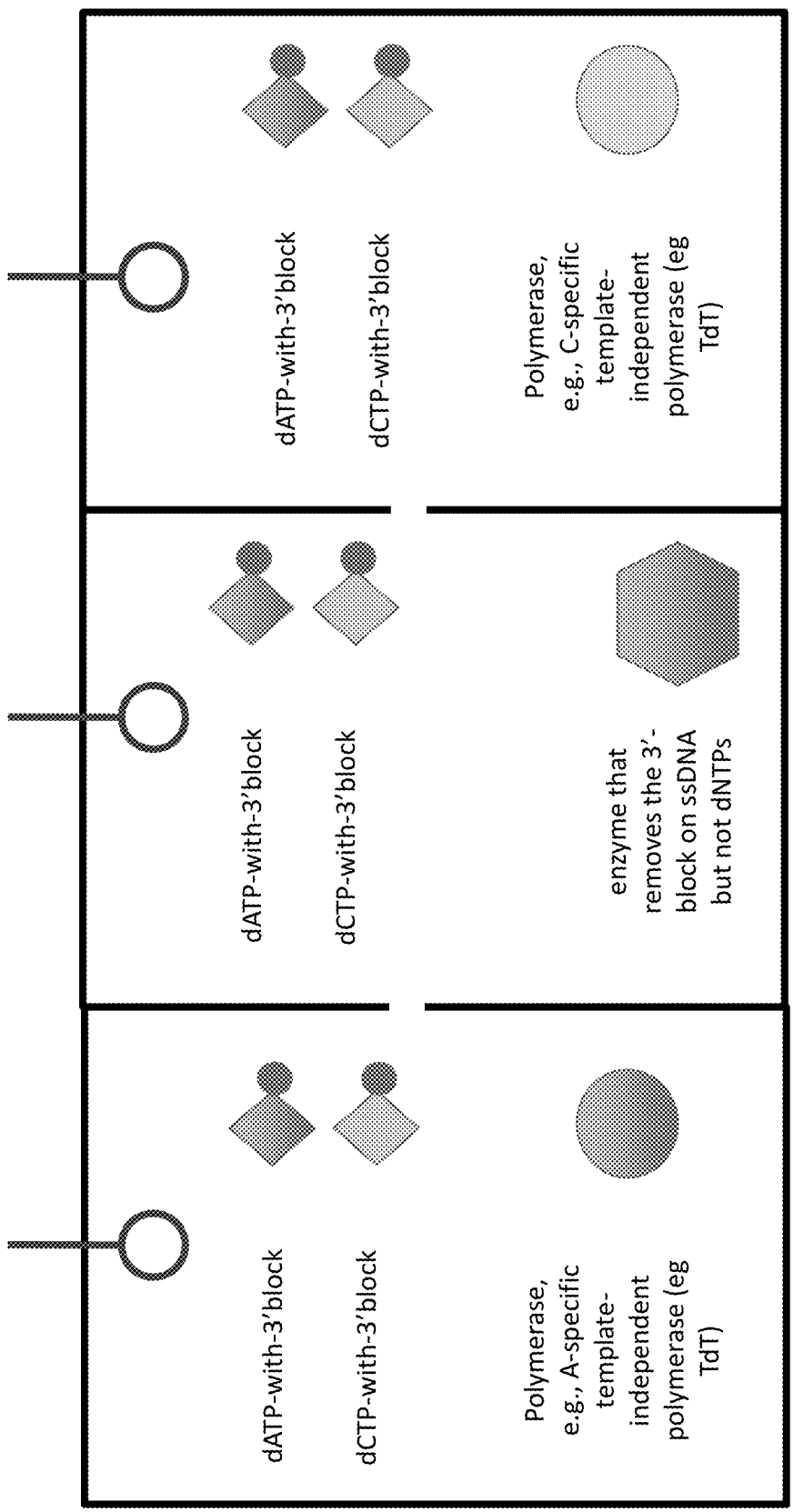
FIG. 17 shows an example of how reagents could be configured in a three compartment arrangement.
Figure 18:
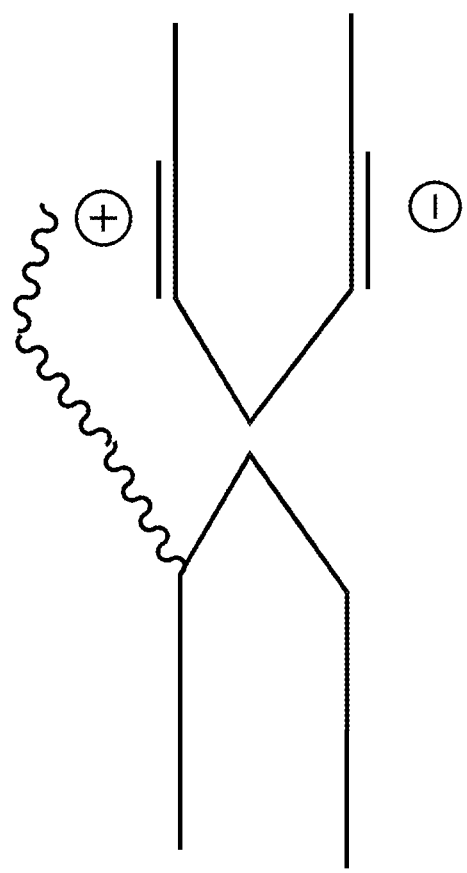
FIG. 18 depicts an oligonucleotide tethered adjacent to a nanopore, where the nanopore has electrode elements on either side of the membrane.
Figure 19:
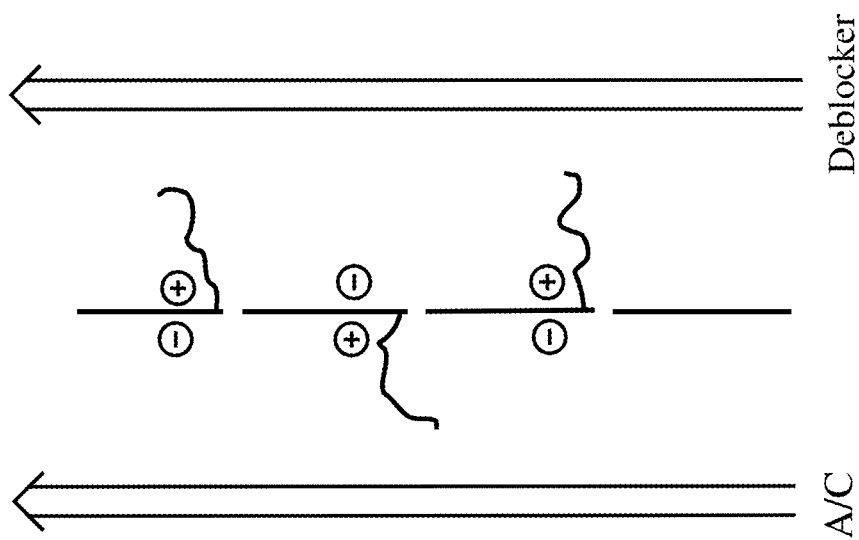
FIG. 19 depicts a series of DNA molecules attached along a membrane comprising nanopores and each under control of electrodes adjacent to a nanopore, with a flow lane on either side of the membrane. For example, as depicted, the left flow lane provides a flow of buffer wash/3'-blocked dATP (A)/buffer wash/3'-blocked dCTP (C)/buffer wash, wherein the DNA molecules are brought into the flow chamber only when the desired nucleotide is present. The right lane provides deblocking agent(s) to deprotect the 3' end of the nucleotide and allow for addition of another nucleotide. In one embodiment, the deblocking agent(s) flow when the left lane is being washed with buffer. In another embodiments, the deprotecting agent(s) are too bulky to cross to the left lane via the nanopores.

In some embodiments, the DNA or other polymer is anchored to a surface proximate to the nanopore during synthesis. For example, in one embodiment, single stranded DNA molecules are each attached at the 5' end to a surface proximate to a nanopore, wherein the current at each nanopore can be independently regulated by electrodes for that nanopore, so that the 3'end of the DNA molecule can be pulled forward through the nanopore from a retaining chamber into a flow chamber containing a flow of 3'-protected dNTPs together with a polymerase or terminal transferase enzyme to add a 3'-protected dNTPs, or retained in the retaining chamber where the nanopore excludes the enzyme, so that the dNTP is not added. See, e.g., depictions at FIGS. 12-16 and also FIGS. 18 and 19. In other embodiments, single stranded DNA is built by addition to the 5' end (with the 3' end attached), using topisomerase, as described more fully below. By controlling whether or not each DNA molecule participates in each cycle, the sequence of each DNA molecule can be precisely controlled, e.g., as follows:

| Step | Flow Chamber | Nanopore 1 | Nanopore 2 |
|---|---|---|---|
| 0 | | Retain | Retain |
| 1 | flow 'A' | | |
| 2 | | Forward into flow chamber 'A' gets added | retain |
| 3 | | Reverse back into resting chamber; oligo is deprotected | retain |
| 4 | Flush with buffer | retain | retain |

-continued

| Step | Flow Chamber | Nanopore 1 | Nanopore 2 |
|---|---|---|---|
| 5 | flow 'C' | forward 'C' gets added | forward 'C' gets added |
| 6 | | reverse oligo is deprotected | reverse oligo is deprotected |
| 7 | | retain | forward 'C' gets added |
| 8 | | retain | reverse oligo is deprotected |
| 9 | Flush with buffer | retain | retain |

Flow A = 3'-protected dATP
Flow C = 3'-protected dCTP
Nanopore 1 and Nanopore 2 in this schematic are associated with different DNA strands and the positions of which (in or out of the flow chambers) are separately controllable. The DNA can be deprotected either by a specific enzyme in the retaining chamber, or by changing the flow in the flow chamber to provide deprotection by enzymatic, chemical, light-catalyzed or other means. In one embodiment, the deblocking agent(s) flow between cycles of Flow A and Flow C, e.g., when the flow chamber is being washed with buffer, so that the deblocking agent does not deprotect the nucleotide building blocks. In other embodiments, the deprotecting agent(s) are too bulky to cross to the flow chamber via the nanopores.

The end result in the foregoing example would be that an A and a C were added to the DNA at Nanopore 1, and a C and a C were added to the DNA at Nanopore 2.

In another embodiment, the chamber configuration is similar, but with double stranded DNA anchored to the surface proximate to a nanopore, and oligonucleotide fragments, for example of two or more types, each corresponding to a binary code, are added sequentially, e.g., using site-specific recombinases, i.e., enzymes that spontaneously recognize and cleave at least one strand of a double strand of nucleic acids within a sequence segment known as the site-specific recombination sequence, for example using topoisomerase-charged oligonucleotides as described below.

In certain embodiments, it may be desirable to keep the electrically charged polymer, e.g., DNA, in a condensed state subsequent to synthesis. There are several reasons for this:
  the polymer should be more stable in this form,
  condensing the polymer will keep down crowding and allow use of longer polymers in small volumes,
  orderly condensation can reduce potential that the polymer will form knots or tangles,
  if any of the chambers are interconnected it will help keep the polymer from getting so long that it goes through a different pore than it is supposed to when current is applied,
  condensation will help keep polymer away from the electrodes, where electrochemistry could damage the polymer.

A human cell is about 10 microns but contains 8 billion base pairs of DNA. Stretched out it would be over a meter long. The DNA fits into the cell because it is wound around histone proteins. In certain embodiments, histones or similar proteins provide a similar function in the nanochips of the invention. In some embodiments, the interior surfaces of the nanochips are slightly positively charged so that electrically charged polymer, e.g., DNA tends to stick weakly to them.

In certain embodiments, the charged polymer, e.g., single or double stranded DNA, bound to a surface proximate to a nanopore. This can be accomplished in various ways. Generally, the polymer is localized to the nanopore by attaching the polymer to a relatively bulky structure (e.g. a bead, a protein, or a DNA origami structure (described below), having a diameter too large to fit through the nanopore, e.g., >10 nm, e.g., about 20-50 nm), pulling the charged polymer through the nanopore using current, anchoring the end of the polymer distal to the bulky structure to the surface adjacent to the nanopore, for example wherein the surface is modified to accept a linker group attached to the distal end of the polymer strand, thereby attaching the polymer strand, and cleaving off the bulky structure.

The step of anchoring the end of the polymer distal to the bulky structure to the surface adjacent to the nanopore, can be accomplished in various ways. In one embodiment, the polymer is a single stranded DNA, and there are pre-attached DNA strands (about 50 bp) which are complementary to part of the single stranded DNA, so that the single stranded DNA and the pre-attached DNA strands can join via base pairing. If the pairing is strong enough, it will be sufficient to keep the DNA anchored even while being manipulated. An advantage of this method of attachment is that it allows the DNA to be removed from the nanopore chip if desired for long term storage of the DNA. Alternatively, the strand is attached to the surface covalently, either using conjugation chemistry, e.g., streptavidin-biotin conjugation as described in Example 1 below, or 'click' chemistry (see Kolb, et al. Angew. Chem. Int. Ed. (2001)40: 2004-2021, incorporated herein by reference, and/or using enzymatic attachment, for example by pre-attaching oligos covalently to the distal surface, and then using DNA ligase to connect them.

Once the distal end of the strand is attached to the surface adjacent to the nanopore, the bulky structure is cleaved off, e.g., using an endonuclease which cleaves at a restriction site near the bulky structure.

The bulky structure may be a bead, a bulky molecule, e.g., a protein which is reversibly bound to a DNA strand, or a DNA origami structure. DNA origami involves the use of base pairing to create three dimensional DNA structures. DNA origami techniques are generally described in Bell, et al, Nano Lett. (2012)12: 512-517, incorporated herein by reference. For example, in the current invention, DNA origami can be used to attach the single DNA molecule to a surface adjacent to the nanopore. In one embodiment, the structure is a 'honey comb cube', e.g., about 20 nm on each side. This prevents this part of the DNA from going through the nanopore (just like in the attached paper). There is a long strand of DNA (single or double stranded) attached to the origami structure. The DNA strand goes through through the nanopore, until the origami cube meets the nanopore and blocks further progress. The current is then turned off and the strand is attached to the surface adjacent to the nanopore.

In another embodiment, the electrically charged polymer, e.g., DNA, with the origami structure is in the middle chamber of a three chamber configuration. The origami will keep the DNA from completely entering the other 2 chambers (or other one chamber in the 2 chamber example). Thus, in this example the polymer doesn't need to be anchored to the surface. This reduces the risk that the polymer will knot up and avoids the need for the step of binding one end of the polymer to the surface and cleaving off the bulky portion at the other end. The volume of the chamber with the origami should be kept as small as practical so that the polymer stays relatively close to the pore, which will help ensure that it translocates quickly when current is applied. It should be noted that while the middle chamber containing the origami portion of the polymer can't be interconnected with other middle chambers (or else the different polymers will get mixed up), the other chambers (or sets of chambers in the 3 chamber example) can be interconnected. These other chambers can have larger volumes if desired, as the polymer will necessarily be close to the pore (some of it will be in the pore in fact) when the DNA is moved to that chamber.

In some embodiments, the device comprises three in-line chambers, wherein the addition chambers are contiguous to allow for flow, and have common electrodes, while the 'deprotect' chambers are fluidically isolated except for the flow through the nanopore and have unique electrodes.

In other embodiments, the DNA or other charged polymer is not anchored but can move between synthesis chamber(s) and deprotection chamber(s), under control of electrodes in the chambers, while the polymerase and the deprotecting agents are restricted from movement between chambers because they are too bulky to pass through the nanopores connecting the chambers and/or are anchored to a surface in a chamber. See, e.g., FIGS. 1-9 and 16-17.

The current needed to move the charged polymer through the nanopore depends on, e.g., the nature of the polymer, the size of the nanopore, the material of the membrane containing the nanopore, and the salt concentrations, and so will be optimized to the particular system as required. In the case of DNA as used in the examples herein, examples of voltage and current would be, e.g., 50-500 mV, typically 100-200 mV, and 1-10 nA, e.g., about 4 nA, with salt concentrations on the order of 100 mM to 1M.

The movement of charged polymer, e.g., DNA, through the nanopore is normally very rapid, e.g., 1 to 5 μs per base, so on the order of one million bases per second (1 MHz, if we adopt the nomenclature of frequency), which presents challenges for getting an accurate reading distinct from the noise in the system. Using current methods, either (i) a nucleotide needed to be repeated in a sequence, e.g., ca. 100 times successively, in order to produce a measurable characteristic change, or (ii) using protein pores, such as Alpha hemolysin (αHL) or *Mycobacterium smegmatis* porin A (MspA), which provide a relatively long pore with potential for multiple reads as the base moves through the polymer, and in some cases, can be adapted to provide a controlled feed of DNA through the pore one base at a time, in some cases using an exonuclease to cleave each base as it passes through. Various approaches are possible, e.g., slowing down the speed of the polymer, from ca. 1 MHz to ca. 100-200 Hz, for example using a medium comprising an electrorheological fluid in which becomes more viscous when a voltage is applied, thereby slowing down the speed of the polymer through the nanopore, or a plasmonic fluid system, wherein the viscosity of the medium can be controlled by light; or a molecular motor or ratchet;

providing a sequence in the polymer, e.g., in single stranded DNA, which will form a bulky secondary structure, e.g., a "hairpin", "hammerhead", or "dumbbell" configuration, which will have to be linearized in order to fit through the nanopore, thereby making the information less dense and providing a signal having a longer duration;

providing many reads of the same sequence, e.g., by using rapidly alternating current, allowing for many reads of the same sequence frame, and combined with brief bursts of direct current to pull the molecule to the next sequence frame, by reading the entire sequence multiple times, or by reading multiple identical sequences in parallel, in each case collating the reads to provide a consensus read that amplifies the signal;

measuring an impedance change in a high frequency signal induced by a change in capacitance as monomers (e.g., nucleotides) pass through the nanopore, rather than measuring changes in current flow or resistance directly;

enhancing the differences in current, resistance or capacitance between different bases, e.g., by using non-natural bases which have a greater difference in size or are otherwise modified to give different signals, or by forming larger secondary structures within the DNA, such as a "hairpin", "hammerhead", or "dumbbell" configuration, which provide an enhanced signal because of their larger size;

using an optical reading system, for example using an integrated optical antenna adjacent to the nanopore, which acts as an optical transducer (or optical signal enhancer) to complement or replace standard ion current measurements, e.g., as described in Nam, et al., "*Graphene Nanopore with a Self-Integrated Optical Antenna*", Nano Lett. (2014)14: 5584-5589, the contents of which are incorporated herein by reference. In some embodiments, the monomers, e.g. DNA nucleotides, are labeled with fluorescent dyes so that each different monomer fluoresces at a signature intensity as it passes through the junction of the nanopore and its optical antenna. In some embodiments, a solid-state nanopore strips off fluorescent labels, leading to a series of detectable photon bursts, as the polymer passes through the nanopore at high speed, e.g. as described in McNally et al., "*Optical recognition of converted DNA nucleotides for single molecule DNA sequencing using nanopore arrays*", Nano Lett. (2010)10(6): 2237-2244, and Meller A., "*Towards Optical DNA Sequencing Using Nanopore Arrays*", J Biomol Tech. (2011) 22(Suppl): S8-S9, the contents of each of which are incorporated herein by reference.

In one embodiment, the charged polymer is a nucleic acid, e.g., single stranded DNA, wherein the sequences provide a secondary structure. Bell, et al., Nat Nanotechnol. (2016)11(7):645-51, incorporated herein by reference, describes using a relatively short sequence of dumbbell configurations detectable in a solid state nanopore format, to label antigens in an immunoassay. The nanopores used in Bell, et al. were relatively large, so the entire dumbbell structure could pass through the pore, but using nanopores smaller than the diameter of the dumbbell configuration, the DNA will "unzip" and become linearized. More complex configurations can be used, e.g. wherein each bit corresponds to a sequence similar to a tRNA (see, e.g., Henley, et al. Nano Lett. (2016)16: 138-144, incorporated herein by reference). Thus the invention provides charged polymers, e.g. single stranded DNA, having at least two types secondary structure, wherein the secondary structure encode data (e.g. binary data, wherein one secondary structure type is a 1 and a second is a 0). In other embodiments, secondary structures are used to slow down the passage of the DNA through the nanopore or to provide breaks in the sequence, to facilitate reading of the sequence.

In another embodiment, the invention utilizes a DNA molecule comprising a series of at least two different DNA motifs, wherein each motif specifically binds to a particular ligand, for example a gene regulatory protein for double stranded DNA or a tRNA for single stranded DNA, wherein the at least two different DNA motifs encode information, e.g. in a binary code, wherein one motif is a 1 and a second is a 0, e.g., wherein the ligand enhances the signal difference (e.g. change in current or capacitance) across the nanopore as the DNA passes through the nanopore.

As discussed above, when different monomers pass through the nanopore, they affect the current flow through the nanopore, primarily by physically blocking the nanopore and changing the conductance across the nanopore. In existing nanopore systems, this change in current is measured directly. The problem with current reading systems is that there is considerable noise in the system, and in the case of DNA, for example, when measuring current fluctuations as different nucleotide units pass through the nanopore, a relatively long integration time, on the order of one hundredth of a second, is needed to accurately detect differences between different monomers, e.g., between different bases. Recently, it has been shown that changes in impedance and capacitance can be useful to study cells and biological systems, despite the potential for complex interactions with salts and biological molecules. For example, Laborde, et al. Nat Nano. (2015)10(9):791-5 (incorporated herein by reference), demonstrates that high-frequency impedance spectroscopy can be used to detect small changes in capacitance under physiological salt conditions and image microparticles and living cells beyond the Debye limit.

In one embodiment of the invention, therefore, we measure capacitive variance rather than measuring current variance directly, for example, wherein the sequence of the charged polymer is identified by measuring the phase change in a radiofrequency signal induced by change in capacitance as the monomers (e.g., nucleotides) pass through the nanopore.

Simply stated, capacitance exists in any circuit where there is a gap between one electrical conductor and another. While current varies directly with capacitance, it does not vary simultaneously with capacitance. For example, if we were to plot the current and voltage over time in a capacitive circuit with an alternating electrical current, we would see that while both current and voltage each form a sine wave, the waves are out of phase. When there is a change in current, there is a change in capacitance, which is reflected in a change in the phase of the signal. A radiofrequency alternating current provides a signal with fixed frequency and amplitude, while the phase of the signal will vary with the capacitance of the circuit. In our system, we use a pulsating direct current (i.e., an AC signal with a DC bias) rather than a pure alternating current (i.e., the voltage alternates between two values, but the voltage does not cross the "zero" line, such that polarity is maintained and one electrode remains positive and the other negative), so that the charged polymer can be drawn through the nanopore (towards the positive electrode in the case of DNA). When there is nothing in the nanopore, the capacitance has one value, which changes as the different monomers of the polymer pass through the nanopore. In some embodiments, suitable frequency ranges are in the radiofrequency range, e.g. 1 MHz to 1 GHz, e.g. 50-200 MHz, for example about 100 MHz, e.g. below higher microwave frequencies that could cause significant dielectric heating of the medium. Other frequencies may be used, as discussed herein. To reduce the potential for interference, different frequencies can be applied at different nanopores so that multiple nanopores can be measured simultaneously with a single radiofrequency input line.

Measuring impedance changes (due to, e.g. changes in capacitance) at high frequencies increases the signal to noise available within a certain time span, as it reduces the effects of 1/f noise, or 'pink' noise that is inherent in electronic measurement circuits. Using a high frequency signal enhances the signal-to-noise ratio, as many measurements are made within a given time span, providing a more stable signal which is readily distinguished from impedance changes due to environmental or device variation and fluctuation.

Applying these principles to the instant invention, the invention provides in one embodiment, a method of measuring an impedance change in a high frequency signal induced by a change in capacitance as monomers (e.g., nucleotides) pass through a nanopore, for example, a method of reading a monomer sequence of a charged polymer comprising at least two different types of monomers, for example a DNA molecule, comprising applying a radiofrequency pulsating direct current, e.g. at a frequency of 1 MHz to 1 GHz, e.g. 50-200 MHz, for example about 100 MHz, across a nanopore, wherein the pulsating direct current draws the charged polymer through the nanopore and the monomer sequence is read by measuring the capacitive variance across the nanopore as the charged polymer goes through the nanopore.

For example, referring to FIGS. 48A, 48B, 48C, a nanopore-based cell 4800 is shown having an upper (or top) chamber 4802 and a lower (or bottom) chamber 4804 and a membrane 4806, which separates the two chambers 4802, 4804. The membrane is made of a material as described herein above. Also in the cell is a nanopore 4808 (or nanometer-sized hole) through the membrane, having a shape and dimensions such at that described herein, which allows for fluid communication between the chambers 4802, 4804.

Inside the cell 4800, is a polymer molecule, e.g., a single-stranded DNA molecule 4810 (or ssDNA), such as that described herein above. In this example, the DNA 4810 has three units or bases, an upper base 4812, a middle base 4814, and a lower base 4816. Each of the bases 4812-4816 in the DNA 4810, or a collection of bases, may be referred to as a "bit" of information used to represent or store data, as also discussed herein. Any other polymer or DNA molecule (single or double-stranded) may be used if desired, as discussed herein above.

The chambers 4802, 4804, of the cell 4800 may be filled with a fluid, such as that describe herein, that allows the DNA 4810 to float and move between the chambers 4802, 4804. The cell 4800 also has a pair of electrodes 4818, 4820, an upper (or top) electrode 4818 connected to an input voltage Vin, and a lower (or bottom) electrode 4820 connected to ground (or GND or 0 volts). In some embodiments, the lower electrode 4820 may also be connected to a non-zero DC voltage, but may still be at AC (or rf or radio frequency) "ground" through use of an AC coupling capacitor, connected to the electrode, having a capacitance value which passes the AC voltage (discussed more hereinafter). Voltage applied to the electrodes 4818,4820 determines the movement of the DNA 4810 in the cell 4800. In particular, when the DNA strand 4810 is in the presence of an electric field or voltage or charge difference, the DNA 4810 will be attracted to the positive charge or voltage, because the DNA molecule 4810 has a net negative charge, as described hereinbefore with FIGS. 1-5.

In this case, when the top electrode 4818 has a positive voltage relative to the bottom electrode 4820 (shown here at ground or 0 volts), the DNA 4810 will move through the nanopore 4808 (if it was in the lower chamber 4804) toward the top electrode 4818, and into the upper chamber 4802. Conversely, when the top electrode 4818 has a negative voltage relative to the bottom electrode 4820, the DNA 4810 will move through the nanopore 4808 toward the bottom electrode 4818, and into the lower chamber 4804. FIGS. 48A, 48B and 48C shows the DNA 4810 moving through the nanopore 4808 from the upper chamber 4802 to the lower chamber 4804.

Referring to FIGS. 48A-48C, the cell 4800 (or the nanopore and DNA system) may be electrically modeled as an equivalent circuit diagram 4830, shown as a capacitor C1 and resistor R1 connected in parallel. In particular, the top electrode 4818 sees a capacitance C1 and resistance R1 to ground that is set by its local environment, where the capacitor C1 represents the capacitance of the cell 4800 as determined by the properties of the two electrodes 4818, 4820 (i.e., the capacitor plates) and the properties of dielectric material there-between, defined at least by the fluid within the cell 4800 and the membrane 4806 with the nanopore 4808. The resistor R1 represents the DC resistance associated with the cell 4800, defined at least by the losses associated with the dielectric material of the cell described above, which appear as a DC leakage current between the two electrodes.

When the DNA 4810 passes through the nanopore 4808, both the cell capacitance and resistance (or the cell impedance, Zcell) changes. Different DNA bases have different sizes, and thus have different effects on the capacitance and resistance, resulting in different equivalent circuit models as illustrated in FIGS. 48A-48C. In particular, in FIG. 48A, the DNA 4810 is outside the nanopore 4808, resulting in a set of values C1,R1 (or Zcell1). In FIG. 48B, the base 4814 of the DNA 4810 is in the nanopore, resulting in another set of values C2,R2 (or Zcell2). Similarly, in FIG. 48C, the base 4812 of the DNA 4810 is in the nanopore, resulting in another set of values C3,R3 (or Zcell3).

Referring to FIGS. 49A and 49B, the capacitance C and resistance R of the cell 4800 (nanopore and DNA system) may be combined with an inductor L to create an "inductor-cell" or "cell-inductor" RLC resonant circuit or resonator or filter (or band-stop, or notch, or band-reject filter) as shown by the circuit 4900 (FIG. 49A), having a magnitude frequency response shown by a graph 4952, and a phase frequency response shown by a graph 4954. The center or resonant frequency $f_{res}$ of the circuit 4900 is given by the equation:

$$\omega_{res} = 2\pi f_{res} = \text{Sqrt}(1/LC) \times \text{Sqrt}(1-(L/C)/R^2) \qquad \text{Eq.1}$$

where C and R are the capacitance and resistance of the cell, respectively, at a given time, and L is the value of the inductor (which is a constant with respect to the position of the DNA in the cell). There may also be an equivalent coil resistor (not shown) in series with the inductor L, indicative of the DC resistance of the inductor coil winding. However, if the coil resistance is negligible, it need not be shown in the circuit diagram or in the resonant frequency $f_{res}$ equation.

When the value of the cell resistance R is large, Eq.1 becomes:

$$\omega_{res} = 2\pi f_{res} = \text{Sqrt}(1/LC) \qquad \text{Eq.2}$$

Referring to FIG. 49B, the magnitude response 4952 of the resonant circuit 4900 (for a given value of C and R) has maximum attenuation (minimum impedance) at the resonant frequency $f_{res}$, and a steep magnitude attenuation response over a narrow frequency band (or stop band) $\Delta f_{stp}$ around the resonant frequency $f_{res}$, which is the frequency range over which the magnitude response (Vout/Vin) is below a standard threshold, e.g., 3 dB (or 20 Log[SQRT(2)]). For all other frequencies, the output magnitude is substantially constant and non-attenuating. The corresponding phase shift response curve 4954 of the resonant circuit 4900 has a phase shift of 45 degrees at the resonant frequency $f_{res}$ (when the reactance or imaginary portion of the complex impedance is equal to zero), and has a steep phase response over the narrow stop band $\Delta f_{stp}$ on each side of the resonant frequency $f_{res}$, such that at frequencies above $f_{res}$ and outside the band $\Delta f_{stp}$, the phase shift is at or near 180 deg., and at frequencies below $f_{res}$ and outside the band $\Delta f_{stp}$, the phase shift is at or near 0 deg. Otherwise, the phase response output is substantially constant and non-shifting over all other frequencies.

Referring to FIG. 50, a family of resonant frequency response magnitude curves 5002 and phase curves 5003 of the resonant circuit (or filter) are shown in response to DNA (or other polymer or molecule having varying sizes along its length) passing through a nanopore and changing the capacitance (or impedance) measured to ground (e.g., 0 volts), and thereby changing the resonant frequency $f_{res}$, as shown by the magnitude response curves 5010-5018 and the corresponding phase response curves 5020-5028. In particular, as shown by Eq. 2 above, increasing the capacitance measured to ground, decreases the resonant frequency $f_{res}$. Also, increasing the DNA "base" size (blocking the nanopore more), may increase the cell capacitance (depending on the dielectric constant of the DNA), which would decrease the resonant frequency $f_{res}$. Conversely, decreasing the DNA base size (un-blocking the nanopore more), may decrease the cell capacitance (depending on the dielectric constant of the DNA), which would increase the resonant frequency $f_{res}$. Using standard DNA bases (G,C,A,T), the size order would be: G (largest), A, T, C (smallest). Accordingly, presuming the dielectric constant of the DNA changes appropriately with the DNA bases, when DNA is in the nanopore, $f_{res}$ would be lowest when the largest base, e.g., Base G, is in the nanopore and $f_{res}$ would be the highest when the smallest base, e.g., Base C, is in the nanopore. Also, when the nanopore is open (unblocked), i.e., no DNA or polymer in the nanopore, $f_{res}$ would be the highest frequency. This range or band of resonant frequencies is shown as $\Delta f_{res}$ in FIG. 50. Also, for the resonator response curves 5010-5018 for magnitude and 5020-5028 for phase shown in FIG. 50, the overall bandwidth of the resonator (over which magnitudes and phase are materially affected by the resonator) is shown in FIG. 50 as $\Delta f_{BW}$.

In addition, the overall resonant frequency band $\Delta f_{res}$ for a given cell-inductor resonant circuit (or resonator or filter), presuming all other cell conditions affecting impedance remained fixed, would have a maximum resonant frequency $f_{res-max}$ when the nanopore is open (or unblocked by the polymer), and a minimum resonant frequency $f_{res-min}$ when the nanopore is closed (or blocked by the polymer), and the cell resonant frequency $f_{res}$ is varied (or tuned or changed) by the size of the polymer in the nanopore at a given time, and thus may be referred to herein as a nanopore-polymer resonator (or NPR). Also, the overall bandwidth $\Delta f_{BW}$ of the resonator (over which magnitudes and phase are materially affected by the resonator) would similarly be determined based on the resonant frequency band $\Delta f_{res}$.

When there is an AC voltage applied to the resonator and the output voltage signal (Vout) of the resonator is observed (or monitored) at a fixed frequency $f_{probe}$, e.g., near the center of the resonant frequency range for the DNA bases shown, shown as a dashed vertical line 5004, not necessarily aligned with one of the center (or resonant) frequencies $f_{res}$, the resonator provides four different possible output signals (or magnitude attenuation or phase shift amounts) at that frequency $f_{probe}$, depending on the specific DNA base (size) passing through the nanopore, and a fifth output voltage state when the DNA is not in the nanopore ("open pore" condition). These five output signals are shown by where the family of response curves 5002,5003 intersect with the line 5004 corresponding to the monitor frequency $f_{probe}$, i.e., magnitudes V1-V5, and phases Ph1-Ph5.

Alternatively, if the output voltage is monitored at a different frequency $f_{probe2}$, e.g., near the resonant frequency of the lowest frequency response curve 5010, shown as a dashed vertical line 5006, which is, e.g., at a lower frequency than $f_{probe}$, the output voltage at the frequency $f_{probe2}$ would be five magnitude output voltages V6-V10 (different from the output voltages V1-V5 seen at $f_{probe}$) and five output phase shifts Ph6-Ph10 (different from the output voltages Ph1-Ph5 seen at $f_{probe}$). In particular, these different five output signals are shown by where the family of response curves 5002, 5004 intersect with the line 5006 corresponding to the monitor frequency $f_{probe2}$, i.e., magnitudes V6-V10, and phases Ph6-Ph10. The values of V1-V10 and Ph1-Ph10 are arbitrary designations and are used for identification or labeling purposes only. The value or location for the probe or monitoring frequency $f_{probe}$, $f_{probe2}$ may be set based on the desired response values, as described below. As shown below, using values for the probe or monitoring frequencies in the range of resonant frequencies seen when the polymer is in the nanopore, may provide a useful range of output values. Other measurement or probe frequencies may be used if desired provided it meets the desired functional and performance requirements.

In particular, if the four bases were to pass through the nanopore sequentially in size order (i.e., G, A, T, C), when the largest base (e.g., Base G) passes through the nanopore, the resonant frequency $f_{res}$ will be the lowest (capacitance highest), and the corresponding response is shown by the (far left) magnitude and phase curves 5010, 5020, respectively. In that case, the output voltage at the frequency $f_{probe}$ where the curves 5010, 5020 intersect with the line 5004 would correspond to an output voltage V2 and output phase Ph1, respectively. Alternatively, if the output voltage is monitored at the monitor frequency $f_{probe2}$, the output voltage at the frequency $f_{probe2}$ where the curves 5010, 5020 intersect with the line 5006 would correspond to an output voltage V10 and output phase Ph6, respectively.

Similarly, when the next smaller base (e.g., Base A) passes through the nanopore, the resonant frequency $f_{res}$ will be a little higher than that of the previous base, and the response is shown by the magnitude and phase curves 5012, 5022, respectively. In that case, the output voltage at the frequency $f_{probe}$ where the curves 5012, 5022 intersect with the line 5004 would correspond to an output voltage V5 and output phase Ph2, respectively. Alternatively, if the output voltage is monitored at the monitor frequency $f_{probe2}$, the output voltage at the frequency $f_{probe2}$ where the curves 5012, 5022 intersect with the line 5006 would correspond to an output voltage V9 and output phase Ph7, respectively.

Similarly, when the next smaller base (e.g., Base T) passes through the nanopore, the resonant frequency $f_{res}$ will be a little higher than that of the previous base, and the response is shown by the magnitude and phase curves 5014, 5024, respectively. In that case, the output voltage at the frequency $f_{probe}$ where the curves 5014, 5024 intersect with the line 5004, would correspond to an output voltage V4 and output phase Ph3, respectively. Alternatively, if the output voltage is monitored at the monitor frequency $f_{probe2}$, the output voltage at the frequency $f_{probe2}$ where the curves 5014, 5024 intersect with the line 5006 would correspond to an output voltage V8 and output phase Ph8, respectively.

When the smallest base (e.g., Base C) passes through the nanopore, the resonant frequency $f_{res}$ will be a little higher than that of the previous base, and the response is shown by the magnitude and phase curves 5016, 5026, respectively. In that case, the output voltage at the frequency $f_{probe}$ where the curves 5016, 5026 intersect with the line 5004 would correspond to an output voltage V3 and output phase Ph4, respectively. Alternatively, if the output voltage is monitored at the monitor frequency $f_{probe2}$, the output voltage at the frequency $f_{probe2}$ where the curves 5016, 5026 intersect with the line 5006 would correspond to an output voltage V7 and output phase Ph9, respectively.

Lastly, when there is no DNA in the nanopore, the resonant frequency $f_{res}$ will be the highest (capacitance lowest), and the response is shown by the magnitude and phase curves 5018, 5028, respectively. In that case, the output voltage at the frequency $f_{probe}$ where the curves 5018, 5028 intersect with the line 5004, would correspond to an output voltage V1 and output phase Ph5, respectively. Alternatively, if the output voltage is monitored at the monitor frequency $f_{probe2}$, the output voltage at the frequency $f_{probe2}$ where the curves 5018, 5028 intersect with the line 5006 would correspond to an output voltage V6 and output phase Ph10, respectively.

Referring to FIG. 51, an overview example of a DNA-reading time sequence 5100 in accordance with embodiments the present disclosure is shown for reading data stored in DNA using two-bits (e.g., two bases) in the DNA strand 4810 via the "inductor-cell" resonator or "capacitive-resonance" DNA data reading technique of the present disclosure measured at a fixed probe (or monitor) frequency $f_{probe}$. The DNA-reading time sequence has 5 time segments or stages T1-T5, shown as five columns 5102 to 5110, and the progression between time segments is shown by dashed lines 5111. For each of the time stages T1-T5, there is an image showing the DNA 4810 (FIG. 48) and its location relative to the nanopore 4808 for that time stage, there are also magnitude and phase response curves 5112-5120 for the time stages T1-T5, respectively, showing the intersection of the response curve at the monitor frequency $f_{probe}$ (corresponding to a curve from the family of curves shown in FIG. 50), and two output value graphs 5130, 5132 showing corresponding output signals (e.g., voltage values) for the magnitude and phase responses, respectively, at the monitor frequency $f_{probe}$ across each of the time stages T1-T5. The values V1-V5 and Ph1-PH5 for the graphs 5130, 5132 may be any voltage values indicative of the output value for that parameter having the appropriate range and scaling to provide the functions described herein.

Regarding the location and movement of the DNA 4810 at each of the five time states T1-T5 in the example of FIG. 51, at time stage T1 (5102)=no DNA in nanopore (Open Pore), at time stage T2 (5104)=Base A in nanopore, at time stage T3 (5106)=Base G in nanopore, at time stage T4 (5108)=Base A in nanopore, and at time stage T5 (5110)=No DNA in nanopore (Open Pore).

Referring to FIGS. 50 and 51, starting at time stage T1, the DNA 4810 is outside of the pore 4808, the capacitance to ground is low (as discussed herein), the resonance frequency f high, and the measured magnitude output signal is high and the phase value is very low (e.g., about is about 0 deg.) at the monitoring frequency $f_{probe}$, which corresponds to the response curves 5018, 5028 shown in FIG. 50, having output values at $f_{probe}$ where the curves 5018, 5028 intersect with the line 5004, corresponding to an output voltage V1 and output phase Ph5, respectively. At time T2, the DNA base 4816 (Base A, in this example) enters the pore 4808, the capacitance to ground increases, the resonance frequency $f_{res}$ shifts to lower central frequency, and the measured magnitude output signal is low and the phase value is intermediate (e.g., about 90 deg.) at $f_{probe}$, which corresponds to the response curves 5012, 5022 shown in FIG. 50, having output values at $f_{probe}$ where the curves 5012, 5022 intersect with the line 5004, corresponding to an output voltage V5 and output phase Ph2, respectively. At time T3, the DNA base 4814 (Base G, the largest base, in this example), enters the pore 4808, the capacitance to ground extremely high, and the resonance frequency $f_{res}$ shifts lower, but the magnitude output signal is an intermediate output value is upper-mid (e.g., about 135 deg.) at $f_{probe}$, which corresponds to the response curves 5010, 5020 shown in FIG. 50, having output values at $f_{probe}$ where the curves 5010, 5020 intersect with the line 5004, corresponding to an output voltage V2 and output phase Ph1, respectively.

At time T4, the DNA base 4812 (Base A in this example) enters the pore 4808 (again), the capacitance to ground decreases (from the value at T3), the resonance frequency $f_{res}$ shifts to central frequency, and the measured magnitude output signal is low and the phase value is intermediate (e.g., about 90 deg.) at $f_{probe}$, which corresponds to the response curves 5012, 5022 shown in FIG. 50, having output values at $f_{probe}$ where the curves 5012, 5022 intersect with the line 5004, corresponding to an output voltage V5 and output phase Ph2, respectively. At time T5, the DNA 4810 is outside of the pore 4808 (again), the capacitance to ground is low, the resonance frequency $f_{res}$ shifts (again) to high frequency, and the measured magnitude output signal is high at $f_{probe}$, which corresponds to the response curves 5018, 5028 shown in FIG. 50, having output values at $f_{probe}$ where the curves 5018, 5028 intersect with the line 5004, corresponding to an output voltage V1 and output phase Ph5, respectively.

Referring to FIG. 52, another overview example 5200 of a time sequence (T1-T5) is shown for reading data stored in DNA using two-bits (e.g., two bases) in the DNA strand via the capacitive-resonance DNA data reading technique of the present disclosure using a different fixed probe (or monitor) frequency $f_{probe2}$. The sequence has 5 time segments or stages T1-T5, shown as five columns 5202-5210, and the progression between time segments is shown by dashed lines 5211. For each of the time stages T1-T5, there is an image showing the DNA 4810 (FIG. 48) and its location relative to the nanopore 4808 for that time stage, there are also magnitude and phase response curves 5212-5220 for the time stages T1-T5, respectively, showing the intersection of the response curve at the monitor frequency $f_{probe2}$ (corresponding to a curve from the family of curves shown in FIG. 50), and two value graphs 5230, 5232 showing corresponding output signals (e.g., voltage values) for magnitude and phase responses, respectively, at the monitor frequency $f_{probe2}$ across each of the time stages T1-T5. The values V1-V5 and Ph1-PH5 for the graphs 5130, 5132 may be any voltage values indicative of the output value for that parameter having the appropriate range and scaling to provide the functions described herein.

Regarding the location and movement of the DNA 4810 at each of the five time states T1-T5 in the example of FIG. 52, more specifically, at time stage T1 (5202)=no DNA in nanopore (Open Pore), at time stage T2 (5204)=Base A in nanopore, at time stage T3 (5206)=Base G in nanopore, at time stage T4 (5208)=Base A in nanopore, and at time stage T5 (5210)=No DNA in nanopore (Open Pore).

Referring to FIGS. 50 and 52, starting at time stage T1, the DNA 4810 is outside of the pore 4808, the capacitance to ground is low (as discussed herein), the resonance frequency $f_{res}$ is high, and the measured magnitude output signal is high and the phase shift value is very low (e.g., about 0 deg.), which corresponds to the response curves

5018, 5028 shown in FIG. 50, having output values at $f_{probe2}$ where the curves 5018, 5028 intersect with the line 5006, corresponding to an output voltage V6 and output phase Ph10, respectively. At time T2, the DNA base 4816 (Base A, in this example) enters the pore 4808, the capacitance to ground increases, the resonance frequency $f_{res}$ shifts to lower central frequency, and the measured magnitude output signal is intermediate and the phase value is low-mid value (e.g., about 45 deg) at $f_{probe2}$, which corresponds to the response curves 5012, 5022 shown in FIG. 50, having output values at $f_{probe2}$ where the curves 5012, 5022 intersect with the line 5006, corresponding to an output voltage V9 and output phase Ph7, respectively.

At time T3, the DNA base 4814 (Base G, the largest base, in this example), enters the pore 4808, the capacitance to ground is extremely high, and the resonance frequency $f_{res}$ shifts lower, and the magnitude output signal at $f_{probe2}$ is at a low output value and the output phase is at about an intermediate or mid value (e.g., about 90 deg.), which corresponds to the response curves 5010, 5020 shown in FIG. 50, having output values at $f_{probe2}$ where the curves 5010, 5020 intersect with the line 5006, corresponding to an output voltage V10 and output phase Ph6, respectively. At time T4, the DNA base 4812 (Base A, in this example) enters the pore 4808 (again), the capacitance to ground decreases (from value at T3), the resonance frequency $f_{res}$ shifts to central frequency, and the measured magnitude output signal is intermediate and the phase is low at $f_{probe2}$, which corresponds to the response curves 5012, 5022 shown in FIG. 50, having output values at $f_{probe2}$ where the curves 5012, 5022 intersect with the line 5006, corresponding to an output voltage V9 and output phase Ph7, respectively. At time T5, the DNA 4810 is outside of the pore 4808, the capacitance to ground is low, the resonance frequency $f_{res}$ shifts to a higher frequency, and the measured magnitude output signal is high and the phase signal is very low (e.g., about 0 deg.) at $f_{probe2}$, which corresponds to the response curves 5018, 5028 shown in FIG. 50, having output values at $f_{probe2}$ where the curves 5018, 5028 intersect with the line 5006, corresponding to an output voltage V6 and output phase Ph10, respectively.

Referring to the two examples of FIGS. 51 and 52, and comparing the output graphs 5130,5132, and 5230,5232, it can be seen that the desired output values can be selected based on the measurement or monitoring frequency $f_{probe}$, $f_{probe2}$.

While DNA using two and four bits (or bases) representing data to be read have been described above, any number of "bits" (or monomers or bases) may be used if desired for the data storage polymer, provided the change in cell capacitance or impedance (and corresponding resonance frequency, or frequency response) is sufficient to produce an output magnitude and/or phase for each bit that is distinguishable over each of the other bits. While such capacitance change may be accomplished by changing the physical molecular size of the bases (e.g., the diameter), any property of the bases that creates a unique capacitance value of the cell when passing through the nanopore may be used if desired. For example, bases that have different dielectric properties, different ionic (or charge) properties, and/or different quantum mechanical/electrical properties, may be used, provided they meet the desired functional and performance requirements.

Referring to FIG. 53, an equivalent circuit and block diagram 5300 of a DNA data reading network array of the present disclosure is shown, having a parallel array of resonant circuits or Nanopore Polymer Resonators (NPRs) 5302-5306 (NPR1-NPR3) each connected in parallel, through a individual coupling capacitors $C_{CPL}$ (discussed hereinafter), to a common AC input voltage source 5308, which provides an AC voltage Vin having a frequency that includes at least the desired measurement frequency(ies) ($f_{probe}$) for each of the resonant circuits NPR1-NPR3 (discussed more hereinafter). Each of the resonators NPR1-NPR3 has a unique inductor values L1-L3, respectively, connected in series with equivalent circuits 5312-5316 of corresponding cells (similar to the cell 4800 described in FIGS. 48A-48C, and similar to the equivalent circuit 4900 described in FIG. 49A), having a variable capacitor C and variable resistor R, which vary based on the location of the polymer (or DNA) 4810 (FIG. 48A) in the cell 4800 with respect to the nanopore 4808 in the cell 4800 (as discussed herein above). Each of the unique inductor values L1-L3 sets a unique resonant frequency band $\Delta f_{res}$ (FIG. 50) and a corresponding overall resonator bandwidth $\Delta f_{BW}$ (FIG. 50), discussed more hereinafter with FIG. 54. Thus, the plurality of resonators NPR1-NPR3 are connected in parallel in a frequency-multiplexed (or frequency-division multiplexed) arrangement creating an array of the resonators NPR1-NPR3, all driven by a single AC input voltage 5308, and each responding to its own probe input frequency.

Referring to FIG. 53, an optional AC RF attenuator 5310 may be provided in series with the AC input source 5308 prior to the connection to the parallel array of resonators NPR1-NPR3 to provide a voltage divider or impedance matching with the resonators NPR1-NPR3 and/or to adjust the AC output voltage Vout range based on the range of impedance values of the resonators over the operational frequency range of interest. The attenuator 5310 may be a constant or switched or variable type RF attenuator, depending on the frequency range used, the impedance of the array and load, and/or the desired functional and performance characteristics.

Referring to FIG. 53, an AC output voltage Vout from the parallel array of resonators NPR1-NPR3, may be provided to an amplifier (or pre-amp) 5320, which performs signal conditioning on the output signal Vout, such as remove noise, filter around the measurement frequency(ies) of interest, isolate impedance of resonator array from down-stream devices or components, improve measurement sensitivity, amplify or attenuate the Vout signal, and/or perform other desired signal conditioning of the AC output voltage signal Vout as needed to provide the desired functions and/or performance. In some embodiments, the amplifier may also be an active filter which filters the AC output voltage signal around one or more of the probe frequencies. The amplifier 5320 provides an analog AC conditioned output voltage Vout signal on line 5322 to an A/D Converter 5324 (e.g., an integrated circuit or chip), which digitally samples the conditioned AC output voltage Vout and provides digital output data on a line 5326 indicative of the sampled conditioned AC output voltage Vout signals. The sample rate of the A/D converter may be any rate that provides sufficient sampling of the output signal to preserve the ability to perform frequency analysis at the desired measurement frequencies (e.g., the probe frequencies). The AC output voltage may also be down-converted to a lower intermediate frequency or DC, e.g., if the fundamental probe frequency (ies) is/are too high (or fast) to be directly sampled accurately by the A/D converter (or for other design or performance reasons), by mixing the AC output signal with the same (or similar) frequency, e.g., homodyne or heterodyne demodulation, or any other type or demodulation or frequency conversion, provided it preserves the magnitude and/or phase components needed to accurately measure the desired parameters. The A/D converter 5324 may have on-board memory that stores the sampled output data and/or may be connected to or communicate with a separate memory device (not shown) which may store all or a portion of the sampled output data. The digital sampled output data is provided on the line 5326 to digital signal processing frequency analysis (or decomposition) logic 5328, such as an FFT (or Fast Fourier Transform) logic or chip, which performs digital signal processing (DSP) on the digital sampled data and provides digital data on a line 5330 indicative of the magnitude and/or phase of the frequency components (or harmonics) that exist in the sampled AC output signal Vout. Instead of the FFT logic 5328, any other frequency analysis hardware, firmware and/or software may be used if desired, provided it provides the functions and performance described herein and adequately measures the magnitude and/or phase of the output signal at the desired frequencies of interest (e.g., at least at the desired probe or measurement frequencies).

The amplifier 5320, the A/D converter 5324, and the FFT logic 5329 are all known hardware or firmware components (which may have computer programmable portions) that may be obtained from an integrated circuit provider, such as Texas Instruments, Inc., Analog Devices, Inc., National Instruments Corp., Intel Corp, or other similar manufacturers. One example of components for digitization that may be used include: Xilinx FFT LogiCORE, part no. 4DSP FMC103, 1126, Alazartec 9360, 9370. Other components may be used if desired, provided they provide the functions and performance described herein. Also, the FFT logic may be performed by a field programmable gate array (FPGA).

Also, instead of sampling the output voltage with an A/D converter and performing digital signal processing to determine the frequency components, the output signal Vout may be provided to one or more analog filters (not shown) tuned to the desired frequencies to identify the magnitude and/or phase of the desired frequency components and provide an analog output voltage signal indicative of same.

Referring to FIG. 54, a frequency plot 5400 shows a sample frequency separation for the plurality of resonators NPR1-NPR3 of FIG. 53 of the present disclosure. In particular, as discussed above with FIG. 53, each of the resonators NPR1-NPR3 has a unique resonator bandwidth $\Delta f_{BW1}$, $\Delta f_{BW2}$, $\Delta f_{BW3}$, which are set or determined by the unique inductor values L1-L3, respectively. The bandwidths $\Delta f_{BW1}$, $\Delta f_{BW2}$, $\Delta f_{BW3}$, of the resonators NPR1-NPR3, respectively, may be separated from adjacent resonator bandwidths by a frequency separation or gap $\Delta f_{gap}$ such that the resonator bandwidth $\Delta f_{BW}$ of adjacent resonators do not overlap and cause interference or cross-talk between the adjacent resonators. In some embodiments, the bandwidths may overlap provided the frequency response of each base is different and thus, they do not affect the ability to identify the response of each resonator.

Similarly, in FIG. 54 there is shown a set of probe or monitor frequencies $f_{p1}$, $f_{p2}$, $f_{p3}$ corresponding to the bandwidths $\Delta f_{BW1}$, $\Delta f_{BW2}$, $\Delta f_{BW3}$, of the resonators NPR1-NPR3, respectively, which may be a frequency (or frequencies) within each of the resonator bandwidths $\Delta f_{BW1}$, $\Delta f_{BW2}$, $\Delta f_{BW3}$, that provides the desired output signals as discussed herein, such as in the range of resonant frequencies seen when the polymer is in the nanopore (as discussed herein above with FIGS. 50-52). Other measurement or probe frequencies may be used if desired provided it meets the desired functional and performance requirements.

While the gap frequency is determined primarily by the choice of inductor L value, the amount of separation between adjacent frequency bands needed to avoid undesired overlap during operation caused by system parameter variations that may occur over the system operating conditions may also be determined by various factors, including but not limited to cell design parameter tolerances (e.g., electrodes, inductors, capacitors, fluids, cell walls, membranes, materials, dimensions, and any other cell design parameters that may vary from cell to cell), environmental operating ranges, e.g., temperature, pressure, humidity, and the like, electro-magnetic interference or noise parameters/effects, any cell-to-cell (or chamber-to-chamber) interactions, and/or any other design practice, safety or regulatory requirements or tolerances, or any other factors that may affect the desired function or performance. Such factors can cause the bandwidth of a given resonator to change from its ideal conditions, and thus should be considered in the overall design tolerance parameters for the frequency separation over time and environments.

Referring to FIGS. 55A and 55B, the AC input voltage Vin of the present disclosure includes at least desired measurement or probe frequencies at which the output AC voltage Vout will be frequency analyzed (e.g., by the FFT logic 5330—FIG. 53). Referring to FIG. 55A, the AC input voltage Vin may be a continuous broadband AC frequency signal shown by a curve 5502 having all frequencies from the minimum possible measurement frequency $f_{MIN}$ to the minimum possible measurement frequency $f_{MAX}$, or from the first probe frequency $f_{p1}$ to the last probe frequency $f_{pN}$. In that case, all the resonators NPR1-NPR3 are excited by the broadband frequency signal and will exhibit a response in the frequency components of the output signal. Alternatively, the AC input voltage Vin may be a broadband AC frequency signal shown by a curve 5510 having only the desired probe or monitor frequencies $f_{p1}$, $f_{p2}$, $f_{p3}$, $f_{pN}$ f as shown by the individual frequency components 5512,5514, 5516, 5518, respectively. Also, the overall frequency range for the AC input voltage Vin for all the resonators in the array may be from about 1.0 MHz to 100 GHz (or higher). Other frequencies may be used if desired, provided it meets the function and performance described herein. The AC input voltage Vin may be provided by a known oscillator chip (which may be adjustable and/or programmable) that provides the desired AC frequency components for the desired design configuration and excitation, such as FMC 2850, TIDAC900, or Xilinx DS558. For the case where Vin contains a plurality of individual probe frequencies, Vin may be created by combining separate AC frequencies together electronically, or directly synthesized mathematically and programmed into the oscillator (either hard wired or programmed by a microprocessor connected thereto).

Referring to FIG. 55B, the AC input voltage Vin may be a time swept AC frequency signal shown by a curve 5550, sweeping the input frequency from the minimum possible measurement frequency $f_{MIN}$ to the minimum possible measurement frequency $f_{MAX}$, or from the first probe frequency $f_{p1}$ to the last probe frequency $f_{pN}$, and then repeated having a repeat-period of time T. In that case, the frequency of the input voltage Vin is at only one frequency at any given time, and all the resonators NPR1-NPR3 respond to that single input frequency and will exhibit a response to that frequency at the output signal. Also, in that case, because the system only responds to one frequency at a time, and the system knows the frequency sweep timing of the input voltage Vin, there is no need for frequency analysis as the system can sample the magnitude and/or phase at the time associated with the desired probe frequency and determine the value directly.

Alternatively, the AC input voltage Vin may be a time-stepped AC frequency signal shown by a curve 5570, where the input frequency is stepped from the first probe frequency $f_{p1}$ to the last probe frequency $f_{pN}$, and waits a predetermined dwell time $T_D$ at each frequency, and then is repeated having a repeat-period of time T. In that case, similar to the swept-frequency curve 5550, the frequency of the input voltage Vin is at only one frequency at any given time, all the resonators NPR1-NPR3 respond to that single input frequency and will exhibit a response to that frequency at the output signal at that time. The dwell time $T_D$ allows more time for system to sample the output signal at each probe frequency. Also, in that case, because the system only responds to one frequency at a time, and the system knows the timing, there is no need for frequency analysis (or decomposition) as the system can sample the magnitude and/or phase at the time associated with the desired probe frequency and determine the value directly.

Also, the overall frequency range for the AC input voltage Vin for all the resonators (and also the probe measurement frequency) in the array may be from about 1.0 MHz to 100 GHz (or higher). Other frequencies may be used if desired, provided they meet the functional and performance requirements described herein. The AC input frequency should be set at a value that enables sufficient number of cycles (or periods) of the input frequency to allow the impedance of the cell to be adequately sampled. This will be based in part on the speed at which the DNA (or other polymer) is moving through the nanopore. For example, if the DNA is moving through the nanopore at a rate of about 1 MHz (i.e., one million bases every second), and if the AC input frequency is 100 MHz, then the cell impedance will receive (or experience) 100 cycles of the input frequency for each base, which corresponds to a 100:1 "sample" rate. Other input frequencies and sample rates may be used if desired, provided they provide the desired function and performance. For example, the minimum sample frequency required to digitally resolve a given input frequency is the Nyquist sample frequency, which is 2× the input frequency. In this case, for a 1 MHz input signal (rate of DNA passage through nanopore), the minimum (or Nyquist) sample rate would be 2 MHz.

Referring to FIG. 56, an example of frequency spectrum graphs of the AC output voltage Vout magnitude and phase 5600, 5620, respectively, are shown, for some embodiments of the present disclosure. In particular, for the AC output voltage signal Vout, there are three magnitudes lines 5602, 5604, 5606 shown, corresponding to the frequency responses of NPR1, NPR2, NPR3, respectively. For this example, the probe frequency used is $f_{probe2}$, and there are only two bits, like the example shown in FIG. 52. At the time this output was obtained for this example, NPR1 had the scenario shown in column 5206 at time T3 (FIG. 52), and the corresponding frequency response line 5602 indicates a magnitude of V10 and a phase of Ph6. At the same time, NPR2 had the scenario shown in column 5204 at time T2 (FIG. 52), and the corresponding frequency response line 5604 indicates a magnitude of V9 and a phase of Ph7. Also at the same time, NPR3 had the scenario shown in column 5210 at time T5 (FIG. 52), and the corresponding frequency response line 5606 (FIG. 56) indicates a magnitude of V6 and a phase of Ph10.

In some embodiments, the probe or measurement frequency used may vary based on the resonator frequency response, polymer properties, and other factors such as system noise that may affect the quality of the output signal. In some embodiments, the system may switch between measurement frequencies in real time to ensure the best quality output signal is obtained, or multiple different measurement frequencies may be used to perform error checking or validation of the data read. In that case, the AC input frequency of Vin should include the measurement frequency, e.g., by changing or adjusting accordingly (in synch with the measurement) or having the measurement frequency be part of the continuous AC input frequency components provided.

Referring to FIG. 57, a top level block diagram 5700 is shown for embodiments of the present disclosure. In particular, when the array of resonators (or NPRs) is laid-out on a chip, it may be configured in a 2-Dimensional array of M×N resonators, where there are M rows 5702-5708 and each row having N resonators, all connected in parallel (as shown by lines 5716) and all NPRs driven by the same AC input voltage Vin 5308 (FIG. 53) on the line 5710 and all NPRs contributing to a common frequency division multiplexed AC output voltage Vout on a line 5712, which may be fed to the amplifier (or pre-amp) 5320 (FIG. 53). In that case, each of the rows 5702-5708 may correspond to a frequency band, such as 100 MHz-199 Mhz (for row 5702), 200 MHz-299 MHz (for row 5704), 300 Mz-399 MHz (for row 5706), and the like for the other rows. Within each of the rows 5702-5708, there may be a plurality of resonators (or NPRs), each shown as a box 5714 with the designation $f_{row,column}$. Each of the NPRs in a given row have a resonator bandwidth $\Delta f_{BW}$ within the frequency band associated with that row, and is separated in frequency from the adjacent NPR by a gap frequency band $\Delta f_{gap}$, to avoid interference or cross-talk between the adjacent resonators, as discussed herein above with FIG. 54.

For example, if the first row at the top 5702 is designated with the frequency band 100 MHz-199 Mhz, the NPRs $f_{1,1}$ to $f_{1,N}$ in that row 5702 would be within this band and be separated from each other by a gap frequency band, as discussed herein above and with FIG. 54. Thus, in this format, the reading system may be viewed as a 2D array of data elements that are individually readable with a single input and output line. Other frequency bands and ranges may be used if desired.

Referring to FIG. 58, a cross-sectional view of a multi-layer chip structure 5800 is shown, including the cell 4800 (FIG. 48A), the inductor L (FIGS. 49A, 53), and the coupling capacitor $C_{CPL}$, and including a top contact 5802, where the input (and output) I/O voltage line may be connected, which may collectively referred to herein as the nanopore-polymer resonator (NPR). Matching components of the cell 4800 (FIG. 48A) are labeled the same in FIG. 58. Above the upper electrode 4818 is a vertical connection 5806 to the center of the chip inductor 5808 (see FIG. 59) L and the other end of the chip inductor 5808 is connected to coupling chip capacitor 5812. The upper side of the chip capacitor 5812 is connected to the I/O contact 5802. 3-D stacking of multiple layers allows for increased packing of the cell 4800 and circuit components which permits close packing of the cells 5804. In particular, referring to FIGS. 48A and 58, the cell 4800. There may also be dielectric layers 5804 that separate each of the functional circuit elements. A plurality of copies of the resonator or NPR structure 5800 may be connected together, in one or two dimensional arrays, to create a "chip" having the NPR arrays discussed herein above, e.g., with FIGS. 53 and 57. Also, the amplifier 5320 (FIG. 53), e.g., a CMOS amp or pre-amp, may be integrated into the chip structure in the output line contact layer 5802 at an appropriate location, e.g., after the last NPR 5800 in the array, via "flip chip" bonding or any other technique that provides the desired function and performance. Also, Referring to FIG. 59, a top view of the inductor L that may be used in the chip 5800 is shown, which may be fabricated using known chip-inductor fabrication techniques, such as lithographic fabrication or other fabrication techniques. As discussed herein, there may also be a DC voltage applied to the electrodes to move or steer the DNA or polymer floating in the chambers to a particular desired chamber. As discussed herein, the AC voltage is applied to all the NPRs 5800 via the I/O contact which may be common to all NPRs and which is fed by the AC input voltage on a line 5812, and the DC voltage may be applied individually to each electrode on a line 5810, with each NPR have its own separate DC voltage input line 5810 to uniquely control the electrode 4818.

Referring to FIGS. 60 and 61, to allow both the AC and DC voltages to drive the same cell, the AC and DC lines may be connected to the structure 5800 using a "bias tee" connection, having a circuit 6000 shown in FIG. 60 and a sample physical chip implementation 6100 shown in FIG. 61. Referring to FIG. 60, the AC RF (high frequency) input signal Vin is coupled to the inductor L through a coupling capacitor Cam (as discussed previously herein) and the DC input may be connected to the same side of the inductor L through a highly resistive wire Rw, which has enough self-inductance to "block" the high frequency AC signals from leaving the circuit via the DC input source path. Alternatively, the resistive wire Rw may be connected to the other side (electrode side) of the inductor L, if desired. However, in that case, the value of the resistive wire Rw would act to dampen the resonance (as another resistor in parallel with the cell capacitance to AC ground).

Referring to FIG. 61, an example of a physical implementation 6100 of the "bias tee" connection is shown, which shows a magnified view of the "bias tee" connection. High frequency AC input signal Vin is capacitively coupled to the inductor L via a transmission line (e.g., the top I/O contact 5802—FIG. 58) with a gap to a second plate 6102 to create the coupling capacitor CCPL which coupled the AC and blocks the DC voltage. Also, the DC input voltage (or DC "steering" voltage) may be connected to the same side of the inductor L through the highly resistive wire Rw, which has enough self-inductance to "block" the high frequency AC signals from leaving the circuit via the DC input source path, as also discussed above with FIG. 60. The result of the "bias tee" connection is that the voltage applied to the inductor L is AC input voltage having a DC bias determined by the DC input voltage.

Referring to FIG. 62, a cross-sectional view of a multi-layer chip structure 6200 is shown, including a cell having three chambers similar to that shown in FIGS. 24, 25, 28, and 29 and described herein, and having two integrated inductors L1A,L1B. In that case, there is an upper (or top) left chamber 6202 with a top left electrode 6210 and a nanopore 6203 (for adding a bit, e.g., "0"), a top right chamber 6204 with a top right electrode 6212 and a nanopore 6205 (for adding a bit, e.g., "1"), and a lower "de-blocking" chamber 6206, common to both top left 6002 and top right 6004 chambers, with a corresponding electrode 6214, which may be connected to ground (e.g., 0 volts). For the three-chamber cell, it can be viewed as having two capacitors in parallel, each having their own impedance which changes with time. In this case, the left inductor L1A is connected to the left top electrode 6210, and the right inductor L1B is connected to the right top electrode 6212.

The remainder of the components and elements may be the same as discussed hereinbefore with the two-chamber cell design. The AC RF I/O input line may be capacitively coupled to the inductor with each DC 6220, 6222 input line coupled by a resistor or resistive wire, using the "bias tee" connection as discussed herein above. If the inductors L1A, L1B have different values, the left and right chambers will have different resonant frequencies and different resonant bandwidths. In that case, each three-chamber cell would have two resonators with two resonant bandwidths, that may be positioned in the frequency space to be interrogated or monitored to read the data on the polymer (or DNA) as discussed herein above. If the inductors L1A, L1B have the same values, the DNA can still be read for each chamber because the system can only read one chamber at a time, as there is only one polymer (or DNA) strand per cell. So it is inherently time sequenced or time dependent, and thus they do not need to be separated in frequency to accomplish the data reading. However, it may be desirable to separate them to ensure (or validate) the correct chamber is actually being read.

Referring to FIG. 63, a cross-sectional view of a multi-layer chip structure 6300 is shown, including a three-chamber cell having similar to that shown in FIG. 62, having a single integrated inductor L1A. In some embodiments, depending on the data read and write protocol, it may be desirable to use only one cell, e.g., the top left cell 6002, to read the polymer data, and the other cell, e.g., 6004, may be not be configured for reading, and thus does not have an inductor and does not form a resonator. In that case, the AC input voltage Vin and the DC steering voltage, may be coupled to the inductor L1A using the "bias tee" connection, as described herein above with other embodiments, to drive the left top electrode 6210, the DC steering voltage coming in on line 6302, and for the right top electrode 6212, the DC steering input voltage may be connected directly as shown by a line 6304. The rest of the components and elements may be the same as discussed hereinbefore with FIG. 62 for the three-chamber cell design.

Referring to FIGS. 64 and 64A, instead of having the inductor attached to one or two of the top electrodes, a single integrated inductor L1 may be connected to the bottom electrode 6214 and the top electrodes 6210,6212 are connected individually to the respective DC steering voltage for that electrode on lines 6410,6412, respectively. In that case, there would be "bias tee"-type connection at the top and bottom of the circuit (see FIG. 64A). In that case, the AC RF input voltage may be provided to the bottom electrode, which may be AC coupled to the inductor L1 via a coupling capacitor $C_{CPL}$ and a coupling capacitor at the top couples the AC to AC RF ground. The DC lines 6410, 6412 (FIG. 64), are each coupled through Rw (FIG. 64A) to their respective electrode, and the DC is passed through the cell and inductor and through a bottom Rw to DC ground. The bottom contact may act as the AC rf I/O line, and the top contact 4610 may act as the DC I/O line. Also, the DC ground could also be a DC input line, the only requirement is to define the DC potential difference between the top and bottom electrodes. With a common inductor L1, the DNA can still be read for each chamber because the system can only read one chamber at a time, as there is only one polymer (or DNA) strand (or memory string, as discussed herein) per cell (as discussed above). Thus, it is inherently time sequenced or time dependent. Referring to FIGS. 63, 63A, and 63B, in some embodiments, instead of using a unique inductor L for each resonator (such as is shown in FIG. 63) to set unique resonance frequency and frequency bandwidth, a single common inductor $L_{common}$ may be used for all resonators in the array and a unique capacitor $C_R$ may be provided in parallel to each cell having a value that sets the resonant frequency of each resonator. In that case, the memory chip may have a built-in fixed chip resonator capacitor $C_R$ from the top electrode to the bottom electrode for each chamber being measured to set the resonance frequency with the common inductor for each cell. As the polymer moves through the nanopore 6203, 6205, and the capacitance of the cell changes, this capacitance change would adjust the overall parallel capacitance combination and adjust the resonance frequency accordingly. Like the case with the unique inductors L, the value of the fixed resonance capacitor $C_R$ would be set to provide a unique resonance frequency response for each resonator in the resonator array. As discussed for the inductor embodiment herein above, there may only need to be one capacitor (one resonator) that performs the measurement, or if two are used, they may be the same value (due to inherent time sequencing as discussed above), or may be different values if desired for validation, redundancy or other purposes. FIG. 63A shows an example of an equivalent circuit diagram for several cells with fixed resonance capacitors $C_{R1}$, $C_{R2}$, $C_{R3}$, and a common inductor $L_{common}$.

Referring to FIGS. 64, 64B, 64C, in some embodiments, instead of using a unique inductor L on the bottom of each resonator (such as is shown in FIG. 64) to set unique resonance frequency and frequency bandwidth, a single common bottom inductor $L_{common}$ may be used for all resonators in the array and a unique capacitor $C_R$ may be provided in parallel to each cell having a value that sets the resonant frequency of each resonator. a similar variation using a fixed may be done for the inductor at the bottom, where resonance capacitors $C_{R1}$, $C_{R2}$, $C_{R3}$, and a common inductor $L_{common}$ may be used. In that case, the memory chip may have a built-in fixed chip resonator capacitor $C_R$ (FIG. 64C) from the top electrode to the bottom electrode for each chamber being measured to set the resonance frequency with the common inductor $L_{common}$ for each cell.

The present disclosure does not require the cells to be individually addressable to read the data in each of the cells. Also, the present disclosure allows the reading of data stored on polymers located in each of the cells by using a single source input line and single output line, using frequency division multiplexing. Further, the data reading technique of the present invention will work with any type of nanopore, e.g., solid state, protein-based, or any other type of nanopore. In addition, the system and method of the present disclosure uses high rf frequencies to read the memory string (or DNA or polymer), e.g., about 1 MH-100 GHz (or higher), which substantially eliminates the 1/f noise, so the system will likely have higher sensitivity (or granularity or fidelity) than systems not using such a high frequency measurement approach. In addition, using such a high frequency approach also provides a fast time scale for reading (or sampling) the memory string as it passes through the nanopore, thereby not requiring the string to be intentionally slowed down for sampling or measurement purposes.

In some embodiments, the invention provides a nanochip for sequencing an electrically charged polymer, e.g., DNA, comprising at least two distinct monomers, the nanochip comprising at least a first and second reaction chambers, each comprising electrolytic medium, and separated by a membrane comprising one or more nanopores, wherein a pair of electrodes (for example in the form of opposing plates), connected in circuit, is disposed on either side of the membrane comprising one or more nanopores, the electrodes being separated by a distance of 1-30 microns, e.g., about 10 microns, such that the gap between the electrodes has a capacitance when a radiofrequency pulsating direct current, e.g. about 1 MHz to 100 GHz (or higher), is applied to the electrodes so as to draw the electrically charged polymer through the nanopore, e.g., from one chamber to the next, and such that the phase of the pulsating direct radiofrequency current changes with changes in capacitance as the electrically charged polymer passes through the nanopore, thereby allowing detection of the monomer sequence of the electrically charged polymer. In certain embodiments, the nanochip comprises multiple sets of reaction chambers wherein the reaction chambers within a set are separated by membrane having one or more nanopores, and the sets of reaction chambers are separated by a screening layer to minimize electrical interference between the sets of reaction chambers and/or to separate multiple linear polymers and allow them to be sequenced in parallel.

For example, in one embodiment the electrodes form the top and bottom plates of a capacitor embedded in a resonant circuit, and the change in capacitance is measured as the DNA passes through the pore between the plates.

In certain embodiments, the nanochip further comprises reagents for synthesizing the polymer, e.g. DNA, e.g., according to any of Nanochip 1, et seq., below.

In one embodiment, therefore the invention provides a method (Method 1) for synthesizing a charged polymer [e.g., a nucleic acid (e.g., DNA or RNA)] comprising at least two distinct monomers in a nanochip, e.g., a nanopore-based device, e.g., any of Nanochip 1, et seq., the nanochip comprising
   one or more addition chambers containing reagents for addition of one or more monomers [e.g. nucleotides] or oligomers [e.g., oligonucleotides] to the charged polymer in a buffer solution in terminal protected form, such that only a single monomer or oligomer can be added in one reaction cycle; and
   one or more reserve chambers containing buffer solution but not all reagents necessary for addition of the one or more monomers or oligomers,
   wherein the chambers are separated by one or more membranes comprising one or more nanopores and
   wherein the charged polymer can pass through the nanopore but the least one of the reagents for addition of one or more monomers or oligomers cannot,
   the method comprising
   a) moving the first end of a charged polymer having a first end and a second end, by electrical attraction, into an addition chamber, whereby monomers or oligomers are added to said first end in blocked form,
   b) moving the first end of the charged polymer with the added monomer or oligomer in blocked form into a reserve chamber,
   c) deblocking the added monomer or oligomer, and
   d) repeating steps a-c, wherein the monomers or oligomers added in step a) are the same or different, until the desired polymer sequence is obtained.

For example, the invention provides
   1.1. Method 1, wherein the polymer is nucleic acid, e.g., wherein the polymer is DNA or RNA, e.g., wherein it is DNA, e.g dsDNA or ssDNA.
   1.2. Any foregoing method wherein the second end of the polymer, e.g. the nucleic acid, is either protected or bound to a substrate adjacent to the nanopore.
   1.3. Any foregoing method wherein the electrical attraction is provided by applying an electric potential between the electrodes in each chamber, wherein the polarity and current flow between the electrodes can be controlled, e.g., such that the nucleic acid is attracted to a positive electrode.

1.4. Any foregoing method wherein the polymer is a nucleic acid and
   (i) the said first end of the nucleic acid is the 3'-end, the addition of nucleotides is in the 5' to 3' direction and is catalyzed by a polymerase, e.g., wherein the polymerase is hindered (e.g. due to its size or due to being tethered to a substrate in the first chamber) from passing through the nanopore, the nucleotides are 3'-protected when added, and following addition of the 3'-protected nucleotide to the 3'-end of the nucleic acid, the 3'-protecting group on the nucleic acid is removed, e.g., in the reserve chamber; or
   (ii) the said first end of the nucleic acid is the 5' end, the addition of nucleotides is in the 3' to 5' direction, the nucleotides are 5'-protected when added, and following addition of the 5'-protected nucleotide to the 5'-end of the nucleic acid, the 5'protecting group is removed, e.g., in the second chamber; (for example wherein the phosphate on the 5'-protected nucleotide is a nucleoside phosphoramidite coupled via the 5'-protecting group to a bulky group which cannot pass through the nanopore, so that following coupling to the nucleic acid, the unreacted nucleotides are flushed away, the bulky 5'-protecting group is cleaved from the nucleic acid, and flushed away, and the 5'-end of the nucleic acid can be moved into the reserve chamber);
   wherein the addition of nucleotides to the nucleic acid is controlled by movement of the first end of the nucleic acid into and out of the one or more addition chambers, and the cycle is continued until the desired sequence is obtained.

1.5. Any foregoing method wherein the sequence of monomers or oligomers in the polymer [e.g., the sequence of nucleotides in the nucleic acid] thus synthesized corresponds to a binary code.

1.6. Any foregoing method wherein the polymer thus synthesized is single stranded DNA.

1.7. Any foregoing method wherein the sequence of the polymer [e.g. the nucleic acid] is checked during the process or synthesis by sequencing the monomers or oligomers [e.g., nucleotide bases] as they pass through the nanopore to identify errors in sequencing.

1.8. Any foregoing method wherein the polymer thus synthesized is single stranded DNA, wherein at least 95%, e.g at least 99%, e.g., substantially all of the bases in the sequence are selected from two bases that do not hybridize with other bases in the strand, e.g. bases selected from adenine and cytosine.

1.9. Any foregoing method wherein a multiplicity of polymers [e.g. oligonucleotides] are synthesized independently in parallel, such that polymers [oligonucleotides] having different sequences are obtained by separately controlling whether they are present in one or more addition chambers or one or more reserve chambers.

1.10. Any foregoing method wherein there are at least two addition chambers that contain reagents suitable for adding different monomers or oligomers, e.g. different nucleotides, e.g., wherein there are one or more addition chambers containing reagents suitable for adding a first monomer or oligomer and one or more addition chambers containing reagents suitable for adding a second different monomer or oligomer, for example wherein there are one or more addition chambers containing reagents suitable for adding adenine nucleotides and one or more addition chambers containing reagents suitable for adding cytosine nucleotides.

1.11. Any foregoing method wherein at least one addition chamber is a flow chamber, providing a flow cycle comprising (i) providing to the flow chamber reagents suitable for adding a first monomer or oligomer, (ii) flushing, (iii) providing to the flow chamber reagents suitable for adding a second different monomer or oligomer, and (iv) flushing, and repeating the cycle, until the synthesis is complete, wherein the sequence of monomers or oligomers in the polymer is controlled by introducing or excluding the first end of the polymer from the flow chamber during step (i) or (iii) in each cycle;

1.12. Any foregoing method wherein the polymer is DNA and at least one addition chamber is a flow chamber, providing a flow cycle comprising (i) providing to the flow chamber reagents suitable for adding a first type of nucleotide, (ii) flushing, (iii) providing to the flow chamber reagents suitable for adding a second type of nucleotide, and (iv) flushing, and repeating the cycle until the synthesis is complete, wherein the sequence is controlled by controlling the presence or absence of the first end of the DNA (e.g. the 3'-end) in the flow chamber.

1.13. Any foregoing method wherein the polymer is DNA and at least one addition chamber is a flow chamber, providing a flow cycle comprising (i) providing to the flow chamber reagents suitable for adding a first type of nucleotide, (ii) flushing, (iii) providing to the flow chamber reagents suitable for adding a second type of nucleotide, and (iv) flushing, (i) providing to the flow chamber reagents suitable for adding a third type of nucleotide, (ii) flushing, (iii) providing to the flow chamber reagents suitable for adding a fourth type of nucleotide, and (iv) flushing, and repeating the cycle until the synthesis is complete, wherein the sequence is controlled by controlling the presence or absence of the first end of the DNA (e.g. the 3'-end) in the flow chamber when reagents suitable for adding the different types of nucleotides are present.

1.14. Any foregoing method wherein the polymer is DNA and the nanochip comprises two addition chambers which are flow chambers, (a) the first flow chamber providing a flow cycle comprising (i) providing to the first flow chamber reagents suitable for adding a first type of nucleotide, (ii) flushing, (iii) providing to the first flow chamber reagents suitable for adding a second different type of nucleotide, and (iv) flushing, and repeating the cycle until the synthesis is complete, and (b) the second flow chamber providing a flow cycle comprising (i) providing to the second flow chamber reagents suitable for adding a third type of nucleotide, (ii) flushing, (iii) providing to the second flow chamber reagents suitable for adding a fourth different type of nucleotide, and (iv) flushing, and repeating the cycle until the synthesis is complete, wherein the nucleotides are selected from dATP, dTTP, dCTP, and dGTP and wherein the sequence is controlled by directing the first end of the DNA (e.g. the 3'-end) into the flow chamber where the next desired nucleotide is provided.

1.15. Any foregoing method wherein the polymer is DNA and the nanopore chip comprises one or more addition chambers for adding dATP, one or more addition chambers for adding dTTP, one or more addition chambers for adding dCTP, and one or more addition chambers for adding dGTP.

1.16. Any foregoing method wherein the polymers [e.g. nucleic acids] synthesized are each bound via their second end to a surface proximate to a nanopore.

1.17. Any foregoing method wherein the sequence of the polymer [e.g. nucleic acid] is determined following each cycle by detecting the change in electric potential, current, resistance, capacitance, and/or impedance as the polymer passes through the nanopore.

1.18. Any foregoing method wherein the polymer is a nucleic acid and synthesis of the nucleic acid takes place in a buffer solution, e.g., a solution comprising a buffer for pH 7-8.5, e.g. ca. pH 8, e,g, a buffer comprising tris(hydroxymethyl)aminomethane (Tris), a suitable acid, and optionally a chelator, e.g., ethylenediaminetetraacetic acid (EDTA), for example TAE buffer containing a mixture of Tris base, acetic acid and EDTA or TBE buffer comprising a mixture of Tris base, boric acid and EDTA; for example a solution comprising 10 mM Tris pH 8, 1 mM EDTA, 150 mM KCl, or for example, 50 mM Potassium Acetate, 20 mM Tris-acetate, 10 mM Magnesium Acetate, pH 7.9 @ 25° C.

1.19. Any foregoing method wherein the polymer is single stranded DNA further comprising converting the synthesized single stranded DNA into double stranded DNA.

1.20. Any foregoing method further comprising removing the polymer [e.g. the nucleic acid] from the nanochip after the polymer synthesis is complete.

1.21. Any foregoing method wherein the polymer is a nucleic acid, further comprising amplifying and retrieving copies of synthesized nucleic acid using an appropriate primer and a polymerase (e.g. Phi29).

1.22. Any foregoing method wherein the polymer is a nucleic acid, further comprising cleaving the synthesized nucleic acid with a restriction enzyme and removing the the nucleic acid from the nanochip.

1.23. Any foregoing method wherein the polymer is a nucleic acid, further comprising amplifying the nucleic acid thus synthesized.

1.24. Any foregoing method further comprising removing the polymer [e.g., the nucleic acid] from the nanochip and crystallizing the polymer.

1.25. Any foregoing method wherein the polymer is a nucleic acid, further comprising stabilizing the nucleic acid, e.g., by drying a solution comprising the nucleic acid together with one or more of a buffer (e.g., a borate buffer), an antioxidant, a humectant, e.g. a polyol, and optionally a chelator, for example as described in U.S. Pat. No. 8,283,165 B2, incorporated herein by reference; or by forming a matrix between the nucleic acid and a polymer, such as poly(ethylene glycol)-poly(l-lysine) (PEG-PLL) AB type block copolymer; or by addition of a complementary nucleic acid strand or a protein that binds the DNA.

1.26. Any foregoing method comprising:
(i) reacting a nucleic acid with a 3'-protected nucleotide in an addition chamber, in the presence of a polymerase which catalyzes the addition of the 3'-protected nucleotide to the 3' end of the nucleic acid;
(ii) drawing at least the 3' end of the 3'-protected nucleic acid thus obtained out of the addition chamber, through the at least one nanopore, into a reserve chamber, wherein the polymerase is hindered (e.g. due to its size or due to being tethered to a substrate in the first chamber) from passing through the nanopore;
(iii) deprotecting the 3'-protected nucleic acid, e.g., chemically or enzymatically; and
(iv) if it is desired that an additional 3'-protected dNTP be added to the oligonucleotide, drawing the 3' end of the oligonucleotide into the same or different addition chamber, so that steps (i)-(iii) are repeated, or if it is not so desired, allowing the 3' end of the nucleic acid to remain in the reserve chamber until a further cycle wherein the desired 3'-protected dNTP is provided to the addition chamber; and
(v) repeating the cycle of steps (i)-(iv) until the desired nucleic acid sequence is obtained.

1.27. Any foregoing method wherein the polymer is nucleic acid single-stranded DNA (ssDNA) and the one or more nanopores have a diameter allowing ssDNA to pass but not double stranded DNA (dsDNA), e.g., a diameter of about 2 nm.

1.28. Any foregoing method wherein the monomer is a 3'-protected nucleotide, e.g., deoxynucleotide triphosphate (dNTP), e.g. selected from deoxyadenosine triphosphate (dATP), deoxyguanosine triphosphate (dGTP), deoxycytidine triphosphate (dCTP), deoxy-thymidine triphosphate (dTTP), for example dATP or dCTP.

1.29. Any foregoing method wherein the polymer is a nucleic acid and the addition of the nucleotide to the nucleic acid is catalyzed by a polymerase, e.g., a template independent polymerase, e.g., terminal deoxy-nucleotidyl transferase (TdT), or polynucleotide phosphorylase, e.g., wherein the polymerase catalyzes the incorporation of a deoxynucleotide at the 3'-hydroxyl terminus of DNA.

1.30. Any foregoing method wherein the membrane contains a multiplicity of nanopores and a multiplicity of polymers each bound to a surface proximate to a nanopore, e.g., a multiplicity of nucleic acids each bound via their 5' end to a surface proximate to a nanopore.

1.31. Any foregoing method wherein a multiplicity of polymers each bound to a surface proximate to a nanopore, e.g., a multiplicity of nucleic acids each bound at the 5' end to a surface proximate to a nanopore, are synthesized independently, wherein each nanopore has an associated pair of electrodes, wherein one electrode in the pair is located proximate to one end of the nanopore and the other electrode located proximate to the other end of the nanopore, such that each polymer can be independently moved between the first and second chamber by current provided by the pair of electrodes.

1.32. Any foregoing method wherein the polymer is a 3'-protected nucleic acid bound at the 5' end to a surface proximate to a nanopore and the 3' end of the 3'-protected nucleic acid is drawn through the nanopore by using an electrical force, e.g., by using an electrical force applied from an electrode in an adjacent chamber.

1.33. Method 1.20 wherein the new 3'-protected dNTP is the same or different from the first 3'-protected dNTP.

1.34. Method 1.20 wherein the 3'-protected dNTP used in step (i) of the cycle alternates with each cycle between 3'-protected dATP and 3'-protected dCTP.

1.35. Any foregoing method wherein the polymer is a nucleic acid and deprotection of the nucleic acid is carried out by an enzyme that removes a 3'-protecting group on ssDNA but not on a 3'protected dNTP.

1.36. Any foregoing method further comprising the step of detecting the sequence of the polymer as it passes through a nanopore to confirm that the desired sequence has been synthesized.

1.37. Any foregoing method comprising the step of detecting the sequence of the polymer as it passes through a nanopore to confirm that the desired sequence has been synthesized by measuring the measuring the capacitive variance in a resonant RF circuit as the DNA is drawn through the nanopore.

1.38. Any foregoing method wherein the reagents for addition of one or more monomers or oligomers to the charged polymer comprise reagents selected from a topoisomerase, a DNA polymerase, or combinations thereof.

1.39. Any foregoing method wherein the addition of one or more monomers or oligomers to the charged polymer is carried out according to any of Method 2, et seq or Method A et seq.

For example, the invention provides a method for synthesizing a nucleic acid in a nanochip, comprising at least a first chamber and a second chamber separated by a membrane comprising at least one nanopore, the synthesis being carried out in a buffer solution by a cycle of nucleotide addition to a first end of a nucleic acid having a first end and a second end, wherein the first end of the nucleic acid is moved by electrical attraction between one or more addition chambers (which contains reagents capable of adding nucleotides) and one or more reserve chambers (which do not contain reagents necessary to add nucleotides), the chambers being separated by one or more membranes each comprising one or more nanopores, wherein the nanopore is large enough to permit passage of the nucleic acid but is too small to permit passage of at least one reagent essential for adding a nucleotide, e.g, wherein the method corresponds to any of Method 1, et seq.

For example, Method 1A, which is a method, e.g., according to any of Method 1, et seq., for synthesizing a charged polymer comprising at least two distinct monomers or oligomers in a nanopore-based device, the nanopore-based device comprising one or more addition chambers or channels containing buffer solution and reagents for addition of one or more monomers or oligomers to the charged polymer in blocked form, such that only a single monomer or oligomer can be added in one reaction cycle; and one or more deblocking chambers or channels containing buffer solution and deblocking reagents for removing the blocker group from the one or more monomers or oligomers added to the charged polymer in blocked form, wherein the addition chambers or channels are separated from the deblocking chambers by one or more membranes comprising one or more nanopores, and wherein the charged polymer can pass through a nanopore and at least one of the reagents for addition of one or more monomers or oligomers cannot pass through a nanopore, and at least one of the deblocking reagents cannot pass through a nanopore, the method comprising a. moving the first end of a charged polymer having a first end and a second end, by electrical attraction, into an addition chamber or channel, whereby monomers or oligomers are added to said first end in blocked form, b. moving the first end of the charged polymer with the added monomer or oligomer in blocked form into a reserve chamber, whereby the blocking group on the added monomer or oligomer is removed, and c. repeating steps a and b, wherein the monomers or oligomers added in step a) are the same or different, until the desired polymer sequence is obtained;

e.g., wherein the device comprises one or more first addition chambers or channels containing reagents suitable for adding a first type of monomer or oligomer and one or more second addition chambers containing reagents suitable for adding a second different type of monomer or oligomer, and wherein in step a, the first end of the charged polymer is moved into either the first addition chamber or the second addition chamber, depending on whether it is desired to add a first type of monomer or oligomer or a second different type of monomer or oligomer.

In certain embodiments, the sequence of the polymer corresponds to a binary code, for example where the polymer is a nucleic acid and the sequence corresponds to a binary code, where each bit (0 or 1) is represented by a base, e.g. A or C.

In certain embodiments, the polymer is DNA.

In certain other embodiments, each bit is represented by a short sequence of monomers rather than by a single monomer. For example, in one such embodiment, blocks of DNA are synthesized, where each block generates a unique signal via the nanopore and corresponds to a zero or a one. This embodiment has certain advantages in that single nucleotides are more difficult to detect in nanopores, especially solid-state nanopores, so using blocks is less prone to reading errors, although the information density in the polymer is correspondingly reduced.

For example, blocks of (double stranded) nucleotides can be added, using site-specific recombinases, i.e., enzymes that spontaneously recognize and cleave at least one strand of a double strand of nucleic acids within a sequence segment known as the site-specific recombination sequence. In one such embodiment, the site specific recombinase is a topoisomerase used to ligate a topo-conjugated dsDNA oligonucleotide block to the sequence. These oligonucleotides themselves will not have a structure compatible with further ligation until they are cleaved with a restriction enzyme. Vaccinia virus topoisomerase I specifically recognises DNA sequence 5'-(C/T)CCTT-3'. The topoisomerase binds to double-stranded DNA and cleaves it at the 5'-(C/T)CCTT-3' cleavage site. Note that the cleavage is not complete, as the topoisomerase only cleaves the DNA on one strand (although having a nearby nick on the other strand does cause a double-strand break of sorts), and when it cleaves, the topoisomerase attaches covalently to the 3' phosphate of the 3' nucleotide. The enzyme then remains covalently bound to the 3' end of the DNA, and can either religate the covalently held strand at the same bond as originally cleaved (as occurs during DNA relaxation), or it can religate to a heterologous acceptor DNA having compatible overhangs, creating a recombinant molecule. In this embodiment, we create dsDNA donor oligonucleotides (e.g., comprising one of at least two different sequences, one for '0' and the other for '1') flanked by a topoisomerase recombination site and a restriction site that generates a topoisomerase ligation site. The cassettes are Topo-charged; that is, they are covalently bound to a topoisomerase, which will bind them to a topoisomerase ligation site on the receiver oligonucleotide. When the growing DNA chain of the receiver is cleaved with a restriction enzyme it becomes capable of ligation to a Topo-charged cassette. So, one just needs to cycle the growing DNA from restriction enzyme to Topo-charged cassette successively, with each cycle adding another donor oligonucleotide. A related approach has been described for cloning, see, e.g., Shuman S., *Novel approach to molecular cloning and polynucleotide synthesis using vaccinia DNA topoisomerase*. J Biol Chem. (1994); 269(51): 32678-84, the contents of which are incorporated by reference.

Single bases can be added using a similar strategy. In the presence of a suitable single stranded 'deprotected' 'acceptor' DNA, the topo-charged DNA is enzymatically and covalently ligated ('added') to the acceptor by the topoisomerase, which in the process becomes removed from the DNA. A type IIS restriction enzyme can then cleave all of the added DNA with the exception of a single base (the base which is being 'added'). This process of deprotect-add can be repeated to add additional bases (bits). As demonstrated in the examples herein, it is feasible to use a Topo/TypeIIS restriction enzyme combination to add a single nucleotide to the 5' end of a target single stranded DNA. The use of a TypeIIS restriction enzyme enables cleavage of DNA in a location different from that of the recognition sequence (other TypeIIS restriction enzymes can be found at https://www.neb.com/tools-and-resources/selectioncharts/type-iis-restriction-enzymes). The use of inosines (which act as 'universal bases' and pair with any other base) in this system allows this reaction to occur without any specific sequence requirements in the target DNA. The identity of the nucleotide added to the single strand target DNA is the 3' nucleotide to which vaccinia topoisomerase conjugates via the 3' phosphate. Since the recognition sequence of vaccinia topoisomerase is (C/T)CCTT, we have used this system to add a 'T' to the target DNA. There is a related topoisomerase, SVF, that can use the recognition sequence CCCTG (https://www.ncbi.nlm.nih.gov/pubmed/8661446). Thus SVF can be used to add a 'G' instead of a 'T'. Paired with vaccinia topo, binary data can be encoded in T's and G's.

In another approach to single base addition, a 5'phosphate provides a blocking group to provide single base addition in the 3' to 5' direction. The charging reaction charges the topoisomerase with a single T (or G, or other nucleotide as desired), having a 5' phosphate group. When the charged topoisomerase 'sees' a free 5' unblocked (unphosphorylated) single stranded DNA chain it will add the T to that chain, providing a DNA with a T added to the 5'. This addition is facilitated by the presence of an adapter DNA having sequences to which the topoisomerase and the single stranded acceptor DNA can bind. (Note that the adapter DNA is catalytic—it can be reused as a template in repeated reactions.) The added nucleotide has a 5' phosphate on it, so it won't be a substrate for further addition until it is exposed to a phosphatase, which removes the 5' phosphate. The process is repeated, using vaccinia topoisomerase to add a single "T" to the 5' end of a target single stranded DNA and SVF topoisomerase to add a single 'G', thus allowing construction of a sequence encoding binary information with T and G. Other topoisomerases can be used to add A's or C's, although this reaction is less efficient.

When the topoisomerase is charged, there is a mix of charged and uncharged product, which represents an equilibrium between the two species. The 'overhang' that the topoisomerase leaves can be designed in many ways, to optimize the efficiency of the reaction. Overhangs that are rich in GC tend to have faster charging reactions, but have charging equilibriums that tend to generate lower yield of product. We have found that having some base mismatches (or using inosines) instead of the 'proper' pairs decreases the 'reverse' reaction and improves yield. Also, performing the reaction in the presence of polynucleotide kinase (plus ATP) improves yield by phosphorylating the reaction 'byproduct' which decreases the reverse reaction rate. In certain embodiments, the topoisomerase enzymes can be "bulked up" by adding additional amino acid sequences that do not impair function, so as to ensure that they are large enough that they cannot pass through the nanopore.

One advantage of using a topoisomerase-mediated strategy is that the monomer is covalently attached to the topoisomerase, and therefore cannot "escape" to interfere with other reactions. When polymerase is used, the monomers can diffuse so the polymerases and/or the deblocking agents should be specific (e.g. selective for A vs C, for example) or alternatively, the monomers are provided by a flow so they don't have a chance to mix.

In one aspect, the invention provides a topoisomerase charged with a single nucleotide, i.e., a topoisomerase conjugated to a single nucleotide, e.g., wherein the topoisomerase is conjugated via the 3'-phosphate of the nucleotide, and the nucleotide is protected, e.g., phosphorylated, at the 5'-position.

In another aspect the invention provides a method (Method A) of synthesizing a DNA molecule using topoisomerase-mediated ligation, by adding single nucleotides or oligomers to a DNA strand in the 3' to 5' direction, comprising (i) reacting a DNA molecule with a topoisomerase charged with the desired nucleotide or oligomer wherein the nucleotide or oligomer is blocked from further addition at the 5' end, then (ii) deblocking the 5' end of the DNA thus formed, and repeating steps (i) and (ii) until the desired nucleotide sequence is obtained, e.g., A1.1. Method A which is a method of synthesizing a DNA molecule by adding single nucleotides in the 3' to 5' direction comprising (i) reacting a DNA molecule with a topoisomerase charged with the desired nucleotide in 5'protected form, e.g., 5'phosphorylated form, such that the desired nucleotide in 5'protected form is added to the 5' end of the DNA, then (ii) deprotecting the 5' end of the DNA thus formed through the use of a phosphatase enzyme, and repeating steps (i) and (ii) until the desired nucleotide sequence is obtained; or A1.2. Method A which is a method of synthesizing a DNA molecule by adding oligomers in the 3' to 5' direction comprising (i) reacting a DNA molecule with a topoisomerase charged with the desired oligomer, thereby ligating the oligomer to the DNA molecule, then (ii) using a restriction enzyme to provide a 5' site for a topoisomerase-mediated ligation for another oligomer, and repeating steps (i) and (ii) until the desired oligimer sequence is obtained.

A1.3. Any foregoing method comprising providing ligase and ATP to seal nicks in the DNA [NB: the topoisomerase ligation only ligates one strand].

A1.4. Any foregoing method wherein the topoisomerase-charged donor oligonucleotide comprises a 5' overhang on the strand complementary to the strand bearing the topoisomerase, comprising a polyinosine sequence [NB: inosines act as 'universal bases' and pair with any other base].

A1.5. Any foregoing method wherein the restriction enzyme is a type IIS restriction enzyme which can cleave all of the added DNA with the exception of a single base (the base which is being 'added').

A1.6. Any foregoing method wherein the topoisomerase is selected from vaccinia topoisomerase and SVF topoisomerase I.

A1.7. Any foregoing method wherein vaccinia topoisomerase (which recognizes (C/T)CCTT) is used to add dTTP nucleotides and SVF topoisomerase I (which recognizes CCCTG) is used to add dGTP nucleotides, e.g., to provide binary code A1.8. Any foregoing method wherein the DNA is double stranded and the reserve chamber further comprises a ligase and ATP, to repair the DNA strand not joined by the topoisomerase.

A1.9. Any foregoing method comprising use of a topoisomerase inhibitor to suppress binding and activity of free topoisomerase to the DNA oligomer, e.g., wherein the inhibitors is selected from novobiocin and coumermycin.

A1.10. Any foregoing method wherein the DNA strand thus provided has a sequence comprising thymidine (T) nucleosides and deoxyguanisine (G) nucleosides.

A1.11. Any foregoing method wherein the topoisomerase adds a single base, but the restriction enzyme cleaves at a position which is one nucleotide in the 5' direction from the base added by topoisomerase.

A1.12. Any foregoing method wherein the DNA strand thus provided has a sequence comprising a sequence of 'TT' and 'TG' dinucleotides.

A1.13. Any foregoing method wherein the DNA is single stranded, A1.14. Any foregoing method wherein the DNA double stranded.

A1.15. Any foregoing method wherein the DNA is on a substrate or magnetic bead, where it can be selectively exposed to or removed from the reagents as required to provide the desired sequence.

A1.16. Any foregoing method wherein some or all of the reagents for adding or deblocking the DNA are supplied by flow and removed by flushing.

A1.17. Any foregoing method wherein the attachment of the single nucleotides or oligomers to a single-stranded DNA is facilitated by the presence of an adapter DNA having sequences to which the topoisomerase and the single stranded acceptor DNA can bind.

A1.18. Any foregoing method carried out in a system where a nanopore separates a chamber comprising the topoisomerase from a chamber comprising the phosphatase or restriction enzyme, wherein the nanopore allows movement of the DNA by electrical attraction, but not the enzymes, e.g. as described in any of Method 2, et seq.

One possible concern is poly-G sequences may form G-quartet secondary structures. By moving the restriction enzyme back one base (to the 5' of the topo sequence) and following a similar Topo/IIS strategy a 'TT' or 'TG' can be added, each of which can represent a different bit. While this would require 2 bases to encode a bit, it has the advantage of avoiding poly-G sequences. In other embodiments, other bases in the 3' end of the topo recognition sequence—although less efficient than (C/T)CCTT, can allow conjugation using poxvirus topoisomerase with (C/T)CCTA, (C/T)CCTC and (C/T)CCTG (https://www.ncbi.nlm.nih.gov/pubmed/17462694). Protein engineering/selection techniques can be used to improve the efficiency of these reactions as well, and similar approaches can be used to add non-canonical bases.

In certain embodiments, the method of synthesizing DNA by this method includes treating the DNA with a ligase and ATP. The topoisomerase only joins together one side of the DNA (the other is essentially nicked). The ligase would repair the nick and ensure that the topoisomerase itself doesn't recut the reaction product and cleave it.

In certain embodiments, the method comprises using a topoisomerase inhibitor to suppress binding and activity of free topoisomerase to the DNA oligomer. Suitable inhibitors include novobiocin and coumermycin. Note that complete inhibition is not desirable, as a low level of topoisomerase activity can help 'relax' coiled DNA, which is useful especially when synthesizing long DNA chains.

Thus, in another embodiment, the disclosure provides a method (Method 2) for synthesizing DNA in a nanochip, comprising one or more addition chambers containing a topoisomerase-charged oligonucleotide (i.e. oligonucleotide bound at the 3' end to a topoisomerase), and one or more reserve chambers comprising a restriction enzyme or deblocker, e.g., phosphatase, said chambers also containing compatible buffer solution and being separated by a membrane comprising at least one nanopore, wherein the topoisomerase and the restriction enzyme are prevented from passing through the nanopore (e.g. because they are too large and/or because they are tethered to a substrate in the first and second chambers respectively), the synthesis being carried out by a cycle of adding single nucleotides or short oligonucleotide blocks to a first end of a nucleic acid having a first end and a second end, wherein the first end of the nucleic acid is moved by electrical attraction between an addition chambers and a reserve chamber, for example in one embodiment as follows:

(i) moving the 5' end of a receiver DNA (e.g., a double-stranded DNA) into a first addition chamber, by means of an electrical force, (ii) providing in the first addition chamber a topoisomerase-charged donor oligonucleotide, wherein the donor oligonucleotide comprises a topoisomerase binding site, an informational sequence (e.g., selected from at least two different nucleotides or sequences, e.g., wherein one sequence corresponds to '0' and the other to '1' in a binary code), and a restriction site which when cleaved by a restriction enzyme will yield a topoisomerase ligation site;

(iii) allowing sufficient time for the donor olignucleotide to ligate to and thereby extend the receiver DNA;

(iv) moving the 5' end of the receiver DNA thus extended into the reserve chamber, by means of an electrical force, e.g., so that the restriction enzyme cleaves the receiver DNA to provide a topoisomerase ligation site, or in the case of single nucleotide addition, the deblocker, e.g., phosphatase, generates a 5' unblocked nucleotide on the single stranded DNA; and (v) repeating the cycle of steps (i)-(iv), adding oligonucleotides having the same or different informational sequence, until the desired DNA sequence or sequences are obtained.

For example, the invention provides 2.1. Method 2 wherein the 3' end of the receiver DNA is attached proximate to a nanopore and the 5'end of the receiver oligonucleotide comprises a topoisomerase ligation site, and comprising a step after step (iv) of adding an additional oligonucleotide to the 5' end of the receiver DNA by flushing the first addition chamber and providing new topoisomerase-charged donor oligonucleotide to the first addition chamber, wherein the new donor oligonucleotide has a different informational sequence from the previous donor oligonucleotide; and if desired that the new donor oligonucleotide be added to the receiver DNA, drawing the 5' end of the receiver nucleic acid back into the first chamber, and repeating steps (i)-(iii), or if not so desired, allowing the receiver DNA to remain in the second chamber until the desired donor oligonucleotide is provided to the first chamber.

2.2. Any foregoing method wherein a multiplicity of receiver DNA molecules are synthesized independently in parallel, such that DNA molecules having different sequences are obtained by separately controlling whether they are present in the first chamber.

2.3. Any foregoing method wherein a multiplicity of receiver DNA molecules each bound at the 3' end to a surface proximate to a nanopore are synthesized independently, wherein each nanopore has an associated pair of electrodes, wherein one electrode in the pair is located proximate to one end of the nanopore and the other electrode located proximate to the other end of the nanopore, such that each receiver DNA molecule can be independently moved between the first and second chamber by current provided by the pair of electrodes.

2.4. Any foregoing method wherein the donor oligonucleotides used in step (i) of the cycle alternate with each cycle between donor oligonucleotides comprising a first informational sequence and donor oligonucleotides comprising a second informational sequence.

2.5. Method 2 comprising the step of adding an additional oligonucleotide to the 5' end of the receiver DNA by returning the 5' end of the receiver DNA to the first addition chamber to add an oligonucleotide having the same informational sequence or moving the 5' end of the receiver DNA to a second addition chamber to having a donor oligonucleotide bound at the 3' end to a topoisomerase, wherein the donor oligonucleotide in the second addition chamber has a different informational sequence from the donor oligonucleotide in the first addition chamber.

2.6. Any foregoing method wherein the donor oligonucleotide comprises a structure as follows:

```
                                              (SEQ ID NO 1)
5' CGAAGGG <Informational sequence A or B>

GTCGACNNNNN

3' GCTTCCC <----------Complement---------->

CAGCTGNNNNN
``` wherein N refers to any nucleotide and the restriction enzyme is Acc1, which can cut the DNA (e.g. GTCGAC in the above sequence) so as to provide an appropriate overhang.

2.7. Any foregoing method wherein the donor oligonucleotide has a hairpin structure, e.g., 2.6 wherein the NNNNN groups on the top and bottom strands are joined.

2.8. Any foregoing method wherein at least one of the topoisomerase charged oligonucleotides has a structure as follows:

```
                                              (SEQ ID NO 1)
5' CGAAGGG <Informational sequence A or B>

GTCGACNNNNN

3' *TTCCC <---------Complement---------->

CAGCTGNNNNN (* = topoisomerase)
```

2.9. Any foregoing method wherein at least one of the topoisomerase charged oligonucleotides has a structure as follows:

```
5' pCACGTCAGGCGTATCCATCCCTT*

3' GTGCAGTCCGCATAGGTAGGGAAGCGC
```

2.10. The preceding method wherein the topoisomerase charged oligonucleotide 2.11. Any foregoing method wherein the sequence of DNA synthesized is determined following each cycle by detecting the change in electric potential, current, resistance, capacitance and/or impedance as the oligonucleotide passes through the nanopore.

2.12. Any foregoing method wherein the synthesis of the DNA takes place in a buffer solution, e.g., a solution comprising a buffer for pH 7-8.5, e.g. ca. pH 8, e,g, a buffer comprising tris(hydroxymethyl)aminomethane (Tris), a suitable acid, and optionally a chelater, e.g., ethylenediaminetetraacetic acid (EDTA), for example TAE buffer containing a mixture of Tris base, acetic acid and EDTA or TBE buffer comprising a mixture of Tris base, boric acid and EDTA; for example a solution comprising 10 mM Tris pH 8, 1 mM EDTA, 150 mM KCl, or for example, 50 mM Potassium Acetate, 20 mM Tris-acetate, 10 mM Magnesium Acetate, pH 7.9 @ 25° C.

2.13. Any foregoing method further comprising removing the DNA from the nanochip.

2.14. Any foregoing method further comprising amplifying the DNA thus synthesized.

2.15. Any foregoing method further comprising removing the DNA from the nanochip and crystallizing the DNA.

2.16. Any foregoing method further comprising stabilizing the DNA, e.g., by drying a solution comprising the DNA together with one or more of a buffer (e.g., a borate buffer), an antioxidant, a humectant, e.g. a polyol, and optionally a chelator, for example as described in U.S. Pat. No. 8,283,165 B2, incorporated herein by reference, or by forming a matrix between the nucleic acid and a polymer, such as poly(ethylene glycol)-poly(l-lysine) (PEG-PLL) AB type block copolymer.

2.17. Any foregoing method comprising providing ligase and ATP to seal nicks in the DNA [NB: the topoisomerase ligation only ligates one strand].

2.18. Any foregoing method wherein the topoisomerase-charged donor oligonucleotide comprises a 5' overhang on the strand complementary to the strand bearing the topoisomerase, comprising a polyinosine sequence [NB: inosines act as 'universal bases' and pair with any other base].

2.19. Any foregoing method wherein the restriction enzyme is a type IIS restriction enzyme which can cleave all of the added DNA with the exception of a single base (the base which is being 'added').

2.20. Any foregoing method wherein the topoisomerase is selected from vaccinia topoisomerase and SVF topoisomerase I.

2.21. Any foregoing method wherein vaccinia topoisomerase (which recognizes (C/T)CCTT) is used to add dTTP nucleotides and SVF topoisomerase I (which recognizes CCCTG) is used to add dGTP nucleotides, e.g., to provide binary code information.

2.22. Any foregoing method wherein the reserve chamber further comprises a ligase and ATP, to repair the DNA strand not joined by the topoisomerase.

2.23. Any foregoing method comprising use of a topoisomerase inhibitor to suppress binding and activity of free topoisomerase to the DNA oligomer, e.g., wherein the inhibitors is selected from novobiocin and coumermycin.

2.24. Any foregoing method wherein the DNA strand thus provided has a sequence comprising thymidine (T) nucleosides and deoxyguanisine (G) nucleosides.

2.25. Any foregoing method wherein the topoisomerase adds a single base, but the restriction enzyme cleaves at a position which is one nucleotide in the 5' direction from the base added by topoisomerase.

2.26. Any foregoing method wherein the DNA strand thus provided has a sequence comprising a sequence of 'TT' and 'TG' dinucleotides.

2.27. Any foregoing method which is a method of synthesizing a DNA molecule by adding single nucleotides in the 3' to 5' direction comprising (i) reacting a DNA molecule with a topoisomerase charged with the desired nucleotide in 5'protected form, e.g., 5'phosphorylated form, such that the desired nucleotide in 5'protected form is added to the 5' end of the DNA, then (ii) deprotecting the 5' end of the DNA thus formed through the use of a phosphatase enzyme, and repeating steps (i) and (ii) until the desired nucleotide sequence is obtained.

2.28. Any foregoing method which is a method of synthesizing a DNA molecule by adding oligomers in the 3' to 5' direction comprising (i) reacting a DNA molecule with a topoisomerase charged with the desired oligomer, thereby ligating the oligomer to the DNA molecule, then (ii) using a restriction enzyme to provide a 5' site for a topoisomerase-mediated ligation for another oligomer, and repeating steps (i) and (ii) until the desired nucleotide sequence is obtained.

2.29. Any foregoing method which is a method in accordance with any of Method A, et seq.

The product of the synthesis reactions can be detected, reviewed for quality control purposes, and read to extract the data encoded on the polymer. For example the DNA may be amplified and sequenced by conventional means to confirm that the nanopore sequencing is robust.

In another embodiment, the invention provides an oligonucleotide comprising a topoisomerase binding site, an informational sequence (e.g., selected from at least two different sequences, e.g., wherein one sequence corresponds to '0' and the other to '1' in a binary code), and a restriction site which when cleaved by a restriction enzyme will yield a topoisomerase ligation site, e.g., comprising the following sequence:

```
                                        (SEQ ID NO 2)
5' CGAAGGG <Informational sequence A or B> GTCGAC 3' GCTTCCC <---------Complement---------> CAGCTG
``` wherein the Informational Sequence A or B is a sequence of 3-12, e.g., about 8 nucleotides.

In another embodiment, the invention provides a topoisomerase charged oligonucleotide wherein the oligonucleotide comprises a topoisomerase binding site, an informational sequence (e.g., selected from at least two different sequences, e.g., wherein one sequence corresponds to '0' and the other to '1' in a binary code), and a restriction site which when cleaved by a restriction enzyme will yield a topoisomerase ligation site; for example a topoisomerase charged oligonucleotide having a structure as follows:

```
                                        (SEQ ID NO 1)
5' CGAAGGG <Informational sequence A or B> GTCGACN

NNNN

3' *TTCCC <---------Complement---------> CAGCTGN

NNNN
``` wherein the Informational Sequence A or B is a sequence of 3-12, e.g., about 8 nucleotides and * is topoisomerase covalently bound to the oligonucleotide; e.g., wherein the topisomerase is Vaccinia virus topoisomerase I.

In certain embodiments, the nanopore chips are controlled to carry out a method of synthesizing and/or reading the polymer, e.g., in accordance with any of Methods 1, et seq., Method A, et seq., or Method 2, et seq., using a computerized chip controller.

For example, referring to FIG. 65, a partial perspective drawing having selective transparent surfaces of a grouping of 3-chamber nanopore-based cells 6500 (each cell similar to that discussed herein above), of nanopore memory chip is shown for some embodiments of the present disclosure. In particular, a group of four 3-chamber cells 6506,6508,6510, 6512 are connected together, such that the upper (or top) left chambers 6502 (Add "0" chambers) of each of the connected cells 6506-6512 are fluidically connected together to form an Add "0" flow channel or Add "0" chambers 6502. In addition, the upper (or top) right chambers 6504 (Add "1" chambers) of each of the connected cells 6506-6512 are also fluidically connected together to form a separate Add "1" flow channel or Add "1" chambers 6504. In addition, the Add "0" chambers (or channel) 6502 have a common electrode 6520, and the Add "1" chambers (or channel) 6504 have a different common electrode 6522. In some embodiments there may be a single metallic or conductive strip providing the common electrode for each add channel, and in some embodiments there may be separate electrodes, which are connected by in-chip wiring.

Below the collective Add channels 6502,6504, are individual "deblock" chambers 6530-6536, similar to that discussed herein above, that are both fluidically and electrically isolated from the other chambers. On the bottom of each of the deblock chambers 6530-6536 are corresponding individually controllable "deblock" electrodes, e.g., deblock electrodes 6514,6516 visible in FIG. 65 correspond to deblock chambers 6534,6536, respectively. Also, the upper chambers for the cells 6506-6512 each have a corresponding nanopore 6528 through a membrane 6529. Also, in this example, the fluidic cell 6512 has a left top Add "0" chamber 6537 and a right top Add "1" chamber 6539. While the Add "0" chambers for the fluidic cells 6502-6512 are fluidically connected via the fluidic channels 6502, and the Add "1" chambers for the fluidic cells 6502-6512 are fluidically connected via the fluidic channels 6504, each of the fluidic cells 6506-6512 has an independent memory storage string (e.g., DNA or polymer) 6550, which has one end that traverses through the nanopore 6550 to enter the Add "1" or Add "0" chambers, and returns to its corresponding deblock chamber 6530-6536, which is fluidically and electrically isolated from the other chambers (in this example). Thus, each of the 3-chamber fluidic cells 6506-6512 represents an independent memory storage cell, or memory cell (discussed more hereinafter).

As the configuration of FIG. 65 has all the Add "0" electrodes connected together and, separately, all the Add "1" electrodes connected together, and the deblock electrodes are individually controlled, the writing (or adding) may occur in write (or add) "cycles," such as an Add "0" cycle, when all the cells that need to write a "0" may be written at the same time, followed by an Add "1" cycle, when all the cells that need to write a "1" may all be written at the same time. Other data writing cycles or approaches may be used if desired.

In addition, the Add "0" and Add "1" channels 6502, 6504, may be filled with fluid (or flushed, or washed or emptied) from the front or back, as shown by the arrows 6503-6505, respectively, and the deblock chambers 6530-6536 may be filled with fluid (or flushed, or washed or emptied) from the side, as shown by the arrows 6540-6546, respectively. It is not required that every Add "1" chamber be fluidically and electrically connected or that every Add "0" chamber be fluidically and electrically connected. If a large number of them are so connected it provides efficiencies; in general, the more cells that are connected the more efficiencies that can be realized.

Also, the entire polymer (or DNA) or "string" or memory string 6550 may be prevented from completely exiting the central deblock chamber by binding (or tethering or attaching) one end of the polymer 6550 to the surface of the central deblock chamber 6536, e.g., shown as point 6552 in deblock chamber 6536. Other locations in deblock chamber 6536 may be used to tether the polymer provided it meets the desired functional and performance requirements. In some embodiments, a structure 6554, e.g., a bead, particle, or origami, or other structure, may be attached to one end of the polymer 6550 and prevent the polymer from leaving the deblock chamber 6536 through the nanopore 6550. Similar criteria apply for the polymer memory string 6550 in the other deblock chambers 6530-6534.

The polymer 6550 used to store the data may be DNA as discussed herein, or it may be any other polymer or other material that has the properties described herein. The polymer 6550 used to store data may also be referred to herein as a "memory polymer" or "memory string" (due to its string-like appearance).

Figure 27:
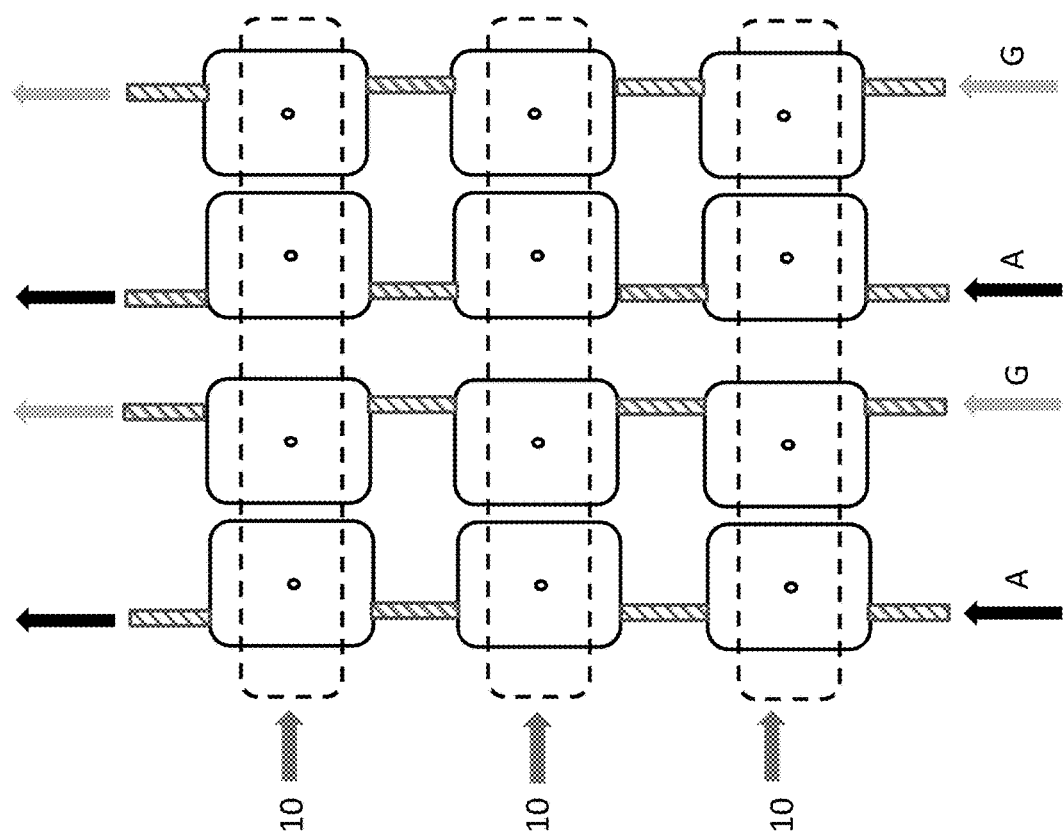
FIG. 27 depicts a top view of a nanopore chip having multiple sets of dual addition chambers as depicted in FIGS. 24 and 25, allowing multiple polymers to be synthesized in parallel. The monomers are (here dATP and dGTP nucleotides represented as A and G) are loaded into each chamber via serial flow paths. One or more common deblocker flow cells allows for the polymers to be deprotected after addition of a monomer or oligomer in one of the addition chambers. This also allow the polymers to be detached on demand (for example using a restriction enzyme in the case of DNA, or a chemical detachment from the surface adjacent to the nanopore, and collected externally. In this particular embodiment, the deblocker flow cells are perpendicular to the fluidics loading channels used to fill the addition chambers.
Figure 29:
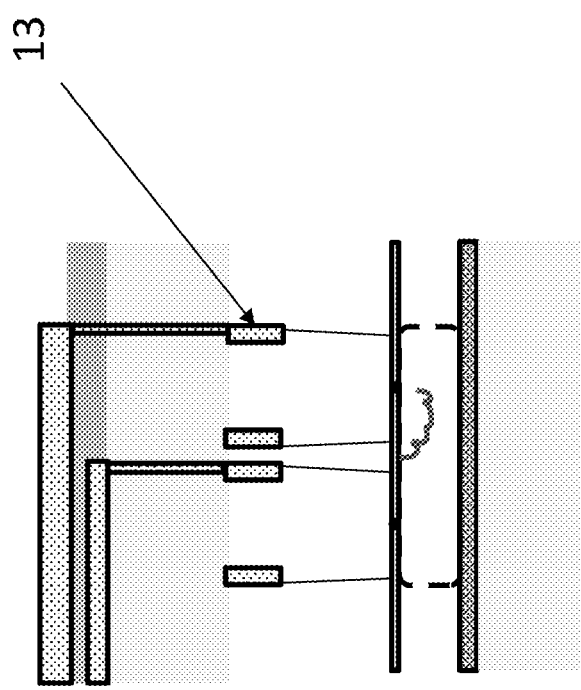
FIG. 29 depicts an alternative configuration where the control electrodes (13) for the addition chambers may be deposited on the side of the chamber in a wrap around fashion instead of at the top of the chamber.

Referring to FIG. 66, a partial perspective drawing having selective transparent surfaces of a grouping of 3-chamber nanopore-based cells 6600 (each cell similar to that discussed herein above), of nanopore memory chip is shown for some embodiments of the present disclosure. In particular, similar to FIG. 65, a group of four 3-chamber cells 6606, 6608, 6610, 6612 are connected together, such that the upper (or top) left chambers 6602 (Add "0" chambers) of each of the connected cells 6606-6612 are fluidically connected together to form an Add "0" flow channel 6602. In addition, the upper (or top) right chambers 6604 (Add "1" chambers) of each of the connected cells 6606-6612 are also fluidically connected together to form a separate Add "1" flow channel 6604. However, in this embodiment, the Add "0" chambers associated with the cells 6606-6612 have separate electrodes 6620-6626, and the Add "1" chambers associated with the cells 6606-6612 also have separate electrodes 6630-6636. This fluidic and electrode arrangement is similar to that described and shown herein above with FIG. 27. In some embodiments, the upper chambers (Add "0" and Add "1") may be fluidically separated or isolated from each other to avoid potential electrical-cross talk between adjacent Add chambers when trying to control the path of the DNA.

Also, for FIG. 65, deblock chambers may be fluidically connected even though the electrodes are separately controlled. In that case, there may be cross-talk between the channels, e.g., nearby DNA gets attracted by electric fields and/or current flow seen by adjacent cells.

In some embodiments, the electrodes may be have 3D shapes, such as a triangle or pyramid rising up from the bottom of the cell or protruding down into the cell. In that case, the electrode may be constructed to produce a more targeted, focused or closer electric field to the nanopore for that cell, which may reduce cross talk between adjacent cells that are fluidically connected but electrically separated.

If the memory string (or DNA or polymer) gets so long it may wrap around from one add chamber and though the top of another. To avoid that issue, there may be partial walls disposed between adjacent cells along the flow channel, to make the distance between adjacent nanopores that much longer for long DNA.

Below the Add chambers is a common "deblock" chamber 6640, which is common to all the upper Add chambers, similar to that discussed herein above. On the bottom of the common deblock chamber 6540 is a common deblock electrode 6642. Also, the upper chambers for the cells 6606-6612 may each have the nanopore 6528, similar to that discussed herein above, through the membrane 6529.

In addition, the deblock chamber 6540 may be filled with fluid from a side (depending on the structural configuration of the cell). In some embodiments, it may be filled from the left (or right side), as shown by the arrow 6650. In other embodiments, it may be filled from the front (or back) side, as shown by the arrow 6652.

Also, the entire DNA or polymer "string" (or memory string) 6550 may be kept from completely exiting the central deblock chamber by binding (or tethering) one end of the polymer 6550 to the surface of the central deblock chamber 6640, e.g., shown as point 6552 for the cell 6612. A similar arrangement would apply for the other cells 6606-6610. Other locations may be used to tether the polymer provided it meets the desired functional and performance requirements.

Referring to FIG. 67, a schematic circuit block diagram of a nanopore-based "memory chip" 6700, is shown for embodiments of the present disclosure. In particular, the memory chip 6700 may have a plurality of nanopore-based "memory cells" 6702 (or "storage cell" or "data storage cell"), each having the ability to store data. Each of the "memory cells" 6702 has a multi-chamber nanopore-based fluidic cell 6704 with a cell structure similar to that discussed herein above (e.g., having a membrane with a nanopore and the "memory string" 6550 (e.g., DNA or other polymer, as discussed herein). The "memory cells" 6702 may also include any solid-state or semiconductor passive or active circuitry or chip layers or components, which interface with the fluidic cell 6704 to provide the data storage (or writing or adding) and/or data retrieval (or reading or sequencing) functions described herein.

The memory cells 6702 may be connected together (electrically and fluidically), such as 3-chamber cells having common fluidic "Add" channels and common "Add" electrodes, and independent "deblock" chambers, such as is shown and described with FIG. 65. Any number of chambers and any cell configurations described herein may be used if desired.

The "memory cells" 6702 may be configured as an M×N array, with M rows and N columns, each of the cells 6702 being labeled $C_{M,N}$. More specifically, the cells 6702 in the first row are labeled $C_{1,1}$-$C_{1,N}$, and the cells 6702 in the last row are labeled $C_{M,1}$-$C_{M,N}$. M and N may be any values that provide the desired functions and performance, and M,N may each be as small a 1 and as large as 1 million, 10 million, 100 million, 1 billion, or 1 trillion, or larger, depending on the desired footprint size of the memory chip and the size of each memory cell.

The memory chip 6700 has an Add "0" input DC voltage on line 6710, which is electrically connected (directly or through on-chip circuitry or components, as described herein) to each of the Add "0" electrodes. The Add "0" input DC voltage on the line 6710 drives the Add "0" electrode to the desired voltage state (discussed herein), to help position (or move or steer) the memory string 6550 (DNA or other polymer, as discussed herein) to the desired chamber of the fluidic cell 6704. In this configuration, all the Add "0" electrodes for each of the memory cells are shared or common, or electrically connected, as shown in FIG. 65.

The memory chip 6700 also has an Add "1" input DC voltage on line 6712 which is electrically connected (directly or through on-chip circuitry or components as described herein) to each of the Add "1" electrodes. The Add "1" input DC voltage on the line 6710 drives the Add "1" electrode to the desired voltage state (discussed herein), to help position (or move or steer) the memory string 6550 (DNA or other polymer, as discussed herein) to the desired chamber of the fluidic cell 6704. In this configuration, all the Add "1" electrodes 6522 for each of the memory cells is shared or common, as shown in FIG. 65.

The memory chip 6700 also has a "Deblock" input DC voltage on a plurality of lines (or bus) 6714, each of which is electrically connected (directly or through on-chip circuitry or components as described herein) to a corresponding "deblock" electrode in each of the cells 6702. The deblock input DC voltage drives the corresponding deblock electrode for a given cell to the desired voltage state (discussed herein), to help position (or move or steer) the memory string 6550 (DNA or other polymer, as discussed herein) to the desired chamber of the fluidic cell 6704. In this configuration, each of the deblock electrodes are independently driven, as shown in FIG. 65, thus the need for the plurality of electrical connections or bus (or deblock bus) 6714. Each row of memory cells 6702 will have a corresponding number of deblock input DC voltage lines provided. For example, the first row there is a set of N deblock lines 6716 feeding the N cells 6702 in that row, and in the last row M, there is a separate set of N deblock lines 6718 feeding the N cells 6702 in the row M.

The DC input voltages Add "0", Add "1", and deblock, on the lines 6710, 6712, 6714, respectively, may be referred to herein as DC "steering" voltages $V_{ST}$ (or polymer or DNA steering voltages or memory string steering voltages) as they are used to "steer" the polymer memory string to the appropriate chamber of the fluidic cell 6704 at the appropriate time to achieve the desired result, e.g., write or add a "0" or "1" onto the memory string, or do nothing, or move the memory string to a particular chamber to enable writing or reading data, or perform validation testing, or the like. DC input voltages Add "0", Add "1", and deblock, on the lines 6710, 6712, 6714, respectively, may be provided from a computer-based controller circuit or logic or device, as described herein, which has the appropriate logic to perform the functions described herein.

The memory chip 6700 also has an AC input voltage Vin, and an AC output voltage Vout, on line 6720, 6722, respectively. The AC input voltage Vin on the line 6720 is electrically connected, as described herein, to each of the memory cells 6702 in parallel. The AC Vin provides an AC signal, e.g., rf or radio frequency signal, on the line 6720 to each of the memory cells 6702 and the memory cells are configured to be a resonator or nanopore polymer resonator (NPR), each having a different frequency response to the input AC Vin, as discussed herein. The line 6720 may connect the memory cell 6702 and/or the electronic components on the chip, the electrodes, and the fluidic cell 6704 therein, differently from that shown in FIG. 67, depending on the circuit configuration used for the nanopore polymer resonator (NPR), fluidic cell configuration, electrode configuration, or other factors, as described herein. The AC input voltage Vin on the line 6720 may be provided from a computer-based controller circuit or logic or device, as described herein, which has the appropriate logic to provide the appropriate AC input voltage Vin and perform the functions described herein.

The combined frequency response from each of the memory cell 6702 may be provided to an on-chip amplifier (or pre-amp) 5320 (FIG. 53), which provides the AC output voltage Vout on the line 6722 indicative of the combined frequency response. The AC output voltage Vout on the line 6722 may be provided to a computer-based processing circuit or logic or device, which has the appropriate logic, e.g., analog-to-digital (A/D) conversion and digital signal processing (DSP) logic, as described herein, which reads the data stored on the memory string 6550 and may perform other functions as described herein.

Referring to FIG. 68, a top level hardware block diagram is shown of a read/write memory storage system 6800 having the nanopore-based memory chip 6700 (FIG. 67) and a memory read/write controller 6802, in accordance with embodiments of the present disclosure. In particular, the memory read/write controller 6802 may have a write controller logic 6804, which receives input data to be written to the memory chip 6700 on lines and an address to store the data (or label or pointer or the like) on lines 6808, and provides the DC steering voltages Add "0", Add "1", and deblock, on the lines 6710, 6712, 6714, respectively, to the nanopore memory chip 6700. The write controller 6804 has the appropriate hardware, software and firmware (including any microprocessor or micro-computer based processor chips or devices and/or memory storage) as needed to provide the functions described herein, as indicated by a box 6810.

In addition, the write controller 6804 may also provide a write (or add) cycle clock 6812 (or oscillator), which determines when the memory chip 6700 writes (or adds or stores) "0" or "1" bits. In particular, the write controller chip 6804 provides the DC steering voltages (Add "0", Add "1", Deblock) based on the write cycle clock 6812 to cause the memory chip 6700 to write "1" or "0" to the memory cells. As discussed herein above with FIG. 65, in certain cell configurations, such as when all the Add "0" electrodes are connected together and, separately, all the Add "1" electrodes are connected together, and the deblock electrodes are individually controlled (such as in FIG. 65), the writing (or adding) of data bits may occur in write (or add) "cycles," such as an Add "0" cycle, when all the cells that need to write a "0" may be written at the same time, followed by an Add "1" cycle, when all the cells that need to write a "1" may all be written at the same time. The write cycle clock provides a write cycle signal on a line 6814 to enable the write requesting device or platform or computer bus, to determine the writing status of the memory chip. Other data writing cycles, timing, or approaches may be used if desired.

In some embodiments, the write controller 6802 may also receive control signals from the system or computer bus, such as a Write Request (W-REQ) signal on a line 6820 to request certain data be written to the memory chip 6700, and the write controller 6802 may also provide a Write (or Add) Complete (W-COM) signal on a line 6822, to indicate when the requested data has been written to the memory chip 6700.

The memory read/write controller 6802 may also have memory read controller logic 6850, which may receive a read address (or label or pointer or the like) on lines 6852 corresponding to the storage location of the data desired to be read from the memory chip 6700, and provides the requested data read from the memory chip 6700, on the lines 6854. The read controller 6850 may also have the necessary logics and components to provide the AC input voltage signal Vin to the memory chip 6700 on the line 6720. The AC input voltage Vin, as described herein, is an AC rf (radio frequency) signal that has frequency components corresponding to the bandwidth of the nanopore resonators (NPRs) in the memory chip 6700. To provide the Vin signal, the read controller 6850 may have a frequency oscillator logic 6858 (programmable or non-programmable), which provides the necessary frequency components (discussed herein) to enable the read controller logic to read the requested data from the nanopore memory chip 6700. As discussed herein, the AC Vin signal may be directly synthesized, combine multiple probe frequencies, and may be a single broadband signal, or a time swept or stepped frequency signal, or any other AC signal the provides the functions described herein.

The read controller 6850 also receives the output AC Vout voltage from the memory chip 6700 on the line 6722, and performs A/D conversion and digital signal processing (e.g., using on-board A/D conversion logic 6862 and FFT logic 6864), as discussed herein, on the Vout signal to determine the values of the desired data at the specified read address and provide the output data on Read Data Out the lines 6854.

The read controller 6850 has the appropriate hardware, software and firmware (including any microprocessor or micro-computer based processor chips or devices and/or memory storage) as needed to provide the functions described herein, as indicated by a box 6856.

In addition, the read controller 6850 may also receive the write (or add) cycle clock signal on the line 6814 from the write cycle clock 6812 (or oscillator), which, as discussed above, determines when the memory chip 6700 will write (or add or store) "0" or "1" bits. In particular, controller chip 6804 will provide the DC steering voltages (Add "0", Add "1", Deblock) based on the write cycle clock 6812 to cause the memory chip 6700 to write "1" or "0" to the memory cells. Because the act of writing with the present disclosure requires the DNA (or polymer or memory string) to pass through the nanopore to enter the desired chamber to Add bits and also to pass through the nanopore when exiting back to the deblock chamber, the write cycle clock signal may also be used by the read controller 6850 to determine when is the best time to read the data, discussed more hereinafter with FIG. 69.

In some embodiments, the read controller may provide a read signal 6860 to the write controller 6804 to request the controller 6804 provide the necessary steering voltages (Add "0", Add "1", Deblock) on the lines 6710-6714 to cause the memory string to pass through the nanopore to enable reading of the memory string.

In some embodiments, the read controller 6850 may also receive a Read Request (RD-REQ) signal on a line 6870 to request certain data be read from the memory chip 6700, and the read controller 6850 may also provide a Read Complete (RD-COM) signal on a line 6822, to indicate when the requested data has been read from the memory chip 6700. The Memory Controller 6802 may perform only one function, e.g., read or writing to the nanopore chip if desired, or it may perform both of these functions (Read and Write), if desired.

Referring to FIG. 68A, the Nanopore memory system 6800 may be part of a larger computer system which may interact with an Address/Data/Control Bus 6870, and may also interact with separate memory controllers 6876, all of which interact with one or more CPU/Processors 6874. For example, one or more of the read/write address and/or data inputs, outputs and/or control lines, such as numerals 6820, 6822, 6806, 6808, 6814, 6852, 6854, 6872, 6870, shown in FIG. 68, may be received from or provided to the bus 6872 or the memory controller 6876. The computer system 8670 may interface with a user 6878 and a display screen 6880.

Referring to FIG. 69, a table 6900 of sample DC steering voltages ($V_{ST}$) for the configuration shown in FIG. 65 and corresponding time graphs 6902 for the steering voltages $V_{ST}$ and associated results on the memory chip 6700, in accordance with embodiments of the present disclosure, is shown. In particular, the table 6900 shows the DC steering voltages $V_{ST}$ (e.g., Add "0", Add "1", Deblock, or $V_{ST0}$, $V_{ST1}$, $V_{STDB}$, respectively) 6904 to be provided to the respective electrodes of the memory cell, based on the write cycle timing to cause the memory chip 6700 to write "1" or "0" to the memory cells, such as an Add "0" cycle, when all the cells that need to write a "0" may be written at the same time, followed by an Add "1" cycle, when all the cells that need to write a "1" may all be written at the same time.

Referring to FIG. 69 and FIG. 65, sample steering voltages for the Add "1" cycle are shown in column 6906 (FIG. 69), and steering voltages for the Add "0" cycle are shown in column 6908. More specifically, during Add "1" cycle, it is desired to cause the memory string (DNA or polymer) 6550 to traverse through the nanopore 6528 to the Add "1" chamber 6539 (FIG. 65) of the fluidic cell 6512. This may be done by having the Add "1" electrode voltage $V_{ST1}$ be at ground (GND) or 0 Volts, the Add "0" electrode voltage $V_{ST0}$ be at a negative voltage (relative to the Add "1" voltage), and the deblock electrode voltage $V_{STDB}$ be at a negative voltage (relative to the Add "1" voltage), until the "1" bit is written (or added) to the string 6550. After the "1" bit is written, the string 6550 may be pulled back into the deblock chamber 6536 (to be ready for the next write command) by having the deblock voltage change to a positive voltage (relative to the Add "1" voltage and the Add "0" voltage), which will attract the memory string if it has a net negative charge, such as DNA.

The time plots 6902 show the values of the steering voltages for the Add "1" and Add "0" write cycles. In this case, for plot 6910, for the Add "1" cycle, shows the Add "1" voltage value is held at a constant value of GND (0 volts) for the entire Add "1" cycle, and plot 6912 shows the value of the Add "0" voltage is held at a constant value of a negative voltage (e.g., −1.0 volts) for the entire Add "1" cycle. The plot 6914 for the "deblock" voltage shows a square wave having two parts 6916 and 6920, which starts at a negative voltage value (as discussed herein above) to release the memory string from the deblock chamber 6536 (FIG. 65) and allow one end of the memory string 6550 to traverse from the deblock chamber 6536 through the nanopore 6528 to the Add "1" chamber 6539, where the Add "1" bit reaction occurs as shown on the graph 6914, also indicated by a "W1" for write of a "1" bit. A first portion of the graph section 6918 (labeled "T1") is the time it takes for the memory string (DNA or polymer) to traverse the nanopore 6528 into the Add "1" chamber 6539, after which the "addition" chemical reaction occurs, during the time "W1". The amount of time W1 should be set long enough for the "1" bit addition reaction to complete, which may have a reaction time of, e.g., about 0.01-100 Hz, or about 10 seconds to 100 milliseconds. Other addition reaction times for the addition reactions may be used if desired, depending on the chemistry used, as discussed herein.

Next in the Deblock time graph section 6920, the Deblock voltage becomes positive relative to the Add "1" voltage, which pulls memory string 6550 back through the nanopore 6528 into the Deblock chamber, after which it is held for a HOLD time period $T_{H1}$ long enough for the deblock reaction to occur, as discussed herein (similar to the Add reaction time). The time "T2" indicated by numeral 6922 is the time it takes for the memory string 6550 to traverse the nanopore 6528. For the remainder of time (Hold time, $T_{H1}$) in this portion 1920 of the cycle the string is held in the Deblock chamber, waiting for the next write request. Thus, other than the deblock reaction, there is no activity (NA) occurring on the string during this Hold time.

Next the write cycle repeats, this time for the Add "0" cycle, column 6908. Referring to FIG. 69 and FIG. 65, sample steering voltages for the Add "0" cycle are shown in column 6908. More specifically, during Add "0" cycle, it is desired to cause the memory string (DNA or polymer) 6550 to traverse through the nanopore 6528 to the Add "0" chamber 6537 (FIG. 65) of the fluidic cell 6512. This may be done by having the Add "0" electrode voltage $V_{ST0}$ be at ground (GND) or 0 Volts, the Add "1" electrode voltage $V_{ST1}$ be at a negative voltage (relative to the Add "0" voltage), and the Deblock electrode voltage $V_{STDB}$ be at a negative voltage (relative to the Add "0" voltage), until the "0" bit is written (or added) to the string 6550. After the "0" bit is written, the string 6550 may be pulled back into the deblock chamber 6536 (to be ready for the next write command) by having the deblock voltage change to a positive voltage (relative to both the Add "1" voltage and the Add "0" voltage), which will attract the memory string if the string has a net negative charge, such as DNA.

Similarly, for the Add "0" cycle, the plot 6912 for the Add "0" cycle shows the Add "0" voltage value is held at a constant value of GND (0 volts) for the entire Add "0" cycle, and plot 6910 shows the value of the Add "0" voltage is held at a constant value of a negative voltage (e.g., −1.0 volts) for the entire Add "0" cycle. The plot 6914 for the "deblock" voltage for the Add "0" cycle shows a square wave having two parts 6926 and 6930, which starts at a negative voltage value (as discussed herein above) to release the memory string from the deblock chamber 6536 (FIG. 65) and allow one end of the memory string 6550 to traverse from the deblock chamber 6536 through the nanopore 6528 to the Add "0" chamber 6537, where the Add "0" bit reaction occurs as shown on the graph 6914, also indicated by a "W0" for write bit "0". A first portion of the graph section 6924 (labeled "T3") is the time it takes for the memory string (DNA or polymer) to traverse the nanopore 6528 into the Add "0" chamber 6537, after which the "addition" of bit "0" chemical reaction occurs, during the time "W0". The amount of time W0 should be set long enough for the addition reaction to complete, which may have a reaction time of, e.g., about 10-100 Hz, or about 10 to 100 milliseconds. Other addition reaction times for the addition may be used if desired, depending on the chemistry used, as discussed herein.

Next in the Deblock time graph section 6930, the Deblock voltage becomes positive relative to the Add "0" voltage, which pulls memory string 6550 back through the nanopore 6528 into the Deblock chamber 6536, after which it is held for a HOLD time period $T_{H2}$ long enough for the deblock reaction to occur, as discussed herein (similar to the Add reaction time). The time "T4" indicated by numeral 6928 is the time it takes for the memory string 6550 to traverse the nanopore 6528 and reenter the Deblock chamber. For the remainder of time (Hold time, $T_{H2}$) in this portion 1930 of the write cycle, a deblock reaction occurs (as discussed herein) on the string and the string is held in the Deblock chamber, waiting for the next write request. Thus, other than the deblock reaction, there is no activity (NA) occurring on the string during this Hold time.

Thus, for the embodiment described, the deblock voltage may control the writing of a "1" or "0", releasing of the memory string to enter the corresponding Add chamber, and the removal of the memory string from the chamber after writing and the holding of string in the deblock chamber. Thus, the deblock voltage may create a No Activity (NA) state or do nothing state, if desired for a given write cycle or portion thereof, by adjusting the "Hold" time during the cycle. It can also determine the timing of when the write (or add) time begins and ends by adjusting the write times W1, W0 during the cycle. Also, depending on the traverse time T1-T4 it takes the memory string to fully traverse thought the nanopore, the write times W1 (Add "1"), W0 (Add "0") may need to be adjusted to ensure there is adequate time to perform the desired write (or add) reaction in the Add chamber. Accordingly, the read/write controller 6802 (FIG. 68) discuss herein above, may have logic that measures and adjusts for these conditions in real time, for any of the configurations and embodiments of fluidic, electrode, or other configurations described herein or others. Also, the traverse time will depend on the number of bases, the more bases the longer the time. For example, for 100K bases, traveling through the nanopore at 1 million bases per second (typical average velocity for DNA through an nanopore), would take about 100 milliseconds to traverse the nanopore. There may also be a delay for entry into the pore, e.g., about 100 milliseconds, however other values may be used.

In addition, during the traverse times T1-T4 shown on the graph 6914, while the memory string (or DNA or polymer) is traversing through the nanopore the read/write controller 6802 may read (or sequence) the values of the bits as the pass through the nanopore, as discussed herein. Thus, for each write cycle (Add "1" cycle or Add "0" cycle), there are two time periods T1,T2 or T3,T4, respectively, when the system may read the data stored on the memory string. Reading the data on a continuous basis may be useful for verifying the data, providing multiple reads of the data, flagging errors in the data, and other reasons.

There are numerous possible approaches and factors to consider regarding reading the data from the memory string for the present disclosure, including timing (e.g., when and how often to read), fluidic & electrode and other related configurations (e.g., how to provide the steering signals to perform the read), and other factors, which may be determined based on the disclosure herein and the design, functional and performance requirements of the overall memory system.

In some embodiments, the memory string (or DNA or polymer) may only be read when no writing is occurring and the Add chambers have been rinsed and removed of chemical "Add" capability (e.g., addition enzymes, and the like). In that case, the memory string may be steered into and out of the desired nanopore(s) by the read controller and the information stored by the read controller for later use. In that case, the read controller may communicate with another memory storage device for holding the retrieved data for later use.

The traverse (or transport) times T1,T2,T3,T4 it takes the memory string (or DNA or polymer) to traverse the nanopore (into or out of an Add chamber) may vary based on the length of the memory string (the more bits on the string the longer it will take) and the string transport velocity through the nanopore (the slower the string moves through the nanopore, the longer it will take). The transport velocity may vary based on a number of factors, including, the angle of the string approaching the nanopore, the geometry of the nanopore (cone, cylinder, etc.), the diameter of the nanopore compared to the diameter of the string (which may vary along its length), the amount of tangling or wrapping or coils in the string, how the velocity varies along the length of the string, fluid dynamic effects, friction/attraction/binding with walls of chamber, viscosity effects, acoustic waves in the fluid, and other factors.

If the velocity is not known accurately, the system may not be able to accurately determine the number of bits in a word with a long string of the same bit state, such as 000000 or 1111111. However, the velocity may be determined or calibrated by the systems or methods of present disclosure by writing a predetermined "velocity calibration sequence" of data on the memory string (or DNA or polymer) for a cell, such, alternating is and Os, i.e., 101010101010, and placing it in the stored data on the string in a known or determinable location, such as near the beginning of the string or after a certain number of words are written, or after detecting a "special" bit having special properties, such as being extra large, as discussed more hereafter. When the system reads the alternating "1010" pattern, it can determine the velocity of the string because it knows the pattern. Such a velocity calibration sequence may be placed a numerous locations along the memory string to enable multiple realtime calibration of the velocity, if desired.

In some embodiments, it may not be necessary to calibrate the velocity if there is a "baseline resolution" between bits, i.e., if the bit signal goes back to a baseline value prior to the next bit. However, if there is a nanopore with a length equal to or longer than a bit, then baseline resolution would not be expected. In that case, the system would be reading several bits simultaneously and assessing how that changes over time, e.g., 110011 to 100111 to 001110, and the like, for the sequence 1101110. To interpret this scenario effectively, having as many measurements per unit time as possible is desired. Also, the system may perform multiple reads of the same DNA to average out at least some of the variability of the time domain, much of which is random.

The sample voltage values for the steering voltages $V_{ST}$ shown in FIG. 69 are for a memory string that has a net (or overall or average) negative charge, such a negatively charged polymer, such as DNA, or other negatively charged polymer. If the memory string has a net positive charge, the values shown here would be reversed. Other values (and polarities (+/−)) for the memory string (or DNA or polymer) steering voltages shown herein may be used if desired based on the electronic circuits components and other factors, provided the relative voltage differences are sufficient to achieve the desire results. Also, it is not necessary that the steering voltages $V_{ST}$ have negative and positive values. It is only necessary that the relative voltage difference created by the steering voltages are such that they create the necessary electric field force to move the memory string through the nanopore 6528 to the desired chamber.

Referring to FIG. 70, a series of time graphs 7000 is shown, having a write cycle graph 7002 and a corresponding set of bit time graphs 7004-70012 showing how 5-bits words would populate for a corresponding five different bit patterns. In particular, the write (or add) cycle graph, shows a square wave 7002 indicative of an alternating repeating write cycle of Add "0" cycle, Add "1" cycle, Add "0" cycle, and so on. The time graphs 7004-7012 show an example of five, 5-bit binary data words 7020 on the left (11100, 00011, 01010, 1111, 0000), and corresponding time graphs 7004-7012 showing when each bit of the 5-bit data words 7020 would be written in a single cell using the alternating write cycle 7002 (Add "1", Add "0") approach. Cells with an "X" indicate no data is written during that portion of the write cycle 7002. The graph also show when each of the data words 7020 would be completely written into a cell, shown by an arrow 7014. For Data 11100, it took 9 cycles to write, data 00011 took 8 cycles to write, data 01010 took 5 cycles to write, 1111 took 10 cycles to write, and data 0000 took 9 cycles to write. Thus, number of write cycles (or the time) to write the same number of bits can vary based on the pattern of the 1's and 0's in the word, if writing each word to a given cell. In this example, the number of write cycles varied from 5 cycles to 10 cycles (i.e., from the number of bits to twice the number of bits).

However, if the cells are written (or added) in parallel, i.e., each bit is assigned to a different cell and written simultaneously, the maximum number of write cycles would be 2, and the minimum number would be 1, independent of the number of bits or the pattern of the bits. Thus, if writing speed is important and an embodiment is used that has alternating write cycles, formatting the data to be written into parallel cells instead of writing data words in series to a single cell may be advantageous. Thus, for some embodiments, there may be a trade-off between write cycle management and data memory cell format.

Referring to FIG. 70A, a flowchart 7030 is shown for the Write/Vst CNTRL Logic 6804 of the Read/Write Memory Controller 6802 (FIG. 68) for writing bits in accordance with embodiments of the present disclosure. The process/logic 7030 begins at a block 7032, which checks if the write cycle is an Add "0" cycle. If not, the process goes to a block 7034 which checks if the write cycle is an Add "0" cycle. If not, the process exits. If the result of block 7034 is YES, a block 7036 sets the steering voltages $V_{ST}$ to values shown in FIG. 69, e.g., $V_{ST1}$=GND; $V_{ST0}$=Neg. Next, a block 7038 checks if the next bit of data to be written is a "1". If NO, the process exits. If YES, a block 7040 sets $V_{STDB}$=Neg., to release the memory string (or DNA or polymer) into the Add "1" chamber, for a time t=T1+W1, as shown in FIG. 69. Then, after this time has passed, the logic sets $V_{STDB}$=Pos., to pull the memory string out of the Add chamber into the Deblock chamber, and the process exits.

If the result of block 7032 is YES, the write cycle is in an Add "0" cycle, and a block 7042 sets $V_{ST}$ to values shown in FIG. 69, e.g., $V_{ST1}$=Neg.; $V_{ST0}$=GND. Next, a block 7044 checks if the next bit of data to be written is a "0". If NO, the process exits. If YES, a block 7046 sets $V_{STDB}$=Neg., to release the memory string (or DNA or polymer) into the Add "0" chamber, for a time t=T3+W0, as shown in FIG. 69. Then, after this time has passed, the logic sets $V_{STDB}$=Pos., to pull the memory string out of the Add chamber into the Deblock chamber, and the process exits. The process 7030 repeats itself continuously to look for the next write cycle and respond accordingly.

Referring to FIG. 70B, a table showing steps to write "1" and "0" for the nanopore memory device cell configuration shown in FIG. 66, in particular, a cell having a common electrode on the bottom for the deblock chamber and individually controllable electrodes on the top add chambers. There are four steps shown in column 7082 for each type of writing and a corresponding controller action shown in column 7084 for the write controller, and a corresponding result shown in column 7076 explaining what happens inside the chip for that particular step.

Referring to FIG. 71, the format of how data is stored may vary based on various factors and design criteria. In particular, the memory string (or DNA or polymer) 6550 may be shown as a line 7102 on which are a series of ovals, indicative of individual "bits" written (or added) on the memory string 6550 in a given memory cell. In some embodiments, the bits 7104 may be written one after the other to build a "storage word". A first example data format 7110 shows three components to the storage word 7112, an address section 7106, a data section 7108, and an error checking section 7110. The address section 7106 is a label or pointer used by the memory system to locate the desired data. Unlike traditional semiconductor memory storage where hardware address lines on a computer memory bus would address a unique memory location, the memory chip and system of the present disclosure require the address (or label) to be part of the data stored and indicative of where the data desired to be retrieved is located. In the examples shown in FIG. 71, the address is located proximate to or contiguous with the data, as well as error checking data, such as parity, checksum, error correction code (ECC), cyclic redundancy check (CRC), or any other form of error checking and/or security information, including encryption information. In the storage word 7112, each of the components Address 7106, Data 7108, Error Checking 7110, are located after each other in the memory string. As each of the components have a known length (number of bits), e.g., address=32 bits, data=16 bits, error check=8 bits, each storage word 7112 and its components can be determined by counting the number of bits.

Another example data format 7120 shows the same three components, address section 7106, data section 7108, and error checking section 7110. However, in between each of the sections there is a "special bit(s) or sequence" sections S1,S2,S3, shown as numerals 7122,7124,7126, respectively. These special bits S1,S2,S3 may be a predetermined series of bits or code that indicate what section is coming next, e.g., 1001001001 may indicate the address is coming next, where as 10101010 may indicated the data is coming next, and 1100110011 may indicate the error checking section in next. In some embodiments, the special bits may be a different molecular bit or bit structure attached to the string, such as dumbbell, flower, or other "large" molecular structure that is easily definable when it passes through the nanopore. Instead of it being large it may have other molecular properties that provide a unique change the capacitance or resonance different from the 1 bits and 0 bits, as discussed herein above.

Another example data format 7130 shows only Data components 7140 with no address component, and an error checking component 7110. In this structure, the string holds only the "Data" components and no Address components, which may be stored in other strings, as discussed hereafter. In this example there are also Special bits S1,S2,S3, shown as numerals 7132,7134,7136, respectively. Similar to the example 7120, these special bits S1,S2,S3 may be a predetermined series of bits or code that indicate the separation between data sections and indicate when an error checking section is next, or may be a different molecular bit or bit structure attached to the string that is easily definable when it passes through the nanopore, as discussed herein above.

Referring to FIG. 72, a single row of memory cells 7202-7208 is shown, with an sample memory string 7210-7216, respectively, associated with each cell. The memory system of the present disclosure is significantly different from traditional semiconductor memory because instead of each memory cell storing a single bit of information (1 or 0), each memory cell of the present disclosure can store a significant amount of data. Thus, if the traditional semiconductor memory is viewed as a 2D array, the present memory system is 3D array, where each memory cell location in the array has significant storage depth. This provides a large range of options for how to store data and retrieve data.

For the example shown in FIG. 72, each cell may store a linear self contained string of information (storage word), similar to that discussed in the example 7110 of FIG. 71. In that case, each storage word is stored back-to-back on top of other storage words. And each of the cells 7202-7208 in the row replicates this structure, and this is repeated for multiple rows (not shown).

Referring to FIG. 73, in some embodiments, some cells may store only address information, and some cells only data information. In that case, each row may have a cell, e.g., Cell 1, 7310, which has a memory string 7302 of addresses or pointers, and the remainder of the row, e.g., Cell2-CellN, 7310-7316, respectively, have a corresponding string of data 7304-7308, respectively. In that case, the addresses or pointers would have a value indicative of where the data is stored on the memory chip, such as a row, column and entry number, e.g. Row 3, Column 8, Entry 50, meaning the data corresponding to this address resides at the $50^{th}$ data block in Row 3 and Column 8. This effectively decouples the address from being located physically next to the data, which can provide flexibility in storage. Also, each of the strings may have one or more error checking or security components to validate the information stored on the string. This may be repeated for each row in the array.

Referring to FIG. 74, instead of storing information contiguously (or serially) on a given memory string, the data may be stored in the memory cell array in parallel. For example, when a storage word is stored, it may be able to be stored more quickly in a single storage action, storing it across the array, similar to the way traditional semiconductor memory works, but allowing it to do it over and over again due to the 3D depth, each time "pushing" (storing) another storage word onto the strings. Such a format also enables quick parallel retrieval of a given storage word (once located). In that case, certain cells 7402 may be allocated to storing addresses/pointers, certain cells 7204 may be allocated to storing parallel data, and certain cells 7406 may be allocated to storing error checking and security data. For example, the storage word 7210 shown in FIG. 72 (which is stored in series on one string), may be stored as shown as storage word 7410, having Address1, Data1, and Error Check1, and which is stored in parallel across a plurality of cells (1-N, N+1 to M, and M+1 to P). Similarly, for storage word 7412 which would be stacked across the same strings in parallel with the storage word 7410 (either underneath or on top of, depending on the direction of storage on the string). In some embodiments, the data may be stored in parallel in 2 Dimensions, thereby creating a layered 2D array of stored information, such as a multi-layered 2D image capture data may be stored, except allowing a 2D image it to be stored in realtime, with each 2D snapshot layering on top the prior snap shot.

The bits may be binary bits; however, they are not limited to any base numbering system as the present disclosure allows the memory stick to write (or add) more than two different values, as described herein. In that case, the cell design would be adjusted accordingly. For example for a base-4 system (e.g., GCAT, for DNA based system), there would be 4 add chambers and a single de-block chamber, as described herein. This can be extended for any base number system greater than 2, such as 3, 4, 5, 6, 7, 8, 9, 10 (decimal), or more, up to N. Where there would be N add chambers and 1 deblock chamber. The only limitation would be that the chambers are oriented such that the memory string (or DNA or polymer) can reach all the add chambers.

The term "data" as used herein includes all forms of data including data representing addresses (or labels or pointers, including physical or virtual), machine code of any type (including but not limited to object code, executable code and the like), error checking, encryption, libraries, databases, stacks, and the like that may be stored in memory. In certain examples, such as in FIGS. 71-74 (or elsewhere as the context implies), the term "Data" may be shown or described as being separate from the "Address," or "Error Checking". In those cases, these terms may be used to show different forms of data for illustrative purposes only.

Chip Fluidics instrument & control: Referring to FIG. 75, the nanopore chip 6700 (FIG. 67) may interact with the read/write memory controller 6802, as discussed herein above with FIG. 68, which may control the voltages (AC and DC) to steer or control the polymer to Add bits and or read the bits on the memory string as shown collectively by lines 7504. The memory chip may also interface with an instrument 7502 on lines 7506, which may provide fluidics to the memory chip, such as filling the chip with buffers, enzymes, and/or polymers or DNA (or other memory strings), as discussed herein. The Instrument 7502 and the Memory Controller 6802 may be controlled or receive commands from a Computer System 6870, such at that described and shown with FIG. 68A, that may interact with the user 6878 and may have the display 6880. The computer system 6870 may interact with the Read/Write Memory Controller 6802 and the Instrument 7502 via the computer bus 6872 (FIG. 68). The instrument 7502 has the necessary electronics, computer processing power, interfaces, memory, hardware, software, firmware, logic/state machines, databases, microprocessors, communication links, displays or other visual or audio user interfaces, printing devices, and any other input/output interfaces, including sufficient fluidic and/or pneumatic control, supply and measurement capability to provide the functions or achieve the results described herein.

In particular, the instrument may perform the following fluidic actions with the memory chip: initially fill the chip with the necessary fluids, enzymes, reagents, DNA, or the like through capillary action & or micro pumping. For the embodiments where the Add1 and Add0 have flow-through channels and deblock as isolated chambers, the deblock chambers could be filled en-masse (via capillary action) first, then sealed—water and buffers would travel into the add chambers which could then be filled with their enzymes/buffers OR deblock chambers could be individually filled via targeted addition (e.g., ink-jet) and dried and sealed. In that case, the Add chambers may be filled under vacuum to ensure no bubbles get trapped in the deblock chamber, or the deblock chambers may be sealed with a material which allows gas but not water to pass through (such as PDMS). Also, the deblock chambers may be filled by leaving the bottom of the cell open during assembly, and placing the cell bottom in the desired fluid, and the fluid will wick up into the deblock chambers by capillary action.

There are various fluidics designs that will achieve the desired results for fluidic filling and flushing. For example, the Add "0" channels and Add "1" channels may respectively be connected together (like channels together) in a continuous serpentine (back and forth) pattern, and fed fluid through vias from a layer above the channels. The vias may connect to the instrument via standard fluidic interfaces sufficient to supply the desired fluids to the channels. In some embodiments, the Add channels may each be fed through separate vias from a common reservoir for Add "0" channels and from a separate common reservoir for Add "1" channels located on a layer above the channels. Any other fluidic design may be used if desired. Sample dimensions for the Add channels, are: width about 100 nm to about 10 microns, height of about 1 micron to about 50 microns, and length of about 100 mm (1 cm or 1000 microns) from one side of the chip to the other. A serpentine connected channel would be a multiple of this depending on how many channels are connected in series.

The instrument 7502 may also be used during initialization and cell testing if desired. For example, for cell initialization & cell testing Quality Control (QC) for nanopore quality to ensure expected current is observed (current proportional to pore size). Also, QC for DNA presence: ensure that the expected current (or capacitance or impedance, or shift in magnitude or phase of the resonance, as discussed herein) changes characteristic of DNA (or polymer, etc.) moving though the nanopore (e.g., expected reduction in current, or shift in magnitude or phase of the resonance, as discussed herein). In addition, it may be used for QC for circuit formation which would be similar to that performed for nanopore quality.

The instrument 7502 may also be used for DNA addition, as previously described herein, where DNA with origami is introduced via one of the add chambers (or channels), current may be applied to cells until insertion is detected, modified DNA end in deblock chamber diffuses and then attaches to surface, and restriction enzyme introduced to add chamber to cleave origami which is then removed via buffer flow.

In another embodiment, the invention provides a single or double stranded DNA molecule as described above, wherein the single strand or the coding sequence consists essentially of nonhybridizing bases, for example adenines and cytosines (As and Cs), which are arranged in sequence to correspond to a binary code, e.g., for use in a method of data storage. For example, the invention provides DNA (DNA 1), wherein the DNA is single or double stranded, at least 1000 nucleotides long, e.g., 1000-1,000,000 nucleotides or, for example, 5,000 to 20,000 nucleotides long, wherein the sequence of the nucleotides corresponds to a binary code; e.g., 1.1. DNA 1 wherein the DNA is single stranded.
   1.2. DNA 1 wherein the DNA is double stranded.
   1.3. Any foregoing DNA wherein the nucleotides in a single strand or in the coding strand are selected from adenine, thymine and cytosine nucleotides, e.g. are selected from adenine and cytosine nucleotides or thymine and cytosine nucleotides
   1.4. Any foregoing DNA consisting primarily of nonhybridizing nucleotides, so that it will not form significant secondary structures when in the form of a single strand.

1.5. Any foregoing DNA wherein the nucleotides are at least 95%, e.g. 99%, e.g., 100% adenine and cytosine nucleotides.
1.6. Any foregoing DNA comprising a nucleotide or sequence of nucleotides added to separate or punctuate the nucleotides comprising a binary code, e.g., to separate the 1's and 0's or groups of 1's and 0's, so that consecutive 1's or 0's can be more easily read.
1.7. Any foregoing DNA wherein (a) each bit in the binary code corresponds to a single nucleotide, e.g. each of 1 and 0 correspond to A or C; or (b) each bit in the binary code corresponds to a series of more than 1 nucleotides, e.g. 2, 3 or 4 nucleotides, e.g., AAA or CCC.
1.8. Any foregoing DNA which is crystallized.
1.9. Any foregoing DNA which is provided in a dry form together with one or more of a buffer salt (e.g., a borate buffer), an antioxidant, a humectant, e.g. a polyol, and optionally a chelator, for example as described in U.S. Pat. No. 8,283,165 B2, incorporated herein by reference; and/or in a matrix between the nucleic acid and a polymer, such as poly(ethylene glycol)-poly(l-lysine) (PEG-PLL) AB type block copolymer; and/or together with a complementary nucleic acid strand or a protein that binds the DNA.
1.10. Any foregoing DNA which contains an identifying sequence.
1.11. Any foregoing DNA that contains PCR amplification sequences.
1.12. Any foregoing DNA that contains one or more calibrating sequences, e.g., known sequences of nucleotides which can be used to calibrate a nanopore-based sequencing device, e.g. to measure the speed of the DNA passage through the nanopore or the relative effect on capacitance or current attributable to different nucleotides passing through the nanopore.
1.13. Any foregoing DNA which contains a terminal linker group enabling it to be anchored to a surface near the nanopore in a nanopore-based device such as Nanochip 1, et seq; a spacer sequence long enough to permit the DNA strand to reach the nanopore when anchored to a surface, a data storage sequence wherein the sequence encodes data, codons or other information, and optionally a restriction sequence, enabling the DNA to be cleaved and retrieved once synthesized.
1.14. Any foregoing DNA made by any of Method 1 et seq. or Method 2 et seq. or Method A, et seq.

In yet another embodiment, the invention provides the use of any of DNA 1, et seq. in a method for storing information.

In another embodiment, the invention provides the use of a single stranded DNA in a method for storing information, e.g., wherein the sequence is substantially non-self-hybridizing.

The nanochips can be fabricated for example as depicted in FIGS. 23-29. For example, in one format, each polymer strand is associated with two or four addition chambers, wherein the two addition chamber format is useful for encoding binary code in the polymer, and the four addition chamber format is particularly useful for making custom DNA sequences. Each addition chamber contains a separately controllable electrode. The addition chambers contain reagents to add monomers to the polymer in buffer. The addition chambers are separated by a membrane comprising one or more nanopores from a reserve chamber, which may be common to multiple addition chambers, and which contains deprotection reagents and buffer, to deprotect the protected monomers or oligomers added in the addition chambers. The nanochips comprise a multiplicity of addition chamber sets, to allow parallel synthesis of many polymers.

For example, in some embodiments, the nanopore-based memory device of the present disclosure may be fabricated on a polished single-crystal silicon wafer, e.g., approximately 200-400 microns thick. A layer of silicon nitride of about 200 nm thick is deposited onto both sides of the silicon wafer via, e.g., low pressure chemical vapor deposition (LPCVD), or other similar technique. Next, a layer of silicon dioxide, e.g., about 1-5 microns thick, is deposited on the top side of the single-crystal silicon wafer and then polished. Next, on top of the Silicon dioxide layer, a thin (e.g., about 5-20 nm) layer of silicon nitride is deposited. Then, a layer of silicon dioxide (e.g., about 5 micron) is deposited. Next, the fluidic "Add" Channels are created by etching through the silicon dioxide, exposing the thin silicon nitride layer at the bottom of the channels. These channels will become the 'Add 1' and 'Add 0' channels. The silicon wafer is then etched from the bottom to the silicon nitride. After this, individual deblock chambers are etched through the silicon dioxide, exposing the thin silicon nitride layer. Nanopores are then created in appropriate locations in the thin silicon nitride layer using electron beams or other appropriate techniques. A glass wafer (approximately 300 microns thick) with vias filled with conductive metal to serve as wiring, is aligned to the original silicon wafer and the wafers bonded together. An additional glass wafer (approximately 300 microns thick), with vias filled with conductive metal to serve as wiring, is aligned to and bonded to the bottom of the bonded wafer. Fluidic inlets and outlets are introduced by etching or drilling into the top layer of the device, through to the fluidic channels. Connections to the electrodes embedded within the device (which connect internally to the fluidic channels and deblock chambers), can be accessed on the top and bottom surfaces of the device. Other thicknesses may be used for the above layers if desired provided they provide the function and performance described herein.

High-bandwidth and low-noise nanopore sensor and detection electronics are important to achieving single-DNA base resolution. In certain embodiments, the nanochip is electrically linked to a Complementary Metal-Oxide Semiconductor (CMOS) chip. Solid-state nanopores can be integrated within a CMOS platform, in close proximity to the biasing electrodes and custom-designed amplifier electronics, e.g., as described in Uddin, et al., "Integration of solid-state nanopores in a 0.5 μm cmos foundry process", Nanotechnology (2013) 24(15): 155501, the contents of which are incorporated herein by reference.

In another embodiment, the disclosure provides a nanochip (Nanochip 1) for synthesis of and/or sequencing an electrically charged polymer, e.g., DNA, comprising at least two distinct monomers, the nanochip comprising at least a first and second reaction chambers, separated by a membrane comprising one or more nanopores, wherein each reaction chamber comprises one or more electrodes to draw the electrically charged polymer into the chamber and further comprises an electrolytic media and optionally reagents for addition of monomers to the polymer, for example,
1.1. Nanochip 1 wherein the nanopore has a diameter of 2-20 nm, e.g. 2-10 nm, for example 2-5 nm.
1.2. Any foregoing nanochip wherein the some or all of the walls of the reaction chambers of the nanochip comprise a silicon material, e.g., silicon, silicon dioxide, silicon nitride, or combinations thereof, for example silicon nitride.
1.3. Any foregoing nanochip wherein the some or all of the walls of the reaction chambers of the nanochip comprise a silicon material, e.g., silicon, silicon dioxide, silicon nitride, or combinations thereof, for example silicon nitride, and some or all of the nanopores are made by ion bombardment.

1.4. Any foregoing nanochip wherein some or all of the nanopores are comprised of a pore-forming protein, α-hemolysin, in a membrane, e.g. a lipid bilayer.

1.5. Any foregoing nanochip wherein some or all of the walls of the reaction chambers are coated to minimize interactions with the reagents, e.g., coated with a polymer such as polyethylene glycol, or with a protein, such a bovine serum albumin.

1.6. Any foregoing nanochip comprising an electrolyte media.

1.7. Any foregoing nanochip comprising an electrolyte media comprising a buffer, e.g., a buffer for pH 7-8.5, e.g. ca. pH 8, e,g, a buffer comprising tris(hydroxymethyl)aminomethane (Tris), a suitable acid, and optionally a chelater, e.g., ethylenediaminetetraacetic acid (EDTA), for example TAE buffer containing a mixture of Tris base, acetic acid and EDTA or TBE buffer comprising a mixture of Tris base, boric acid and EDTA; for example a solution comprising 10 mM Tris pH 8, 1 mM EDTA, 150 mM KCl, or for example, 50 mM Potassium Acetate, 20 mM Tris-acetate, 10 mM Magnesium Acetate, pH 7.9 @ 25° C.

1.8. Any foregoing nanochip comprising reagents for addition of monomers to the polymer.

1.9. Any foregoing nanochip capable of both synthesizing ("writing", e.g., by adding monomers or groups of monomers sequentially to the polymer) and sequencing ("reading", e.g., by measuring changes in current and/or inductance as the monomers pass through the nanopore) the polymer.

1.10. Any foregoing nanochip wherein the membrane comprising one or more nanopores comprises a metal surface on both sides, the metal surface being separated by an insulator, e.g. a silicon nitride membrane, the metal surfaces being configured, e.g., by lithographic means, to provide electrodes at either end of each nanopore, e.g., such that a current flow across the nanopore may be established through the nanopore via an electrolyte media, e.g., such that the currant can draw the polymer through the nanopore and as the polymer passes through the nanopore, the change in electric potential across the nanopore can be measured and used to identify the sequence of monomers in the polymer.

1.11. Any foregoing nanochip comprising an electrically charged polymer which is DNA.

1.12. Any foregoing nanochip comprising an electrically charged polymer which is single stranded DNA (ssDNA).

1.13. Any foregoing nanochip comprising an electrically charged polymer which is DNA comprising a predetermined restriction site.

1.14. Any foregoing nanochip comprising an electrically charged polymer which is DNA wherein the DNA is a DNA as described in any of DNA 1, et seq., above.

1.15. Any foregoing nanochip comprising an electrically charged polymer which is DNA, wherein the DNA comprises at least 95%, e.g. 99%, e.g., 100% adenines and cytosines.

1.16. Any foregoing nanochip comprising an electrically charged polymer which is DNA, wherein the DNA comprises only adenines and cytosines.

1.17. Any foregoing nanochip comprising one or more ports to permit introduction of and flushing out of buffer and reagents.

1.18. Any foregoing nanochip comprising a buffer solution, e.g., a solution comprising a buffer for pH 7-8.5, e.g. ca. pH 8, e,g, a buffer comprising tris(hydroxymethyl)aminomethane (Tris), a suitable acid, and optionally a chelater, e.g., ethylenediaminetetraacetic acid (EDTA), for example TAE buffer containing a mixture of Tris base, acetic acid and EDTA or TBE buffer comprising a mixture of Tris base, boric acid and EDTA; for example a solution comprising 10 mM Tris pH 8, 1 mM EDTA, 150 mM KCl, or for example, 50 mM Potassium Acetate, 20 mM Tris-acetate, 10 mM Magnesium Acetate, pH 7.9 @ 25° C.

1.19. Any foregoing nanochip which is or is capable of being lyophilized for storage and subsequently rehydrated, e.g., wherein the structure of the nanochip comprises a hydratable or water permeable polymer.

1.20. Any foregoing nanochip which is synthesized in a dry form, e.g., wherein the structure of the nanochip comprises a hydratable or water permeable polymer, followed by hydration prior to use, optionally followed by lyophilization for long term storage once the write process is complete.

1.21. Any foregoing nanochip wherein the electrically charged polymer, e.g., DNA, is stabilized with histone.

1.22. Any foregoing nanochip wherein the interior surface is positively charged.

1.23. Any foregoing nanochip wherein the electrodes are operably connected in a capacitive circuit capable of providing a radiofrequency pulsating direct current, e.g. at a frequency of 1 MHz to 1 GHz, e.g. 50-200 MHz, for example about 100 MHz, across the nanopore, e.g., wherein the pulsating direct current can draw the charged polymer through the nanopore and the monomer sequence can be determined by measuring the capacitive variance across the nanopore as the charged polymer goes through the nanopore.

1.24. Any foregoing nanochip comprising a reserve or deblocker chamber, which contains reagents for deprotection of the polymer following addition of a monomer or oligomer in one of addition chambers.

1.25. Any foregoing nanochip comprising a multiplicity of pairs of addition chambers.

Figure 24:
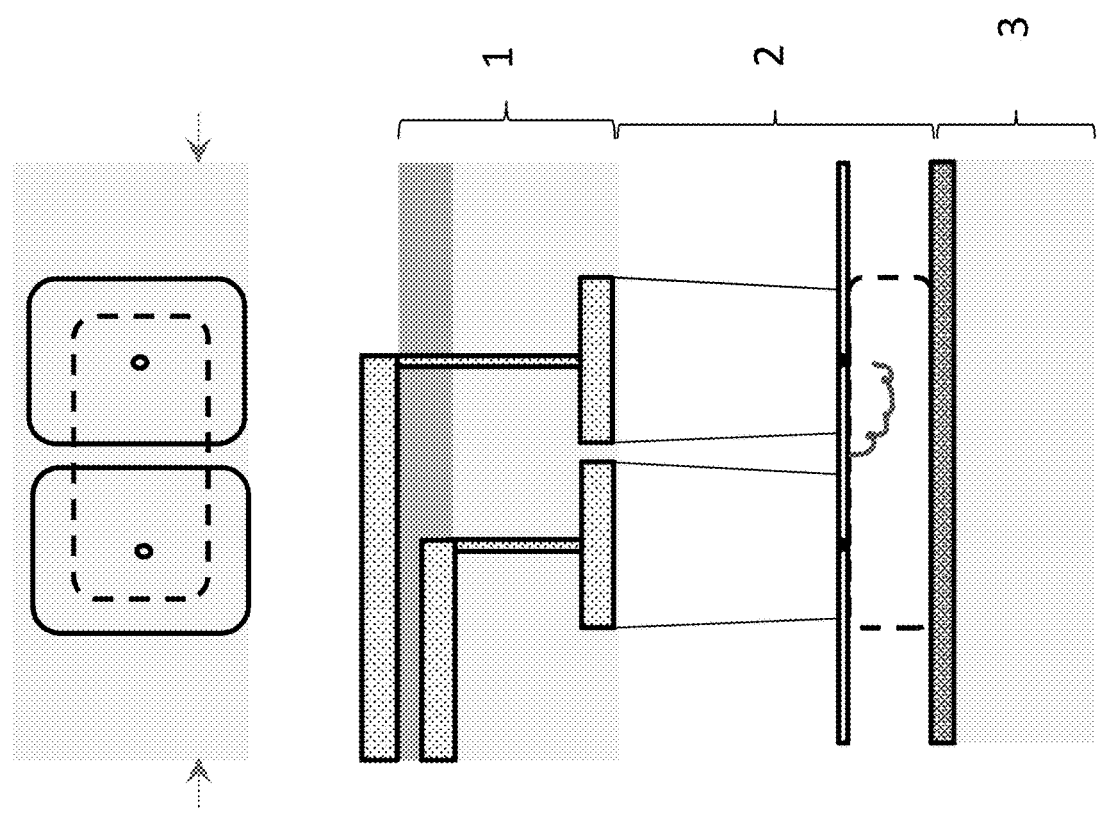
FIG. 24 depicts a dual addition chamber layout, suitable for adding two different types of monomers or oligomers, e.g., for 2-bit or binary encoding. The upper part of the figure shows a top view. The lower part shows a side view cross-section. The full device in this embodiment can be assembled from up to 3 independently fabricated layers and joined by wafer bonding, or may be formed by etching a single substrate. The chip comprises an electrical control layer (1), a fluidics layer (2) which contains the two addition chambers atop a reserve chamber, with the charged polymer (e.g., DNA) anchored between nanopore entrances to the first and second addition chambers, and an electrical ground layer (3).
Figure 25:
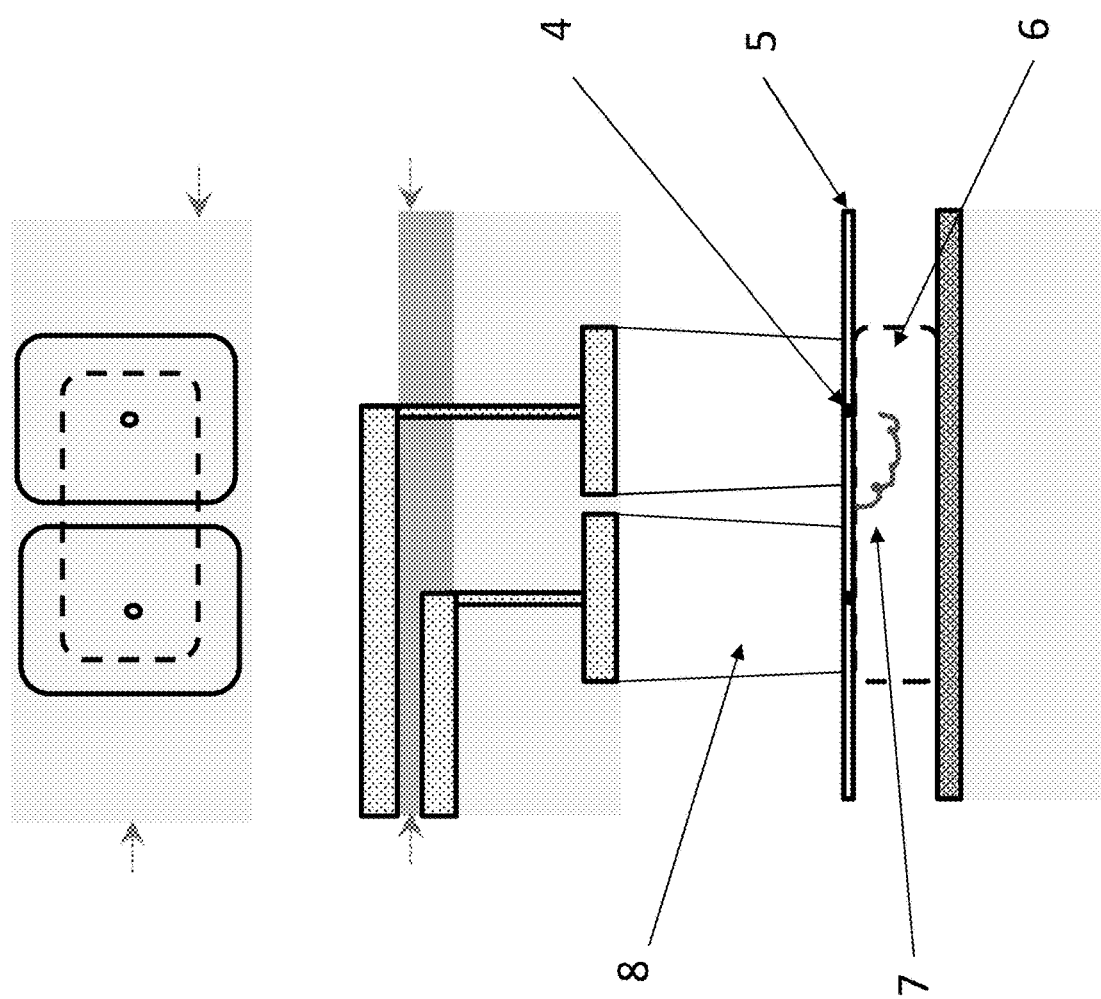
FIG. 25 depicts the operation of the dual addition chamber layout of FIG. 24. It will be observed that at the base of each addition chamber, there is a nanopore (4). The nanopore is made, for example, by drilling with FIB, TEM, wet or dry etching, or via dielectric breakdown. The membrane (5) comprising the nanopores is, e.g., from 1 atomic layer to 10's of nm thick. It is made from, e.g., SiN, BN, SiOx, Graphene, transition metal dichalcogenides e.g. $WS_2$ or $MoS_2$. Underneath the nanopore membrane (5) there is a reserve or deblocker chamber (6), which contains reagents for deprotection of the polymer following addition of a monomer or oligomer in one of addition chambers (it will be recalled that the monomers or oligomers are added in end-protected form, so that only a single monomer or oligimer is added at a time). The polymer (7) can be drawn into or out of the addition chambers by changing the polarity of the electrodes in the electrical control layer (1).
Figure 26:
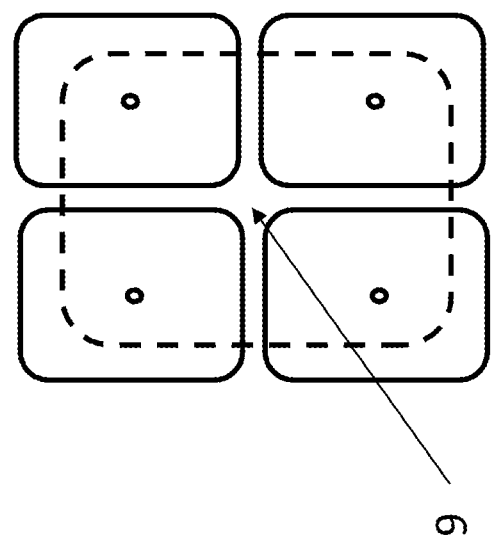
FIG. 26 depicts a top view of similar layout to FIGS. 24 and 25, but here there are four addition chambers which share a common reserve or deblocker chamber and the polymer is tethered at a position (9) with access to each of the four chambers. The cross section of this layout would be as depicted in FIGS. 24 and 25, and the charged polymer can be moved into each of the four addition chambers by operation of the electrodes in the electrical control layer (1 in FIG. 24).

1.26. Any foregoing nanochip comprising an electrical control layer, a fluidics layer and an electrical ground layer, e.g., as depicted in FIG. 24, joined by wafer bonding.

1.27. Any foregoing nanochip wherein the nanopore is made by drilling with FIB, TEM, wet or dry etching.

1.28. Any foregoing nanochip wherein the membrane comprising the nanopores is from 1 atomic layer to 30 nm thick.

1.29. Any foregoing nanochip wherein the membrane comprising the nanopores is made of SiN, BN, SiOx, Graphene, transition metal dichalcogenides e.g. $WS_2$ or $MoS_2$.

1.30. Any foregoing nanochip comprising wiring made from metal or polysilicon.

1.31. Any foregoing nanochip wherein the wiring density is increased by 3D stacking, with electrical isolation provided by dielectric deposition (e.g., via PECVD, sputtering, ALD etc).

1.32. Any foregoing nanochip wherein the contact to the electrode in the addition chamber is made using Through Silicon Via (TSV) by Deep Reactive Ion Etch (DRIE), e.g. using cryo or BOSCH process, or via wet silicon etching.

1.33. Any foregoing nanochip wherein individual voltage control for the electrode in each addition chamber allows the electrode in each addition chamber to be controlled and monitored individually.

1.34. Any foregoing nanochip wherein each polymer is associated with a first addition chamber, a second addition chamber, and a deblocking chamber.

1.35. Any foregoing nanochip wherein one or more chambers have fluid flow.

1.36. Any foregoing nanochip wherein one or more chambers are fluidically isolated.

1.37. Any foregoing nanochip wherein the deblocking chamber has fluid flow.

1.38. Any foregoing nanochip wherein addition chambers have common fluid flow.

1.39. Any foregoing nanochip wherein wiring between chambers is common among chambers of similar type (e.g. among first addition chambers, among second addition chambers, and among deblocking chambers.)

1.40. Any foregoing nanochip wherein the addition chambers have individual voltage control and the deblocking chambers have a common electrical ground.

1.41. Any foregoing nanochip wherein the deblocking chambers have individual voltage control, the first addition chambers have a common electrical ground and the second addition chambers have a common electrical ground.

1.42. Any foregoing nanochip wherein the nanochip is fabricated by wafer bonding, and the chambers are prefilled with desired reagents prior to bonding.

1.43. Any foregoing nanochip wherein one or more internal surfaces are silanized.

1.44. Any foregoing nanochip which has one or more ports for introduction or removal of fluid.

1.45. Any foregoing nanochip wherein the electrodes in the chambers are restricted from direct contact with the charged polymer, e.g., wherein the electrode is placed too far from the nanopore to be reached by a charged polymer bound to a surface adjacent to the nanopore, or wherein the electrode is protected by a material which will permit the passage of water and single atom ions (e.g., Na+, K+ and Cl– ions) but not the passage of the polymer or monomer or oligomer reagents to be joined to the polymer.

1.46. Any foregoing nanochip which is electrically linked to a Complementary Metal-Oxide Semiconductor (CMOS) chip.

1.47. Any foregoing nanochip which is operably linked to a chip controller, as hereinbefore described.

For example, in one embodiment, the invention provides a nanochip, e.g., according to any of Nanochip 1, et seq., for sequencing an electrically charged polymer, e.g., DNA, comprising at least two distinct monomers, the nanochip comprising at least a first and second reaction chambers comprising an electrolyte media and separated by a membrane comprising one or more nanopores, wherein each reaction chamber comprises at least one pair of electrodes disposed on opposite sides of the membrane, wherein the electrodes are operably connected in a capacitive circuit capable of providing a radiofrequency pulsating direct current, e.g. at a frequency of 1 MHz to 1 GHz, e.g. 50-200 MHz, for example about 100 MHz, across the nanopore, e.g., wherein the pulsating direct current can draw the charged polymer through the nanopore and the monomer sequence can be determined by measuring the capacitive variance across the nanopore as the charged polymer goes through the nanopore.

In another embodiment, the invention provides a method of reading a monomer sequence of a charged polymer comprising at least two different types of monomers, for example a DNA molecule, comprising applying a radiofrequency pulsating direct current, e.g. at a frequency of 1 MHz to 1 GHz, e.g. 50-200 MHz, for example about 100 MHz, across a nanopore, wherein the pulsating direct current draws the charged polymer through the nanopore and the monomer sequence is read by measuring the capacitive variance across the nanopore as the charged polymer goes through the nanopore, for example wherein the circuit is a resonant circuit and the capacitive variance is detected by detecting changes in the resonant frequency.

For example, in a particular embodiment, the invention provides a nanopore-based device (Device 1), e.g., a nanochip, e.g., according to any of Nanochip 1, et seq., which is capable of reading data stored in a polymer, the device comprising:

a. a resonator having an inductor and a cell, the cell having a nano-pore and a polymer that can traverse through the nanopore, the resonator having an AC output voltage frequency response at a probe frequency in response to an AC input voltage at the probe frequency;

b. an AC input voltage source configured to provide an AC input voltage at least the probe frequency; and c. a monitoring device configured to monitor the AC output voltage at least at the probe frequency, the AC output voltage at the probe frequency being indicative of the data stored in the polymer at the time monitoring.

For example, in certain embodiments of Device 1 the polymer comprises at least two monomers having different properties causing different resonant frequency responses at the probe frequency the response indicative of at least two different data bits, e.g., two different DNA nucleotides or oligonucleotides; and/or the inductor is connected in series with an effective capacitance to create the resonator, a combination of the inductor and effective capacitance being related to the resonant frequency response at the probe frequency.

For example, in a particular embodiment, the invention provides a method (Method 3) for reading data stored in a polymer, e.g., in conjunction with any of Methods 1, et seq., Method A, et seq., or Method 2, et seq., e.g., using a device according to any of Nanopore 1, et seq., or Device 1, et seq. comprising:

a. providing a resonator having an inductor and a cell, the cell having a nanopore and a polymer that can traverse through the nanopore, the resonator having an AC output voltage frequency response at a probe frequency in response to an AC input voltage at the probe frequency;

b. providing the AC input voltage having at least the probe frequency; and c. monitoring the AC output voltage at least at the probe frequency, the AC output voltage at the probe frequency being indicative of the data stored in the polymer at the time of monitoring; for example, 3.1. Method 3, wherein the polymer comprises at least two different types of monomers or oligomers having different properties causing different resonant frequency responses.

3.2. Method 3.1 wherein the at least two different types of monomers or oligomers comprises at least a first monomer or oligomer having a first property that causes a first resonant frequency response when the first monomer or oligomer is in the nanopore, and a second monomer or oligomer having a second property that causes a second resonant frequency response when the second monomer or oligomer is in the nanopore.

3.3. Method 3.2, wherein a characteristic of the first frequency response at the probe frequency is different from the same characteristic of the second frequency response at the probe frequency.

3.4. Method 3.3 wherein the characteristic of the first and second frequency responses comprises at least one of magnitude and phase response.

3.5. Method 3.4 wherein the first property and the second property of the monomers comprises a dielectric property.

3.6. Any foregoing method wherein the first and second monomers or oligomers each comprises a plurality of monomers or oligomers.

3.7. Any foregoing method wherein the cell comprises at least a top and bottom electrode, the nanopore being disposed between the electrodes, and the cell having a fluid therein, and wherein the electrodes, the nanopore and the fluid having an effective cell capacitance that changes when the polymer passes through the nanopore.

3.8. Any foregoing method wherein the inductor is connected in series with the effective capacitance to create the resonator, a combination of the inductor and effective capacitance being related to the resonant frequency response.

3.9. Any foregoing method wherein the polymer is moved through the nanopore via a DC steering voltage applied to the electrodes.

3.10. Any foregoing method wherein the cell has at least three chambers, at least two nanopores, and at least three electrodes for moving the polymer through the nanopore.

3.11. Any foregoing method wherein at least two of the monomers is indicative of at least two different bits of data.

3.12. Any foregoing method wherein a plurality of monomers is indicative of a bit of data.

3.13. Any foregoing method wherein the polymer comprises DNA, and wherein the DNA comprises bases, at least two of the bases providing a unique frequency response at the probe frequency.

3.14. Any foregoing method wherein the probe frequency is about 1 MHz to 1 GHz.

3.15. Any foregoing method wherein at least two of the monomers have a dielectric property that affects the frequency response of the resonator to produce at least two different frequency responses at the probe frequency.

3.16. Any foregoing method wherein the polymer comprises DNA and the sequence encodes a protein or a biologically functional RNA, e.g., mRNA.

3.17. Any foregoing method wherein the sequence encodes computer-readable data, e.g., in a binary, ternary or quaternary code.

3.18. Any foregoing method which is a method to read or confirm the sequence of a polymer sequenced in accordance with any of Methods 1, et seq., Methods A, et seq, or Methods 2 et seq.

In another embodiment, the invention provides a method for storing and reading data on a polymer in situ in a nanopore-based chip, comprising:
 a. providing a cell having at least three chambers, including an Add "1" chamber arranged to add a "1" bit to the polymer and an Add "0" chamber arranged to add a "0" bit to the polymer, and a "deblock" chamber arranged to enable the polymer to receive the "1" bit and "0" bit when the polymer enters the Add "1" or Add "0" chambers, respectively;
 b. successively steering the polymer from the "deblock" chamber through the nanopore to the Add "1" chamber or to the Add "0" chamber based on a predetermined digital data pattern to create the digital data pattern on the polymer; and
 c. reading the digital data stored on the polymer as it passes through the nanopore using a resonance frequency response of a nanopore-polymer resonator (NPR) on the chip, for example using a method according to Method 3, et seq.

In another embodiment, the invention provides a method of data storage and device, using a nanochip, e.g., any of Nanochip 1 et seq. to make an electrically charged polymer, e.g., DNA, comprising at least two distinct monomers or oligomers, wherein the monomers or oligomers are arranged in sequence to correspond to a binary code, e.g., in accordance with any of the foregoing Methods 1 and/or 2 et seq.

For example, in one embodiment, the nanochip comprising the polymer thus synthesized provides a data storage device, as the nanochip can be activated and the sequence of the polymer detected by passing it through a nanopore at any time. In other embodiments the polymer is removed from the nanochip, or amplified and the amplified polymer removed from the nanochip, stored until required, and then read using a conventional sequencer, e.g., a conventional nanopore sequencing device, In another embodiment, the invention provides a method of storing information comprising synthesizing any of DNA 1, et seq., e.g., in accordance with any of Methods 1, et seq. or Methods 2, et seq.

In another embodiment, the invention provides a method of reading a binary code, e.g., as encoded on any of DNA 1, et seq., using a nanopore sequencer, for example using Nanochip 1 et seq., as described herein.

In another embodiment, the invention provides any foregoing method wherein the nanochip is erased using an enzyme which lyses the charged polymer, e.g., a deoxyribonuclease (DNase) to hydrolyze DNA.

Referring to FIG. 48A and FIG. 58, as discussed herein, the DNA molecule 4810 may move (or traverse or translocate) in the chamber fluid through the nanopore 4808 from the upper chamber 4802 to the lower chamber 4804 by applying a DC steering voltage (Vin or Vst) across the top and bottom electrodes 4818, 4820, which creates an electric field across the nanopore 4808 and drives negatively charged DNA 4810 away from the negative charge and toward the positive charge. In particular, as discussed herein, when the top electrode 4818 has a positive voltage relative to the bottom electrode 4820 (shown here at ground or 0 volts), the DNA 4810 will move through the nanopore 4808 (if it was in the lower chamber 4804) toward the top electrode 4818, and into the upper chamber 4802. Conversely, when the top electrode 4818 has a negative voltage relative to the bottom electrode 4820, the DNA 4810 will move through the nanopore 4808 toward the bottom electrode 4818, and into the lower chamber 4804.

Referring to FIGS. 77A and 58, a graph 7700 of Vin vs. Time is shown, where Vin is a combination of an AC signal (or AC component or RF input) 7712 "AC In/Out" on the line 5812 (FIG. 58) and a DC bias (or steering) voltage 7714 "DC In" on the line 5810, as seen at the electrode 4818 (FIG. 58), after the "bias tee" connection discussed herein with FIGS. 58-61, for several DC values of Vin (e.g., −V1, 0, +V1), over several time periods 7702-7710. The AC component of Vin may be a single frequency, a time-varying frequency, or a broadband frequency signal, as described herein with FIGS. 55A and 55B, or any other frequency band signal having any desired shape signal (e.g., sinusoidal wave, square wave, triangle wave, or the like), that provides the desired results. When the DC value of Vin is −V1 (during time periods 7702,7710), the DNA 4810 would be in the bottom chamber 4804, and when the DC value is of Vin is +V1 (during time period 7706), the DNA 4810 would be in the top chamber 4802. When the DC value is of Vin is 0 v (ground) (during time periods 7704,7708), no voltage is applied across the nanopore 4808, and thus the DNA 4810 is not being driven in any particular direction, i.e., the DNA would be "floating" in the liquid/fluid of the chamber it was last driven into. In that case, the DNA 4810 may move or float around the chamber based on Brownian motion, stray electrical or magnetic forces, fluidic forces, thermodynamic forces, or other forces acting locally on the DNA 4810 strand.

In addition, DNA translocation time (or speed) through the nanopore 4808 may be adjusted or stopped at any time while not affecting the AC resonance measurement or sensitivity of the present disclosure. In particular, the speed (or velocity) at which the DNA molecule 4810 (FIG. 48A), 6550 (FIG. 65), moves (or travels or traverses or translocates) through the nanopore 4808 (FIGS. 48A, 58), 6528 (FIG. 65), may be determined in-part by the magnitude of the electric field (or voltage) applied across the nanopore 4808 by the top and bottom electrodes 4818,4820 (FIG. 48A), respectively, i.e., the DC value (or DC component or DC bias or DC input) of Vin.

It is known that the DNA translocation speed through the nanopore may be slowed down or stopped by controlling the DC voltage. For example, in FIG. 77A, if the DC component of Vin was reduced from +/−V1 to a lower magnitude value of +/−V2, as shown by the dashed lines 7716, the DNA may move more slowly through the nanopore 4808, while maintaining the AC component 7712 of Vin as before (not shown on 7716). Such a change in the DC component voltage from V1 (7714) to V2 (7716) does not affect the resonance measurement as it is based only on the AC component 7712 of the input voltage Vin. Thus, the speed of the DNA 4810 may be adjusted while not affecting the AC resonance frequency shift measurement.

Other techniques for adjusting the DNA translocation speed through a nanopore may be used if desired with the measurement techniques of the present disclosure, such as that described in US Patent Publication 2014/0099726 to Heller, or in U.S. Pat. No. 8,961,763, to Dunbar et al., which are each incorporated herein by reference to the extent necessary to understand the present disclosure.

Referring to FIG. 78A, more specifically, a top level block diagram and side view of a dual-pore device or cell 7800 is shown with corresponding voltage sources. In particular, there may be three chambers, e.g., an upper chamber 7802, a middle chamber 7804, and a lower chamber 7806, each filled with fluid (similar to that discussed herein), and three corresponding electrodes, e.g., upper electrode 7808, middle electrode 7810, and lower electrode 7812, and two nanopores 7814,7816 through respective membranes 7815,7817, which fluidically connect the three chambers 7802-7806. The middle electrode 7810 may be attached to the side of the middle chamber 7804 or may penetrate into the fluid of the middle chamber 7804 (e.g., a "wet" or "bath" electrode) shown as an electrode 7809 connected by conductive wires 7811 and the electrode 7809 may be located close to the nanopores 7814,7816, and may come from one side or multiple sides of the middle chamber 7804 and may partially or completely surround the perimeter of the nanopores 7814,7816.

A first DC voltage V1dc, 7816, is applied across the nanopore 7814 between the chambers 7802,7804, and a second DC voltage V2dc, 7818, is applied across the nanopore 7816 between chambers 7806,7804. The DC voltages V1dc (7816), V2dc (7818), have opposite polarities and thus apply opposite forces on the DNA 7820, as indicated by the arrows 7822, 7824, such that the net force on (and thus resultant velocity of) is determined by the difference between V1dc and V2dc, which can be set very precisely allow the DNA 7820 to be controlled very precisely, as described in the aforementioned patent application and patent. In addition, the input voltages may also have one or two corresponding AC components V1ac (7826), V2ac (7828), respectively, and the AC and DC components may be combined at respective "bias-tee" connections 7830, 7832, to provide the DC biased AC input signal to the respective electrodes 7808,7810. The bias-tee connections 7830,7832 may also contain inductors L1, L2, respectively, which may, together with the total capacitance of the respective resonator, set (or tune) the resonance frequencies of the respective resonators, as described herein. In particular, there may be two resonators (or nanopores resonators or NPRs), one NPR associated with the upper chamber 7802, and one NPR associated with the lower chamber 7804, in which case two AC voltages V1ac, V2ac would be used, as shown in FIGS. 78A and 78B. The NPRs may be set (or tuned) to the same resonant frequency or they may be set to different resonant frequencies, depending on the desired function and performance requirements. Alternatively, the resonators NPR1, NPR2, may be run at separate times to reduce the risk of electrical cross-talk or interference between adjacent resonators running on the same device or cell (or electro-chemical multi-chamber structure) 7800.

In some embodiments, only one nanopore resonator (NPR) may be used, corresponding to one of the chamber-pairs 7802,7804 or 7806,7804, in which case only of the corresponding one of the AC voltages V1ac,V2ac, and a corresponding one of the "bias-tee" connections 7830,7832, would be used. Use of a single resonator may minimize the risk of electrical (or electro-magnetic) cross-talk or interference between the adjacent resonators in the same device 7800, which such cross-talk may be enhanced when the electrically charged DNA string 7820 is passing through both pores 7814,7816. Such cross-talk may be minimized or filtered-out by filtering or signal processing or may be a common-mode effect that does not impact the resonant frequency shift caused when a DNA base passes by the electrodes in the nanopore and the corresponding measurement of such shift as discussed herein.

Referring to FIG. 78B, an AC equivalent circuit 7850 is shown for the AC portion of the dual-pore (or two-pore) device 7800 (FIG. 78A) having two resonators. In particular, the upper and middle chambers 7802, 7804 of the device 7800 (FIG. 78A) form a first nanopore resonator NPR1 (7852) having a coupling capacitor Ccpl1, an inductor L1, and a cell or chamber variable capacitance C1 and resistance R1, which vary as the DNA 7820 traverses through the first nanopore 7814, as discussed hereinbefore. Also, the lower and middle chambers 7806, 7804 of the device 7800 (FIG. 78A) form a second nanopore resonator NPR2 (7854) having a coupling capacitor Ccpl2, an inductor L2, and a cell or chamber variable capacitance C2 and resistance R2, which vary as the DNA 7820 traverses through the second nanopore 7816, as discussed hereinbefore with other NPR embodiments. If the two resonators NPR1, NPR2 are set to the same frequency, the values of the two inductors L1, L2 will be set to the same value. In the case where a single resonator is used for each device or cell 7800, then only one of the NPR resonators 7852, 7854 would in the equivalent circuit for that device.

Other dual-pore devices (or cells) 7800 may be electrically connected in parallel (by a common set of input/output lines) and interrogated simultaneously for frequency response (using frequency division multiplexing), as indicated by the dashed lines 7856-7860, similar to that discussed hereinbefore with FIG. 53, which may be done for either single or double resonator devices or cells 7800.

Because each of the resonators operates independently, they can be tuned to different frequencies to provide specific desired measurement performance. For example, as the nanopores 7814,7816 are measuring the same DNA string 7820, the first resonator NPR1 may be tuned to optimize the detection sensitivity (e.g., maximize the output magnitude or phase change for a given resonant frequency shift) of one DNA base type (e.g., larger purines, G's and A's), and the second resonator NPR2 may be tuned to optimize the detection sensitivity of the other DNA base type (e.g., smaller pyrimidines, C's and T's). Such maximum output signal change may be seen where the slope of the frequency response curve is the highest (closest to vertical), e.g., about half-way between the minimum and maximum of the frequency response curve for a given DNA base and a given probe measurement frequency as shown in FIG. 50.

In some embodiments, the resonators may be tuned to the same resonant frequency and monitored at the same or different probe frequencies, and the second resonator used as a delayed second measurement of the same data or a predictable variant thereof, e.g., for quality control or redundancy purposes or for other purposes. In particular, when the probe frequencies are the same for both resonators, the output signal data should be the same, and when the probe frequencies are different, the output signal data will be changed (or different) in a predictable way, knowing the second probe frequency and the expected DNA base being measured determined from the first resonator output data.

In some embodiments, the resonators may be tuned to the same resonant frequency and measured at different probe frequencies selected to optimize the detection sensitivity of a given DNA base type (e.g., maximize the output magnitude or phase change for a given resonant frequency shift). For example, the probe/measurement frequency for the first resonator NPR1 may be tuned to optimize the detection sensitivity of one DNA base type (e.g., larger purines, G's and A's), and the probe/measurement frequency for the second resonator NPR2 may be tuned to optimize the detection sensitivity of the other DNA base type (e.g., smaller pyrimidines, C's and T's). In that case, the first resonator may be used to detect G's and A's, and the second resonator used to detect C's and T's.

In the case where a single resonator is used for each device or cell 7800, then only one resonant frequency would be set using the associated inductor for that cell. In that case, each DNA base may be interrogated (or monitored or measured) at multiple probe frequencies, depending on the speed of the output signal frequency detection and the DNA translocation speed passing through the nanopore and/or the ability to re-run, re-interrogate, or "ping-pong" the DNA back and forth through the nanopore. In the limit, the full frequency response profile (such as that shown in FIG. 50) for each DNA base in the string may be determined through multiple samples.

Referring to FIG. 79A, in some embodiments, the effective capacitance (or effective impedance) change causing the resonance shift may be measured transversely across the diameter of the nanopore, as shown by a dual-chamber transverse measurement cell 7900. In particular, the cell 7900 has an upper (top) and lower (bottom) fluidic chambers 7902,7904, similar to the upper and lower chambers of the cell 4800 (FIG. 48A), and a membrane 7906, which separates the two chambers 7902, 7904. The membrane 7906 is made of a material as described herein and having a nanopore 7908 (or nanometer-sized hole) through the membrane 7906, the nanopore 7908 having a shape and dimensions such at that described herein, which allows for fluid communication between the chambers 7902, 7904. Inside the cell 7900, is a polymer molecule in solution, e.g., a single-stranded DNA molecule 7910 (or ssDNA), such as that described herein. Any other molecule or polymer maybe used if desired provided they provide similar performance and/or function to that described herein.

The chambers 7902, 7904, of the cell 7900 may be filled with a fluid, such as that described herein, that allows the DNA 7910 to float and move between the chambers 7902, 7904. The cell 7900 also has an upper (or top) electrode 7918 connected to a DC input voltage source V1dc 7922, and a lower (or bottom) electrode 7920 connected to the other side of the DC voltage source 7922, which in this embodiment is connected to DC ground (or GND or 0 volts).

The cell 7900 also has "transverse" electrodes 7902 (left), 7904 (right), located inside the membrane 7906, which run along the membrane from the outer edge of the cell 7900 to the edge of the nanopore 7908, as discussed more hereinafter. The transverse electrodes 7912, 7914 may be embedded in membrane 7906 having the nanopore 7908. In some embodiments, the transverse electrodes 7912, 7914 may be attached to, etched on, or otherwise disposed on the upper or lower surface of the membrane 7906. The electrodes 7912, 7914 may be located in close proximity to the nanopore 7908, and may come from multiple sides or angles around the nanopore 7908. In some embodiments, the electrodes 7912,7914 may be separate from the membrane 7906 and may penetrate into the chamber fluid between the two chambers 7902,7904 as "wet" or "bath" electrodes (not shown) and be located near the nanopore inlet or exit to measure the capacitance across the nanopore 7908.

The transverse electrodes 7912,7914, are connected to an AC input voltage source V1ac 7924. In addition, a DC voltage V1dc is applied to the top and bottom electrodes 7918, 7920 to drive or steer the movement of the DNA 7910 in the cell 7900, as discussed herein.

Referring to FIG. 79B, the transverse measurement cell 4900 (or the nanopore and DNA system) may be electrically modeled in the transverse direction across the transverse electrodes 7912,7914, as an equivalent circuit diagram 8000, shown as a transverse capacitor Ct and transverse resistor Rt connected in parallel, similar to the model used for the vertical or longitudinal measurement electrical model shown in FIGS. 48A-48C. In particular, the left transverse electrode 7912 sees a transverse capacitance Ct and transverse resistance Rt to ground that is set by its local environment, where the transverse capacitor Ct represents the transverse capacitance of the cell 7900 as determined by the properties of the two transverse electrodes 7912,7914 (i.e., the capacitor "plates") and the properties of dielectric material therebetween, defined at least by the fluid within the cell 7900 and the membrane 7906 with the nanopore 7908. The resistor Rt represents the DC transverse resistance associated with the cell 7900, defined at least by the losses associated with the dielectric material of the cell described above, which appear as a DC leakage current between the two electrodes.

When the DNA 7910 passes through the nanopore 7908, both the cell transverse capacitance and transverse resistance (or the overall transverse cell impedance, Ztcell) changes. Different DNA bases have different sizes, and thus have different effects on the transverse capacitance Ct and transverse resistance Rt, resulting in different transverse equivalent circuit models for each DNA base, similar to that discussed hereinbefore with FIGS. 48A-48C, where the values of C1,R1, C2,R2, and C3,R3, would be replaced by Ct1,Rt1, Ct2,Rt2, and Ct3,Rt3, but otherwise equivalent, resulting in three different impedance values (Ztcell1, Ztcell2, Ztcell3).

Referring to FIG. 79C, similar to FIGS. 49A and 49B, the transverse capacitance Ct and transverse resistance Rt of the cell 7900 (nanopore and DNA system) may be combined with an inductor Lt to create a transverse "inductor-cell" or "cell-inductor" RLC (or LC) resonant circuit or resonator or filter (or band-stop, or notch, or band-reject filter) as shown by the circuit 7970 (similar to FIG. 49A), having a transverse resonator impedance Ztres, which includes the transverse cell impedance Ztcell, and having a magnitude frequency response shown by the graph 4952 (FIG. 49B), and a phase frequency response shown by a graph 4954 (FIG. 49B). The center or resonant frequency fres of the transverse resonant circuit 7970 is shown in equations Eq. 1 and Eq. 2, described hereinbefore, with the values for L,C,R replaced with Lt,Ct,Rt.

In some embodiments, the transverse inductor (or inductance) Lt for the transverse resonator may be a spiral inductor or other inductance configuration described herein that provides the desired resonator characteristics (together with the other parts of the resonator effective impedance) and may be disposed within or on the surface of the membrane 7906, similar to that shown and described in FIGS. 58 and 59, or may be in other locations in the cell or have other configurations, such as part of the effective impedance of a split-ring resonator, as discussed more hereinafter.

The magnitude and phase frequency responses of the transverse resonant equivalent circuit 7970 (for a given value of Ct and Rt, or a given value of Ztcell) are substantially the same as those shown in graphs 4952, 4954 of FIG. 49B and described hereinbefore. Similarly, the family of resonant frequency response magnitude curves 5002 and phase curves 5003 of the resonant circuit (or filter), shown in FIG. 50 in response to DNA (or other polymer or molecule having varying sizes along its length) passing through a nanopore and changing the capacitance (or impedance) measured to ground (e.g., 0 volts), and thereby changing the resonant frequency fres, is also substantially the same. The transverse resonant circuit configuration shown in FIGS. 79A-79C may also be referred to herein as a transverse nanopore resonator (or transverse NPR or TNPR).

Also, the transverse nanopore resonator (TNPR) may also be multiplexed (or frequency division multiplexed) similar to that shown in FIG. 53, where each of the TNPRs (TNPR1-TNPR3) resonators may be connected in parallel (like NPR1-NPR3 resonators in FIG. 53) and fed by (or connected to) a common AC voltage source. In some embodiments, the coupling capacitors CCPL for each of the multiplexed resonators TNPR1-TNPR3 as the AC input (or RF input) signal may be applied directly to the inductor, as there is no "bias-tee" connection as the AC and DC voltage sources are not combined at a common electrode. Accordingly, there is no transverse DC voltage (or steering voltage) that needs to be blocked by the coupling capacitors CCPL. However, certain resonator design embodiments may still require an equivalent coupling capacitor CCPL, (even when no DC steering voltage is being blocked), as discussed hereinafter, such as with certain split-ring resonator (SRR) designs or other designs that may require an equivalent coupling capacitor CCPL in series with the resonator in the equivalent circuit model.

The transverse nanopore resonator TNPR has the same frequency response and frequency division multiplexing (FDM) properties as that of the longitudinal (or vertical or "along the pore length") nanopore resonator NPR (or longitudinal NPR or LNPR) configuration discussed herein with FIGS. 48A-48C, 49A-49B, 50, 51, 52, 53, 54 55A,55B, 56, 57 and related drawings. Also, any of the embodiments and cell designs disclosed herein may be used with the transverse resonator design(s) (TNPR) described herein for measurement or reading molecules structures or data. For example, the embodiments shown in FIGS. 65 and 66 may be modified to add transverse electrodes 6590 around one or more of the nanopores 6528. Also, the hardware and software logic and control logics and embodiments shown herein may also be used with the TNPR configurations.

One potential difference between the longitudinal (or vertical or "along the pore length") nanopore resonator (LNPR) configuration discussed herein with FIGS. 48A-48C and related drawings, and the transverse (or horizontal or "across the pore diameter") nanopore resonator configuration (TNPR) discussed herein with FIGS. 79A-79C and related drawings, is that the effective total (or average) cell capacitance value for a given cell design may be larger in the longitudinal configuration LNPR due at least partially to a potentially larger surface area of the electrodes (or capacitor "plates") and/or a potentially larger gap spacing between the electrodes that may exist in some embodiments of the LNPR configuration. However, even if the average effective capacitance value is larger in one configuration, the amount of capacitance change (or impedance change) and corresponding resonant frequency shift (magnitude and/or phase) as the measured molecule (e.g., each NDA base or other molecular structure) travels through the nanopore may be substantially similar between the LNPR and TNPR configurations.

One advantage of using the TNPR configuration is that is separates (or decouples) the DC steering voltage from the AC sensing or measurement voltage. Thus, there is no need for a "bias-tee" connection as the AC and DC voltage sources do not need to be combined to drive a common electrode.

Referring to FIG. 80, in some embodiments, the present disclosure may use both LNPR and TNPR configurations in the same cell. More specifically, a top level block diagram and side view of a dual-resonator device or cell 8000 is shown with the corresponding voltage sources. In particular, the cell 7900 shown in FIG. 79A may be modified as shown in FIG. 80 to create the dual-resonator cell 8000 configuration having both the transverse resonator TNPR shown in FIGS. 79A-79C and the longitudinal resonator LNPR shown in FIG. 48A to FIG. 61.

The transverse AC voltage V2ac 7924 is applied across the transverse electrodes 7912,7914 as described with FIG. 79A herein. Also, the DC steering voltage V1dc is applied across the electrodes 7918,7920 to steer the DNA between the two chambers 7902,7904, as also described with FIG. 79A. In addition, the input voltages may also have a corresponding AC components V1ac (8002), and the AC and DC components are combined at a "bias-tee" connection 8004 (such as is described herein with FIGS. 58-61, to provide the combined DC-biased AC input signal to the electrode 7918. The "bias-tee" connection 8004 may also contain the inductor Lv, which, together with the total capacitance of the vertical resonator, set (or tune) the resonance frequency of the vertical resonator VNPR, as described herein.

Referring to FIG. 80A, in some embodiments, the two resonators LNPR, TNPR may be run (or excited by the respective AC source V1ac, V2ac) at separate times (time multiplexed) to reduce the risk of electrical cross-talk or interference between adjacent resonators running on the same device or cell (or electro-chemical multi-chamber structure) 8000, or for other reasons. Also, the two resonators LNPR, TNPR in each cell may be set (or tuned) to the same resonant frequency (e.g., using the same resonator inductor L values for each) or they may be set to different resonant frequencies (e.g., using different resonator inductor L values for each), and/or the probe measurement frequency may be the same or different for the two resonators output signals, depending on the desired function and performance requirements, such as those described herein with FIG. 78B when two resonators were used. For the embodiment shown in FIG. 80A, the output voltages from the two resonators LNPR, TNPR associated with the AC input sources V1ac, V2ac, respectively, are V1out, V2out, respectively, and may be carried on separate lines as shown in FIG. 80A.

Referring to FIG. 80B, in some embodiments, the two resonators LNPR, TNPR may be run at (or driven or excited by) a single common AC source V2ac using the same lines to drive all the desired resonators in the cell array. In that case, the two resonators LNPR, TNPR in each cell may be set (or tuned) to different resonant frequency bands (e.g., using different resonator inductor L values for each resonator) to avoid overlap and interference between the resonator frequency output signals from the two resonators, as the output signals may be on the same return line V2out (as shown in FIG. 80B). Also, the probe measurement frequencies for the two resonators LNPR, TNPR may likely be at different frequencies as well for measuring the two resonators output signals, for similar reasons.

When the two resonators LNPR, TNPR are used in a given cell, the output measurement results of frequency shift or frequency response from the two resonators may be taken (or obtained or sampled) simultaneously (i.e., at the same time) when the DNA molecule 7910 (e.g., a give DNA base or monomer) is traversing through the nanopore 7908. The two output results may then be used as a redundancy or quality check to verify the results. In some embodiments, the two simultaneous measurement results may be combined, averaged, filtered, correlated, cross-correlated, or otherwise signal processed to more precisely identify the type of monomer passing by the electrodes 7912,7914 at a given time. Such correlation or processing may be helpful to remove common-mode effects or anomalous data between the two measurements.

In that case, the read logic, e.g., the read control logic 6850 (FIG. 68), would control when the read occurs to ensure they are at the same time for the same sample window. Referring to FIG. 68, for the case of a two-chamber device or cell, or cell array, such as that described herein, the Write/Vst Control Logic 6804 may have only one or two DC output steering voltage lines to control the DNA between the upper and lower chambers (instead of the three lines 6710-6714, Add0, Add1, Deblock, shown). Also, the Read Control Logic 6856 may have multiple AC source voltage Vin lines for driving the cell (e.g., V1ac, V2ac, FIG. 80A), and multiple AC response measurement lines for reading/measuring the frequency response AC output voltage from the cell (e.g., V1out, V2out, FIG. 80A) and/or make various other adjustments known by those skilled in the art to accommodate the designs or embodiments described herein. Similarly, in FIG. 75, the Read/Write Memory Controller 6802 may be used for moving or steering or driving the DNA between chambers for the purpose of reading the DNA (or molecule or sample of interest), and the Nanopore Memory Chip (Nanochip) may be the two-chamber chips described herein which may be used for the purpose of reading the DNA (or molecule or sample of interest), and the Instrument 7502 may be used for holding samples and providing them fluidically to the cells or devices described herein for the purpose of reading the DNA (or molecule or sample of interest), and those skilled in the art may make various other adjustments to FIGS. 68 and 75, as well as to FIG. 67 (showing an array of three chamber cells), to accommodate the various different cell designs or embodiments described herein.

It should be understood by those skilled in the art that the embodiments described herein for the transverse resonator TNPR and dual resonator LNPR,TNPR, for a two-chamber device or cell or cell array, may also be readily applied to the three chamber devices described herein (e.g., Add0, Add1, Deblock), as well as to four or more chamber devices, cells or cell arrays, such as is shown in FIG. 65 showing transverse electrodes 6590 in a three-chamber based array device.

Referring to FIGS. 81A and 81B, a plurality of transverse nanopore resonators TNPRs may be disposed in a common cell 8100, the cell 8100 is similar to the TNPR cell 7900 discussed hereinbefore (FIG. 79A); but having a plurality of transverse electrode pairs 8102-8110 on opposite sides of respective nanopores 8112-8120 within the cell 8100. The electrode pairs 8102-8110 may be embedded in or disposed on a membrane having the nanopores 8112-8120, as discussed hereinbefore in FIG. 79A. A DNA molecule (or other molecule of interest) 8122 in the cell 8100 may be driven (or steered) through each of the nanopores 8112-8120 and measured by each of the transverse resonators TNPRs. Also, the spacing De between pairs of transverse electrodes (and corresponding ring-resonators, if used) may be set to be large enough to minimize the effects of electro-magnetic interference between adjacent pairs of electrodes. Also, there may be a common AC input voltage Vac 8124 connected in parallel across each of the transverse electrode pairs 8102-8110. The AC output voltage signal Vout may be processed through an amplifier A 8216, similar to the amplifier A 5320 discussed hereinbefore with FIGS. 53 and 67. The common AC input voltage Vac may also be provided to other cells in an array, if desired, as indicated by a line 8128, as discussed hereinbefore. Also, there may be a DC input (or steering or driving) voltage Vdc 8134 applied across electrodes 8130, 8132, at the top and bottom, respectively, of the cell 8100, which may be used to drive the DNA 8122 (or other molecule of interest) through the nanopores 8112,8120. The DC steering voltage Vdc may also be provided to other cell in an array, if desired, as indicated by a dashed line 8136. In some embodiments it may be desired to have each of the steering control voltage for each cell to be individually controlled. In that case, there would be a separate Vdc steering voltage for each of the cells 8100 in the array. As a common AC input voltage Vac 8124 is used as the AC source to drive for each of the transverse resonators TNPRs in the cell 8100, each of the TNPRs should be tuned to a different resonant frequency band to avoid overlapping output signals, as discussed hereinbefore.

Referring to FIG. 81B, in some embodiments, the cell 8100 of FIG. 81A may be connect such that there are separate AC input voltages V1ac-VNac connected to each of the transverse electrode pairs 8102-8110 for each of the respective TNPRs. In that case, there may be separate AC output voltage signals Vout1-VoutN 8150, which may be processed through their respective amplifiers A 8252, similar to the amplifier A 5320 discussed hereinbefore with FIGS. 53 and 67. The separate AC input voltages V1ac-VNac may also be provided to a respective resonator other cells in an array, if desired, as indicated by a line 8154. For example, the first AC input voltage V1ac may be provided to the first TNPR in each cell in an array, which would share a common output voltage.

Also, the DC input (or steering or driving) voltage Vdc 8134 may be applied across the electrodes 8130,8132, at the top and bottom, respectively, of the cell 8100 to drive the DNA 8122 (or other molecule of interest) through the nanopores 8112,8120. The DC steering voltage Vdc may also be provided to other cell in an array, if desired, as indicated by a dashed line 8156. In some embodiments, it may be desired to have each of the steering control voltage for each cell to be individually controlled. In that case, there would be a separate Vdc steering voltage for each of the cells 8100 in the array. As different AC input voltages Vac1-VacN 8148 are used as the AC source to drive each of the transverse resonators TNPRs in the cell 8100, and have separate output signals, each of the TNPRs may be tuned to the same (or overlapping frequency bands) resonant frequency (or overlapping frequency bands or bandwidths), if desired. Alternatively, each of the TNPRs may be tuned to a different resonant frequency, if desired.

Having a plurality of TNPRs in series as shown in FIGS. 81A and 81B allows for multiple sequential measurement reads of the same DNA or molecule, which may be used for quality control and/or redundancy, if desired. In some embodiments, the resonant frequency of each TNPR resonator may be tuned to a frequency that provides maximum sensitivity to frequency shift (magnitude and/or phase) to optimize the accuracy of the measurement, and while not having overlapping frequency bands (when necessary depending on the configuration), as discussed hereinbefore. For example, for a DNA string, the first TNPR 8102 may be tuned to DNA Base G, TNPR 8104 may be tuned to DNA Base C, TNPR 8106 may be tuned to DNA Base A, TNPR 8108 may be tuned to DNA Base T. As discussed above, each may be in a different frequency band that does not overlap with the other TNPRs in the cell 8100, and/or in the other cells in the array (if connected in an array of cells), depending on the configuration used (e.g., FIG. 81A or 81B).

Referring to FIG. 82A, in some embodiments, a cell 8200 having multiple transverse electrodes 8202-8210 (and corresponding transverse resonators TNPRs) that interact with a fluidic nano-channel (or nano-tube) 8201 (or nano-fluidic channel) is shown. The cell 8200 is similar to the cell 8100 of FIGS. 81A and 81B, having the DC voltage Vdc 8134, and the AC voltage Vac 8124, but is modified such that instead of having nanopores located in a membrane, there may be a fluidic nano-sized channel or tube 8201 along which the DNA 8222 (or other molecule or cells) travels or flows in fluid between an upper chamber 8252 and lower chamber 8254. In that case, the transverse electrode pairs 8202-8210 may be disposed along opposite sides of the walls of the nano-channel 8201. Referring to FIGS. 82B and 82C, perspective views of embodiments of the nano-channel 8201 is shown, having a square (or rectangular) cross-section (FIG. 82B) and a circular (or oval) cross-section (FIG. 82C), respectively. The nano-channel 8201 may have a length Lc longer than the length of a typical nanopore, e.g., longer than about 50-100 nm (or greater), and a width (between side walls) Wc of about 10 nm to 1000 nm, and a height (or depth) Hc (from top of side wall to floor of nano-channel) of about 10 nm to about 1000 nm. Other dimensions may be used if desired, provided they provide the function and performance described herein. The width Wc of the channel may be set to at least partially linearize or elongate the DNA so it is not tangled or knotted or folded on itself in the fluidic nano-channel 8201, or the like, to allow the DNA to be substantially linearly flowed along same, such that only one monomer occupies a section of a nano-channel at a time, e.g., entropic confinement. For example, for double stranded DNA the width Wc of the nano-channel 8201 may be about 40 nm, and for single stranded DNA the width Wc may be about 20 nm. Other widths may be used if desired. In some embodiments, the width Wc and height Hc may be about the same dimensions to assist in providing substantially linear flow of the DNA. There may be an upper fluidic chamber 8252 which holds the DNA (or other molecule) 8222. When a voltage Vdc is applied across the upper and lower electrodes 8240,8242, e.g., negative voltage at electrode 8240 relative to electrode 8242 (as discussed hereinbefore for DNA movement), one end of the DNA 8222 is drawn into the top of nano-channel 8201, and flows past each pair of electrodes 8202-8210 (where it is read by each of the transverse resonators TNPRs) and then exits the bottom of the nano-channel 8201 where it is held in the lower fluidic chamber 8254.

The nano-channel 8201 may be similar to the nano-channels described in U.S. Pat. No. 8,722,327, to Cao et al, and U.S. Pat. No. 9,725,315, to Austin et al, which are incorporated herein by reference to the extent necessary to understand the present invention. The nano-channel 8201 may be formed by any technique that provides the functional and performance requirements described herein. In some embodiments, the nano-channels 8201 may be patterned or etched into a substrate 8250, e.g., fused-silica or other material that provides the function and performance described herein. Also, the spacing Dc between electrodes may be set to be large enough to avoid unacceptable electro-magnetic interference between adjacent rows of electrodes 8202-8210. Also, the electrodes 8202-8210 (and corresponding split-ring resonator or transverse resonators TNPRs) may be applied or lithographically fabricated on a layer of the substrate material 8250. In addition, the substrate material 8250 between rows of the electrodes 8202-8210 may be made of an insulating material (or doped with appropriate dopants added thereto) to limit electro-magnetic interference between adjacent rows of electrodes 8202-8210 to acceptable levels, or to minimize such interference. In some embodiments, the nano-channel 8201 may be one of a plurality of nano-channels, each channel 8201 having its own set of measurement electrodes 8202-8210, configured in the form of an array in the substrate 8250, e.g., plurality of parallel channels. In some embodiments, there may be an array or network of nano-channels, if desired, to hold or guide or transport the DNA (or other molecule) being measured by the present disclosure. In some embodiments, the nano-channels may be nano-sized tubes having an outer diameter and inner diameter 8260, within which the DNA flows. In some embodiments, the channel 8201 may be a series of short nano-channels or nano-tubes arranged in series and may be separated by a predetermined spacing. The channel 8201 may be any cross-sectional shape, e.g., square, rectangular, circular, oval, polygon, or other shape or any combination of same. When used with a nano-channel, the NPR or nanopore resonator may be referred to as a nano-channel resonator or, more generally, a "nano-path" resonator (NPR), which may apply to both nanopores or nano-channels or other nano-sized opening discussed herein. In addition, the cell 8200 having the nano-channel 8201 may also be electrically connected as shown in FIG. 81B to have separate AV input voltages V1ac-VNac and have separate output voltages Vout1-VoutN, if desired.

Referring to FIGS. 83-85, in some embodiments, one type of LC resonator design that may be used for the transverse nanopore resonator TNPR is a split-ring resonator (or SRR) which is configured to have the nanopore located in the gap of the split-ring portion of the resonator. In particular, FIG. 83 shows a partial top view of a layer of a split-ring resonator 8300 having an AC feedline 8306, which receives an AC input voltage AC IN (or Vin as discussed herein) provided at an input port 8302 and provides an AC output voltage at an output port 8304. The AC input voltage on the feedline 8306 is AC-coupled to a split-ring 8308 portion or structure (also referred to as the "resonator" portion herein) of the SRR 8300 having a square shape. The AC feedline 8306 is disposed a predetermined coupling distance Dcp1 8316 for a predetermined coupling length Lcp1 along one side of the split-ring 8308, to form an AC coupling capacitance to the split-ring 8308. There is a gap "g" (or split) 8310 in the split ring in which the nanopore 8312 is located. As the DNA (or other molecule) passes through the nanopore, it alters the capacitance across the gap g 8310 in the split-ring 8306 thereby changing the resonant frequency of the split-ring resonator LC circuit. The dimensions of the split-ring 8308 may be set to provide the desired resonant frequency and the desired electric field strength in the gap "g" 8310, as discussed more herein. Also, the coupling length Lcp1 and coupling distance Dcp1 along one side of the split-ring 8308 are set to provide the appropriate amount of energy transfer between the feedline 8306 and the resonator (split-ring) 8308. This may be referred to as the geometric capacitance, which would be a determined by a standard parallel plate capacitance formula. In some embodiments, the feedline 8306 may couple the AC voltage along more than one side of the resonator 8308, e.g., to ensure sufficient AC voltage is coupled to the resonator 8308, as shown by the dashed line 8305, in which case the output voltage AC OUT would be at a port 8307.

Referring to FIG. 84, a partial top view of an alternate embodiment of a split-ring resonator 8300 of FIG. 83 is shown, having split-ring (or resonator) portion 8308 being a circular shape. Other shapes may be used if desired provided it provides the desired function and performance.

Referring to FIG. 85, a partial front cut-away view along the line 8314 of FIGS. 83 and 84 is shown, having the split-ring 8308 disposed on top of a membrane 8324 in which the nanopore 8312 is located. The membrane 8324 separates an upper chamber 8326 and a lower chamber 8328 of a fluid-filled dual chamber cell 8330, similar to other dual chamber cells described herein, having a upper electrode 8320 and lower electrode 8322 which may be used to steer or drive the DNA (or other molecule of interest) 8332 between the two chambers 8326,8328.

Referring to FIGS. 86 and 87, in some embodiments, the feedline 8306 may be located on a different vertical plane from the split-ring 8308 portion. In that case, the feedline 8306 may be disposed above or below the split-ring portion 8308 of the SRR. In particular, FIG. 86 shows the SRR of FIG. 83 having the feedline 8306 displaced above the split-ring 8308. FIG. 87 shows a partial front cut-away view along the line 8602 of FIG. 86, showing the vertical displacement of the feedline 8306 above the split-ring 8308, which are separated by a vertical AC coupling distance Dvcp1 8604, which is analogous to the lateral AC coupling distance Dcp1 8316 shown in FIG. 83.

Referring to FIGS. 88,89,90,91,91A, the split-ring resonators SRRs of the present disclosure may be connected in an array configuration as shown in FIG. 88 for a square/rectangle shaped split-ring 8308 and FIG. 90 for a modified square/rectangular shaped split-ring 8308. In FIGS. 88 and 90, the feedline 8306 receives the AC input voltage VAC in from the input port 8302 and AC couples the AC voltage along the feedline 8306 to each of the split-rings 8308 in the array and provides the output voltage VAC out at the output port 8304. The nanopore 8312 is located in the gap g as discussed hereinbefore. Referring to FIGS. 89 and 90, the length Lg of the gap g of the split-ring 8306 may be made long enough to allow the nanopore 8312 to be located in the gap g along a straight line 8802 (FIG. 88), 9002 (FIG. 90).

The resonators 8308 may be frequency division multiplexed along the common feedline 8306 by making the split-rings of different geometries, such as that shown in FIGS. 88 and 90. In particular, the different area loops shown for the resonators 8308 create different resonant frequencies, similar to using different values of the inductor L or capacitor C to set the resonant, as discussed hereinbefore. In FIG. 90 the top row 9004, the shape varies by aspect ratio, in the middle row 9006, the shape varies by width (having a common height), and in the bottom row 9008, the shape varies by length (having a common width). Other variations may be used if desired.

The various dimensions h,w,s,g,L (and materials) of the split-ring (or resonator) 8308, shown in FIGS. 91 and 91A, may be set to provide the desired resonant frequency and desired electric field strength in the gap "g" 8310, where E is the electric field, H is the magnetic field, and k is the wave vector, of an incident field, shown in an x,y,z coordinate system, as is discussed in Bagiante, "Giant Electric Field Enhancement in Split Ring Resonators Featuring Nanometer-sized Gaps", Scientific Reports, 5:8051, DOI:10.1038/srep. 08051, which is incorporated herein by reference. The resonant frequency of a split-ring resonator may be determined by the dimensions and geometry of the split-ring (resonator) 8306 and the materials used, such as is discussed in Shamonin, "Resonant Frequencies of a Split-Ring Resonator: Analytical Solutions and Numerical Simulations", Microwave and Opt. Tech. Letters. Vol. 44, pp. 133-136, 2005, which is incorporated herein by reference. Also, to maximize the sensitivity of the change in resonance frequency of the split-ring resonator caused by the DNA (or other molecule) passing through the nanopore 8312 in the gap g, it is desirable to maximize the value of the electric field (or E-field) strength in the gap g 8310 where the nanopore 8312 is located, shown as region 8902 (FIG. 89), 9102 (FIG. 91). The gap electric field strength may be maximized by making the gap g as small as possible, e.g., 100 nm, such as is discussed in Bagiante, where a substrate was made of a highly resistive silicon, and the relevant dimensions of the gold structures were L=200 microns, w=10 microns, s=20 microns, and h=60 nm, where significant THz electric field enhancement (e.g. about 14,000) was observed at a lowest order resonance, e.g., at about 50 GHz. Other values for the gap g may be used if desired provided it provides sufficient electric field strength sufficient across the gap where the nanopore (or nano-channel) is located to provide sufficient shift in resonant frequency to measure the desire molecule traversing through the nanopore or nano-channel.

Other LC resonators may be used for the present disclosure, if desired, such as micro-strip, coplanar waveguide, pseudo-lumped element LC (where the inductor and capacitor are made geometrically using geometric shapes on the chip itself, rather than using lumped-element chip components), provided they provide the function and performance described herein.

Referring to FIGS. 92A,92B,92C,92D,92E,92F, various possible top-view geometries are shown for the electrodes near the nanopore 8312. Referring to FIG. 92G, a side view of the membrane having a nanopore 8312 is shown. In particular, FIG. 92A shows electrodes 9202,9204 wider than the diameter of the nanopore 8312 and electrodes having perpendicular (or square) edges. FIG. 92B shows electrodes 9202,9204 the same width as the nanopore 8312 diameter. FIG. 92C shows electrodes 9202,9204 stepped down to the nanopore size near the nanopore, and having square edges. FIG. 92D shows electrodes 9202,9204 tapered down to the nanopore size near the nanopore, and having square edges. FIG. 92E shows electrodes 9202,9204 with the ends rounded or contoured to the nanopore geometry at the nanopore. FIG. 92F stepped down to nanopore diameter size near the nanopore, where both the nanopore and the electrodes have square edges.

Referring to FIG. 92G, a side view of the electrodes 9202,9204 in the membrane that has the nanopore 8312 is shown, showing the nanopore 8312 cross section that begins wide and narrows in the center to the desired nano-pore diameter size discussed herein (e.g., an "X" shape or two cones intersecting at a common apex), and showing the electrodes being near the center where the nanopore 8312 is at the smallest diameter. In some embodiments, the edges of the nanopore cross-section may also be rounded instead of straight lines, and may follow a similar outer and central diameter as indicated by dashed lines 9212. Also, in some embodiments, the electrodes may stop before reaching the edge of the nanopore as indicated by dashed lines 9210 (FIGS. 92A-92G).

Referring to FIG. 93, an example of a fabrication process to create a chip that implements portions of the present disclosure is shown. In particular, in step 1, SiN layer 9306 is formed on top of a Silicon base 9302 and a resonator layer 9304 is formed having a thickness of about 50 nm of Au using LPCVD (Low Pressure Chemical Vapor Deposition) low stress silicon nitride (other thicknesses may be used if desired). Next, in step 2, the resonator layer 9304 is etched 9308 to define the resonator (or split-ring) geometry using lithography, such as wet etching the Au (gold) with KI (potassium iodide). Next, in step 3, a heterostructure 9312 is grown of TEOS Silicon Oxide (about 150 nm), followed by LPCVD low stress silicon nitride layer 9310 of about 20 nm. Next, in step 4, the backside of the cavity is etched in the silicon base 9302 to form a backside (or bottom side) cavity (or chamber) 9314 using standard etching techniques. Next, in step 5, the front side (or top side) is etched to form a second cavity (or chamber) 9316 and define the nanopore 9318. Next, in step 6, feedline contacts 9320 are added to connect (or couple) the resonator to the feedline (not shown; see feedline 8306 in FIG. 83), located in the CMOS chip 9324 to complete the main portions of the fluidic chip/layer 9322 (top/bottom electrodes may be added later, as discussed below). In this case, the feedline contacts 9320 may couple the feedline to more than one portion (or side) of the resonator.

Next, in step 7, the fluidic chip/layer 9322 is flipped upside-down and wafer bonded to a CMOS readout layer chip 9324 and then packaged with a field programmable gate array (FPGA) printed circuit board (PCB) layer 9326 using known standard integrated circuit fabrication, connection and assembly techniques. In particular, the multi-chamber fluidics chip portion 9322 is used for DNA control, and the resonator structure used for impedance measurements (via resonance shift) is integrated into the fluidics chip 9322. The readout of the resonator output is performed by the CMOS chip 9324 containing amplifiers, impedance matching circuits wafer bonded to the fluidics chip 9322, and the fluidics/CMOS chip stack 9322,9324, is then packaged with the FPGA readout PCB 9326, where the FPGA controls signal generation, and processes the data read from the resonators. The bottom electrode (not shown) may be part of the CMOS chip 9324 facing the chamber 9316, and the top electrode (not shown) may be added with a top layer (not shown) bonded to the top of the silicon layer 9302 (and fluidic chip 9222).

As discussed herein, the transverse electrodes described herein for the transverse resonators TNPRs may have various different geometries depending on the desired performance and sensitivity and materials and resonator designs used. When used with the split-ring resonator described herein, the electrodes may define a portion of the split-ring (resonator) 8306 near the gap g.

Referring to FIGS. 94 and 95, the three chamber device described herein, such as that shown in FIGS. 62, 65 and 66, having an Add 0 and Add 1 upper chambers 9402,9404, and a common lower (or deblock) chamber 9406, may have a nanometer sized fluidic channel, or nano-channel 9408 in the lower chamber 9406, having a width "Wc" of about 40 nanometers, to help keep the DNA from becoming tangled or knotted, similar to the nano-channel described herein before with FIGS. 82A, 82B, and 82C. In particular, the nano-channel 9408 may have a length Lc of least about 10 nm long (longer than length of a nanopore), and a width (between side walls) Wc of about 10 nm to 1000 nm, and a height (or depth) Hc (FIG. 95), from top of side wall to floor of nano-channel of about 10 nm to about 1000 nm. Other dimensions may be used if desired, provided they provide the function and performance described herein. The width Wc of the channel 9408 may be set to at least partially linearize or elongate the DNA so it is not tangled or knotted or folded on itself, or the like, in the fluidic nano-channel 9408, to allow the DNA to be linearly flowed along same, such that only one monomer occupies a section of a nano-channel at a time, e.g., entropic confinement. For example, for double stranded DNA the width Wc of the nano-channel 8201 may be about 40 nm, and for single stranded DNA the width Wc may be about 20 nm. Other widths may be used if desired. In some embodiments, the width Wc and height Hc may be about the same dimensions to assist in providing substantially linear flow of the DNA along the nano-channel 9408. The nano-channel 9408 may be similar to the nano-channels described in the aforementioned U.S. Pat. No. 8,722,327, to Cao et al, and U.S. Pat. No. 9,725,315, to Austin et al, which are incorporated herein by reference to the extent necessary to understand the present invention. In some embodiments, there may be an array or network of nano-channels, if desired, to hold or guide or transport the DNA (or other molecule) being measured by the present disclosure. The nano-channel 9408 may be formed by any technique that provides the functional and performance requirements described herein, such as that described herein with FIGS. 82A-82C. In some embodiments, the nano-channel 9408 may be nano-sized tube having an outer diameter and inner diameter, within which the DNA flows. The channel 9408 may be any cross-sectional shape, e.g., square, rectangular, circular, oval, polygon, or other shape or any combination of same. The DNA (or other polymer or molecule) 9408 may have a bead or DNA origami or other particle or molecule attached to one end (such as the bead 6554 shown in FIG. 65) that causes that portion of the DNA to be retained in the lower common deblock chamber 9406 and does not pass through the nanopores 9410,9412. In some embodiments, the bead may be magnetic or charged, such that it is attracted to the bottom electrode 9416 to ensure the DNA is pulled into the nano-channel. In FIG. 94, a vertical channel 9408 is provided having a length Lc and width Wc. In FIG. 95, the nano-channel 9408 runs into the page and the DNA would lay flat along the bottom of the lower channel 9406. In some embodiments, the nano-channel 9408 may be oriented from left to right along the bottom of the lower chamber 9406, similar to that shown for the bottom electrode 6514 in FIG. 65.

Instead of using an FFT (Fast Fourier Transform) logic 5328 (FIG. 53) to measure (or monitor or determine or calculate) the frequency content of the output voltage signal, any other technique may be used, such as one or more fixed or tunable digital or analog bandpass filters set or tuned the appropriate monitor or probe frequency or frequencies or frequency band(s) of interest. Any other technique may be used to measure the desired frequency content of the frequency division multiplexed output voltage signal.

Also, as described herein, the resonant frequency shift (see FIGS. 50-52) of the various nanopore or nano-channel (or nano-path) resonators (NPRs) described herein may be measured and multiplexed, and the measurement sensitivity optimized, in numerous different ways, each of which may be applied to any of the embodiments and resonators and cell configurations discussed herein. In some embodiments, the probe or monitoring or measurement frequency may be set at a fixed value or tuned or changed dynamically to optimize the measurement sensitivity for reading one or more DNA bases (or other molecule of interest), by monitoring at a probe frequency where the frequency response (magnitude and/or phase) has the highest slope (i.e., maximum change in signal strength when resonant frequency shifts). Also, in some embodiments, the frequency response (or a portion thereof) of a given DNA base (or monomer) may be "mapped" out by obtaining multiple probe sample points at different frequencies, thereby creating a frequency response curve or frequency response "signature" for a given monomer. The above may be accomplished by performing multiple separate reads of the DNA molecule (i.e., re-interrogation) with the same resonator and shifting the probe measurement frequency for each measurement to optimize the sensitivity for the desired detection monomer, or by having a plurality of resonators in series each being measured at a different probe frequency, or by simultaneously measuring a plurality of probe frequencies from a single resonator at a given time when the molecule passes by.

Also, the present disclosure may be used with nanopores, nano-tubes, nano-gaps, nano-channels, or any other nano-size opening (collectively, "nano-path") between two chambers and may have any desired side-view or top-view geometric shape, such as circle, oval, square, rectangle, polygon, polygon with rounded-corners, triangle, parallelogram, rhombus, diamond, star, a combination of any of these, or any other desired shape, provided it provides the function or performance described herein, any of which may be referred to herein as a "nanopore" or a "nano-path".

In particular, in some embodiments, the nanopore 4808 (FIG. 58) in the two chamber device 5800 of FIG. 58 may be created using a vertical nano-channel in the membrane where the membrane 4806 may be made thicker than the length of a typical nanopore (e.g., greater than about 50 nm), e.g., about 100-1000 nm (or greater) and the nano-channels etched in the membrane 4806 material (e.g., fused-silica or other material that provides the function and performance described herein such as discussed hereinbefore) to provide the nano-sized fluidic path (or nano-path) between the chambers 4802,4804, which may also be used for the nanopores 6203,6205 of the three-chamber devices 6200, 6300 of FIGS. 62,63, respectively. In that case, the DNA may be detected using one or more transverse electrodes along the nano-channel as discussed hereinbefore with FIGS. 82A and 82B. In some embodiments, the nanopore 4808 (FIG. 58) may be created by a combination of a nanopore and a nano-channel, e.g., having a nanopore drilled, created or disposed, in the bottom (or floor), or in one of the walls, of a horizontal nano-channel etched in the membrane 4806, depending on the orientation of the nano-channel.

The present disclosure may be used with frequencies up to or exceeding 100 GHz, provided specific frequencies or energy are avoided that would cause heating of or damage to the liquid or materials of the cell or damage to the molecules being measured. In particular, it has been shown, as referenced hereinbefore, e.g., the aforementioned paper by Laborde, that the deleterious effects of ionic screening of electric fields caused when charged molecules, such as DNA which carries a negative charge, are moved through or exist in an ionized solution (such as the fluids that may be used in the chambers described herein), are reduced at high frequencies. Accordingly, the present disclosure may operate at frequencies as high as will be supported by integrated circuit technology.

In some embodiments, the present disclosure may be implemented using a nano-capacitor array CMOS chip, made by NXP Semiconductors, such as the chip discussed in the aforementioned paper by Laborde, where the electrode pads of the NXP chip become (or interface with) ground electrodes of the fluidics chip or cell 5800, such as that shown in FIG. 58.

The present disclosure does not require the cells to be individually addressable to read the data in each of the cells. Also, the present disclosure allows the reading of data stored on polymers located in each of the cells by using a single source input line and single output line, using frequency division multiplexing.

It should be understood by those skilled in the art that each of the cell configurations and embodiments described herein may be used for interrogating, evaluating, reading or sequencing DNA, proteins, polymers, or other molecules or moieties residing in fluid samples that are presented or provided to the cells described herein. In that case, there may be fluidic interfaces which fluidically connect one or more input sample chambers or reservoirs to the cells to fluidically provide the samples to the cells for interrogation, measurement or evaluation.

All dimensions described herein are shown for exemplary embodiments of the present disclosure, other dimensions, geometries, layouts, and orientations may be used if desired, provided they provide the functions described herein.

Also, the present disclosure is not limited to use with DNA based data storage, and may be used with any type of molecular data storage, such as any polymer or other material that has the necessary properties to achieve the functions or performance described herein.

Any automated or semi-automated device or component described herein may be a computer-controlled device having the necessary electronics, computer processing power, interfaces, memory, hardware, software, firmware, logic/state machines, databases, microprocessors, communication links, displays or other visual or audio user interfaces, printing devices, and any other input/output interfaces, including sufficient fluidic and pneumatic control, supply and measurement capability to provide the functions or achieve the results described herein. Except as otherwise explicitly or implicitly indicated herein, process or method steps described herein may be implemented within software modules (or computer programs) executed on one or more general purpose computers. Specially designed hardware may alternatively be used to perform certain operations. In addition, computers or computer-based devices described herein may include any number of computing devices capable of performing the functions described herein, including but not limited to: tablets, laptop computers, desktop computers and the like.

Although the disclosure has been described herein using exemplary techniques, algorithms, or processes for implementing the present disclosure, it should be understood by those skilled in the art that other techniques, algorithms and processes or other combinations and sequences of the techniques, algorithms and processes described herein may be used or performed that achieve the same function(s) and result(s) described herein and which are included within the scope of the present disclosure.

Any process descriptions, steps, or blocks in process flow diagrams provided herein indicate one potential implementation, and alternate implementations are included within the scope of the preferred embodiments of the systems and methods described herein in which functions or steps may be deleted or performed out of order from that shown or discussed, including substantially concurrently or in reverse order, depending on the functionality involved, as would be understood by those reasonably skilled in the art.

It should be understood that, unless otherwise explicitly or implicitly indicated herein, any of the features, characteristics, alternatives or modifications described regarding a particular embodiment herein may also be applied, used, or incorporated with any other embodiment described herein. Also, the drawings herein are not drawn to scale, unless indicated otherwise.

EXAMPLES

Example 1

Immobilizing One End of DNA Adjacent to Nanopore and Controlled Back and Forth Movement of DNA Via Electrical Current Experimental procedures are developed to demonstrate that DNA is moved back and forth between two chambers separated by a nanopore, via an electrical current, under conditions that a relevant protein does not move between chambers.

A nanochip comprising two chambers is fabricated from silicon nitride. Nanopores of <4 nm (for dsDNA or ssDNA) and 2 nm (for ssDNA only) are prepared as described in Briggs K, et al. *Automated fabrication of 2-nm solid-state nanopores for nucleic acid analysis*, Small (2014)10(10): 2077-86. The two chambers are referred to as a 'near' and 'far' chamber, the far chamber being the chamber where 3' end of DNA is conjugated.

It is shown that ssDNA (2 nm pore) and ssDNA+dsDNA (4 nm pore) but not protein pass through the nanopore. Passing through the nanopores is detected by electrical current disruption.

Conjugation of DNA to pore surface: Attach 5' amino modified DNA to carboxy-coated polystyrene beads (Fluoresbrite® BB Carboxylate Microspheres 0.05µm, from Polysciences, Inc.) via carbodiimide mediated attachment. 3' of DNA is labeled with biotin. DNA is of a pre-specified length.

Strepatividin conjugation: Conjugation was performed on the 'far' side of a silicon nitride nanopore conjugate streptavidin to the surface, as described in Arafat, A. *Covalent Biofunctionalization of Silicon Nitride Surfaces*. Langmuir (2007) 23 (11): 6233-6244.

Immobilization of DNA near the nanopore: DNA conjugated polystyrene beads in buffer is added to 'near' chamber and buffer is added to 'far' chamber (standard buffer: 10 mM Tris pH 8, 1 mM EDTA, 150 mM KCl). Voltage (~100 mV) is applied until current disruption is observed (use an Axon Nanopatch200B patch-clamp amplifier). 50 nm beads cannot pass through the nanopore, so when a DNA strand has gone through and a bead is pressed against an end of the nanopore the current is highly disrupted. Current is maintained 1-2 mins until DNA is irreversibly bound to immobilized streptavidin on the far side via binding of biotin. To confirm that the DNA has been immobilized, the current is reversed. Different currents are observed if DNA is in or out of the pore. If it appears that DNA is not immobilized, then the process is repeated.

Release the bead via endonuclease: Restriction enzyme in restriction enzyme buffer is added to the chamber where the DNA is attached. In one embodiment, the DNA is single stranded and contains a restriction site cleavable by an enzyme that will cleave single stranded DNA. See, e.g., Nishigaki, K., *Type II restriction endonucleases cleave single-stranded DNAs in general*. Nucleic Acids Res. (1985) 13(16): 5747-5760. In an alternative embodiment, a complementary oligonucleotide is added to the chamber where the DNA is attached and allowed to hybridize for 30 minutes to create dsDNA, then the restriction enzyme is added. Once the bead is released, it is washed away. Current is switched between forward and reverse to confirm that the DNA goes into/through and out of the pore.

Demonstrate controlled back and forth movement: Using standard buffer, current is applied in forward direction until signal disruption is observed and then reverted to 'normal' after the DNA passes. Reverse current is applied until signal disruption is observed. It is observed that the signal does not go back to normal as the DNA remains in the pore. Application of current in forward and reverse direction is repeated for several cycles to confirm that DNA moves back and forth through the nanopore.

Example 1a

Immobilizing DNA Strand Adjacent to Nanopore in a Silicon Dioxide Chip

A nanochip interior wall is fabricated from silicon dioxide. Both sides are silanized, but the oligonucleotide is conjugated to just one side of the chip wall, then a nanopore is created.

Silanization: The surface of the chip wall is cleaned with piranha solution (various brands commercially available, generally comprising a mixture of sulfuric acid ($H_2SO_4$) and hydrogen peroxide ($H_2O_2$), which remove organic residues from the surface) at 30° C., and washed with double-distilled water. A stock solution of (3-aminopropyl)triethoxysilane (APTES) is prepared, with 50% methanol (MeOH), 47.5% APTES, 2.5% nanopure H2O, and aged >1 hour at 4° C. The APTES stock is then diluted 1:500 in MeOH and applied to and incubated with the chip wall at room temperature. The chip wall is then rinsed with MeOH and dried at 110° C. for 30 minutes.

Conjugation: The chip wall is then incubated for 5 hours at room temperature in a 0.5% w/v solution of 1,4-phenylene diisothiocyanate (PDC) in dimethyl sulfoxide (DMSO). It is washed briefly twice with DMSO and the briefly twice with double distilled water. The chip wall is then incubated with 100 nM amine-modified single stranded DNA oligomers (ca. 50-mers) in double distilled water (pH 8) overnight at 37° C. Then the chip wall is washed twice with 28% ammonia solution to deactivate any unreacted material, and washed twice with double distilled water. One or more nanopores are then created in the wall.

Once the fabrication of the nanochip is complete, the interior wall is coated with DNA oligomers ca. 50 bp long. This permits a single stranded DNA having an end-terminal sequence complementary to the surface bound DNA to be localized to a nanopore by attaching the ssDNA to a relatively bulky structure (e.g. a bead, a protein, or a DNA origami structure having a diameter too large to fit through the nanopore,), wherein the sequence complementary to the surface-bound DNA is distal to the bulky structure, pulling the charged polymer through the nanopore using current, allowing the ssDNA to bind to a complementary surface bound DNA oligomer adjacent to the nanopore, and cleaving off the bulky structure.

Example 2

DNA Synthesis—Single Nucleotide Addition

DNA is moved to 'reserve' chamber by applying appropriate current and detecting DNA movement.

Terminal transferase enzyme (TdT, New England Biolabs) in appropriate buffer (50 mM Potassium Acetate, 20 mM Tris-acetate, 10 mM Magnesium Acetate, pH 7.9 @ 25° C.), plus reversibly blocked-dATP* is added to the 'addition' chamber. The buffer is also added to the 'reserve' chamber.

dNTPs that have reversible blocks on the 3'-OH are used to add nucleotides to the DNA. When added to the DNA chain, the next dNTP cannot be added until the blocked dNTP is unblocked.

Deblocking can be chemical or enzymatic. Different approaches are utilized:

a. 3' 0-allyl: Allyl is removed by Pd-catalyzed deallylation in aqueous buffer solution as described in Ju J, *Four-color DNA sequencing by synthesis using cleavable fluorescent nucleotide reversible terminators*. Proc Natl Acad Sci USA. (2006);103(52):19635-40; or by using using iodine (10 mol %) in polyethylene glycol-400, as described in Shankaraiah G., et al., *Rapid and selective deallylation of allyl ethers and esters using iodine in polyethylene glycol*-400. Green Chem. (2011)13: 2354-2358 b. 3' O—NH2: Amine is removed in buffered NaNO$_2$, as described in U.S. Pat. No. 8,034,923.

c. 3'-phosphate. Phosphate is hydrolyzed with Endonuclease IV (New England Biolabs). Other possible 3' modifications which can also be removed with Endonuclease IV include phosphoglycoaldehyde and deoxyribose-5-phosphate.

d. 3'-O-Ac: Acetate is removed by enzymatic hydrolysis as described in Ud-Dean, *A theoretical model for template free synthesis of long DNA sequence*. Syst Synth Biol (2008) 2:67-73, The DNA is then moved to the 'far' chamber by applying appropriate current and detecting DNA movement. DNA is deprotected by switching out buffers and adding deblocking buffer/solution as described in a.-d. above.

Process is repeated as desired to make sequence of interest.

Example 3

DNA Synthesis: Block Oligonucleotide Addition

The 3' end of double stranded DNA is attached adjacent to a nanopore with 4 nm aperture. The 5' end of the DNA has an overhang of CG (reading from 5' to 3').

Oligo cassettes A and B are made as follows:

```
                                              (SEQ ID NO 1)
5' CGAAGGG <CODE A OR B> GTCGACNNNNN

3' GCTTCCC <COMPLEMENT> CAGCTGNNNNN
```

CodeA and CodeB each represent an informational sequence. Ns refer to any nucleotide. The 5' sequence comprises a topoisomerase recognition site and the 3' sequence comprises an Acc1 restriction site. The oligo is exposed to topoisomerase and the topoisomerase binds to 3' thymidine:

```
5' CGAAGGG <CODEA OR B> GTCGACNNNNN

3'  *TTCCC <COMPLEMENT>  CAGCTGNNNNN (* = topoisomerase)
```

DNA is moved to 'near' chamber by applying appropriate current and detecting DNA movement. The topoisomerase-charged 'codeA' oligo is provided in the 'addition' chamber. The DNA is moved into the addition chamber by applying appropriate current and detecting DNA movement, whereupon the code A oligo is bound to the DNA, Acc1 is added to the 'reserve' chamber, where it cleaves at the restriction site to provide a topoisomerase ligation site.

The process is repeated until the desired sequence is reached, adding other 'code A' or 'code B.' Note that it is not required to continually add new Acc1 to the 'reserve' chamber; it is just needed to flush out codeA or codeB oligos in 'addition' chamber when switching from codeA or codeB.

For sequencing a pore that only allows ssDNA to pass, some modifications to the protocol above are required. It is already known that when dsDNA encounters a small pore (2 nm) only ssDNA will go through and the complement will be 'stripped' off. Thus, if doing this synthesis with a 2 nm pore one must ensure that the proper dsDNA is able to 'reform' on the other side. To do this one would add "CGAAGGG <CODEA OR B> GTCGACNNNNN" (SEQ ID NO 1) to the near chamber (to ensure a restriction site is created) and "CGAAGGG <CODEA OR B> GT" (SEQ ID NO 3) to the far chamber (to ensure a topo-compatible site is generated).

Elaborating on the foregoing method, we demonstrate the sequential 'addition' of DNA-encoded information into a growing DNA chain with ≥2 sequential additions (representing 2 bits of data), each of which comprise an 'add' and a 'deprotect' step. Initial experiments for optimization and proof of concept are performed in microtubes.

In the approach described in this example, one bit of information is encoded in a string of nucleotides. The DNA bit to be 'added' is a short dsDNA sequence conjugated to vaccinia topoisomerase I (topo). In the presence of a suitable 'deprotected' 'acceptor' DNA, the topo-charged DNA 'bit' is enzymatically and covalently linked ('added') to the acceptor by the topoisomerase, which in the process becomes removed from the DNA. A restriction enzyme can then cleave the added bit to 'deprotect' it and create of suitable 'acceptor' sequence for addition of the next bit.

Figure 22:
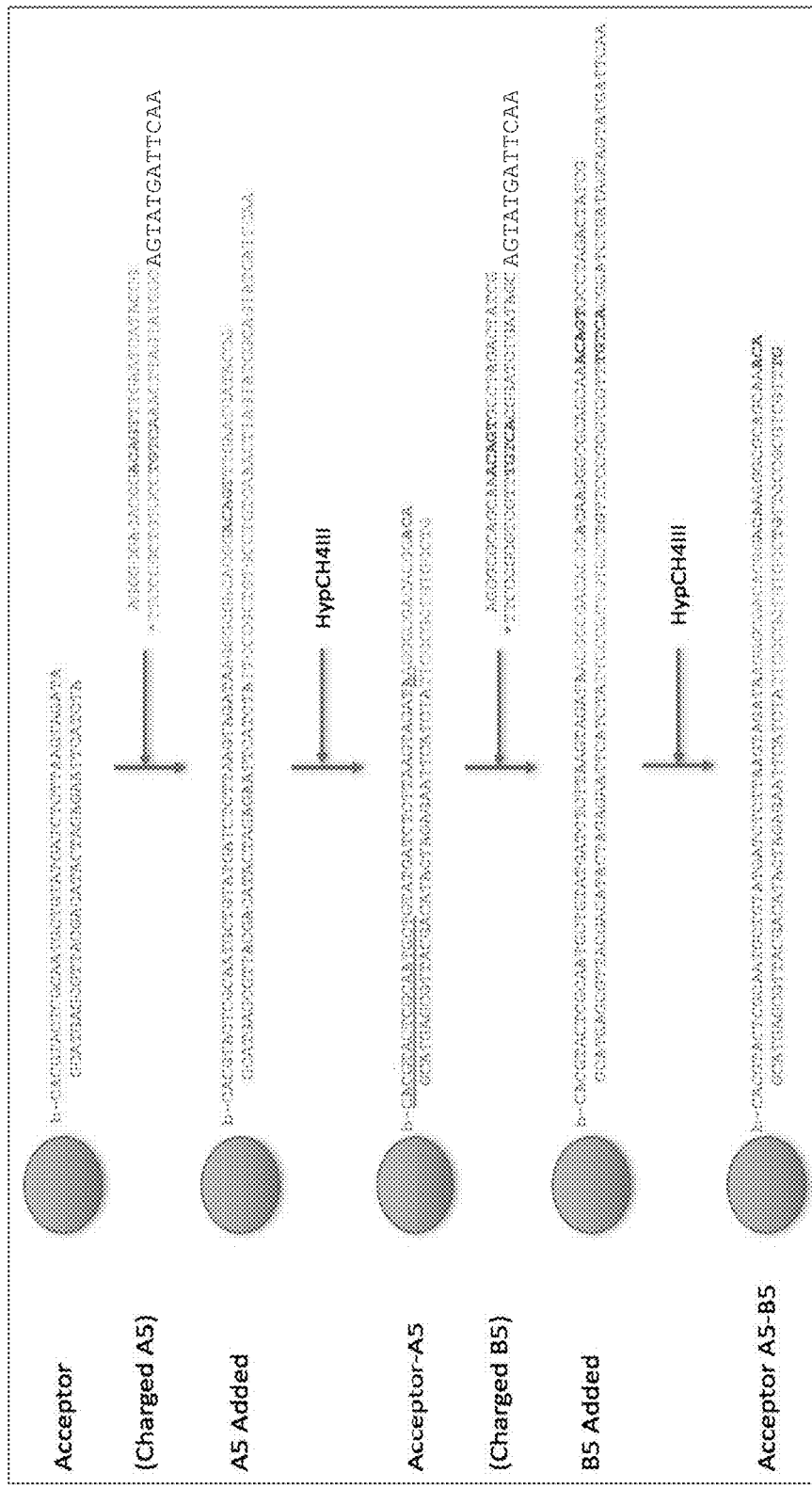
Figure 23:
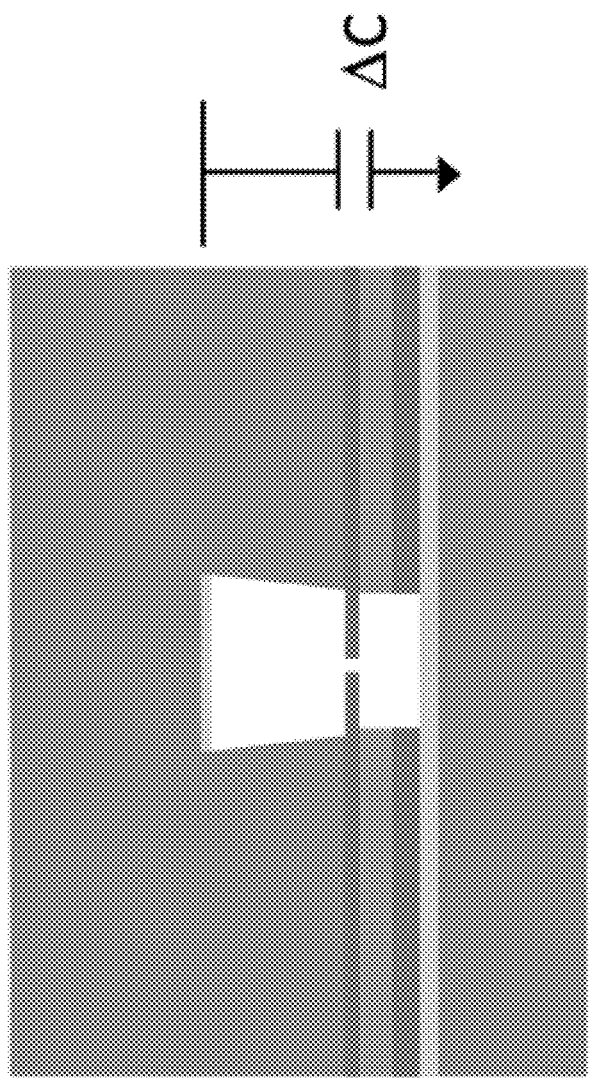
FIG. 23 depicts a format for a nanopore sequencer wherein the polymer sequence is read using capacitive variance. In this capacitive readout scheme, electrodes form the top and bottom plates of a capacitor, separated by a membrane comprising a nanopore. The capacitor is embedded in a resonant circuit, wherein a pulsating direct current can draw the charged polymer through the nanopore. The change in capacitance is measured as the polymer, e.g. DNA, passes through the nanopore, using high frequency impedance spectroscopy. A major advantage of this approach, particularly with DNA, is that the measurement frequency can be very high (effectively a measurement for every cycle, so a 100 MHz frequency corresponds to 100 million measurements per second), and much greater than the rate of transfer of monomers through the nanopore (DNA, for example, unless somehow constrained, will pass through the nanopore in response to electrical current at a speed on the order of 1 million nucleotides per second).

Topo Charging: A generic charging scheme is as follows, depicted schematically in FIG. 22 and below, where N indicates any nucleotide, and A, T, G, and C represent nucleotides with adenine, thymine, guanine and cytosine bases respectively. N's on top of one another are complementary. While this example uses the restriction enzyme HpyCH4III, the basic strategy will work with other restriction enzymes, e.g., as demonstrated in Example 4.

```
N-N-N-N-N-N-N-N-N    A-G-G-G-N-N-N-N-N-N-N-N-N
N-N-N-N-N-N-N-N-N-T-T-C-C-C-N-N-N-N-N-N-N-N-N
+
Topoisomerase *
=
N-N-N-N-N-N-N-N-N
N-N-N-N-N-N-N-N-N
+
    A-G-G-G-N-N-N-N-N-N-N-N-N
*-T-T-C-C-C-N-N-N-N-N-N-N-N-N
(topo charged)
(N's on top of one another are complementary)

Addition
Generic 'add' reaction:
N-N-N-N-N-N-N-N-N-A
N-N-N-N-N-N-N-N-N-N..
(acceptor)
+
    A-G-G-G-N-N-N-N-N-N-N-N-N
*-T-T-C-C-C-N-N-N-N-N-N-N-N-N
(topo charged)
=
N-N-N-N-N-N-N-N-N-A A-G-G-G-N-N-N-N-N-N-N-N-N
N-N-N-N-N-N-N-N-N-T-T-C-C-C-N-N-N-N-N-N-N-N-N
+
*
(free topo)

Deprotection
Generic 'deprotection' reaction:
...N-N-A-C-A-G-T-N-N-N-N-N-N-N-N-N
...N-N-T-G-T-C-A-N-N-N-N-N-N-N-N-N
+
HpyCH4III
(restriction enzyme)
=
...N-N-A-C-A
...N-N-T-G..
(deprotected)
+
..G-T-N-N-N-N-N-N-N-N-N
T-C-A-N-N-N-N-N-N-N-N-N
(side product)
```

The following oligonucleotides are ordered from Integrated DNA Technologies (IDT). The "b" at the end of some of the oligonucleotides indicates biotin):

(SEQ ID NO 4) BAB:
CGATAGTCTAGGCACTGTTTGCTGCGCCCTTGTCCGTGTCGCCCTTATCT

ACTTAAGAGATCATACAGCATTGCGAGTACG

B1: b-CACGTACTCGCAATGCTGTATGATCTCTTAAGTAGATA (SEQ ID NO 5):
B2: ATCTACTTAAGAGATCATACAGCATTGCGAGTACG

TA1: b-CACACTCATGCCGCTGTAGTCACTATCGGAAT (SEQ ID NO 6):
TA2: AGGGCGACACGGACAGTTTGAATCATACCG (SEQ ID NO 7): TA3b:
AACTTAGTATGACGGTATGATTCAAACTGTCCGTGTCGCCCTTATTCCG

ATAGTGACTACAGCGGCATGAG

TB1: b-CACACTCATGCCGCTGTAGTCACTATCGGAAT (SEQ ID NO 8):
TB2: AGGGCGCAGCAAACAGTGCCTAGACTATCG (SEQ ID NO 9): TB3b:
AACTTAGTATGACGATAGTCTAGGCACTGTTTGCTGCGCCCTTATTCCGA

TAGTGACTACAGCGGCATGAG (SEQ ID NO 10):
FP1: CACGTACTCGCAATGCT (SEQ ID NO 11):
FP2: CGGTATGATTCAAACTGTCCG (SEQ ID NO 12):
FP3: GCCCTTGTCCGTGTC

Oligonucleotides are solubilized to 100 uM in TE buffer and stored at −20 C.

Hybridized oligonucleotides are made by mixing oligonucleotides as described below, heating to 95° C. for 5 minutes, and then dropping the temperature by 5° C. every 3 minutes until the temperature reaches 20° C. Hybridized oligonucleotides are stored at 4° C. or −20° C. The combinations of oligonucleotide are as follows:

B1/2
48 uL B1
48 uL B2
4 uL 5M NaCl
A5
20 uL TA1
20 uL TA2
5 uL TA3b
4 uL 5M NaCl
51 uL TE
B5
20 uL TB1
20 uL TB2
5 uL TB3b
4 uL 5M NaCl
51 uL TE

The following buffers and enzymes are used in this example:
TE: 10M Tris pH 8.0, 1 mM EDTA, pH 8.0
WB: 1M NaCl, 10 mM Tris pH8.0, 1 mM EDTA pH8.0
1×Topo: 20 mM Tris pH7.5, 100 mM NaCl, 2 mM DTT, 5 mM MgCl2
1×RE: 50 mM K-acetate, 20 mM Tris-acetate, 10 mM Mg-acetate, 100 ug/ml BSA pH 7.9 @ 25 C.
Vaccinia DNA Topoisomerase I (topo) is purchased from Monserate Biotech (10,000 U/mL)
HypCH4III is purchased from NEB
Streptavidin-coated magnetic beads (s-MagBeads) are purchased from ThermoFisher.

Figure 20:
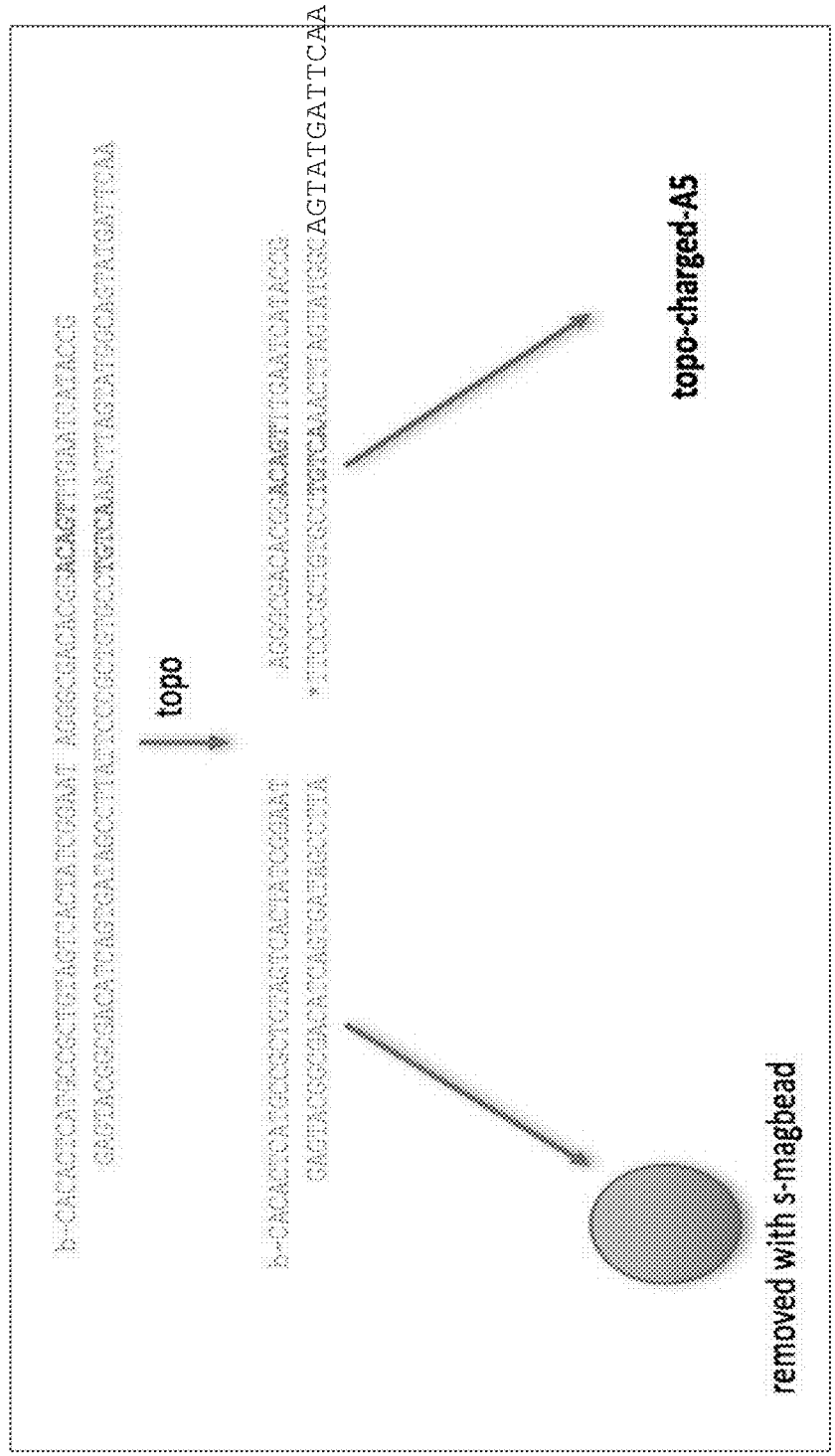
FIGS. 20-22 depict the schematically the proof of concept experiments wherein the bits used to encode the data are short oligomers attached using topoisomerase.

Acceptor is prepared as follows: 5 uL of s-magbeads are washed one time in 200 uL WB (binding time 1 minute). 5 uL B1/2+195 uL WB is added to beads and incubated 15 minutes at room temperature, then washed one time with 200 uL WB, then washed one time with 200 uL 1×Topo, and resuspended in 150 uL of 1×Topo Topo-charged A5 (see FIG. 20) is prepared as follows: 4 uL 10×topo buffer+23 uL water+8 uL A5+5 uL topo are incubated at 37° C. for 30 minutes, added to to 5 uL s-magbeads (washed 1× with 200 uL WB, 1× with 200 uL 1×Topo, resuspended in 150 uL 1×topo), and allowed to bind for 15 minutes at room temperature.

'Add' charged A5 to Acceptor: s-magbeads are removed from Topo-charged-A5, added to Acceptor, and incubated at 37° C. for 60 minutes. The aliquot is removed, diluted 1/200 in TE, and stored at −20 C Deprotection: The material is washed one time with 200 uL of WB, when washed one time with 200 uL of 1×RE, and resuspended in 15 uL 10×RE and 120 uL water). 15 uL HypCH4III is added. The mixture is incubated at 37° C. for 60 minutes, then washed one time with 200 uL WB, washed one time with 200 uL 1× topo, to produce a product which we term 'Acceptor-A5'.

Figure 21:
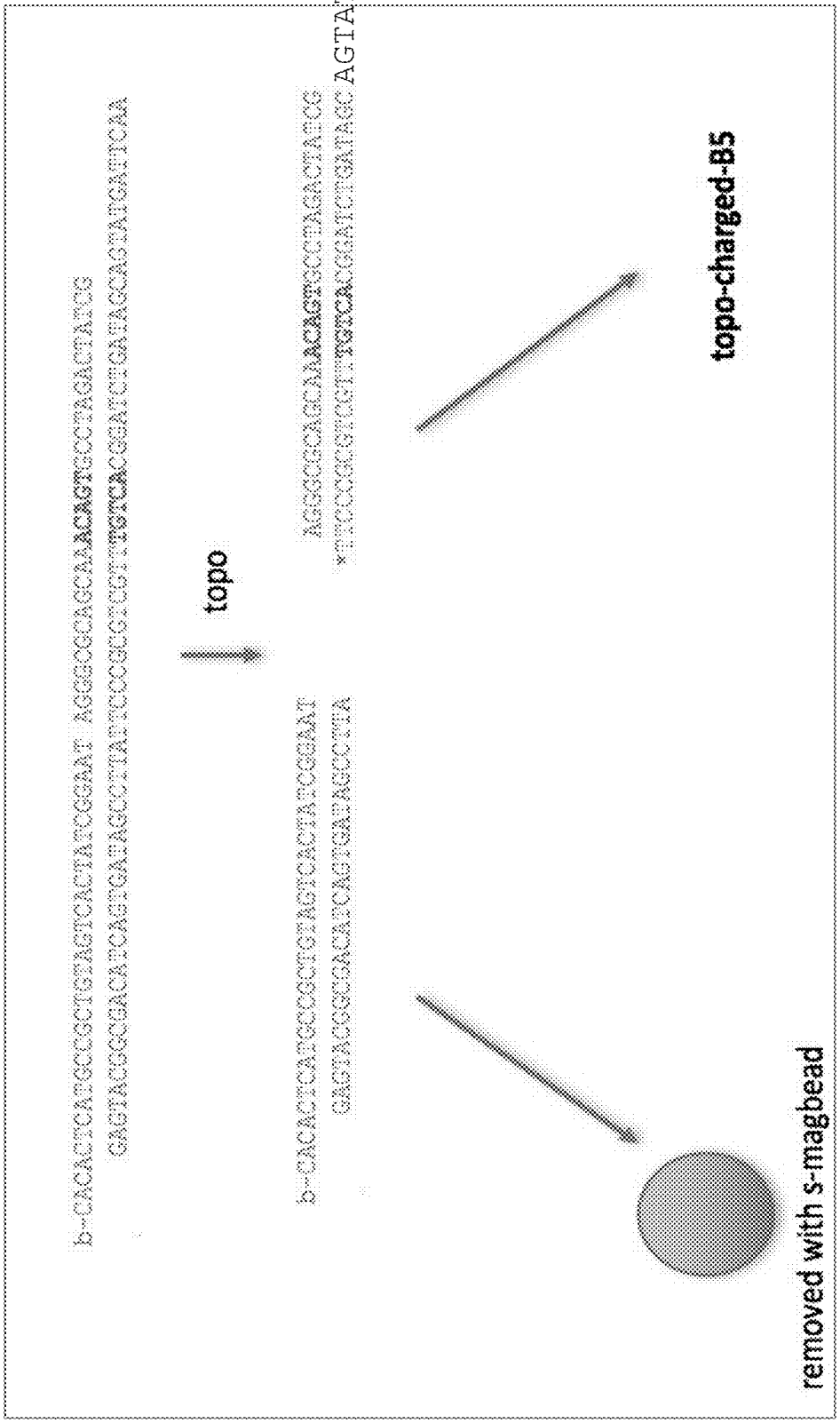

Topo charged B5 (see FIG. 21) is prepared as follows: 4 uL 10× topo buffer. 23 uL water and 8 uL B5+5 uL topo are combined and incubated at 37° C. for 30 min. the product is added to 5 uL s-magbeads (washed one time with 200 uL WB, one time with 200 uL 1× Topo, and resuspended in 150 uL 1× topo) and allowed to bind for 15 minutes at room temperature.

'Add' charged B5 to Acceptor-A5: s-magbeads are removed from Topo-charged-B5, added to Acceptor-A5 and incubated at 37° C. for 60 minutes. The aliquot is then removed, diluted 1/200 in TE, and stored at −20° C.

Deprotection: The material is washed one time with 200 uL of WB, then washed one time with 200 uL of 1×RE, and resuspended in 15 uL 10×RE and 120 uL water. 15 uL HypCH4III is added, and the mixture is incubated at 37° C. for 60 minutes.

Confirmation that the above reactions worked is provided by PCR amplification of aliquots from A5 (Acceptor with A5 added: step iii, 'A5 Added' in schematic) and B5 (Acceptor-A5 with B5 added: step vi, 'B5 Added' in schematic). 'No template' is used as negative control for A5, A5 is used as negative control for B5, oligo BAB is used as positive control for B5. The expected product size for A5 PCR is 68 bp, the expected product size for B5 PCR is 57 bp. (B1/2 is also run on the gel, expected size is ~47 bp, but this may be approximate as there are overhangs and it is biotinylated). PCR reactions (30 cycles of 95/55/68 (1 minutes each) are carried out as follows:

|  | A5 (—) ctrl | A5 | B5 (—) ctrl | B5 |
|---|---|---|---|---|
| Template |  | 1 uL | 1 uL | 1 uL |
| FP1 | 1 uL | 1 uL | 1 uL | 1 uL |
| FP2 | 1 uL | 1 uL |  |  |
| FP3 |  |  | 1 uL | 1 uL |
| Water | 8 uL | 7 uL | 7 uL | 7 uL |
| Maxima MM | 10 uL | 10 uL | 10 uL | 10 uL |

Figure 30:
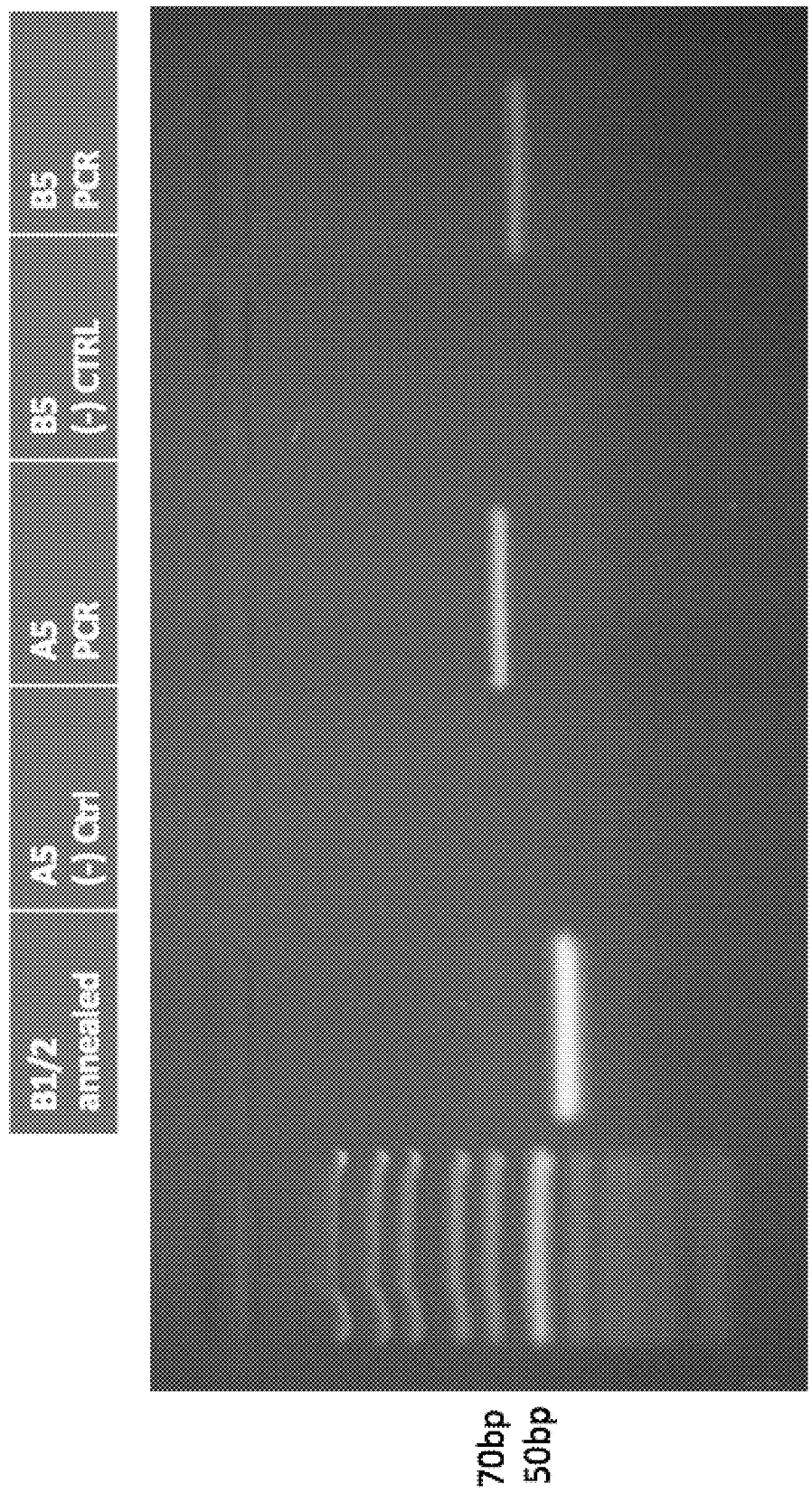
FIG. 30 depicts a SDS-PAGE gel confirming that topoisomerase addition protocol as described in Example 3 works, with bands corresponding to the expected A5 and B5 products being clearly visible.

SDS-PAGE using 4-20% Tris-glycine gels is used to confirm that expected size oligonucleotides are produced. Charging is performed as described above, but directly after charging (37° C. incubation step), loading buffer is mixed in and samples are heated to 70° C. for 2 minutes and allowed to cool prior to running the gel. Gel is stained with Coomassie. For the negative control, water is added to the reaction instead of topo. FIG. 30 depicts the results, clearly showing bands corresponding to the expected product sizes for A5 PCR and for B5 PCR.

DNA bit addition via topoisomerase-charged DNA cassettes and deprotection performed via restriction enzyme are thus shown to be feasible. In these proof of concept experiments the DNA is immobilized via streptavidin-conjugated magnetic beads, and moved sequentially into different reaction mixes, but in the nanopore chip format, we create separate reaction chambers and use electrical current to move the DNA into those different reaction chambers.

Finally, PCR demonstrates that the expected DNA sequences are created when performing sequential additions of DNA sequences corresponding to 'bits' of information. These reactions have worked as designed, even with minimal optimization.

DNA made as described in examples 2 and 3 is recovered and sequenced, using a commercial nanopore sequencer (MinION from Oxford Nanopore), confirming that the desired sequence is obtained.

Example 4

DNA Synthesis: Block Oligonucleotide Addition, Using a Different Restriction Enzyme The following synthesis is carried analogously to Example 3, but using the restriction enzyme MluI, which cuts at 'ACGCCT' to form:

```
...NNNA      CGCGTNNN...
...NNNTGCGC     ANNN...
```

In this example TOPO is charged to form a complex with sequence complementarity that will enable the charged TOPO to transfer DNA to DNA cut with MluI:

```
5'  pCACGTCAGGCGTATCCATCCCTTCGCGTTCACGTACTCGCAATGCTGTAG
3'   GTGCAGTCCGCATAGGTAGGGAAGCGC AGTGCATGAGCGTTACGAGATCb
        +
TOPO
        =
5'  pCAGTCAGGCGTATCCATCCCTT*         (
3'   GTGCAGTCCGCATAGGTAGGGAAGCGC
('*' indicates TOPO bound at 3' phosphate)
        +
CGCGTTCACGTACTCGCAATGCTGTAG
    AGTGCATGAGCGTTACGAGATCb
(b = biotin. This can be removed with streptavidin)
```

By a process analogous to the preceding example, the charged TOPO is then used to add the oligomer to the 5' end of strand being synthesized, having a complementary acceptor sequence, thereby releasing the TOPO, and the strand is then "deprotected" using the WA and the cycle repeated until the desired sequence of oligomers is obtained.

Example 5

Addition of Single Base Using Topoisomerase Strategy

We have found that the topoisomerase system can also be designed to add single bases to a single stranded DNA chain (in comparison to Example 3, which describes adding 'cassettes'). The DNA bit to be 'added' is contained in a short DNA sequence conjugated to vaccinia topoisomerase I (topo). In the presence of a suitable single stranded 'deprotected' 'acceptor' DNA, the topo-charged DNA is enzymatically and covalently ligated ('added') to the acceptor by the topoisomerase, which in the process becomes removed from the DNA. A type IIS restriction enzyme can then cleave all of the added DNA with the exception of a single base (the base which is being 'added'). This process of deprotect-add is repeated to add additional bases (bits).

Topo Charging: A generic charging protocol is as follows, similar to Example 3:

```
...N-N-N-N-N-N-N-N-N-C-C-C-T-T-N-N-N-N-N-N-N-N-N-N-N-N-N...
...N-N-N-N-N-N-N-N-N-N-N-N-N-I-I-I-I   N-N-N-N-N-N-N...biotin
         +
Topoisomerase (*)
         =
N-N-N-N-N-N-N-N-N-N-N-N-N-N
N-N-N-N-N-N-N-N-N...biotin
(by-product)
         +
...N-N-N-N-N-N-N-N-N-C-C-C-T-T*
...N-N-N-N-N-N-N-N-N-N-N-N-N-I-I-I-I
(topo charged)
```

As in Example 3, the N's on top of one another are complementary. I is inosine. The biotin is used to remove unreacted product and byproduct. Addition of a single base is carried out as follows

```
N-N-N-N-N-N-N-N-N-N...
(acceptor sequence nucleotides indicated in italics)
         +
...N-N-N-N-N-N-N-N-N-C-C-C-T-T*
...N-N-N-N-N-N-N-N-N-N-N-N-N-I-I-I-I
(topo charged)
         =
...N-N-N-N-N-N-N-N-N-C-C-C-T-T-N-N-N-N-N-N-N-N-N-N...
...N-N-N-N-N-N-N-N-N-N-N-N-N-I-I-I-I
         +
         *
         (free topo)
```

Deprotection is illustrated as follows, using BciVI restriction enzyme (site in bold):

```
...N-G-T-A-T-C-C-N-N-C-C-C-T-T-N-N-N-N-N-N-N-N-N-N...
...N-N-N-N-N-N-N-N-N-N-N-N-N-I-I-I-I
+
BciVI
(restriction enzyme)
=
T-N-N-N-N-N-N-N-N-N-N...
(note a 'T' has been added to the 5' of the acceptor DNA)
+
N-N-I-I-I-I
(dissociated*)
+
...N-G-T-A-T-C-C-N-N-C-C-C-T
...N-N-N-N-N-N-N-N-N-N-N-N-N
--------------------------------------------------------
T-N-N-N-N-N-N-N-N-N-N...
    N-N-I-I-I-I
=
T-N-N-N-N-N-N-N-N-N-N... + N-N-I-I-I-I
(NNIIIII dissociates from the single strand with added base)
```

The following oligonucleotides are synthesized commercially (B=biotin, P-phosphate, I=inosine):

(SEQ ID NO 13): NAT1:
CACGTCAGGCGTATCCATCCCTTCACGTACTCGCAATGCTGTATGGCGAT

NAT1b P-CACGTCAGGCGTATCCATCCCTTCACGTACTCGCAATGCTGTATGGCGAT-B (SEQ ID NO 35):
NAT9cI: P-IIIIIAAGGGATGGATACGCCTGACGTG (SEQ ID NO 14):
NAT9x: P-ATCGCCATACAGCATTGCGAG (SEQ ID NO 15):
NAT9: ACGTGAAGGGATGGATACGCCTGACGTG (SEQ ID NO 16):
Nat9Acc: CACGTAGCAGCAAACAGTGCCTAGACTATCG (SEQ ID NO 17):
Nat1P: CACGTCAGGCGTATCCATCC (SEQ ID NO 18):
FP4: CGATAGTCTAGGCACTGTTTG

The oligonucleotides are solubilized to 100 μM in TE buffer and stored at −20° C.

Hybridization: The following hybridized oligonucleotides are made by mixing the oligonucleotides as described, heating to 95° C. for 5 minutes, and then dropping the temperature by 5° C. every 3' until the temperature reaches 20° C. Hybridized oligonucleotides are stored at 4° C. or −20° C.

NAT1b/NAT9cI/NAT9x

8 μL NAT1B
10 μL NAT9cI
10 μL NAT9x
48 μL TE
4 μL 5M NaCl

NAT1/NAT9cI
10 μL NAT1
10 μL NAT9cI
80 μL PBS
NAT1/NAT9
10 μL NAT1
10 μL NAT9
80 uL PBS
Buffers & Enzymes: The following buffers are used:
TE: 10M Tris pH 8.0, 1 mM EDTA, pH 8.0
PBS: phosphate buffered saline (137 mM NaCl, 2.7 mM KCl, 10 mM $Na_2HPO_4$, 1.8 mM $KH_2PO_4$) (pH 7.4)

10× Cutsmart: 500 mM KAc, 200 mM Tris-Ac, 100 mM Mg—Ac, 1 mg/mL BSA pH 7.9

BciVI is purchased from NEB and Streptavidin-coated magnetic beads (s-MagBeads) are purchased from ThermoFisher The addition reaction is carried out as follows.

1. Topo charge: The reagents are assembled as per table:

|  | Experiment | (—) control #1 | (—) control #2 |
|---|---|---|---|
| 10x topo buffer | 3 | 3 | 3 |
| Water | 17 | 21 | 23 |
| NAT1B/NAT9cI/NAT9x | 6 | 6 | — |
| Topo | 4 | — | 4 |

The reagents are then incubated at 37° C. for 30 minutes. The byproducts are removed using streptavidin magnetic beads (5 uL) in 1× topo buffer after 10 minutes at room temperature to allow binding.

2. Reaction: The reagents are assembled as per table:

|  | Experiment | (—) control #1 | (—) control #2 |
|---|---|---|---|
| From A.1.c | 1 | 1 | 1 |
| NAT9Acc | 1 | 1 | 1 |
| 10x topo buffer | 1 | 1 | 1 |
| water | 7 | 7 | 7 |

The reagents are then incubated at 37° C. for 30 minutes. The addition reaction is expected to proceed as follows:

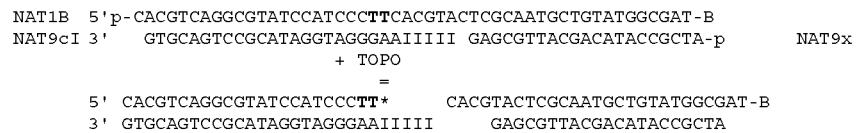

The asterisk (*) represents topoisomerase. Note that NAT9cI is phosphorylated, but this isn't shown for illustration purposes.

When the charged topo is in the presence of an acceptor sequence, it undergoes the following reaction:

PCR amplification and measurement of the molecular weights of the product on agarose gel confirms the expected product is produced. See FIG. 30, depicting correct sized band in lane 1 (experiment), no bands in negative controls.

B. Deprotection Reaction: The reagents are assembled as per table:

|  | 1 | 2 | 3 | 4 |
|---|---|---|---|---|
| NAT1/NAT9 | 1 | 1 | — | — |
| NAT1/NAT9cI | — | — | 1 | 1 |

|  | 1 | 2 | 3 | 4 |
|---|---|---|---|---|
| 10x cutsmart | 2 | 2 | 2 | 2 |
| water | 17 | 16 | 17 | 16 |
| BciVI | 0 | 1 | 0 | 1 |

The reagents are incubated at 37° C. for 90 minutes. For the deprotection reaction, a representative product of an addition reaction is created using purchased oligonucleotides, and tested for digestion with the BciVI restriction enzyme:

```
(SEQ ID NO 13): NAT1
5' CACGTCAGGCGTATCCATCCCTTCACGTACTCGCAATGCTGTATGGCGAT
NAT9cI
3' GTGCAGTCCGCATAGGTAGGGAAIIIII
     +
BciVI
     =
(SEQ ID NO 13): NAT1
5' CACGTCAGGCGTATCCATCCCT    TCACGTACTCGCAATGCTGTATGGCGAT
NAT9cI
3' GTGCAGTCCGCATAGGTAGGG  AAIIIII
```

It was not known whether the restriction enzyme would cut the DNA as intended, given that 3' of the cut site are a series of inosines as opposed to 'regular' bases. As a positive control, the 'appropriately' base-paired equivalent of NAT1/NAT9cI is made (NAT1/NAT9c):

```
(SEQ ID NO 13): NAT1
5' CACGTCAGGCGTATCCATCCCTTCACGTACTCGCAATGCTGTATGG

CGAT (SEQ ID NO 19): NAT9c
3' GTGCAGTCCGCATAGGTAGGGAAGTGCA
```

Figure 31:
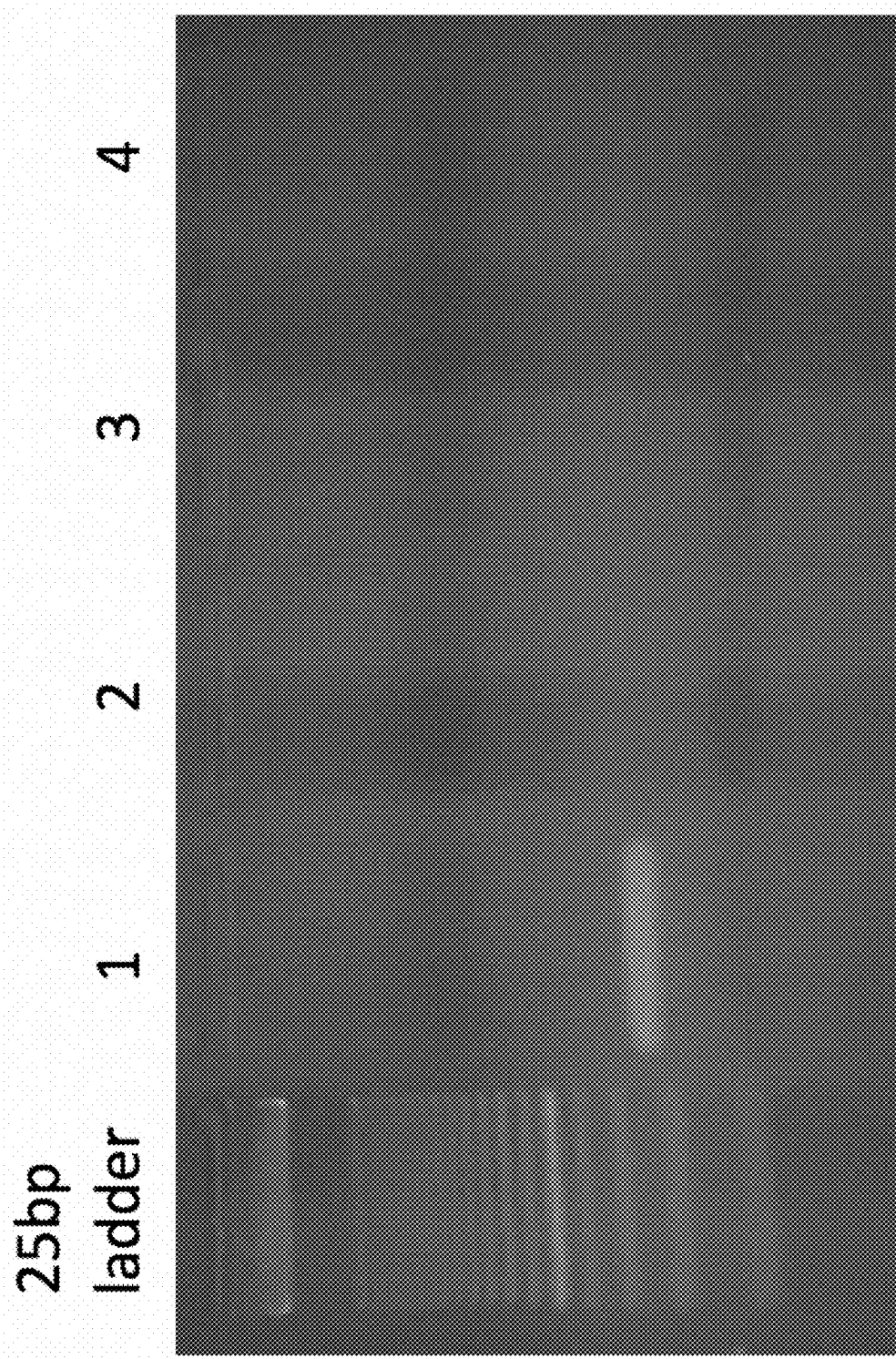
FIG. 31 depicts an agarose gel confirming that the PCR product of Example 5 is the correct size. Lane 0 is a 25 base pair ladder; lane 1 is product of experiment, line corresponding to expected molecular weight; lane 2 is negative control #1; lane 3 is negative control #2; lane 4 is negative control #4.
Figure 32:
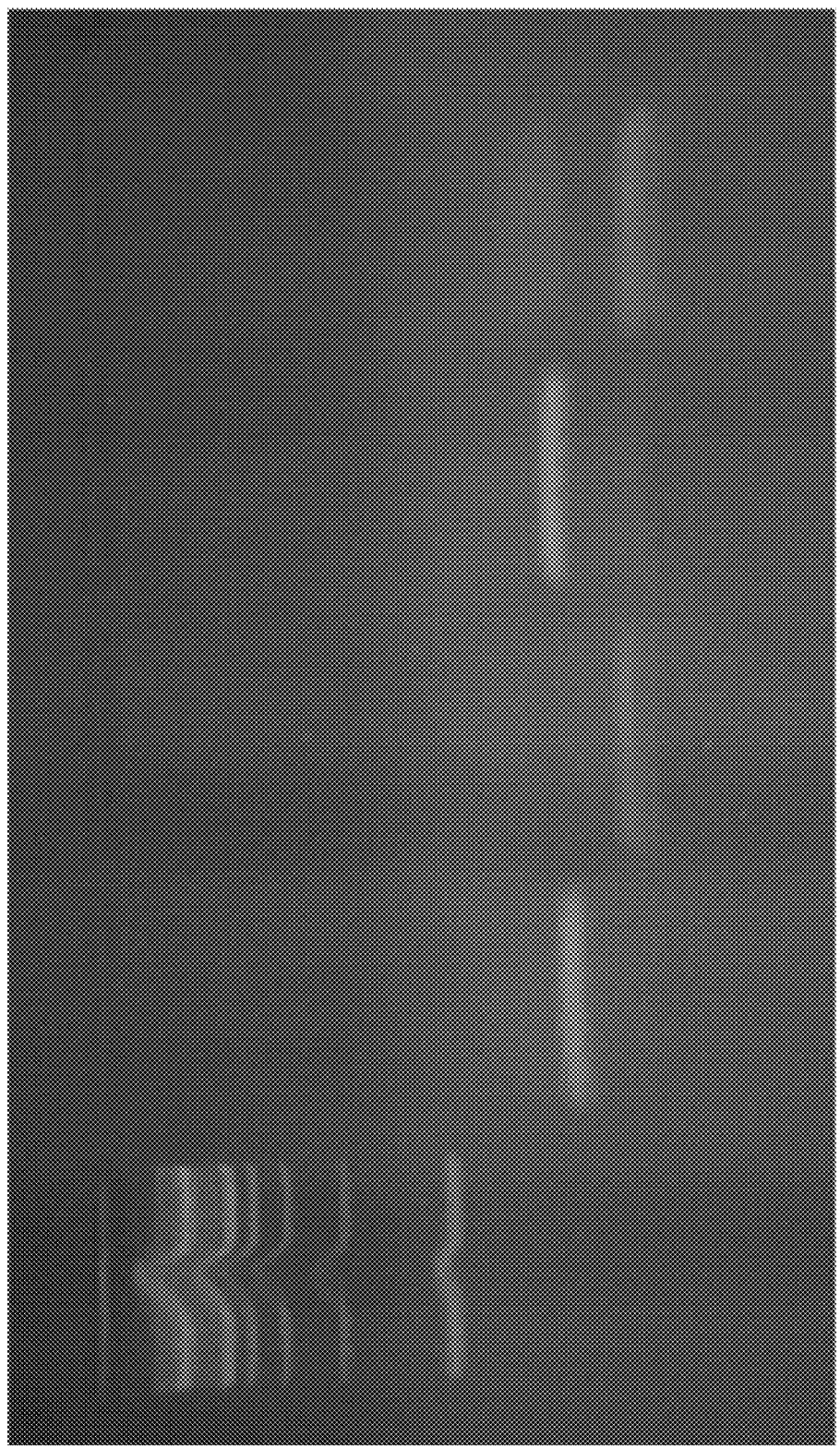
FIG. 32 depicts an agarose gel confirming that the restriction enzyme as described in Example 5 produces the expected product. The ladder on the left is a 100 base pair ladder. Lane 1 is undigested NAT1/NAT9c, Lane 2 is digested NAT1/NAT9c. Lane 3 is undigested NAT1/NAT9cI, Lane 4 is digested NAT1/NAT9cI.

PCR amplification of the product followed by measurement of molecular weight on agarose gels (FIG. 31) shows that the enzyme works as intended. For the positive control, a larger band is observed when undigested (lane 1), but a smaller band/s are observed with digestion. The same pattern is observed with NAT1/NAT9cI, showing that the presence of inosines does not negate or interfere with digestion. A small amount of undigested product seems to remain with NAT1/NAT9cI, suggesting that the cleavage is not as effective, at least under these conditions, as with NAT1/NAT9c. Cleavage efficiency may be improved by altering buffer conditions and/or addition of more inosines at the 5' end of NAT9cI.

The foregoing example demonstrates that it is feasible to use a Topo/TypeIIS restriction enzyme combination to add a single nucleotide to the 5' end of a target single stranded DNA. A related topoisomerase, SVF, that recognizes the sequence CCCTG (https://www.ncbi.nlm.nih.gov/pubmed/8661446) is used to add a 'G' instead of a 'T', using an analogous process, thus allowing construction of a sequence encoding binary information with T and G.

As noted above, where dsDNA is generated using topoisomerase strategies, nicks in DNA on the opposing strand can be repaired using a ligase together with ATP. But when doing the single nucleotide addition, as in this example, we are building a single stranded DNA, so there are no nicks that need to be repaired and no need to use ligase.

Example 6

Addition of Single Base Using Topoisomerase Strategy Couple with 5' Phosphate Coupling In another approach to single base addition, we use a 5'phosphate as a blocking group to provide single base pair addition in the 3' to 5' direction. The charging reaction charges the topoisomerase with a single T (or G, or other nucleotide as desired), having a 5' phosphate group. When the charged topoisomerase 'sees' a free 5' unblocked (unphosphorylated) single stranded DNA chain it will add the T to that chain, providing a DNA with a T added to the 5'. This addition is facilitated by the presence of an adapter DNA having sequences to which the topoisomerase and the single stranded acceptor DNA can bind. (Note that the adapter DNA is catalytic—it can be reused as a template in repeated reactions.) The added nucleotide has a 5' phosphate on it, so it won't be a substrate for further addition until it is exposed to a phosphatase, which removes the 5' phosphate. The process is repeated, using Topo to add a single "T" to the 5' end of a target single stranded DNA and SVF topoisomerase to add a single 'G', thus allowing construction of a sequence encoding binary information with T and G. The process is depicted schematically as follows:

```
GENERICALLY:
    CHARGING:
        N-N-N-N-N-N-N-C-C-C-T T-N-N-N-N-N-N-N-N   (T is 5' phosphorylated)
        N-N-N-N-N-N-N-N-N-N-N-N-N-N-N-N-N-N-N-N
        +
        TOPO
        =
        N-N-N-N-N-N-N-C-C-C-T    N-N-N-N-N-N-N-N
        N-N-N-N-N-N-N-N-N-N-N-N-N-N-N-N-N-N-N-N
        +
        T-TOPO  (T is 5' phosphorylated)

TRANSFER:
        T-TOPO  (T is 5' phosphorylated)
```

```
                                -continued
    +
    N-N-N-N-N-N-N-N-N-N-N    (5' N has 5' OH)
    =
    T-N-N-N-N-N-N-N-N-N-N-N  (T is 5' phosphorylated)
    +
    TOPO DEBLOCKING:
    T-N-N-N-N-N-N-N-N-N-N-N  (T is 5' phosphorylated)
    +
    Phosphatase
    =
    T-N-N-N-N-N-N-N-N-N-N-N  (T is 5' dephosphorylated, now has 5' OH)
*ALTERNATE TRANSFER MECHANISM*

T-TOPO  (T is 5 phosphorylated)
    +
    N-N-N-N-N-N-N-N-N-N-N    (acceptor) (5' N has 5' OH)
    +
    N-N-N-N-N-N-N-C-C-C-T
    N-N-N-N-N-N-N-N-N-N-A-I-I-I-I-I
    (adapter)
    =
    TOPO
    +
    N-N-N-N-N-N-N-C-C-C-T T-N-N-N-N-N-N-N-N-N-N-N
    N-N-N-N-N-N-N-N-N-N-A-I-I-I-I-I
        this transient intermediate that breaks down to -->
        T-N-N-N-N-N-N-N-N-N-N-N  (T is 5' phoshorylated)
        +
        N-N-N-N-N-N-N-C-C-C-T
        N-N-N-N-N-N-N-N-N-N-A-I-I-I-I-I
```

Example 7

Using DNA Origami to Aid in Attaching DNA Adjacent to Nanopore

A DNA strand with a large origami structure on one end is captured in a nanopore, and immobilized to surface-conjugated streptavidin through a terminal biotin moiety on the DNA. After restriction enzyme cleavage of the origami structure, the immobilized DNA can be moved back and forth through the pore, as confirmed by current disruption. The immobilization enables a controlled movement of a single DNA molecule through the pore, which in turn enables both the 'reading' and 'writing' of information to DNA.

Figure 33:
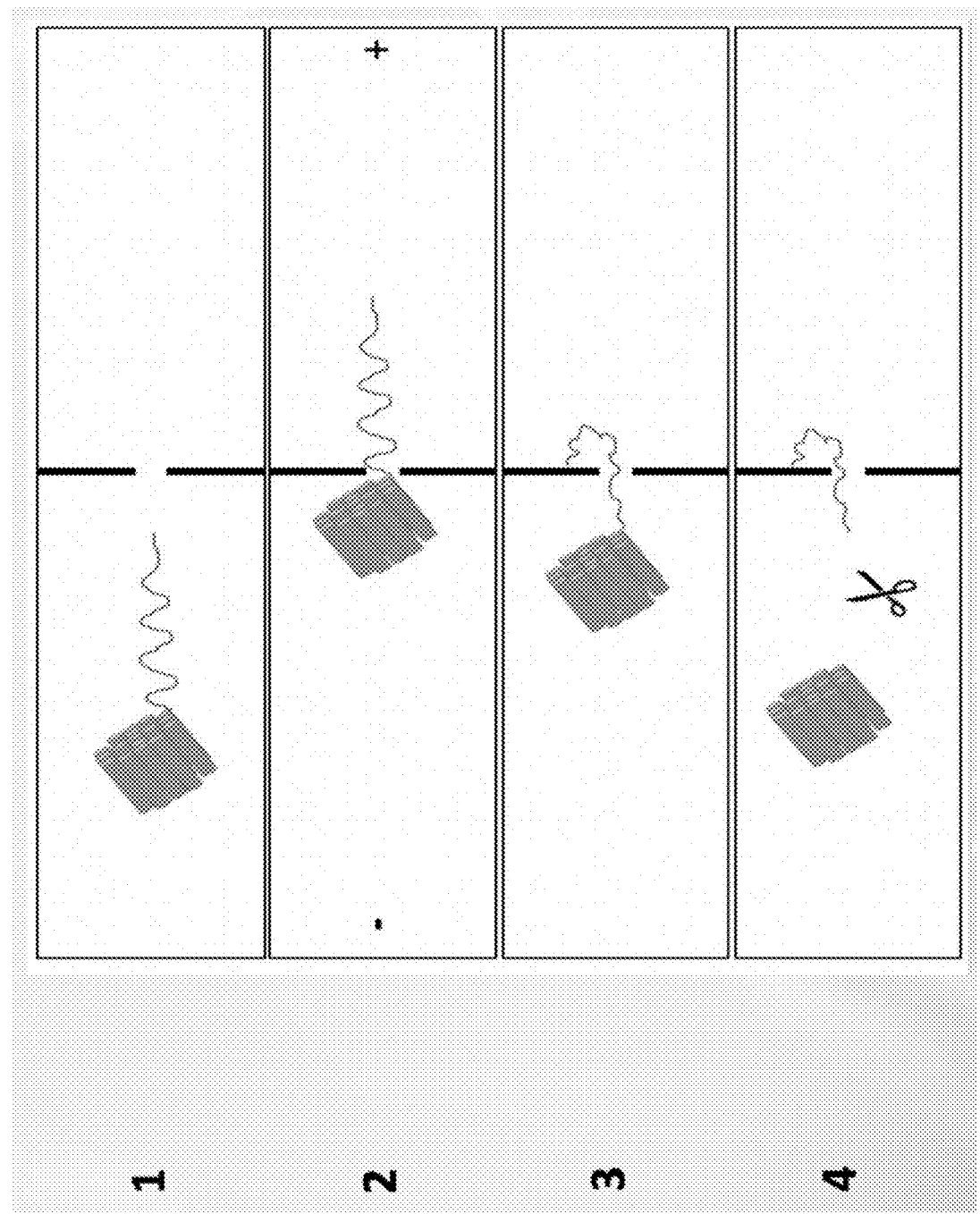
FIG. 33 depicts Immobilization of DNA near nanopore. Panel (1) shows DNA with an origami structure on one end in the left chamber (in the actual nanochip, there initially are many such origami structures in the left chamber). Panel (2) illustrates the system with anode on the right, which drives the DNA to the nanopore. While the DNA strand is able to transit the nanopore, the origami structure is too large to pass through, so the DNA is 'stuck'. Turning the current off (panel 3) allows the DNA to diffuse. With suitable chemistry, the end of the DNA strand is able to bind when it comes in contact with the surface near the nanopore. In panel (4) a restriction enzyme is added, which cuts the origami structure from the DNA. The chamber is washed to remove enzyme and residual DNA. The final result is a single DNA molecule attached near a nanopore, able to be moved back and forth through the nanopore.

As depicted in FIG. 35, a bulky double-stranded DNA unit is formed, which is too large to fit through the nanopore, with a single stranded region, linked to the bulky portion by two short double stranded regions having which serves to anchor the DNA to be added to in the synthesis. The single stranded region can then be detached and anchored to the surface adjacent to the nanopore, and the origami structure released. See FIG. 33.

Nanopores are formed in 3 mm chips with 20 nm SiO2, with 50*50 µm windows. Chip are provided by Nanopore Solutions. Nanopore cassette holders and flow cells are provided by Nanopore Solutions. The amplifier is a Tecella Pico 2 amplifier. This is a usb-powered amplifier that uses a usb-computer interface for control. Tecella supplies (Windows) software to control the amplifier. The multimeter is a FLUKE 17B+ Digital Multimeter, capable of detecting current as low as 0.1 uA. For screening of radiofrequency noise we use a Concentric Technology Solutions TC-5916A Shield Box (Faraday Cage) with USB interface. Oligonucleotides are obtained from IDT.com. "PS" is Proparyl Silane-O-(PROPARGYL)-N-(TRIETHOXYSILYLPROPYL) CARBAMATE from http://www.gelest.com/product/o-propargl-n-triethoxysilylpropylcarbamate-90/.

The origami structure is based on single-stranded m13 with a 'honeycomb' cube origami structure which is ~20 nm on one side. There are double stranded regions adjacent to the honeycomb each containing a unique restriction site. One of those sites is used to attach modified DNA to enable attachment near the nanopore, the other is used for cleaving off the origami structure once the DNA is attached.

Nanopore Formation: Nanopores are formed in the chips using dielectric breakdown, as follows:

1. Chips are carefully mounted in the cassettes
2. Wetting: 100% ethanol is carefully pipetted on the chip. Bubbles must be removed. However, direct pipetting of solution on the chip should be avoided or the chip can crack (SiO2 is only 20 nm).
3. Surface treatment: ethanol is removed, and freshly prepared Piranah solution (75% sulfuric acid, 25% hydrogen peroxide (30%)) is pipetted onto the chip. (let piranha solution come to room temperature). Leave on for 30 minutes.
4. Rinse 4 times with distilled water.
5. Rinse 2 times with HK buffer (10 mM HEPES pH 8, 1M KCl)
6. Assemble cassette into flow cell.
7. Add 700 µL HK buffer to each chamber of the flow cell.
8. Insert silver electrodes attached to the amplifier and close the Faraday cage.
9. Test resistance with 300 mV. No current should be detected. If it is detected, the chip is likely cracked and one must start again.
10. Connect electrodes to a DC current of 6 V and test the current with a multimeter. Current should be low and should not change. Increase voltage by 1.5 V and hold the voltage until the resistance increases. If resistance does not increase after 5-10 minutes, increase the voltage another 1.5 V and try again. Repeat until resistance increases, at which point the applied voltage should be stopped immediately. (with sufficient voltage, dielectric breakdown occurs and a 'hole' is created in the SiO2 membrane. When initially created the hole is small, but will increase in size as the voltage is maintained.)

11. Test the pore using the amplifier. At 300 mV one should see current of a few to several nA. The more current, the larger the pore.

Figure 34:
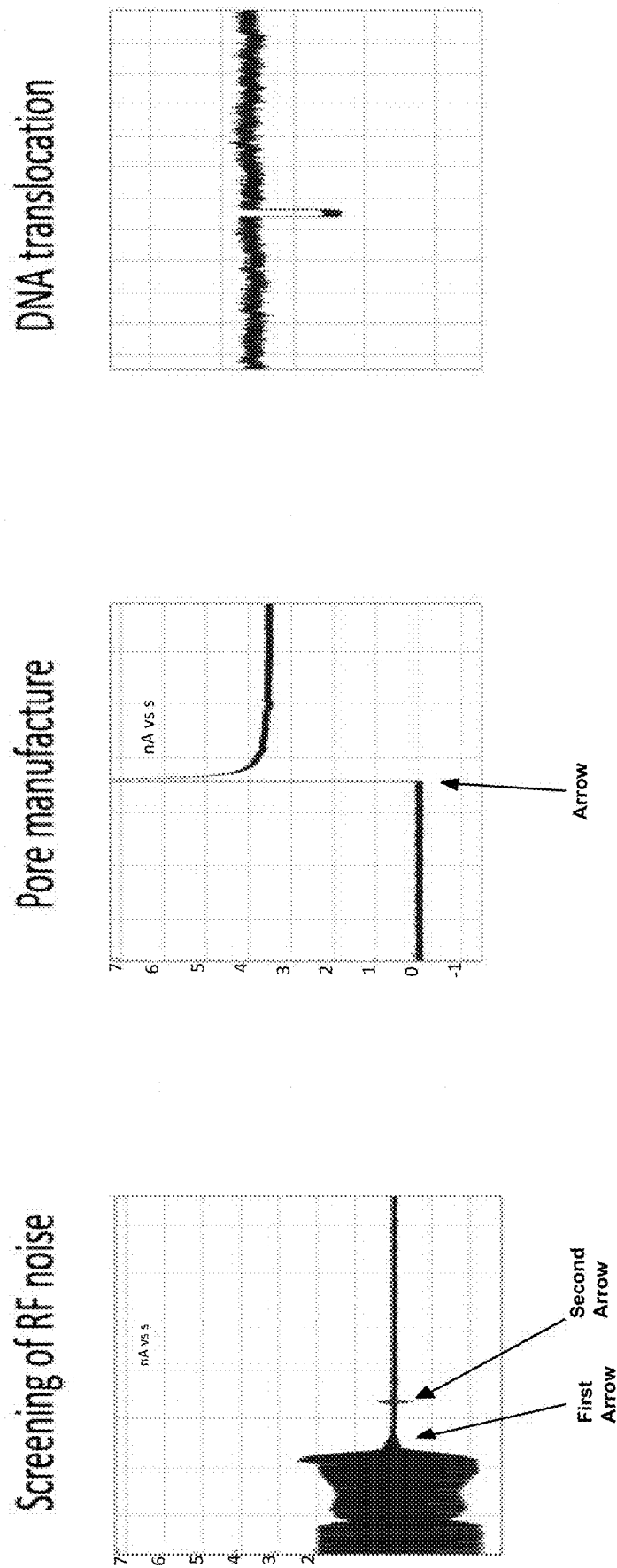
FIG. 34 depicts a basic functioning nanopore. In each panel, the y-axis is current (nA) and the x-axis is time (s). The left panel "Screening of RF Noise" illustrates the utility of the Faraday cage. A chip with no nanopore is placed in the flow cell and 300 mV applied. When the lid of the Faraday cage is closed (first arrow) the noise reduction can be seen. A small spike occurs when the latch is closed (second arrow). Notice the current is ~0 nA. After pore manufacture (middle panel), application of 300 mV (arrow) results in a current of ~3.5 nA. When DNA is applied to the ground chamber and +300 mV is applied DNA translocations (right panel) can be observed as transient decreases in the current.

FIG. 34 depicts a basic functioning nanopore. In each panel, the y-axis is current (nA) and the x-axis is time (s). The left panel "Screening of RF Noise" illustrates the utility of the Faraday cage. A chip with no nanopore is placed in the flow cell and 300 mV applied. When the lid of the Faraday cage is closed (first arrow) the noise reduction can be seen. A small spike occurs when the latch is closed (second arrow). Notice the current is ~0 nA. After pore manufacture (middle panel), application of 300 mV (arrow) results in a current of ~3.5 nA. When DNA is applied to the ground chamber and +300 mV is applied DNA translocations (right panel) can be observed as transient decreases in the current. (Note, in this case the TS buffer is used: 50 mM Tris, pH 8, 1M NaCl). Lambda DNA is used for this DNA translocation experiment.

Silver Chloride Electrodes:
1. Silver wire is soldered to insulated copper wire.
2. Copper wire is grounded, and silver is dipped into fresh 30% sodium hypochlorite for 30 minutes.
3. Silver should acquire a dark gray coating (silver chloride).
4. Silver wire is rinsed extensively in distilled water and dried.
5. It is now ready for use.

Silanization of Beads: The silanization method is initially developed/tested on $SiO_2$ coated magnetic beads (GBioscience). The following protocol is adopted:
1. Pretreat beads in fresh pirannah solution for 30 minutes.
2. Wash 3× with distilled water.
3. Wash 2× in methanol.
4. Dilute APTES stock 1:500 in methanol.
5. Add diluted APTES to beads, incubate at RT for 45 minutes.
6. Rinse with methanol.
7. 100° C. for 30 minutes.
8. Store under vacuum.

Silanization of Silicon Chip
1. Mount chip with nanopore in a cassette.
2. Rinse with methanol, carefully removing any air bubbles.
3. Add fresh pirannah solution (equilibrated to room temperature) and incubate for 30 minutes.
4. Wash 4× with distilled water.
5. Wash 3× with methanol.
6. Dilute APTES stock 1:500 in methanol and use to wash chip 2×. Incubate at RT for 45 minutes.
7. Rinse 2× with methanol.
8. Dry under and air stream.
9. Store under vacuum overnight.

Streptavidin Conjugation of beads: The streptavidin conjugation is initially developed/tested on the silanized beads prepared above.
1. Wash silanized beads with Modified Phosphate-Buffered Saline (MPBS)
2. Make a fresh solution of 1.25% glutaraldehyde in MPBS (using 50% glutaraldehyde stock, stored frozen).
3. Add 1.25% glutaraldehyde to beads and let stand for 60' with gentle up-down pipetting every 15 minutes.
4. Wash 2× with MPBS.
5. Wash 2× with water.
6. Let dry under vacuum.
7. Add streptavidin (500 µg/mL in MPBS) to beads and incubate 60 minutes. (For negative control beads, use bovine serum albumin (BSA) (2 mg/mL in MPBS) in place of streptavidin).
8. Remove streptavidin and add BSA (2 mg/mL in MPBS). Incubate 60 minutes.
9. Wash 2× in MPBS.
10. Store at 4° C.

Streptavidin Conjugation of Silicon Chip
1. Rinse silanized chip with ethanol 2×
2. Rinse silanized chip with MPBS 2×
3. Make a fresh solution of 1.25% glutaraldehyde in MPBS (using 50% glutaraldehyde stock, stored frozen).
4. Rinse chip with 1.25% glutaraldehyde 2×, let stand for 60' with gentle up-down pipetting every 15 minutes
5. Wash 2× with MPBS
6. Wash 2× with water
7. Let dry under air stream
8. To one half of the chip add BSA (2 mg/mL in MPBS), and to the other add streptavidin (500 µg/mL in MPBS). Incubate 60 minutes. Make a marking on the cassette to indicate which half of the chip is streptavidin modified.
9. Rinse both halves of the chip with BSA (2 mg/mL in MPBS). Incubate 60 minutes.
10. Wash in MPBS.

The buffers used herein are made as follows:
MPBS: 8 g/L NaCl, 0.2 g/L KCl, 1.44 g/L disodium-phosphate, 0.240 g/L potassium phosphate, 0.2 g/L polysorbate-20 (pH 7.2)
PBS: 8 g/L NaCl, 0.2 g/L KCl, 1.44 g/L disodium-phosphate, 0.240 g/L potassium phosphate
TS: 50 mM Tris pH 8.0, 1M NaCl
HK: 10 mM HEPES pH 8.0, 1M KCl
TE: 10 mM Tris, 1 mM EDTA, pH 8.0
Pirannah Solution: 75% hydrogen peroxide (30%)+25% sulfuric acid
APTES stock: 50% methanol, 47.5% APTES, 2.5% nano-pure water. Age at 4° C. for at least 1 hour. Store at 4° C.
PDC stock: 0.5% w/v 1,4-phenylene diisothiocyanate in DMSO Oligonucleotides (5' TO 3') are ordered:

```
(SEQ ID NO 20):
o1 CTGGAACGGTAAATTCAGAGACTGCGCTTTCCATTCTGGCTTTAATG (SEQ ID NO 21):
o3 GGAAAGCGCAGTCTCTGAATTTAC (SEQ ID NO 22):
N1  CTTACTGGAACGGCTATCGATATCGCAGCAGGACAGA
BN1 Biotin-CTTACTGGAACGGCTATCGATATCGCAGCAGGACAGA (SEQ ID NO 23):
N2 GTCCTGCTGCGATATCGATAGCCGTTCCAGTAAG
```

Oligonucleotide pair hybridization is carried out as follows:
1. Make stock solutions of oligo's at 100 uM concentration in TE buffer
2. Dilute oligos to 10 µM in PBS
3. Heat to 85° C. for 5' in a thermal cycler
4. Ramp heat down by 5° C. every 3' until 25° C.
5. Store at 4° C. or −20° C.

Streptavidin Conjugation: Streptavidin conjugation to SiO$_2$ is developed and tested using SiO2 coated magnetic beads, and the protocols were then adapted for SiO$_2$ chips. Binding of biotinylated oligos to both streptavidin and BSA conjugated beads are tested. As expected, negligible binding is observed with BSA-conjugated beads, while strong binding is observed with streptavidin conjugated beads. See FIG. 38. Since it would be more convenient to perform the conjugation in high salt (DNA movement is performed in high salt), the ability of the beads to bind in HK buffer is also tested. Binding in HK buffer is comparable to binding in MPBS buffer (FIG. 39).

Origami constructs are made and confirmed operable as described above in FIGS. 35-37. Biotinylation of the origami structure is tested using oligonucleotides. We already know from the 'Orgami' results described above for FIG. 37 that the AlwNI site is active. An oligonucleotide pair that recreates a segment of the exact sequence in the origami DNA is used below (o1/o3). The origami molecule is depicted in FIG. 77:

The oligo pair o1/o3 is

```
o1
                                         (SEQ ID NO 20)
CTGGAACGGTAAATTCAGAGACTGCGCTTTCCATTCTGGCTTTAATG o3
                                         (SEQ ID NO 21)
CATTTAAGTCTCTGACGCGAAAGG
```

The DNA is digested with AlwNI in the presence of T4 DNA ligase, and a biotinylated oligo that is complementary to the overhang on the 3' side of the origami sequence (which itself is attached to a long ssDNA sequence which itself is attached to the other side of the origami), according to the following reaction:

```
CTGGAACGGTAAATTCAGAGACTGCGCTTTCCATTCTGGCTTTAATG  o1  (SEQ ID NO 20)

CATTTAAGTCTCTGACGCGAAAGG             o3  (SEQ ID NO 21)
                + AlwNI
                   =
CTGGAACGGTAAATTCAGAGA     CTGCGCTTTCCATTCTGGCTTTAATG (SEQ ID NO 24)

CATTTAAGTC       TCTGACGCGAAAGG (SEQ ID NO 25)
                +
B-CTTACTGGAACGGCTATCGATATCGCAGCAGGACAGA        BN1 (SEQ ID NO 22)

GAATGACCTTGCCGATAGCTATAGCGTCGTCCTG         N2 (SEQ ID NO 23)
                + ligase
                   =
B-CTTACTGGAACGGCTATCGATATCGCAGCAGGACAGACTGCGCTTTCCATTCTGGCTTTAATG
    GAATGACCTTGCCGATAGCTATAGCGTCGTCCTGTCTGACGCGAAAGG
```

In this strategy, AlwN1 cleaves the target DNA. When the ligase is added it is possible for this DNA to be religated, but the restriction enzyme will cut it again. However, if/when the (right) fragment (of o1/o3) binds to BN1/N2, the restriction site is NOT recreated, thus this product will not be cut. Specific attachment is confirmed, by testing with and without the restriction enzyme:

|  | 1 | 2 |
|---|---|---|
| o1/o3 | 1 | 1 |
| n1/bn2 | 1 | 1 |
| 10x lig buf | 2 | 2 |
| water | 15 | 14.5 |
| AlwNI |  | .5 |
| Ligase | 1 | 1 |

All reagents except ligase are added and solution is incubated at 37° C. for 60 minutes. Ligase is added and solution incubated overnight at 16° C. 10× lig buff refers to NEB 10×T4 DNA ligase buffer. Ligase in NEB T4 DNA ligase. o1/o3 and n1/n2 refer to annealed oligo pairs, as depicted above. Units are microliters. Agarose gel analysis confirms that in the presence of the AlwNI, a larger product is formed, corresponding to the biotinylated oligonucleotide attached to the long ssDNA arm attached to the origami structure. A similar strategy is used for 3' biotinylation, where desired.

Above we demonstrate the ability to form and use a nanopore to detect voltage induced transit of DNA across the pore, the creation of an origami molecule with a long ss region attached at its' far end to a biotin, and the conjugation of streptavidin to silicon dioxide, and to use that to capture biotinylated DNA. These tools are used to attach and control the movement of a single DNA molecule next to a nanopore.

The first step is to conjugate streptavidin to one surface of an SiO2 nanopore (and BSA to the other side). This is accomplished according to the protocol above. The resulting pores tend to have a lower current than they initially have. After some brief 6 v pulses, the currents return to be near their original current. A functioning nanopore at this point is shown in FIG. 40.

Next, the origami DNA is inserted. When the origami DNA is added to the appropriate chamber and the current turned on, the origami will insert into the chamber. A representation of this is shown in FIG. 41. Experimental results when the origami is introduced at a final concentration of 50 pM confirm that the DNA with the origami inserts into the pore relatively soon (typically in seconds), which is detectable by the resulting reduction of current flow across the nanopore (e.g., in these experiments, current before origami insertion is ~3 nA, and ~2.5 nA after insertion). If the current is allowed to run for longer times, double insertions can be observed. If higher concentrations are used, insertion occurs too quickly to be observed.

Binding of inserted DNA to chip. After the origami is inserted into the nanopore, 15 minutes are allowed to elapse before voltage is applied again. The end of the ssDNA region of the origami contains a biotin, and streptavidin is conjugated to the surface of the nanopore. Streptavidin binds to avidin with an affinity constant that approaches that of a covalent bond. The 15 minute time allows the DNA to diffuse and for the biotin end to find and bind to the streptavidin. If the DNA has in fact become attached to the surface, when the voltage is reversed the observed current should be slightly less than what was seen previously. Also, switching the current back and forth should result in currents in both directions that are lower than that seen with a free pore. In the example shown here, a free pore shows a current of ~3 nA. FIG. 42 shows a representation of attached DNA, and FIG. 43 shows experimental results of voltage switching the attached origami DNA. Note that the currents seen in both directions are ~+/−2.5 nA, which is lower than the ~+/−3 nA observed with a free pore. If the DNA hasn't bound to the surface, the original current will be recovered when the voltage is switched (FIG. 44).

In order to remove the origami structure, the buffer in the flow cell chamber containing the origami structure was removed and replaced with 1×Swa1 buffer with 1 uL Swa1/ 20° L. The buffer in the other flow cell chamber is replaced with 1×Swa1 buffer without Swa1. This is incubated at room temperature for 60 minutes, then washed with HK buffer, and voltage applied. Movement of the DNA back and forth as represented in FIG. 45 is confirmed by the experimental data in FIG. 46, showing controlled movement of immobilized DNA through a SiO2 nanopore.

Example 8

Alternative Means to Attach the Polymer to the Surface Adjacent to the Nanopore

The foregoing examples describe attachment of DNA to the surface adjacent to the nanopore by biotinylating the DNA and coating the attachment surface with streptavidin. Some alternative means of attaching the polymer are depicted in FIG. 47.

a) DNA Hybridizaation: In one method, the DNA which is extended in the methods of the invention is hybridized to a short oligonucleotide which is attached near the nanopore. Once the synthesis is complete, the synthesized DNA can be easily removed without a need for restriction enzymes, or alternatively the double strand formed by the bound oligonucleotide and the synthesized DNA can provide a substrate for a restriction enzyme. In this example, the short oligomers are conjugated to the surface using biotin-strepavidin, or ligated using 1,4-phenylene diisothiocyanate as follows:

Conjugation of biotinylated DNA to SiO2:
A. Silanize:
1. Pre-treatment: nha solution for 30 minutes, wash with double distilled H$_2$O (ddH$_2$O)
2. Prepare APTES stock: 50% MeOH, 47.5% APTES, 2.5% nanopure H$_2$O: age >1 hr 4° C.
3. dilute APTES stock 1:500 in MeOH
4. incubate chips at room temperature
5. rinse MeOH
6. dry
7. heat at 110° C. for 30 minutes
Conjugate:
1. Treat chip with PDC stock 5 h (room temperature) (PDC stock: 0.5% w/v 1,4-phenylene diisothiocyanate in DMSO)
2. 2 washes in DMSO (brief!)
3. 2 washes in ddH$_2$O (brief!)
4. 100 nM amino-modified DNA in ddH$_2$O (pH 8) O/N 37° C.
5. 2 washes 28% ammonia solution (deactivate)
6. 2 washes ddH$_2$O Single stranded DNA having a terminal sequence complementary to the attached oligonucleotides is introduced as described above and allowed to hybridize with the attached oligonucleotides.

b) Click chemistry: Click chemistry is a general term for reactions that are simple and thermodynamically efficient, do not create toxic or highly reactive byproducts, and operate in water or biocompatible solvents, and are often used to join substrates of choice with specific biomolecules. The click conjugation in this case uses similar chemistry as used in a) to attach the oligonucleotides, only it is here used to attach the polymer which is extended in the course of synthesis in the methods of the invention. While in this example, DNA is the polymer, this chemistry would work to attach other polymers which have been functionalized by addition of a compatible azide group.

Silanize:
1. Pre-treatment: piranha solution for 30', wash ddH2O
2. Prepare PS (propargyl silane) stock: 50% MeOH, 47.5% PS, 2.5% nanopure H2O: age >1 hr 4 C
3. Dilute APTES stock 1:500 in MeOH
4. Incubate chips at room temperature
5. Rinse MeOH
6. Dry
7. Heat at 110° C. for 30 minutes DNA which is terminated in an azide functional group will covalently bind to this surface (as shown in FIG. 47). Azide terminated oligos are ordered, and attached to the longer origami DNA, as described for the biotin addition to the DNA previously.

Example 9

Optimized Topoisomerase-mediated DNA Synthesis

An oligonucleotide cassette is composed of three oligonucleotides that are hybridized to form a double-stranded DNA cassette. The cassettes are designed with a vaccinia virus topoisomerase recognition sequence (CCCTT) on the plus DNA strand and followed by a GCCG sequence on the minus strand. Upon topoisomerase recognition of its target sequence, the topoisomerase cleaves the oligonucleotide, and forms a covalent bond with the 5' section of the oligonucleotide, resulting in the formation of a "charged" topoisomerase. The addition of unmatched base pairs just 3' of the CCCTT on the plus strand (CGAA matched to the GCCG on the minus strand) results in more efficient topoisomerase charging. The cleaved 3' portion of the oligonucleotide cassette (termed by-product) can be removed from the charged topoisomerase when streptavidin-coated beads are added to the mixture, binding to the biotin attached to the 3' end of the plus DNA strand. This reaction is depicted as follows:

Initial Charging Oligonucleotide:

5' GCGCACGGTCTCCCGGCGTATCCATCCCTTCGAATTCACGTACTCG CCAGTCTACAG-biotin 3'

3' *CGCGTGCCAGAGGGCCGCATAGGTAGGGAAGCCG* AGTGCATGAGC GGTCAGATGTC 5'

The oligonucleotide in italics is 5' phosphorylated.

After Topoisomerase Charges:

```
                                            (SEQ ID NO 26)
        5' GCGCACGGTCTCCCGGCGTATCCATCCCTT        3'

3' CGCGTGCCAGAGGGCCGCATAGGTAGGGAAGCCG 5'
```

Topoisomerase is covalently linked the 3' T of the CCCTT recognition sequence (not shown). The by-product oligonucleotide is removed by the biotin bound to streptavidin beads

```
    5' GCGCACGGTCTCCCGGCGTATCCATCCCTT        3' + CGGCCTCGCAATGCTGTATGGCGATGGAATTCCACAGTCA-
    GCAG
    3' CGCGTGCCAGAGGGCCGCATAGGTAGGGAAGCCG 5'      GAGCGTTACGACATACCGCTACCTTAAGGTGTCAGTCGTC
```

```
5' CGAATTCACGTACTCGCCAGTCTACAG-biotin 3'
bound to S/A coated magnetic beads
3'       AGTGCATGAGCGGTCAGATGTC       5'
```

The charged topoisomerase has the unique ability to add the 5' section of the oligonucleotide to a DNA acceptor strand that has a complementary overhang:

DNA Bound to the Charged Topo (SEQ ID NO 26): DNA Acceptor Strand (SEQ ID NO 27):

The DNA acceptor strand extended by one cassette (or bit):

```
(SEQ ID NO 28):
5' GCGCACGGTCTCCCGGCGTATCCATCCCTTCGGCCTCGCAATGCTGTATGGCGATGGAATTCCACAGTCAGCAG 3'
3' CGCGTGCCAGAGGGCCGCATAGGTAGGGAAGCCGGAGCGTTACGACATACCGCTACCTTAAGGTGTCAGTCGTC 5'
```

The topoisomerase is released by this reaction. The oligonucleotide cassette, or bit, is then "deprotected" by digestion with the restriction enzyme Bsa I, which recognizes the nucleotides GGTCTC. Bsa I is a type IIS restriction enzyme, which recognizes asymmetric DNA sequences (the GGTCTC sequence) and cleaves outside of their recognition sequence. The cassette was designed so that cleavage with Bsa I will result in a CGGC overhang. This overhang, the same as is found in the DNA acceptor strand, allows another cassette, or bit, to be added by another charged topoisomerase.

```
(SEQ ID NO 28): DNA acceptor with one protected cassette (Bsa I restriction site in bold):
5' GCGCACGGTCTCCCGGCGTATCCATCCCTTCGGCCTCGCAATGCTGTATGGCGATGGAATTCCACAGTCAGCAG 3'
3' CGCGTGCCAGAGGCCGCATAGGTAGGGAAGCCGGAGCGTTACGACATACCGCTACCTTAAGGTGTCAGTCGTC 5'

(SEQ ID NO 29): DNA acceptor with one cassette after Bsa I digestion:
5'     CGGCGTATCCATCCCTTCGGCCTCGCAATGCTGTATGGCGATGGAATTCCACAGTCAGCAG 3'
3'         CATAGGTAGGGAAGCCGGAGCGTTACGACATACCGCTACCTTAAGGTGTCAGTCGTC 5'
```

Incubation with charged topoisomerase results in the addition of another cassette (bit), and extends the DNA chain to encode more information.

DNA bound to the Charged Topo DNA Acceptor strand plus one cassette
(SEQ ID NO 26):                    (SEQ ID NO 29):
```
5' GCGCACGGTCTCCCGGCGTATCCATCCCTT +  CGGCGTATCCATCCCTTCGGCCTCGCAATGCTGTATGGCGATGGAATTCCACAGTCAGCAG 3'
3' CGCGTGCCAGAGGGCCGCATAGGTAGGGAAGCCG    CATAGGTAGGGAAGCCGGAGCGTTACGACATACCGCTACCTTAAGGTGTCAGTCGTC 5'
```

DNA acceptor strand extended by two cassettes (or bits) (SEQ ID NO 30):
```
5' GCGCACGGTCTCCCGGCGTATCCATCCCTTCGGCGTATCCATCCCTTCGGCCTCGCAATGCTGTATGGCGATGGAATTCCACAGTCAGCAG 3'
3' CGCGTGCCAGAGGGCCGCATAGGTAGGGAAGCCGCATAGGTAGGGAAGCCGGAGCGTTACGACATACCGCTACCTTAAGGTGTCAGTCGTC
```

This process can be repeated over and over, to extend the DNA strand with "bits" which encode data.

Experimental Details:

Topoisomerase Charging Reaction: Forty microliters of streptavidin-coated magnetic dynabeads (Thermo Fisher) are washed 5 times in B & W buffer (10 mM Tris, pH 8.0, 1 mM EDTA, 2 M NaCl). 2.7 pmole of biotinylated charging oligonucleotide is added to the beads, and the mixture is incubated for 10 minutes at room temperature, gently shaking. The supernatant is drawn off the beads and discarded, leaving only bound charging oligonucleotide. The beads are then incubated in 1× Cutsmart buffer (New England Biolabs, NEB) containing vaccinia virus topoisomerase (6 ug), 10 units T4 polynucleotide kinase (3' phosphatase minus, NEB), 0.1 uM ATP (NEB) and 5 mM DTT, for 30 minutes at 37 C to charge the topoisomerase. After the topoisomerase cleaves the charging oligonucleotide, the polynucleotide kinase phosphorylates the 5' end of the newly formed by-product oligonucleotide, thereby preventing the topoisomerase from ligating the charging oligonucleotide back together again, and increasing the efficiency of the charging reaction. Any uncharged topoisomerase binds to the streptavidin-coated Dynabeads via electrostatic forces. The charged topoisomerase is freed from the streptavidin-coated beads. The polynucleotide kinase (PNK) is neutralized by recombinant shrimp alkaline phosphatase which reverses the activity of PNK or preferably, the charged topoisomerase is purified either by ion exchange chromatography or via Nickel-NTA beads (the topoisomerase is His-6 tagged), Initial binding of Acceptor DNA to beads: Twenty microliters of streptavidin-coated magnetic dynabeads (Thermo Fisher) are washed 5 times in B&W buffer (10 mM Tris, pH 8.0, 1 mM EDTA, 2 M NaCl). 0.03 pmoles of biotinylated DNA acceptor oligonucleotide is added to the washed beads, and incubated for 10 minutes at room temperature shaking. The supernatant is drawn off of the streptavidin-coated beads and discarded, leaving only DNA acceptor strands bound to the beads.

Addition reaction: To prepare addition mix add E coli DNA ligase plus 1 mM NAD to the charged topoisomerase. Optional: add 100 uM Coumermycin or 1 mM Novobiocin. (rationale: E coli DNA ligase (which requires NAD) will 'repair' the nick left when the charged topoisomerase adds DNA to the acceptor. This ensures that if an uncharged topoisomerase encounters this DNA it will not cleave it. Also, coumermycin and novobiocin will inhibit topoisomerase, and preferentially inhibit the 'charging' and not the 'addition' reaction. So the inhibitor also helps ensure that any uncharged topoisomerase formed during the reaction isn't active). Fifty microliters of addition mix is added to the beads, and incubated at 37° C. for 15 minutes, to allow for the addition of a DNA cassette to the DNA acceptor molecule. FIG. 76 shows a 4% agarose gel, proving that the cassettes were added as predicted. In order to release the DNA from the magnetic beads to prepare this gel, the sample is digested with Eco (EcoRI)).

The beads are then placed next to a magnet, and the topoisomerase solution is removed and stored on ice. The beads are then washed 3× with fifty microliters of 1× cutsmart buffer (NEB), to remove any residue of the topoisomerase.

Deblocking reaction: The beads are then incubated with fifty microliters of cutsmart buffer (with NAD and optionally coumermycin/novobiocin), containing 40 units of Bsa I and 1 unit of shrimp alkaline phosphatase. When the restriction enzyme cuts the DNA, a 5' phosphate is left, and this inhibits charged topoisomerase from adding another cassette. The addition of shrimp alkaline phosphatase removes the 5' phosphate, thereby effectively de-protecting the cassette. The use of a phosphatase such as shrimp alkaline phosphatase or calf intestinal phosphatase enhances the efficiency of the reaction; without the phosphatase, the 5' phosphate has an inhibitory effect.

The Bsa I and SAP are removed from the beads, and the beads are washed 3× in cutsmart buffer. They are now ready for the addition of another cassette by charged topoisomerase.

This sequence of adding a cassette by incubating the DNA acceptor strand with charged topoisomerase (/ligase), followed by digestion with BsaI/rSAP is repeated for the number of cassettes to be added.

Example 10

Restriction Enzyme Free Approach

The previous example provides a deblocking protocol that combines a phosphatase enzyme with the restriction enzyme to dramatically increase the efficiency of the system. In some cases, we have found that the ability of the 5'-phosphate on the 'acceptor' DNA to inhibit the addition reaction is strong enough that a restriction enzyme is not even necessary. The simplification of using only a phosphatase instead of the combination of phosphatase and restriction enzyme is advantageous and unexpected. It requires fewer reagents, it speeds up the reaction, and it gives more flexibility in terms of what nucleotide sequences can be used in the 'hybridization' region. This restriction-enzyme free method is shown here:

```
7F-T
5'            pCGGCAGATCTACCCTTCGAATTCACGTACTTG    [SEQ ID NO: 31]
3'                 TCTAGATGGGAAGCCGpAGTGCATGAACp
7F-B1                                7F-B2
+
Topo
=
5'            pCGGCAGATCTACCCTT*                   [SEQ ID NO: 32]
3'                 TCTAGATGGGAAGCCGp
(* = topo)
```

When this oligonucleotide is introduced to an acceptor with a pCGGC overhang, the addition reaction will not take place to any appreciable degree until the phosphate is removed by SAP, CIP or other suitable phosphatase. For example:

```
7F-T              pCGGCAGATCTACCCTTCGAATTCACGTACTTG
[SEQ ID NO: 31]

7F-B1             pGCCGAAGGGTAGATCT
[SEQ ID NO: 33]

7F-B2             pCAAGTACGTGA
[SEQ ID NO: 34]
```

The main restriction on this method is that it would not be appropriate if a restriction enzyme that will cut into and destroy the topoisomerase binding site is required, as described above for building DNA chains by a single nucleotide.

The particular method selected takes into account that when topoisomerase is 'charged', there is a mixture of charged and uncharged product—which represents an equilibrium between the two species, which can be influenced to optimize the efficiency of the reaction. The 'overhang' that the topoisomerase leaves can be designed in many ways. Overhangs rich in GC tend to have faster charging reactions, but have charging equilibriums that tend to generate lower yield of product. In some systems, it may be desirable to having some base mismatches (or to use Inosines) instead of the 'proper' pairs, as this may decrease the 'reverse' reaction and improves yield. Also, performing the reaction in the presence of polynucleotide kinase (plus ATP) improves yield by phosphorylating the reaction 'byproduct' which decreases the reverse reaction rate. The method can also be optimized for scale-up, for example by using column purification rather than magnetic beads to isolate the products.

Example 11

Charging Topo with Non-consensus Bases

The consensus recognition sequence for vaccinia topoisomerase is (C/T)CCTT. When adding a single nucleotide to a chain of DNA (as described previously), the last position of this sequence (a 'T' in this case) will be added to the DNA chain. In order to encode binary data in DNA with maximum efficiency (i.e. one base per bit), it is useful to be able to 'charge' topoisomerase with a sequence having a nucleotide other than 'T' in the final position. Generally, non-consensus sequences show poor reactivity with topoisomerase. However, we show below an efficient method to 'charge' the DNA with sequences other the consensus sequence.

Step 1: Annealing oligonucleotides. Components are introduced into 4 tubes as specified in table below, heated to 94° C. for 5 minutes, and allowed to cool to room temperature.

|        | 7-BT  | 7-BTC | 7-BTC | 7-BTA |
|--------|-------|-------|-------|-------|
| 7F-T*  | 10 μL |       |       |       |
| 7F-B1* | 10 μL |       |       |       |
| 7F-TG* |       | 10 μL |       |       |
| 7F-B1G*|       | 10 μL |       |       |
| 7F-TC* |       |       | 10 μL |       |
| 7F-B1C*|       |       | 10 μL |       |
| 7F-TA* |       |       |       | 10 μL |
| 7F-B1A*|       |       |       | 10 μL |
| 7F-B2* | 10 μL | 10 μL | 10 μL | 10 μL |
| TE     | 66 μL | 66 μL | 66 μL | 66 μL |
| 5M NaCl| 4 μL  | 4 μL  | 4 μL  | 4 μL  |

*100 μM oligos (sequence below) in TE
TE: 10 mM Tris, 1 mM EDTA, pH 8.0

This will yield the annealed DNAs as illustrated below. These DNAs differ from one another in the nucleotides in bold, which is the last (3') position of the topo consensus sequence. Also note the mismatches in the sequence (underlined). When topoisomerase binds it's recognition sequence and undergoes transesterification, the presence of these mismatches decreases the rate of the reverse reaction and hence promotes the formation of 'charged' topoisomerase.

```
7-BT:
7F-T  5' P-CGGCAGATCTACCCTTCGAATTCACGTACTTG    [SEQ ID NO: 34]
7F-B1          TCTAGATGGGAAGCCG AGTGCATGAAC    7F-B2

7-BTC:
7F-TC 5' P-CGGCAGATCTACCCTCCGAATTCACGTACTTG    [SEQ ID NO: 35]
7F-B1C         TCTAGATGGGAGGCCG AGTGCATGAAC    7F-B2

7-BTG:
7F-TG 5' P-CGGCAGATCTACCCTGCGAATTCACGTACTTG    [SEQ ID NO: 36]
7F-B1G         TCTAGATGGGAGGCCG AGTGCATGAAC    7F-B2

7-BTA:
7F-TA 5' P-CGGCAGATCTACCCTACGAATTCACGTACTTG    [SEQ ID NO: 37]
7F-B1A         TCTAGATGGGATGCCG AGTGCATGAAC    7F-B2
```

Step 2: The topoisomerase is then charged with the above oligonucleotides, by combining each of the four oligonucleotides described above with topoisomerase.

|               | C      | G      | A      | T      |
|---------------|--------|--------|--------|--------|
| 7-BTC*        | 1 μL   |        |        |        |
| 7-BTG*        |        | 1 μL   |        |        |
| 7-BTA*        |        |        | 1 μL   |        |
| 7-BT*         |        |        |        | 1 μL   |
| Topoisomerase | 1 μL   | 1 μL   | 1 μL   | 1 μL   |
| 10x buffer    | 2 μL   | 2 μL   | 2 μL   | 2 μL   |
| water         | 16 μL  | 16 μL  | 16 μL  | 16 μL  |

*produced as described in step 1
Topoisomerase: 60 ng/μl in 50 mM sodium phosphate (pH 7.5), 1 mM DTT, 0.5 mM EDTA, 50 mM NaCl, 50% glycerol.
10x buffer: 200 mM Tris (8.0), 1M NaCl, 50 mM MgCl2, 20 mM DTT The ingredients are mixed as per above table, incubated at 37° C. for 30 minutes, and run on SDS-PAGE gel to check that the reaction proceeded as expected. Gel results are shown in FIG. 96. The charged topoisomerase can be purified from the uncharged topoisomerase and other reaction components and products. While the T reaction (corresponding to the consensus CCCTT sequence) generates the best yield of charged topoisomerase (indicated), the other reactions generate significant amount of charged topoisomerase as well, demonstrating that the topoisomerase reactions for synthesizing DNA can be used to add any selected single nucleotides or oligomers to a DNA strand in the 3' to 5' direction, e.g., as described in Method A, et seq. above.

The invention claimed is:

1. A method for synthesizing a charged polymer comprising at least two distinct monomers or oligomers in a nanopore-based device, the nanopore-based device comprising
   one or more addition chambers or channels containing buffer solution and reagents for addition of one or more monomers or oligomers to the charged polymer in blocked form, such that only a single monomer or oligomer can be added in one reaction cycle; and
   one or more deblocking chambers or channels containing buffer solution and reagents for removing the blocker group from the charged polymer,
   wherein the addition chambers or channels are separated from the deblocking chambers or channels by one or more membranes comprising one or more nanopores, and
   wherein the charged polymer can pass through a nanopore and at least one of the reagents for addition of one or more monomers or oligomers cannot,
   the method comprising
   a) moving the first end of a charged polymer having a first end and a second end, by electrical attraction, into an addition chamber or channel, whereby monomers or oligomers are added to said first end in blocked form,
   b) moving the first end of the charged polymer with the added monomer or oligomer in blocked form into a deblocking chamber or channel, whereby the blocking group is removed from the added monomer or oligomer, and
   c) repeating steps a) and b), wherein the monomers or oligomers added in step a) are the same or different, until the desired polymer sequence is obtained, and
   d) detecting the sequence of the polymer as it passes through the nanopore to confirm that the desired sequence has been synthesized.

2. The method of claim 1, wherein the charged polymer is DNA.

3. The method of claim 1, wherein the second end of the polymer is bound to a surface.

4. The method of claim 1, wherein the device comprises one or more first addition chambers or channels containing reagents suitable for adding a first type of monomer or oligomer and one or more second addition chambers containing reagents suitable for adding a second type of monomer or oligomer, and wherein in step a), the first end of the charged polymer is moved into either the first addition chamber or the second addition chamber, depending on whether it is desired to add a first type of monomer or oligomer or a second type of monomer or oligomer.

5. The method of claim 2, wherein the reagents for addition of one or more monomers or oligomers to the charged polymer comprise reagents selected from a topoisomerase, a DNA polymerase, or combinations thereof.

6. The method of claim 2 wherein the step of detecting the sequence of the polymer as it passes through a nanopore to confirm that the desired sequence has been synthesized is performed by measuring the capacitive variance in a resonant RF circuit as the DNA is drawn through the nanopore.

7. The method of claim 1, wherein step of detecting the sequence of the polymer as it passes through the nanopore to confirm that the desired sequence has been synthesized comprises:
   i) providing an LC resonator having an effective impedance;
   ii) providing a cell, the cell having at least the addition chamber, the deblocking chamber, and the nanopore disposed therebetween, the effective impedance being affected by the polymer passing through the nanopore, the resonator having an AC output voltage resonant frequency response at a probe frequency, which is based on the effective impedance, in response to an AC input voltage at the probe frequency;
   iii) providing the AC input voltage having at least the probe frequency; and
   iv) monitoring the AC output voltage at least at the probe frequency, the AC output voltage at the probe frequency being indicative of the data stored in the polymer at the time of monitoring.

8. The method of claim 7 wherein the polymer comprises at least two types of monomers or oligomers having different properties causing different resonant frequency responses.

9. The method of claim 8 wherein the at least two types of monomers or oligomers comprises at least a first monomer or oligomer having a first property that causes a first resonant frequency response when the first monomer or oligomer is in the nanopore, and a second monomer or oligomer having a second property that causes a second resonant frequency response when the second monomer or oligomer is in the nanopore.

10. The method of claim 9 wherein a characteristic of the first frequency response at the probe frequency is different from the same characteristic of the second frequency response at the probe frequency.

11. The method of claim 10 wherein the characteristic of the first and second frequency responses comprises at least one of magnitude and phase response.

12. The method of claim 9 wherein the first property and the second property of the monomers comprises a dielectric property.

13. The method of claim 7 wherein the cell comprises at least a top electrode and a bottom electrode, the nanopore being disposed between the electrodes, and the cell having the buffer solution and reagents therein, and wherein the electrodes, the nanopore, and the buffer solution and reagents have an effective cell capacitance that changes when the polymer passes through the nanopore.

14. The method of claim 13 wherein the effective impedance comprises an inductor connected in series with the effective capacitance to create the resonator, a combination of the inductor and effective capacitance being related to the resonant frequency response.

15. The method of claim 13 wherein the polymer is moved through the nanopore via a DC steering voltage applied to the electrodes.

16. The method of claim 13 wherein the cell has at least three chambers, comprising two of the addition chambers and the deblocking chamber, at least two nanopores, and at least three electrodes for moving the polymer through the nanopores between the addition chambers and the deblocking chamber.

17. The method of claim 8 wherein at least part of the sequence of the at least two types of monomers or oligomers of the polymer stores data in the form of a computer-readable code.

18. The method of claim 7 wherein the polymer comprises DNA, and wherein the DNA comprises at least two types of nucleotides, each type of nucleotide providing a unique frequency response at the probe frequency.

19. The method of claim 7 wherein the probe frequency is about 1 MHz to 100 GHz.

20. The method of claim 8 wherein the at least two types of monomers or oligomers have a dielectric property that affects the frequency response of the resonator to produce at least two different frequency responses at the probe frequency.

21. The method of claim 7 wherein the resonator comprises at least one of a longitudinal resonator and a transverse resonator.

22. The method of claim 21 wherein the transverse resonator comprises a split-ring resonator having the nanopore disposed in a gap of the split-ring resonator.

23. The method of claim 7 wherein the nanopore comprises a nano-channel having dimensions that allow for substantially linear flow of the polymer without folding on itself.

24. The method of claim 7 further comprising a plurality of the resonators in the cell, each resonator driven by a common AC input voltage and monitored from a common AC output voltage.

25. The method of claim 24 wherein the plurality of resonators in the cell comprises at least one longitudinal resonator and at least one transverse resonator.

26. The method of claim 25 wherein the frequency response of the longitudinal resonator and of the transverse resonator are monitored simultaneously.

27. The method of claim 7 further comprising a plurality of cells, each cell having the resonator tuned to a different resonant frequency band, the cells being driven by a common AC input voltage and measured by a common AC output voltage.

* * * * *